US007087765B2

(12) United States Patent
Mueller et al.

(10) Patent No.: US 7,087,765 B2
(45) Date of Patent: *Aug. 8, 2006

(54) COMPOUNDS ACTIVE AT A NOVEL SITE ON RECEPTOR-OPERATED CALCIUM CHANNELS USEFUL FOR TREATMENT OF NEUROLOGICAL DISORDERS AND DISEASES

(75) Inventors: Alan L. Mueller, Salt Lake City, UT (US); Scott T. Moe, Salt Lake City, UT (US)

(73) Assignee: NPS Pharmaceuticals, Inc., Salt Lake City, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/797,355

(22) Filed: Mar. 9, 2004

(65) Prior Publication Data

US 2004/0171670 A1    Sep. 2, 2004

Related U.S. Application Data

(63) Continuation of application No. 09/825,373, filed on Apr. 2, 2001, which is a continuation of application No. 09/186,341, filed on Nov. 4, 1998, now Pat. No. 6,211,245, which is a continuation of application No. 08/873,011, filed on Jun. 11, 1997, now abandoned, which is a continuation-in-part of application No. 08/869,154, filed on Jun. 4, 1997, now abandoned, which is a continuation-in-part of application No. 08/763,480, filed on Dec. 11, 1996, now Pat. No. 6,017,965, which is a continuation-in-part of application No. 08/663,013, filed on Jun. 7, 1996, now abandoned, which is a continuation-in-part of application No. 08/485,038, filed on Jun. 7, 1995, now Pat. No. 6,071,970.

(51) Int. Cl.
*C07D 337/16* (2006.01)
*C07D 495/00* (2006.01)
*C07D 313/00* (2006.01)
*C07D 311/82* (2006.01)
*C07C 211/03* (2006.01)

(52) U.S. Cl. ............................ 549/12; 549/26; 549/354; 549/388; 564/355; 564/360; 564/361; 564/363; 564/379

(58) Field of Classification Search ................ 514/649; 549/12, 26, 354, 388; 564/355, 360, 361, 564/363, 379

See application file for complete search history.

(56) References Cited

U.S. PATENT DOCUMENTS

| | | | |
|---|---|---|---|
| 3,258,488 A * | 6/1966 | Judd et al. ........................ | 564/379 |
| 3,372,193 A | 3/1968 | Moffet et al. ................... | 564/375 |
| 4,018,895 A | 4/1977 | Molloy et al. .................. | 514/649 |
| 4,070,373 A | 1/1978 | Winter et al. ................... | 549/354 |
| 4,313,896 A | 2/1982 | Molloy et al. ................... | 562/597 |
| 5,037,846 A | 8/1991 | Saccomano et al. ........... | 514/419 |
| 5,145,870 A | 9/1992 | Jakobsen et al. ............... | 514/524 |
| 5,185,369 A | 2/1993 | Saccomano et al. ........... | 514/502 |
| 5,310,756 A | 5/1994 | Jakobsen et al. ............... | 514/524 |
| 5,574,173 A * | 11/1996 | Ting et al. ...................... | 549/354 |

FOREIGN PATENT DOCUMENTS

| | | |
|---|---|---|
| AU | 723349 | 1/1998 |
| DE | 1 051 281 | 2/1959 |
| DE | 33 285 | 12/1964 |
| DE | 1 793 735 | 7/1973 |
| DE | 17 93 735 | 7/1973 |
| DE | 1793735 | * 7/1973 |
| DE | 23 35 943 | 1/1975 |
| DE | 4 239 816 | 6/1994 |
| EP | 0 005 658 | 4/1979 |
| EP | 0 208 523 | 1/1987 |
| EP | 0 399 504 | 5/1990 |
| EP | 0 436 332 | 7/1991 |
| FR | 2 277 589 | 2/1976 |
| FR | 2277589 | * 2/1976 |
| GB | 1 169 944 | 7/1967 |
| GB | 1 129 029 | 10/1968 |
| GB | 1 129 210 | 10/1968 |
| GB | 1129029 | * 10/1968 |
| GB | 1134715 | 11/1968 |
| GB | 1135926 | 12/1968 |
| NL | 300541 | 6/1974 |
| WO | 92/14709 | 9/1992 |
| WO | 93/04036 | 3/1993 |
| WO | 93/04041 | 3/1993 |
| WO | 93/04373 | 3/1993 |
| WO | 95/15959 | 6/1995 |
| WO | 95/21612 | 8/1995 |
| WO | WO 95/21612 | 8/1995 |

(Continued)

OTHER PUBLICATIONS

Banciu et al, Carbonium ion reactions, Revue Roumaine de Chimie, 1975, 20(1), 121-7.*

(Continued)

*Primary Examiner*—Alton Pryor
(74) *Attorney, Agent, or Firm*—Holland & Hart LLP

(57) ABSTRACT

Method and compositions for treating a patient having a neurological disease or disorder, such as stroke, head trauma, spinal cord injury, spinal cord ischemia, ischemia- or hypoxia-induced nerve cell damage, epilepsy, anxiety, neuropsychiatric or cognitive deficits due to ischemia or hypoxia such as those that frequently occur as a consequence of cardiac surgery under cardiopulmonary bypass, or neurodegenerative diseases such as Alzheimer's Disease, Huntington's Disease, Parkinson's Disease, or amyotrophic lateral sclerosis (ALS).

6 Claims, No Drawings

FOREIGN PATENT DOCUMENTS

| WO | 96/05818 | 2/1996 |
|---|---|---|
| WO | 96/40097 | 12/1996 |
| WO | 97/46511 | 12/1997 |

OTHER PUBLICATIONS

Tsvetkova et al, Synthesis of aminoalkylxanthenes and aminothioxanthenes, Khimo-Farmatsevticheski Zhurnal, 1969, 3 (12), 17-20.*

U.S. Appl. No. 08/763,480, filed Dec. 11, 1996, Mueller et al.

Akaike et al., "Spider Toxin Blocks Excitatory Amino Acid Responses in Isolated Hippocampal Pyramidal Neurons," *Neuroscience Letters* 79:326-330 (1987).

Anis et al., "Structure-Activity Relationships of Philanthotoxin Analogs and Polyamines on N-Methyl-D-Aspartate and Nicotinic Acetylcholine Receptors," *Journal of Pharmacology and Experimental Therapeutics* 254:764-773 (1990).

Artman et al., "Preferential Inhibitory Effects of Arylamine Spider Toxins on NMDA Receptor-Mediated Increases in Cytosolic Calcium," *Society for Neuroscience Abstracts* 17(Part 1):394 at abstract No. 163.19 (1991).

Ashe et al., "Argiotoxin-636 Blocks Excitatory Synaptic Transmission in Rat Hippocampal CA1 Pyramidal Neurons," *Brain Research* 480:234-240 (1989).

Banciu et al., "Carbonium ion reactions. XII. Acetolysis of 5-(2-bromoethyl)-5H-dibenzol [a,d] cycloheptene and nitrous acid deamination of 5-(2-aminoethyl)-5H-dibenzo [a,d] cycloheptene," *Revue Roumaine de Chimie* 20(1):121-127 (1975).

Banciu et al., Chemical Abstracts, vol. 83 Abstract 146868 (1975).

Beckett and Casy, "Configurational Studies in Synthetic Analgesics," *Journal of the Chemical Society* pp. 900-904 (Feb. 1955).

Blagbrough and Usherwood, "Polyamine amide toxins as pharmacological tools and pharmaceutical agents," *Proceedings of the Royal Society of Edinburgh* 99B(1-2):67-81 (1992).

Blagbrough et al., "Anthropod Toxins as Leads for Novel Insecticides: An Assessment of Polyamine Amides as Glutamate Antagonists," *Toxicon* 30:303-322 (1992).

Blake et al., "2-Methyl-3,3-Diphenyl-3-Propanolamine (2-MDP) Selectively Antagonises N-Methyl-Aspartate (NMA)," *Pharmacology Biochemistry & Behavior* 24:23-25 (1986).

Blaschke et al., "A Single Amino Acid Determines the Subunit-Specific Spider Toxin Block of -Amino-3-Hydroxy-5-Methylisoxazole-4-Propionate/Kainate Receptor Channels," *Proc. Natl. Acad. Sci. USA* 90:6528-6532 (1993).

Boehringer et al., Chemical Abstracts, vol. 70 Abstract 37664 (1969).

Boehringer Mannheim, Chemical Abstracts, vol. 86 Abstract 16562 (1977).

Brackley et al., "Selective Antagonism of Native and Cloned Kainate and NMDA Receptors by Polyamine-Containing Toxins," *Journal of Pharmacology and Experimental Therapeutics* 266:1573-1580 (1993).

Bruce et al., "Structure-Activity Relationships of Analogues of The WASP Toxin Philanthotoxin: Non-Competitive Antagonists of Quisqualate Receptors," *Toxicon* 28(11):1333-1346 (1990).

Burtsev and Savkov, "Calcium Antagonists (Finoptin and Senzit) in the Treatment of Cerebrovascular Disorders," *Klinicheskaia Meditsina* 67(9):51-54 (1989) (abstract from MEDLINE).

Buschauer et al., "Synthesis and histamine $H_2$ agonistic activity of arpromidine analaogues: replacement of the pheniramine-like moiety by non-heterocyclic groups." *Eur. J. Med. Chem.* 27:321-330 (1992).

Camps et al., "A New and Efficient One-Pot Preparation of Alkyl Halides From Alcohols," *Synthesis Communications* pp. 511-512 (May 1987).

*Chemical Abstracts* 5:423 (1959).

*Chemical Abstracts* 54:24555-24556 (1960).

*Chemical Abstracts* 54:424a (1960).

*Chemical Abstracts* 66:4375 (1967).

*Chemical Abstracts* 67:3059 (1967).

*Chemical Abstracts* 69:3322 (1968).

Chemical Abstracts Service, Registry Handbook, Reg. No. 114272-62-7 through 116231-28-8, 1988 Supplement.

Cheng and Prusoff, "Relationship Between the Inhibition Constant ($K_1$) and the Concentration of Inhibitor Which Causes 50 Per Cent Inhibition ($I_{50}$) of an Enzymatic Reaction," *Biochemical Pharmacology* 22:3099-3108 (1973).

Choi et al., "Glutamate Neurotoxicity in Cortical Cell Culture," *J. Neuroscience* 7:357-368 (1987).

Choi et al., "Synthesis and Assay of Hybrid Analogs of Argiotoxin-636 and Philanthotoxin-433: Glutamate Receptor Antagonists," *Tetrahedron* 49:5777-5790 (1993).

Choi, "Glutamate Neurotoxicity and Diseases of the Nervous System," *Neuron* 1:623-634 (1988).

Collingridge and Davis, "Ch. 9—NMDA receptors and long-term potentiation in the hippocampus," in *The NMDA Receptor*, edited by Watkins and Collingridge, IRL Press, p. 123-135 (1989).

Cramer et al., "Kainic Acid and 4-Aminopyridine Seizure Models in Mice: Evaluation of Efficacy of Anti-Epileptic Agents and Calcium Antagonists," *Life Sciences* 54:PL271-PL275 (1994).

Davis et al., "Polyamine Spider Toxins Are Potent Uncompetitive Antagonists of Rat Cortex Excitatory Amino Acid Receptors," *European Journal of Pharmacology—Molecular Pharmacology Section* 227:51-56 (1992).

Deneris et al., "Pharmacological and Functional Diversity of Neuronal Nicotinic Acetylcholine Receptors," *TiPS* 12:34-40 (1991).

Dickenson, "A Cure for Wind-Up: NMDA Receptor Antagonists as Potential Analgesics," *TiPS* 11:307-309 (1990).

Dingledine et al., "Excitatory Amino Acid Receptors in Epilepsy," *TiPS* 11:334-338 (1990).

Donevan and Rogawski, "GYKI 52466, a 2,3-Benzodiazepine, is a Highly Selective, Noncompetitive Antagonist of AMPA/Kainate Receptor Responses," *Neuron* 10:51-59 (1993).

Donevan et al:, "Arcaine Blocks N-Methyl-D-Aspartate Receptor Responses by an Open Channel Mechanism: Whole-Cell and Single-Channel Recording Studies in Cultured Hippocampal Neurons," *Molecular Pharmacology* 41:727-735 (1992).

Draguhn et al., "Argiotoxin$_{636}$ inhibits NMDA-activated ion channels expressed in *Xenopus* oocytes," *Neuroscience Letters* 132:187-190 (1991).

Fingl and Woodbury, "Chapter 1—General Principles," in *The Pharmacological Basis of Therapeutics* 5th edition, Goodman and Gilman editors, MacMillan Publishing Co., Inc., New York, pp. 1-46 (1975).

Fisher and Bogousslavsky, "Evolving Toward Effective Therapy for Acute Ischemic Stroke," *JAMA* 270:360-364 (1993).
Foye et al., *Principals of Medicinal Chemistry*, 4th edition, Lea & Febiger/Williams and Wilkins, Philadelphia, PA, pp. 233, 265, 281-282, 340-341, 418-427 and 430 (1995).
Ginsberg and Busto, "Rodent Models of Cerebral Ischemia," *Stroke* 20:1627-1642 (1989).
Gisvold and Steen, "Drug Therapy in Brain Ischaemia," *Br. J. Anaesth.* 57:96-109 (1985).
Grishin et al., "Isolation and Structure Analysis of Components from Venom of the Spider *Argiope lobata*," *Toxicon* 27:451-549 (1989).
Gullak et al., "CNS Binding Sites of the Novel NMDA Antagonist Arg-636," *Soc. Neurosci. Abst.* 15:1168 at abstract No. 463.23 (1989).
Hayes et al., "Anticonvulsant Properties of Phencyclidine-Like Drugs in Mice," *European Journal of Pharmacology* 117:121-125 (1985).
Helke and Raines, "Antiextensor Effects of 3,3-Diphenyl-n-Propylamine in the Mouse," *European Journal of Pharmacology* 48:231-235 (1978).
Herlitze et al., "Argiotoxin Detects Molecular Differences in AMPA Receptor Channels," *Neuron* 10:1131-1140 (1993).
Herold and Yaksh, "Anesthesia and Muscle Relaxation with Intrathecal Injections of AR636 and AG489, Two Acylpolyamine Spider Toxins, in Rat," *Anesthesiology* 77:507-512 (1992).
Hill, "A New Mathematical Treatment of Changes of Ionic Concentration in Muscle and Nerve Under the Action of Electric Currents, with a Theory as to Their Mode of Excitation," *Journal of Physiology* 40:190-224 (1910).
Honoré et al., "Quinoxalinediones: Potent Competitive Non-NMDA Glutamate Receptor Antagonists," *Science* 241:701-703 (1988).
Hughes, "Merz' Novel Approach to the Treatment of Dementia," Script No. 1666:24-25 (1991).
Jackson and Parks, "Spider Toxins: Recent Applications In Neurobiology," *Ann. Rev. Neurosci.* 12:405-414 (1989).
Jackson and Usherwood, "Spider Toxins as Tools for Dissecting Elements of Excitatory Amino Acid Transmission," *TINS* 11:278-283 (1988).
Janssen et al., *Synthetic Analgesics: Part I—Diphenylpropylamines*, Pergamon Press, pp. 1-109 (1960).
Jasys et al., "Isolation, Structure Elucidation, and Synthesis of Novel Hydroxylamine-Containing Polyamines From the Venom of the *Agelenopsis aperta* Spider," *J. Amer. Chem. Soc.* 112:6696-6704 (1990).
Jasys et al., "The Total Synthesis of Argiotoxins 636, 659 and 673," *Tetrahedron Letters* 29:6223-6226 (1988).
Jones and Lodge, "Comparison of Some Arthropod Toxins and Toxin Fragments as Antagonists of Excitatory Amino Acid-Induced Excitation of Rat Spinal Neurones," *European Journal of Pharmacology* 204:203-209 (1991).
Jones et al., "Philanthotoxin Blocks Quisqualate-, AMPA- and Kainate-, but not NMDA-, Induced Excitation of Rat Brainstem Neurones in vivo," *Br. J. Pharmacol* 101:968-970 (1990).
Jones et al., "Substituted 1,1-Diphenyl-3-aminoprop-l-enes and 1,1-Diphenyl-3-aminopropanes as Potential Antidepressant Agents," *J. Med. Chem.* 14(2):161-164 (1971).
Kalman et al., "Difenil-propil-amin-szarmazekok," *Magyar Kemiai Folyirat* 78:46-49 (1972).

Kanai et al., "An Analogue of Joro Spider Toxin Selectively Suppresses Hippocampal Epileptic Discharges Induced by Quisqualate," *Brain Research* 581:161-164 (1992).
Karpiak et al., "Animal Models for the Study of Drugs in Ischemic Stroke," *Annu. Rev. Pharmocol. Toxicol.* 29:403-414 (1989).
Kawai et al., "Effect of a Spider Toxin on Glutaminergic Synapses in the Mammalian Brain," *Biomedical Research* 3:353-355 (1982).
Kawai et al., "Spider Toxin and the Glutamate Receptors," *Comp. Biochem. Physiol.* 98C:87-95 (1991).
Kawai, "Neuroactive Toxins of Spider Venoms," *J. Toxicol.—Toxin Reviews* 10:131-167 (1991).
Keasling and Moffett, "Central Nervous System Agents. 3. Structure-Activity Relationship of a Series of Diphenylaminopropanols," *Journal of Medicinal Chemistry* 14(11):1106-1111 (1971).
Kiskin et al., "A Highly Potent and Selective N-Methyl-D-Aspartate Receptor Antagonist From the Venom of the *Agelenopsis aperta* Spider," *Neuroscience* 51:11-18 (1992).
Kiskin et al., "Argiopine, Argiopinines and Pseudoargiopinines as Glutamate Receptor Blockers in Hippocampal Neurons," *Neurophysiology* 21:748-754 (1989) (in Russian).
Kovacs and Hesse, "Synthetic Analogues of Naturally Occuring Spider Toxins," *Helvetica Chimica Acta* 75:1909-1924 (1992).
Kurokawa et al., "Synthesis and Biological Activity of 11-[4-(Cinnamyl)-1-piperazinyl]-1-piperazinyl]-6,11-dihydrodibenz[b,e]oxepin Derivatives, Potential Agents for the Treatment of Cerebrovascular Disorders," *Chem. Pharm. Bull.* 39(10):2564-2573 (1991).
Leszkovszky et al., "The Pharmacology of Diphenylalkyl Derivatives," *Acta Physiologica Academiae Scientiarum Hungaricae Tomus* 29(3-4):283-298 (1966).
Marcusson et al., "Inhibition of [$^3$H]paroxetine binding by various serotonin uptake inhibitors: structure-activity relationships," *Europ. J. Pharmacol.* 215:191-198 (1992).
McQuaid et al., "Inhibition of [$^3$H]-MK801 Binding and Protection Against NMDA-Induced Lethality in Mice by a Series of Imipramine Analogs," *Research Communications in Chemical Pathology and Pharmacology* 77(2):171-178 (1992).
Meldrum and Garthwaite, "Excitatory Amino Acid Neurotoxicity and Neurodegenerative Disease," *TiPS* 11:379-387 (1990).
Meldrum, "Excitatory Amino Acid Neurotransmission in Epilepsy and Anticonvulsant Therapy," in *Excitatory Amino Acids*, Meldrum et al. editors, New York, Raven Press, pp. 655-670 (1991).
Melloni et al., "Potential antidepressant agents. Aryloxybenzyl derivatives of ethanolamine and morpholine," *Eur. J. Med. Chem.—Chim. Ther.* 19:235-242 (1984).
*Merck Index*, 11th edition, Merck & Co., Inc., Rahway, New Jersey, p. 218 at No. 1433, p. 337 at No. 2180, p. 623 at No. 3916, p. 655 at No. 4112, p. 1148 at No. 7198, p. 1227 at No. 7744, p. 1444 at No. 9098, and p. 1597 at No. 10024 (1989).
Mikio et al., "Synthesis of Analgesics," *Chemical Abstracts* vol. 83, No. 7, Aug. 18, 1975 at abstract No. XP002016632.
Moffett et al., "Central Nervous System Agents. 1. Synthesis of Diphenyl-*tert*-aminopropanols," *J. Med. Chem.* 14(11):1088-1100 (1971).
Mueller et al., "Arylamine Spider Toxins Antagonize NMDA Receptor-Mediated Synaptic Transmission in Rat Hippocampal Slices," *Synapse* 9:244-250 (1991).

Mueller et al., "Effects of Polyamine Spider Toxins on NMDA Receptor-Mediated Transmission in Rat Hippocampus In Vitro," Soc. Neurosci. Abst. 15:945 at abstract No. 373. 10 (1989).

Nakanishi et al., "Bioorganic Studies of Transmitter Receptors with Philanthotoxin Analogs," Pure & Applied Chemistry vol. 66, #3 (Mar 1994).

Nakanishi, "Molecular Diversity of Glutamate Receptors and Implications for Brain Function," Science 258:597-603 (1992).

Nason et al., "Synthesis of Neurotoxic Nephila Spider Venoms: NSTX-3 and JSTX-3," Tetrahedron Letters 30:2337-2340 (1989).

Nemeth et al."Arylamines Derived From Spider Venom Are Potent and Selective NMDA Receptor Antagonists in The Mammalian CNS," in Neuroreceptors, Ion Channels and the Brain, Kawai et al., editors, pp. 21-28 (1992).

Olney et al., "Pathological Changes Induced in Cerebrocortical Neurons by Phencyclidine and Related Drugs," Science 244:1360-1362 (1989).

Palmer et al., "Anticonvulsant Properties of Calcium Channel Blockers in Mice: N-Methyl-D-, L-Aspartate- and Bay K 8644-Induced Convulsions are Potentially Blocked by the Dihydropyridines," Epilepsia 34:372-380 (1993).

Parks et al., "Arylamine Toxins From Funnel-Web Spider (Agelenopsis aperta)Venom Antagonize N-Methyl-D-aspartate Receptor Function in Mammalian Brain," J. Biol. Chem. 266:21523-21529 (1991).

Parks et al., "Polyamine Spider Toxins Block NMDA Receptor- Mediated Increases in Cytosolic Calcium in Cerebellar Granule Neurons," Soc. Neurosci. Abst. 15:1169 at abstract No. 463.25 (1989).

Paul et al., "Adaptation of the N-Methyl-D-Aspartate Receptor Complex Following Chronic Antidepressant Treatments," J. Pharmacology and Experimental Therapeutics 269:95-102 (1994).

Peterson, "Studies on a New Spasmolytic Compound 1,1-diphenyl-3-dimethylaminobutene-1 (A29) related to Methadon, and on the Combined Use of this Compound and a Potent Analgesic Ketobemidone," Acta Pharmacol. et toxicol, 7:51-64 (1951).

Priestley et al., "Antagonism of responses to excitatory amino acids on rat cortical neurones by the spider toxin, argiotoxin$_{636}$," Br. J. Pharmacol. 97:1315-1323 (1989).

Prous, The Year's Drug News. Therapeutic Targets, 1995 Edition, Prous Science Publishers, Barcelona, Spain, pp. 13, 55-56, 58-59, 74, 89, 144-145, 152, 296-297 and 317 (1995).

Quistad et al., "Paralytic and Insecticidal Toxins from the Funnel Web Spider, Hololena Curta," Toxicon 29:329-336 (1991).

Raditsch et al., "Subunit-Specific Block of Cloned NMDA Receptors by Argiotoxin$_{636}$," FEBS Letters 324(1):63-66 (1993).

Ransom and Stec, "Cooperative Modulation of [$^3$H]MK-801 Binding to the N-Methyl-D-Aspartate Receptor-Ion Channel Complex by L-Glutamate, Glycine and Polyamines," Journal of Neurochemistry 51:830-836 (1988).

Reist et al., "Sodium Azide in Dimethylformamide for the Preparation of Amino-Sugars," Chemistry and Industry pp. 1794-1795 (Oct. 13, 1962).

Reynolds and Miller, "Ifenprodil is a Novel of N-Methyl-D-Aspartate Receptor Antagonist: Interaction with Polyamines," Molecular Pharmacology 36:758-765 (1989).

Reynolds, "Arcaine is a Competitive Antagonist of the Polyamine Site on the NMDA Receptor," European Journal of Pharmacology 177:215-216 (1990).

Reynolds, "The Spider Toxin, Argiotoxin$_{636}$, Binds to a $Mg^{2+}$Site on the N-Methyl-D-Aspartate Receptor Complex," Br. Journal of Pharmacology 103(2):1373-1376 (1991).

Reynolds, Martindale: The Extra Pharmacopoeia, The Pharmaceutical Press, London, pp. 543-544 (1989).

Rock and MacDonald, "Spermine and Related Polyamines Produce a Voltage-Dependent Reduction of N-Methyl-D-Aspartate Receptor Single-Channel Conductance," Molecular Pharmacology 42:157-164 (1992).

Rogawski, "Therapeutic Potential of Excitatory Amino Acid Antagonists: Channel Blockers and 2,3-benzodiazepines," Trends in Pharmacol. Sci. 14:325-331 (1993).

Rozental et al., "Allosteric Inhibition of Nicotinic Acetylcholine Receptors of Vertebrates and Insects by Philanthotoxin," Journal of Pharmacology and Experimental Therapeutics 249:123-130 (1989).

Sacaan and Johnson, "Characterization of the Stimulatory and Inhibitory Effects of Polyamines on [$^3$H]N-(1-[thienyl]cyclohexyl) piperidine Binding to the N-Methyl-D-Aspartate Receptor Ionophore Complex," Molecular Pharmacology 37:572-577 (1990).

Saccomano et al., "Arylamine NMDA Antagonists From Spider Venom," 201s(American Chemical Society National Meeting, Abstracts of Papers —Part 1, Atlanta, Georgia, Apr. 14-19, (1991) (Abstract #10).

Saccomano et al. "Ch. 30—Polyamine Spider Toxins: Unique Pharmacological Tools," in Annual Reports in Medicinal Chemistry 24:287-293 (1989).

Saito et al., "Effects of a Spider Toxin (JSTX) on Hippocampal CA1 Neurons in vitro," Brain Research 481:16-24 (1989).

Saito et al., "Spider Toxin (JSTX) Blocks Glutamate Synapse in Hippocampal Pyramidal Neurons," Brain Research 346:397-399 (1985).

Scatchard, "The Attractions of Proteins For Small Molecules and Ions," Annals New York Academy of Sciences 51:660-672 (1949).

Scatton et al., "NMDA Receptor Antagonists: Treatment for Brain Ischemia," Drug News & Perspectives 4(2):89-95 (1991).

Scatton, Therapeutic Potential of NMDA receptor antagonists in Ischemic Cerebrovascular Disease in Drug Strategies in the Prevention and Treatment of Stroke, IBC Technical Services Ltd., 1990.

Seymour and Mena, "In Vivo NMDA Antagonist Activity of the Polyamine Spider Venom Component, Argiotoxin-636," Soc. Neurosci. Abst.15:1168 at abstract No. 463.24 (1989).

Snell and Johnson, "Ch. 13—Phencyclidine: Behavioral Correlates of NMDA Antagonism," in Excitatory Amino Acids in Health and Diseases, D. Lodge editor, John Wiley & Sons, pp. 261-273 (1988).

Snyder, "Neurotransmitter Receptor Binding and Drug Discovery," J. Med. Chem. 26:1667-1672 (1983).

Srebnik et al., "Chiral Synthesis via Organoboranes. 18. Selective Reductions. 43. Diisopinocampheylchloroborane as an Excellent Chiral Reducing Reagent for the Synthesis of Halo Alcohols of High Enantiomeric Purity. A Highly Enantioselective Synthesis of Both Optical Isomers of Tomoxetine, Fluoxetine and Nisoxetine," J. Org. Chem. 53(13):2916-2920 (1988).

Sutton et al., "Inhibition of voltage-activated Ca$^{2+}$currents from cultured sensory neurones by spermine, argiotoxin-636 and a synthetic arginine polyamine," *Molecular Neuropharmacology* 3:37-43 (1993).

Tang et al., Phencyclidine-Like Behavioral Effects of 2-Methyl-3,3-Diphenyl-3-Propanolamine (2-MDP), *Pharmacology Biochemistry & Behavior* 20:209-213 (1984).

Teyler and DiScenna, "Long-Term Potentiation," *Annu. Rev. Neurosci*, 10:131-161 (1987).

Titeler, *Multiple Dopamine Receptors: Receptor Binding Studies in Dopamine Pharmacology*, vol. 1, Marcel Dekker, Inc., New York, pp. 1-173 (1983).

Tsvetkova et al., "Synthesis of aminoalkylxanthenes and aminothioxanthenes," *Khim. Farm. Zh*. 3(12):17-20 (1969).

Usherwood and Blagbrough, "Spider Toxins Affecting Glutamate Receptors: Polyamines in Therapeutic Neurochemistry," *Pharmac. Ther*. pp. 1-24 (1992).

von Wolfgang J. Fiedler et al., "66. Synthetische Analoga von niedermolekularen Spinnentoxinen mit Acyl-polyamin-Struktur," *Helvetica Chimica Acta* 76:1167-1181 (1993).

von Wolfgang J. Fiedler et al., "98. Synthese von selektiv N-funktionalisierten Polyamin-Derivaten," *Helvetica Chimica Acta* 76:1511-1519 (1993).

Watkins et al., *The NMDA Receptor*, Oxford, IRL Press (1989).

White et al., "Chemicopharmacological Studies on Antispasmodic Action. XII. Structure-Activity Relationship of Aralkylamines," *Chem. Pharm*. 6(2):147-154 (1958).

White et al., "Some Pharmacological Properties of 3:3-Diphenyl-Propanolamines,—Allylamines and -Propyl-amines," *Brit. J. Pharmacol*, 6:560-571 (1951).

Wiley and Balster, "Preclinical Evaluation of N-Methyl-D-Aspartate Antagonists for Antianxiety Effects: A Review," in *Multiple Sigma and PCP Receptor Ligands: Mechanisms for Neuromodulation and Neuroprotection*? NPP Books, Ann Arbor, Michigan, pp. 801-815 (1992).

Willetts et al., "The Behavioral Pharmacology of NMDA Receptor Antagonists," *Trends Pharmacol. Sci*, 11:423-428 (1990).

Williams et al., "Characterization of Polyamines Having Agonist, Antagonist, and Inverse Agonist Effects at the Polyamine Recognition Site of the NMDA Receptor," *Neuron* 5:199-208 (1990).

Williams et al., "Effects of Polyamines on the Binding of [$^3$H]M-801 to the *N*-Methyl-D-Aspartate Receptor: Pharmacological Evidence for the Existence of a Polyamine Recognition Site," *Molecular Pharmacology* 36:575-581 (1989).

Williams, "Effects of *Agelenopsis aperta* Toxins on the *N*-Methyl-D-Aspartate Receptor: Polyamine-Like and High-Affinity Antagonist Actions," *Journal of Pharmacology and Experimental Therapeutics* 266:231-236 (1993).

Williams, "Ifenprodil Discriminates Subtypes of the N-Methyl-D-Aspartate Receptor: Selectivity and Mechanisms at Recombinant Heteromeric Receptors," *Molecular Pharmacology* 44:851-859 (1993).

Yamaguchi et al., "Anticonvulsant Activity of AMPA/Kainate Antagonists: Comparison of GYKI 52466 and NBQX in Maximal Electroshock and Chemoconvulsant Seizure Models," *Epilepsy Research* 15:179-184 (1993).

* cited by examiner

COMPOUNDS ACTIVE AT A NOVEL SITE ON RECEPTOR-OPERATED CALCIUM CHANNELS USEFUL FOR TREATMENT OF NEUROLOGICAL DISORDERS AND DISEASES

This application is a continuation of co-pending U.S. application Ser. No. 09/825,373 filed on Apr. 2, 2001, which is a continuation of U.S. application Ser. No. 09/186,341 filed Nov. 4, 1998, now U.S. Pat. No. 6,211,245, which is a continuation of U.S. application Ser. No. 08/873,011, filed Jun. 11, 1997, now abandoned, which is a continuation-in-part of U.S. application Ser. No. 08/869,154, filed Jun. 4, 1997, now abandoned, which is a continuation-in-part of U.S. application Ser. No. 08/763,480, filed Dec. 11, 1996, now U.S. Pat. No. 6,017,965, which is a continuation-in-part of U.S. application Ser. No. 08/663,013, filed Jun. 7, 1996, now abandoned, which is a continuation-in-part of U.S. application Ser. No. 08/485,038, filed Jun. 7, 1995, now U.S. Pat. No. 6,071,970, which was a National Stage application of International Patent Appl. No. PCT/US94/12293 (WO 95/21612), filed Oct. 26, 1994 and designating the United States, which is a continuation-in-part of U.S. application Ser. No. 08/288,668, filed Aug. 9, 1994, now abandoned, which is a continuation-in-part of U.S. application Ser. No. 08/194,210, filed Feb. 8, 1994, now abandoned, which is a continuation-in-part of U.S. Ser. No. 08/014,813, filed Feb. 8, 1993, now abandoned, each of which are hereby incorporated by reference herein in their entirety, including all Tables, Figures, and claims.

FIELD OF THE INVENTION

This invention relates to compounds useful as neuroprotectants, anticonvulsants, anxiolytics, analgesics, muscle relaxants or adjuvants to general anesthetics. The invention relates as well to methods useful for the treatment of neurological disorders and diseases, including, but not limited to, global and focal ischemic and hemorrhagic stroke, head trauma, spinal cord injury, hypoxia-induced nerve cell damage such as in cardiac arrest or neonatal distress, epilepsy, anxiety, and neurodegenerative diseases such as Alzheimer's Disease, Huntington's Disease, Parkinson's Disease, and amyotrophic lateral sclerosis (ALS). The invention relates as well to methods of screening for compounds active at a novel site on receptor-operated calcium channels, and thereby possessing therapeutic utility as neuroprotectants, anticonvulsants, anxiolytics, analgesics, muscle relaxants or adjuvants to general anesthetics, and/or possessing potential therapeutic utility for the treatment of neurological disorders and diseases as described above.

BACKGROUND OF THE INVENTION

The following is a description of relevant art, none of which is admitted to be prior art to the claims.

Glutamate is the major excitatory neurotransmitter in the mammalian brain. Glutamate binds or interacts with one or more glutamate receptors which can be differentiated pharmacologically into several subtypes. In the mammalian central nervous system (CNS) there are three main subtypes of ionotropic glutamate receptors, defined pharmacologically by the selective agonists N-methyl-D-aspartate (NMDA), kainate (KA), and α-amino-3-hydroxy-5-methyl-isoxazole-4-propionic acid (AMPA). The NMDA receptor has been implicated in a variety of neurological pathologies including stroke, head trauma, spinal cord injury, epilepsy, anxiety, and neurodegenerative diseases such as Alzheimer's Disease (Watkins and Collingridge, *The NMDA Receptor*, Oxford: IRL Press, 1989). A role for NMDA receptors in nociception and analgesia has been postulated as well (Dickenson, A cure for wind-up: NMDA receptor antagonists as potential analgesics. *Trends Pharmacol. Sci.* 11: 307, 1990). More recently, AMPA receptors have been widely studied for their possible contributions to such neurological pathologies (Fisher and Bogousslavsky, Evolving toward effective therapy for acute ischemic stroke. *J. Amer. Med. Assoc.* 270: 360, 1993; Yamaguchi et al., Anticonvulsant activity of AMPA/kainate antagonists: Comparison of GYKI 52466 and NBQX in maximal electroshock and chemoconvulsant seizure models. *Epilepsy Res.* 15: 179, 1993).

When activated by glutamate, the endogenous neurotransmitter, the NMDA receptor permits the influx of extracellular calcium ($Ca^{2+}$) and sodium ($Na^+$) through an associated ion channel. The NMDA receptor allows considerably more influx of $Ca^{2+}$ than do kainate or AMPA receptors (but see below), and is an example of a receptor-operated $Ca^{2+}$ channel. Normally, the channel is opened only briefly, allowing a localized and transient increase in the concentration of intracellular $Ca^{2+}$ ($[Ca^{2+}]_i$), which, in turn, alters the functional activity of the cell. However, prolonged increases in $[Ca^{2+}]_i$, resulting from chronic stimulation of the NMDA receptor, are toxic to the cell and lead to cell death. The chronic elevation in $[Ca^{2+}]_i$, resulting from stimulation of NMDA receptors, is said to be a primary cause of neuronal degeneration following a stroke (Choi, Glutamate neurotoxicity and diseases of the nervous system. *Neuron* 1: 623, 1988). Overstimulation of NMDA receptors is also said to be involved in the pathogenesis of some forms of epilepsy (Dingledine et al., Excitatory amino acid receptors in epilepsy. *Trends Pharmacol. Sci.* 11: 334, 1990), anxiety (Wiley and Balster, Preclinical evaluation of N-methyl-D-aspartate antagonists for antianxiety effects: A review. In: *Multiple Sigma and PCP Receptor Ligands: Mechanisms for Neuromodulation and Neuroprotection?* NPP Books, Ann Arbor, Mich., pp. 801–815, 1992), neurodegenerative diseases (Meldrum and Garthwaite, Excitatory amino acid neurotoxicity and neurodegenerative disease. *Trends Pharmacol. Sci.* 11: 379, 1990), and hyperalgesic states (Dickenson, A cure for wind-up: NMDA receptor antagonists as potential analgesics. *Trends Pharmacol. Sci.* 11: 307, 1990).

The activity of the NMDA receptor-ionophore complex is regulated by a variety of modulatory sites that can be targeted by selective antagonists. Competitive antagonists, such as the phosphonate AP5, act at the glutamate binding site, whereas noncompetitive antagonists, such as phencyclidine (PCP), MK-801 or magnesium ($Mg^{2+}$), act within the associated ion channel (ionophore). There is also a glycine binding site that can be blocked selectively with compounds such as 7-chlorokynurenic acid. There is evidence suggesting that glycine acts as a co-agonist, so that both glutamate and glycine are necessary to fully elicit NMDA receptor-mediated responses. Other potential sites for modulation of NMDA receptor function include a zinc ($Zn^{2+}$) binding site and a sigma ligand binding site. Additionally, endogenous polyamines such as spermine are believed to bind to a specific site and so potentiate NMDA receptor function (Ransom and Stec, Cooperative modulation of [³H]MK-801 binding to the NMDA receptor-ion channel complex by glutamate glycine and polyamines. *J. Neurochem.* 51: 830, 1988). The potentiating effect of polyamines on NMDA receptor function may be mediated via a specific receptor site for polyamines; polyamines demonstrating agonist, antagonist, and inverse agonist activity have been described (Reynolds, Arcaine is a competitive antagonist of the polyamine site on the NMDA receptor. *Europ. J. Pharmacol.* 177: 215, 1990; Williams et al., Characterization of polyamines having agonist, antagonist, and inverse agonist effects at the polyamine recognition site of the NMDA receptor. *Neuron* 5: 199, 1990). Radioligand binding studies have demonstrated additionally that higher concentrations of polyamines inhibit NMDA receptor function (Reynolds and Miller, Ifenprodil is a novel type of NMDA receptor antagonist: Interaction with polyamines. *Molec. Pharmacol.* 36: 758, 1989; Williams et al., Effects of polyamines on the binding of [$^3$H]MK-801 to the NMDA receptor: Pharmacological evidence for the existence of a polyamine recognition site. *Molec. Pharmacol.* 36: 575, 1989; Sacaan and Johnson, Characterization of the stimulatory and inhibitory effects of polyamines on [$^3$H]TCP binding to the NMDA receptor-ionophore complex. *Molec. Pharmacol.* 37: 572, 1990). This inhibitory effect of polyamines on NMDA receptors is probably a nonspecific effect (i.e., not mediated via the polyamine receptor) because patch clamp electrophysiological studies have demonstrated that this inhibition is produced by compounds previously shown to act at the polyamine receptor as either agonists or antagonists (Donevan et al., Arcaine Blocks N-Methyl-D-Aspartate Receptor Responses by an Open Channel Mechanism: Whole-Cell and Single-Channel Recording Studies in Cultured Hippocampal Neurons. *Molec. Pharmacol.* 41: 727, 1992; Rock and Macdonald, Spermine and Related Polyamines Produce a Voltage-Dependent Reduction of NMDA Receptor Single-Channel Conductance. *Molec. Pharmacol.* 42: 157, 1992).

Recent studies have demonstrated the molecular diversity of glutamate receptors (reviewed by Nakanishi, Molecular Diversity of Glutamate Receptors and Implications for Brain Function. *Science* 258: 597, 1992). At least five distinct NMDA receptor subunits (NMDAR1 and NMDAR2A through NMDAR2D), each encoded by a distinct gene, have been identified to date. Also, in NMDAR1, alternative splicing gives rise to at least six additional isoforms. It appears that NMDAR1 is a necessary subunit, and that combination of NMDAR1 with different members of NMDAR2 forms the fully functional NMDA receptor-ionophore complex. The NMDA receptor-ionophore complex, thus, can be defined as a hetero-oligomeric structure composed of at least NMDAR1 and NMDAR2 subunits; the existence of additional, as yet undiscovered, subunits is not excluded by this definition. NMDAR1 has been shown to possess binding sites for glutamate, glycine, $Mg^{2+}$ MK-801, and $Zn^{2+}$. The binding sites for sigma ligands and polyamines have not yet been localized on NMDA receptor subunits, although ifenprodil recently has been reported to be more potent at the NMDAR2B subunit than at the NMDAR2A subunit (Williams, Ifenprodil discriminates subtypes of the N-methyl-D-aspartate receptor: selectivity and mechanisms at recombinant heteromeric receptors. Mol. Pharmacol. 44: 851, 1993).

Several distinct subtypes of AMPA and kainate receptors have been cloned as well (reviewed by Nakanishi, Molecular diversity of glutamate receptors and implications for brain function. *Science* 258: 597, 1992). Of particular relevance are the AMPA receptors designated GluR1, GluR2, GluR3, and GluR4 (also termed GluRA through GluRD), each of which exists in one of two forms, termed flip and flop, which arise by RNA alternative splicing. GluR1, GluR3 and GluR4, when expressed as homomeric or heteromeric receptors, are permeable to $Ca^{2+}$, and are therefore examples of receptor-operated $Ca^{2+}$ channels. Expression of GluR2 alone or in combination with the other subunits gives rise to a receptor which is largely impermeable to $Ca^{2+}$. As most native AMPA receptors studied in situ are not $Ca^{2+}$-permeable (discussed above), it is believed that such receptors in situ possess at least one GluR2 subunit.

Furthermore, it is hypothesized that the GluR2 subunit is functionally distinct by virtue of the fact that it contains an arginine residue within the putative pore-forming transmembrane region II; GluR1, GluR3 and GluR4 all contain a glutamine residue in this critical region (termed the Q/R site, where Q and R are the single letter designations for glutamine and arginine, respectively). The activity of the AMPA receptor is regulated by a number of modulatory sites that can be targeted by selective antagonists (Honore et al., Quinoxalinediones: potent competitive non-NMDA glutamate receptor antagonists. *Science* 241: 701, 1988; Donevan and Rogawski, GYKI 52466, a 2,3-benzodiazepine, is a highly selective, noncompetitive antagonist of AMPA/kainate receptor responses. *Neuron* 10: 51, 1993). Competitive antagonists such as NBQX act at the glutamate binding site, whereas compounds such as GYKI 52466 appear to act noncompetitively at an associated allosteric site.

Compounds that act as competitive or noncompetitive antagonists at the NMDA receptor are said to be effective in preventing neuronal cell death in various in vitro neurotoxicity assays (Meldrum and Garthwaite, Excitatory amino acid neurotoxicity and neurodegenerative disease. *Trends Pharmacol. Sci.* 11: 379, 1990) and in in vivo models of stroke (Scatton, Therapeutic potential of NMDA receptor antagonists in ischemic cerebrovascular disease in *Drug Strategies in the Prevention and Treatment of Stroke*, IBC Technical Services Ltd., 1990). Such compounds are also effective anticonvulsants (Meldrum, Excitatory amino acid neurotransmission in epilepsy and anticonvulsant therapy in *Excitatory Amino Acids*. Meldrum, Moroni, Simon, and Woods (Eds.), New York: Raven Press, p. 655, 1991), anxiolytics (Wiley and Balster, Preclinical evaluation of N-methyl-D-aspartate antagonists for antianxiety effects: A review. In: *Multiple Sigma and PCP Receptor Ligands: Mechanisms for Neuromodulation and Neuroprotection*? NPP Books, Ann Arbor, Mich., pp. 801–815, 1992), and analgesics (Dickenson, A cure for wind-up: NMDA receptor antagonists as potential analgesics. *Trends Pharmacol. Sci.* 11: 307, 1990), and certain NMDA receptor antagonists may lessen dementia associated with Alzheimer's Disease (Hughes, Merz' novel approach to the treatment of dementia. *Script* No. 1666: 24, 1991).

Similarly, AMPA receptor antagonists have come under intense scrutiny as potential therapeutic agents for the treatment of such neurological disorders and diseases. AMPA receptor antagonists have been shown to possess neuroprotectant (Fisher and Bogousslavsky, Evolving toward effective therapy for acute ischemic stroke. *J. Amer. Med. Assoc.* 270: 360, 1993) and anticonvulsant (Yamaguchi et al., Anticonvulsant activity of AMPA/kainate antagonists: comparison of GYKI 52466 and NBQX in maximal electroshock and chemoconvulsant seizure models. *Epilepsy Res.* 15: 179, 1993) activity in animal models of ischemic stroke and epilepsy, respectively.

The nicotinic cholinergic receptor present in the mammalian CNS is another example of a receptor-operated $Ca^{2+}$, channel (Deneris et al., Pharmacological and functional diversity of neuronal nicotinic acetylcholine receptors. *Trends Pharmacol. Sci.* 12: 34, 1991). Several distinct receptor subunits have been cloned, and these subunits can be expressed, in Xenopus oocytes for example, to form functional receptors with their associated cation channels. It is hypothesized that such receptor-ionophore complexes are heteropentameric structures. The possible role of nicotinic receptor-operated $Ca^{2+}$ channels in the pathology of neurological disorders and diseases such as ischemic stroke, epilepsy and neurodegenerative diseases has been largely unexplored.

It has been demonstrated previously that certain spider and wasp venoms contain arylalkylamine toxins (also called polyamine toxins, arylamine toxins, acylpolyamine toxins or polyamine amide toxins) with activity against glutamate receptors in the mammalian CNS (for reviews see Jackson and Usherwood, Spider toxins as tools for dissecting elements of excitatory amino acid transmission. *Trends Neurosci.* 11: 278, 1988; Jackson and Parks, Spider Toxins: Recent Applications In Neurobiology. *Annu. Rev. Neurosci.* 12: 405, 1989; Saccomano et al., Polyamine spider toxins: Unique pharmacological tools. *Annu. Rep. Med. Chem.* 24: 287, 1989; Usherwood and Blagbrough, Spider Toxins Affecting Glutamate Receptors: Polyamines in Therapeutic Neurochemistry. *Pharmacol. Therap.* 52: 245, 1991; Kawai, Neuroactive Toxins of Spider Venoms. *J. Toxicol. Toxin Rev.* 10: 131, 1991). Arylalkylamine toxins were initially reported to be selective antagonists of the AMPA/kainate subtypes of glutamate receptors in the mammalian CNS (Kawai et al., Effect of a spider toxin on glutaminergic synapses in the mammalian brain. *Biomed. Res.* 3: 353, 1982; Saito et al., Spider Toxin (JSTX) blocks glutamate synapse in hippocampal pyramidal neurons. *Brain Res.* 346: 397, 1985; Saito et al., Effects of a spider toxin (JSTX) on hippocampal CAl neurons in vitro. *Brain Res.* 481: 16, 1989; Akaike et al., Spider toxin blocks excitatory amino acid responses in isolated hippocampal pyramidal neurons. *Neurosci. Lett.* 79: 326, 1987; Ashe et al., Argiotoxin-636 blocks excitatory synaptic transmission in rat hippocampal CAl pyramidal neurons. *Brain Res.* 480: 234, 1989; Jones et al., Philanthotoxin blocks quisqualate-induced, AMPA-induced and kainate-induced, but not NMDA-induced excitation of rat brainstem neurones in vivo. *Br. J. Pharmacol.* 101: 968, 1990). Subsequent studies have demonstrated that while certain arylalkylamine toxins are both nonpotent and nonselective at various glutamate receptors, other arylalkylamines are both very potent and selective at antagonizing responses mediated by NMDA receptor activation in the mammalian CNS (Mueller et al., Effects of polyamine spider toxins on NMDA receptor-mediated transmission in rat hippocampus in vitro. *Soc. Neurosci. Abst.* 15: 945, 1989; Mueller et al., Arylamine spider toxins antagonize NMDA receptor-mediated synaptic transmission in rat hippocampal slices. *Synapse* 9: 244, 1991; Parks et al., Polyamine spider toxins block NMDA receptor-mediated increases in cytosolic calcium in cerebellar granule neurons. *Soc. Neurosci. Abst.* 15: 1169, 1989; Parks et al., Arylamine toxins from funnel-web spider (Agelenopsis aperta) venom antagonize N-methyl-D-aspartate receptor function in mammalian brain. *J. Biol. Chem.* 266: 21523, 1991; Priestley et al., Antagonism of responses to excitatory amino acids on rat cortical neurones by the spider toxin, argiotoxin-636. *Br. J. Pharmacol.* 97: 1315, 1989; Draguhn et al., Argiotoxin-636 inhibits NMDA-activated ion channels expressed in *Xenopus* oocytes. *Neurosci. Lett.* 132: 187, 1991; Kiskin et al., A highly potent and selective N-methyl-D-asparate receptor antagonist from the venom of the Agelenopsis aperta spider. *Neuroscience* 51: 11, 1992; Brackley et al., Selective antagonism of native and cloned kainate and NMDA receptors by polyamine-containing toxins. *J. Pharmacol. Exptl. Therap.* 266: 1573, 1993; Williams, Effects of Agelenopsis aperta toxins on the N-methyl-D-aspartate receptor: Polyamine-like and high-affinity antagonist actions. *J. Pharmacol. Exptl. Therap.* 266: 231, 1993). Inhibition of nicotinic cholinergic receptors by the arylalkylamine toxin philanthotoxin has also been reported (Rozental et al., Allosteric inhibition of nicotinic acetylcholine receptors of vertebrates and insects by philanthotoxin. *J. Pharmacol. Exptl. Therap.* 249: 123, 1989).

Parks et al. (Arylamine toxins from funnel-web spider (Agelenopsis aperta) venom antagonize N-methyl-D-aspartate receptor function in mammalian brain. *J. Biol. Chem.* 266: 21523, 1991), describe arylalkylamine spider toxins (α-agatoxins) which antagonize NMDA receptor function in mammalian brain. The authors discuss the mechanism of action of arylalkylamine toxins, and indicate that an NMDA receptor-operated ion channel is the probable site of action of the α-agatoxins, and most probably other spider venom arylalkylamines. They state:

The discovery that endogenous polyamines in the vertebrate brain modulate the function of NMDA receptors suggests that the arylamine toxins may produce their antagonism via a polyamine-binding site on glutamate receptors. Brackley et al. studied the effects of spermine and philanthotoxin 433 on the responses evoked by application of excitatory amino acids in Xenopus oocytes injected with mRNA from rat or chick brain. These authors reported that, at concentrations below those that antagonize glutamate receptor function, both spermine and philanthotoxin potentiate the effects of excitatory amino acids and some other neurotransmitters. On the basis of these and other data, Brackley et al. concluded that the arylamine toxins may, by binding nonspecifically to the membranes of excitable cells, reduce membrane fluidity and alter receptor function. The validity of this intriguing idea for NMDA receptor function is not well supported by two recent binding studies. Reynolds reported that argiotoxin 636 inhibits the binding of [$^3$H]MK-801 to rat brain membranes in a manner that is insensitive to glutamate, glycine, or spermidine. This author concluded that argiotoxin 636 exerts a novel inhibitory effect on the NMDA receptor complex by binding to one of the $Mg^{2+}$ sites located within the NMDA-gated ion channel. Binding data reported by Williams et al. also support the conclusion that argiotoxin 636 does not act primarily at the polyamine modulatory site on the NMDA receptor, but rather acts directly to produce an activity-dependent block of the ion channel. It is already known that compounds such as phencyclidine and ketamine can block the ion channels associated with both arthropod muscle glutamate receptors and mammalian NMDA receptors. Thus, it seems possible that vertebrate and invertebrate glutamate receptors share additional binding sites for allosteric modulators of receptor function, perhaps related to divalent cation-binding sites. Clearly, considerable additional work will be needed to determine if the arylamines define such a novel regulatory site.

Usherwood and Blagbrough (Spider Toxins Affecting Glutamate Receptors: Polyamines in Therapeutic Neurochemistry. *Pharmacol. Therap.* 52: 245, 1991) describe a proposed intracellular binding site for arylalkylamine toxins (polyamine amide toxins) located within the membrane potential field referred to as the QUIS-R channel selectivity filter. The authors postulate that the binding site for polyamine amide toxins may occur close to the internal entrance of the channel gated by the QUIS-R of locust muscle. The authors also note that one such toxin, argiotoxin-636, selectively antagonizes the NMDA receptor in cultured rat cortical neurons.

Gullak et al. (CNS binding sites of the novel NMDA antagonist Arg-636. *Soc. Neurosci. Abst.* 15: 1168, 1989), describe argiotoxin-636 (Arg-636) as a polyamine (arylalkylamine) toxin component of a spider venom. This toxin is said to block NMDA-induced elevation of cGMP in a noncompetitive fashion. The authors state that:

[$^{125}$I]Arg-636 bound to rat forebrain membranes with $K_d$ and $B_{max}$ values of 11.25 µM and 28.95 pmol/mg protein (80% specific). The ability of other known polyamines and recently discovered polyamines from Agelenopsis aperta to inhibit binding paralleled neuroactivity as functional NMDA antagonists. No other compounds tested were able to block specific binding.

The authors then stated that polyamines (arylalkylamines) may antagonize responses to NMDA by interacting with membrane ion channels.

Seymour and Mena (In vivo NMDA antagonist activity of the polyamine spider venom component, argiotoxin-636. *Soc. Neurosci. Abst.* 15: 1168, 1989) describe studies that are said to show that argiotoxin-636 does not significantly affect locomotor activity at doses that are effective against audiogenic seizures in DBA/2 mice, and that it significantly antagonizes NMDA-induced seizures with a minimal effective dose of 32 mg/kg given subcutaneously (s.c.).

Herold and Yaksh (Anesthesia and muscle relaxation with intrathecal injections of AR636 and AG489, two acylpolyamine spider toxins, in rats. *Anesthesiology* 77: 507, 1992) describe studies that are said to show that the arylalkylamine argiotoxin-636 (AR636), but not agatoxin-489 (AG489), produces muscle relaxation and anesthesia following intrathecal administration in rats.

Williams (Effects of Agelenopsis aperta toxins on the N-methyl-D-aspartate receptor: Polyamine-like and high-affinity antagonist actions, J. Pharmacol. Exptl. *Therap.* 266: 231, 1993) reports that the α-agatoxins (arylalkylamines) Agel-489 and Agel-505 enhance the binding of [$^3$H]MK-801 to NMDA receptors on membranes prepared from rat brain by an action at the stimulatory polyamine receptor; polyamine receptor agonists occluded the stimulatory effects of Agel-489 and Agel-505 and polyamine receptor antagonists inhibited the stimulatory effect of Agel-505. Higher concentrations of Agel-489 and Agel-505, and argiotoxin-636 at all concentrations tested, had inhibitory effects on the binding of [$^3$H]MK-801. In *Xenopus* oocytes voltage-clamped at −70 mV, Agel-505 inhibited responses to NMDA with an $IC_{50}$, of 13 nM; this effect of Agel-505 occurred at concentrations approximately 10,000-fold lower than those that affected [$^3$H]MK-801 binding. Responses to kainate were inhibited only 11% by 30 nM Agel-505. The antagonism of NMDA-induced currents by Agel-505 was strongly voltage-dependent, consistent with an open-channel blocking effect of the toxin. Williams states:

Although α-agatoxins can interact at the positive allosteric polyamine site on the NMDA receptor, stimulatory effects produced by this interaction may be masked in functional assays due to a separate action of the toxins as high-affinity, noncompetitive antagonists of the receptor.

Brackley et al. (Selective antagonism of native and cloned kainate and NMDA receptors by polyamine-containing toxins, *J. Pharmacol. Exp. Therap.* 266: 1573, 1993) report that the polyamine-containing toxins (arylalkylamines) philanthotoxin-343 (PhTX-343) and argiotoxin-636 (Arg-636) produce reversible, noncompetitive., partly voltage-dependent antagonism of kainate- and NMDA-induced currents in Xenopus oocytes injected with rat brain RNA. Arg-636 was demonstrated to be selective for NMDA-induced responses ($IC_{50}$=0.04 µM) compared to kainate-induced responses ($IC_{50}$=0.07 µM), while PhTX-343 was selective for kainate-induced responses $IC_{50}$=0.12 µM) compared to NMDA-induced responses ($IC_{50}$=2.5 µM). Arg-636 more potently antagonized responses to NMDA in Xenopus oocytes expressing cloned NMDAR1 subunits ($IC_{50}$=0.09 µM) than responses to kainate in oocytes expressing either cloned GluR1 ($IC_{50}$=3.4 µM) or GluR1+GluR2 subunits ($IC_{50}$=300 µM). PhTX-343, on the other hand, was equipotent at antagonizing NMDAR1 ($IC_{50}$=2.19 µM) and GluR1 ($IC_{50}$=2.8 µM), but much less potent against GluR1+GluR2 subunits ($IC_{50}$=270 µM).

Raditsch et al. (Subunit-specific block of cloned NMDA receptors by argiotoxin-636. *FEBS Lett.* 324: 63, 1993) report that Arg-636 more potently antagonizes responses in Xenopus oocytes expressing NMDAR1+NMDAR2A subunits ($IC_{50}$=9 nM) or NMDAR1+NMDAR2B subunits ($IC_{50}$=2.5 nM) than NMDAR1+NMDAR2C subunits ($IC_{50}$,=460 nM) even though all of the receptor subunits contain an asparagine residue in the putative pore-forming transmembrane region II (the Q/R site, as discussed above). The authors state that the large difference in Arg-636 sensitivity between NMDAR1+NMDAR2A and NMDAR1+NMDAR2C channels "must be conferred by other structural determinants."

Herlitz et al. (Argiotoxin detects molecular differences in AMPA receptor channels. *Neuron* 10: 1131, 1993) report that Arg-636 antagonizes subtypes of AMPA receptors in a voltage- and use-dependent manner consistent with open-channel blockade. Arg-636 potently antagonizes $Ca^2$-permeable AMPA receptors comprised of GluRAi ($K_i$=0.35 µM), GluRCi ($K_i$=0.23 µM), or GluRDi subunits ($K_i$=0.43 µM), while being essentially ineffective against $Ca^2$,—impermeable GluRBi subunits at concentrations up to 10 µM.

Other data reported by these investigators strongly suggest that the Q/R site in the putative pore-forming transmembrane region II is of primary importance in determining Arg-636 potency and $Ca^{2+}$ permeability.

Blaschke et al. (A single amino acid determines the subunit-specific spider toxin block of α-amino-3-hydroxy-5-methylisoxazole-4-propionate/kainate receptor channels. *Proc. Natl. Acad. Sci. USA* 90: 6528, 1993) report that the arylalkylamine JSTX-3 potently antagonizes responses to kainate in Xenopus oocytes expressing GluR1 ($IC_{50}$)=0.04 µM) or GluR3 ($IC_{50}$=0.03 µM) subunits, but that expressed receptors in which a GluR2 subunit is present are essentially unaffected by the toxin. Site-directed mutagenesis studies strongly implicate the Q/R site as the primary site influencing toxin potency.

Nakanishi et al. (Bioorganic studies of transmitter receptors with philanthotoxin analogs. *Pure Appl. Chem.*, in press) have synthesized a number of highly potent photoaffinity labeled philanthotoxin (PhTX) analogs. Such analogs have been studied on expressed nicotinic cholinergic receptors as a model system for receptor-operated calcium channels. These investigators suggest that these PhTX analogs block the ion channel with the hydrophobic headpiece of the toxin binding to a site near the cytoplasmic surface while the polyamine tail extends into the ion channel from the cytoplasmic side.

SUMMARY OF THE INVENTION

Applicant has examined the structural diversity and biological activity of arylalkylamines (sometimes referred to as arylamine toxins, polyamine toxins, acylpolyamine toxins or polyamine amide toxins) in spider and wasp venoms, and determined that some of the arylalkylamines present in these venoms act as potent noncompetitive antagonists of glutamate receptor-operated $Ca^{2+}$ channels in the mammalian CNS. Although these arylalkylamine compounds contain within their structure a polyamine moiety, they are unlike other known simple polyamines in possessing extremely potent and specific effects on certain types of receptor-operated $Ca^{2+}$ channels.

Using native arylalkylamines as lead structures, a number of analogs were synthesized and tested. Initial findings on arylalkylamines isolated and purified from venom were confirmed utilizing synthetic arylalkylamines. These compounds are small molecules (mol. wt. <800) with demonstrated efficacy in in vivo models of stroke and epilepsy. The NMDA receptor-ionophore complex was used as a model of receptor-operated $Ca^{2+}$ channels. Selected arylalkylamines were shown to block NMDA receptor-mediated responses by a novel mechanism. Moreover, the unique behavioral pharmacological profile of these compounds suggests that they are unlikely to cause the PCP-like psychotomimetic activity and cognitive deficits that characterize other inhibitors of the NMDA receptor. Finally, the arylalkylamines are unique amongst NMDA receptor antagonists in that they are able to antagonize certain subtypes of cloned and expressed AMPA receptors, namely, those permeable to $Ca^{2+}$. The arylalkylamines, therefore, are the only known class of compounds able to antagonize glutamate receptor-mediated increases in cytosolic $Ca^{2+}$ regardless of the pharmacological definition of receptor subtype. Additionally, the arylalkylamines inhibit another receptor-operated $Ca^{2+}$ channel, the nicotinic cholinergic receptor. Given that excessive and prolonged increases in cytosolic $Ca^{2+}$ have been implicated in the etiology of several neurological disorders and diseases, such arylalkylamines are valuable small molecule leads for the development of novel therapeutics for various neurological disorders and diseases.

Applicant has determined that the selected arylalkylamines bind with high affinity at a novel site on the NMDA receptor-ionophore complex which has heretofore been unidentified, and that said arylalkylamines do not bind with high affinity at any of the known sites (glutamate binding site, glycine binding site, MK-801 binding site, $Mg^{2+}$ binding site, $Zn^{2+}$ binding site, polyamine binding site, sigma binding site) on said NMDA receptor-ionophore complex. This determination has allowed applicant to develop methods and protocols by which useful compounds can be identified which provide both therapeutically useful compounds and lead compounds for the development of other therapeutically useful compounds. These compounds can be identified by screening for compounds that bind at this novel arylalkylamine binding site, and by determining whether such a compound has the required biological, pharmacological and physiological properties.

The method includes the step of identifying a compound which binds to the receptor-operated $Ca^{2+}$ channel at that site bound by the arylalkylamine compounds referred to herein as Compound 1, Compound 2 or Compound 3, and having the structures shown below.

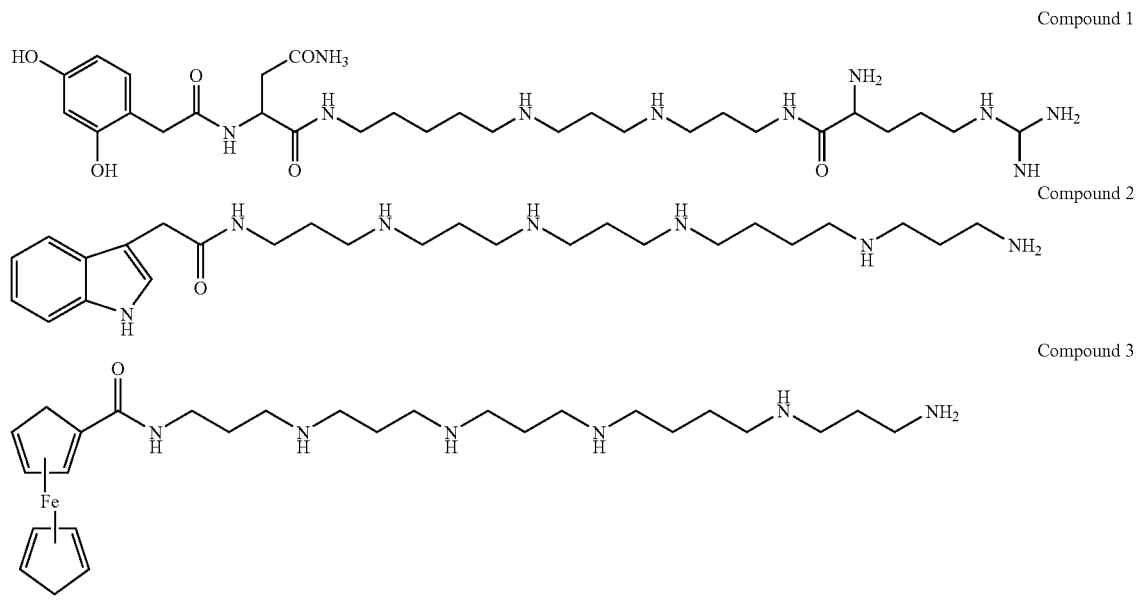

By "therapeutically useful compound" is meant a compound that is potentially useful in the treatment of a disorder or disease state. A compound uncovered by the screening method is characterized as having potential therapeutic utility in treatment because clinical tests have not yet been conducted to determine actual therapeutic utility.

By "neurological disorder or disease" is meant a disorder or disease of the nervous system including, but not limited to, global and focal ischemic and hemorrhagic stroke, head trauma, spinal cord injury, spinal cord ischemia, ischemia- or hypoxia-induced nerve cell damage, hypoxia-induced nerve cell damage as in cardiac arrest or neonatal distress, epilepsy, anxiety, neuropsychiatric or cognitive deficits due to ischemia or hypoxia such as those that frequently occur as a consequence of cardiac surgery under cardiopulmonary bypass, and neurodegenerative disease. Also meant by "neurological disorder or disease" are those disease states and conditions in which a neuroprotectant, anticonvulsant, anxiolytic, analgesic, muscle relaxant and/or adjunct in general anesthesia may be indicated, useful, recommended or prescribed.

By "neurodegenerative disease" is meant diseases including, but not limited to, Alzheimer's Disease, Huntington's Disease, Parkinson's Disease, and amyotrophic lateral sclerosis (ALS).

By "neuroprotectant" is meant a compound capable of preventing the neuronal damage or death associated with a neurological disorder or disease.

By "anticonvulsant" is meant a compound capable of reducing convulsions produced by conditions such as simple partial seizures, complex partial seizures, status epilepticus, and trauma-induced seizures such as occur following head injury, including head surgery.

By "anxiolytic" is meant a compound capable of relieving the feelings of apprehension, uncertainty and fear that are characteristic of anxiety.

By "analgesic" is meant a compound capable of relieving pain by altering perception of nociceptive stimuli without producing anesthesia or loss of consciousness.

By "muscle relaxant" is meant a compound that reduces muscular tension.

By "adjunct in general anesthesia" is meant a compound useful in conjunction with anesthetic agents in producing the loss of ability to perceive pain associated with the loss of consciousness.

By "Potent" or "active" is meant that the compound has activity at receptor-operated calcium channels, including NMDA receptors, $Ca^{2+}$-permeable AMPA receptors, and nicotinic cholinergic receptors, with an $IC_{50}$ value less than 10 µM, more preferably less than 100 nM, and even more preferably less than 1 nM.

By "selective," is meant that the compound is potent at receptor-operated calcium channels as defined above, but is less potent by greater than 10-fold, more preferably 50-fold, and even more preferably 100-fold, at other neurotransmitter receptors, neurotransmitter receptor-operated ion channels, or voltage-dependent ion channels.

By "biochemical and electrophysiological assays of receptor-operated calcium channel function" is meant assays designed to detect by biochemical or electrophysiological means the functional activity of receptor-operated calcium channels. Examples of such assays include, but are not limited to, the fura-2 fluorimetric assay for cytosolic calcium in cultured rat cerebellar granule cells (see Example 1 and Example 2), patch clamp electrophysiolocial assays (see Example 3 and Example 27), rat hippocampal slice synaptic transmission assays (see Example 5), radioligand binding assays (see Example 4, Example 24, Example 25, and Example 26), and in vitro neuroprotectant assays (see Example 6).

By "efficacy" is meant that a statistically significant level of the desired activity is detectable with a chosen compound; by "significant" is meant a statistical significance at the $p<0.05$ level.

By "neuroprotectant activity" is meant efficacy in treatment of neurological disorders or diseases including, but not limited to, global and focal ischemic and hemorrhagic stroke, head trauma, spinal cord injury, spinal cord ischemia, ischemia- or hypoxia-induced nerve cell damage, hypoxia-induced nerve cell damage as in cardiac arrest or neonatal distress, neuropsychiatric or cognitive deficits due to ischemia or hypoxia such as those that frequently occur as a consequence of cardiac surgery under cardiopulmonary bypass, and neurodegenerative diseases such as Alzheimer's Disease, Huntington's Disease, Parkinson's Disease, and amyotrophic lateral sclerosis (ALS) (see Examples 7 and 8, below).

By "anticonvulsant activity" is meant efficacy in reducing convulsions produced by conditions such as simple partial seizures, complex partial seizures, status epilepticus, and trauma-induced seizures such as occur following head injury, including head surgery (see Examples 9 and 10, below).

By "anxiolytic activity" is meant that a compound reduces the feelings of apprehension, uncertainty and fear that are characteristic of anxiety.

By "analgesic activity" is meant that a compound produces the absence of pain in response to a stimulus that would normally be painful. Such activity would be useful in clinical conditions of acute and chronic pain including, but not limited to the following: preemptive preoperative analgesia; peripheral neuropathies such as occur with diabetes mellitus and multiple sclerosis; phantom limb pain; causalgia; neuralgias such as occur with herpes zoster; central pain such as that seen with spinal cord lesions; hyperalgesia; and allodynia.

By "causalgia" is meant a painful disorder associated with injury of peripheral nerves.

By "neuralgia" is meant pain in the distribution of a nerve or nerves.

By "central pain" is meant pain associated with a lesion of the central nervous system.

By "hyperalgesia" is meant an increased response to a stimulus that is normally painful.

By "allodynia" is meant pain due to a stimulus that does not normally provoke pain (see Examples 11 through 14, below).

By "induction of long-term potentiation in rat hippocampal slices" is meant the ability of tetanic electrical stimulation of afferent Schaffer collateral fibers to elicit long-term increases in the strength of synaptic transmission at the Schaffer collateral-CAl pyramidal cell pathway in rat hippocampal slices maintained in vitro (see Example 19).

By "therapeutic dose" is meant an amount of a compound that relieves to some extent one or more symptoms of the disease or condition of the patient. Additionally, by "therapeutic dose" is meant an amount that returns to normal, either partially or completely, physiological or biochemical parameters associated with or causative of the disease or condition. Generally, it is an amount between about 1 nmole and 1 µmole of the compound, dependent on its $EC_{50}$ ($IC_{50}$ in the case of an antagonist) and on the age, size, and disease associated with the patient.

By "impair cognition" is meant the ability to impair the acquisition of memory or the performance of a learned task (see Example 20). Also by "impair congnition" is meant the ability to interfere with normal rational thought processes and reasoning.

By "disrupt motor function" is meant the ability to significantly alter locomotor activity (see Example 15) or elicit significant ataxia, loss of the righting reflex, sedation or muscle relaxation (see Example 16).

By "locomotor activity" is meant the ability to perform normal ambulatory movements.

By "loss of the righting reflex" is meant the ability of an animal, typically a rodent, to right itself after being placed in a supine position.

By "neuronal vacuolization" is meant the production of vacuoles in neurons of the cingulate cortex or retrosplenial cortex (see Example 18).

By "cardiovascular activity" is meant the ability to elicit significant changes in parameters including, but not limited to, mean arterial blood pressure and heart rate (see Examples 21 and 22).

By "hyperexcitability" is meant an enhanced susceptibility to an excitatory stimulus. Hyperexcitability is often manifested as a significant increase in locomotor activity in rodents administered a drug (see Example 15).

By "sedation" is meant a calmative effect, or the allaying of activity and excitement. Sedation is often manifested as a significant decrease in locomotor activity in rodents administered a drug (see Example 15).

By "PCP-like abuse potential" is meant the potential of a drug to be wrongfully used, as in the recreational use of PCP (i.e., "angel dust")by man. It is believed that PCP-like abuse potential can be predicted by the ability of a drug to generalize to PCP in rodents trained to discriminate PCP from saline (see Example 17.)

By "generalization to PCP" is meant that a compound is perceived as being PCP in rodents trained to discriminate PCP from saline (see Example 17).

By "PCP-like psychotomimetic activity" is meant the ability of a drug to elicit in man a behavioral syndrome resembling acute psychosis, including visual hallucinations, paranoia, agitation, and confusion. It is believed that PCP-like psychotomimetic activity can be predicted in rodents by the ability of a drug to produce PCP-like stereotypic behaviors including ataxia, head weaving, hyperexcitability, and generalization to PCP in rodents trained to discriminate PCP from saline (see Example 15 Example 16, and Example 17).

By "ataxia" is meant a deficit in muscular coordination.

By "head weaving" is meant the stereotypic behavior elicited in rodents by PCP in which the head is repeatedly moved slowly and broadly from side to side.

By "pharmaceutical composition" is meant a therapeutically effective amount of a compound of the present invention in a pharmaceutically acceptable carrier, i.e., a formulation to which the compound can be added to dissolve or otherwise facilitate administration of the compound. Examples of pharmaceutically acceptable carriers include water, saline, and physiologically buffered saline. Such a pharmaceutical composition is provided in a suitable dose. Such compositions are generally those which are approved for use in treatment of a specified disorder by the FDA or its equivalent in non-U.S. countries.

In a related aspect, the invention features a method for treating a neurological disease or disorder, comprising the step of administering a pharmaceutical composition comprising a compound which binds to a receptor-operated calcium channel at the site bound by one of the arylalkylamines Compound 1, Compound 2 and Compound 3, said compound being a potent and selective noncompetitive antagonist at such a receptor-operated calcium channel, and having one or more of the following pharmacological and physiological properties: efficacy in in vitro biochemical and electrophysiological assay of receptor-operated calcium channel function, in vivo anticonvulsant activity, in vivo neuroprotectant activity, in vivo anxiolytic activity, and in vivo analgesic activity; said compound also possessing one or more of the following pharmacological effects: the compound does not interfere with the induction of long-term potentiation in rat hippocampal slices, and, at a therapeutic dose, does not impair cognition, does not disrupt motor performance, does not produce neuronal vacuolization, has minimal cardiovascular activity, does not produce sedation or hyperexcitability, has minimal PCP-like abuse potential, and has minimal PCP-like psychotomimetic activity. By "minimal" is meant that any side effect of the drug is tolerated by an average individual, and thus that the drug can be used for therapy of the target disease. Such side effects are well known in the art and are routinely regarded by the FDA as minimal when it approves a drug for a target disease.

Treatment involves the steps of first identifying a patient that suffers from a neurological disease or disorder by standard clinical methodology and then treating such a patient with a composition of the present invention.

In a further aspect, the invention features compounds useful for treating a patient having a neurological disease or disorder wherein said compound is a polyamine-type compound or an analog thereof (i.e., a polyheteroatomic molecule) having the formula

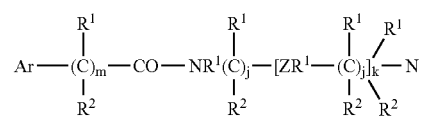

wherein Ar is an appropriately substituted aromatic ring, ring system or other hydrophobic entity; Ar can be an aromatic (e.g., carbocyclic aryl groups such as phenyl and bicyclic carbocyclic aryl ring systems such as naphthyl, 1,2,3,4-tetrahydronaphthyl, indanyl, and indenyl), heteroaromatic (e.g., indolyl, dihydroindolyl quinolinyl and isoquinolinyl, and their respective 1,2,3,4-tetrahydro- and 2-oxo-derivatives), alicyclic (cycloaliphatic), or heteroalicyclic ring or ring system (mono-, bi-, or tricyclic), having 5- to 7-membered ring(s) optionally substituted with 1 to 5 substituents independently selected from lower alkyl of 1 to 5 carbon atoms, lower haloalkyl of 1 to 5 carbon atoms substituted with 1 to 7 halogen atoms, lower alkoxy of 1 to 5 carbon atoms, halogen, nitro, amino, lower alkylamino of 1 to 5 carbon atoms, amido, lower alkylamido of 1 to 5 carbon atoms, cyano, hydroxyl, sulfhydryl, lower acyl of 2 to 4 carbon atoms, sulfonamido, lower alkylsulfonamido of 1 to 5 carbon atoms, lower alkylsulfoxide of 1 to 5 carbon atoms, lower hydroxyalkyl of 1 to 5 carbon atoms, lower alkylketo of 1 to 5 carbon atoms, or lower thioalkyl of 1 to 5 carbon atoms, each m is an integer from 0 to 3, inclusive, each k is an integer from 1 to 10, inclusive, each j is the same or different and is an integer from 1 to 12, inclusive, each $R^1$ and $R^2$ independently is selected from the group consisting of hydrogen, lower alkyl of 1 to 5 carbon atoms, lower alkylamino of 1 to 5 carbon atoms, lower alkylamido of 1 to 5 carbon atoms, lower mono-, di-, or trifluoroalkyl of 1 to 5 carbon atoms, hydroxy, amidino, guanidino, or typical common amino acid side chain or with an associated carbon atom $R^1$ and $R^2$ taken together form a carbonyl, and each Z is selected from the group consisting of nitrogen, oxygen, sulfur, amido, sulfonamido, and carbon.

Preferred aromatic headgroups include, but are not limited to, the following:

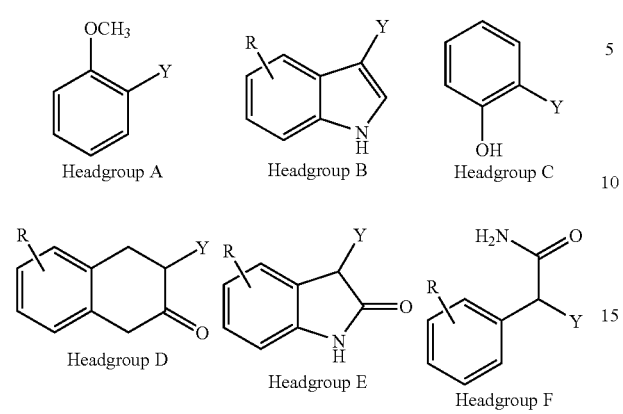

Headgroup A
Headgroup B
Headgroup C
Headgroup D
Headgroup E
Headgroup F

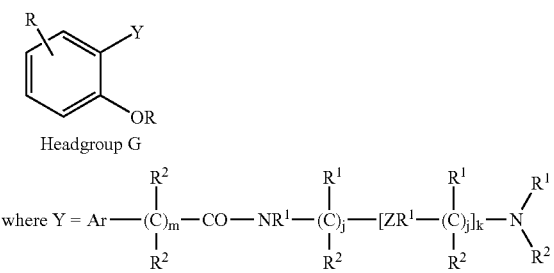

Headgroup G where Y = $Ar-(C)_m-CO-NR^1-(C)_j-[ZR^1-(C)_j]_k-N$ with $R^2$ substituents and terminal $R^1, R^1$ Preferably the claims claiming a compound exclude known compounds whose chemical structures are enabled.

In further preferred embodiments, the compound is selected from the group of Compounds 4 through 18, where such compounds have the formulae:

Compound 4

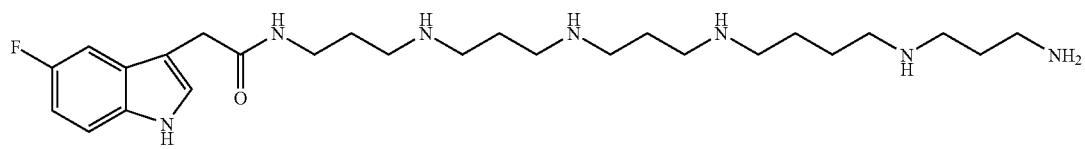

Compound 5

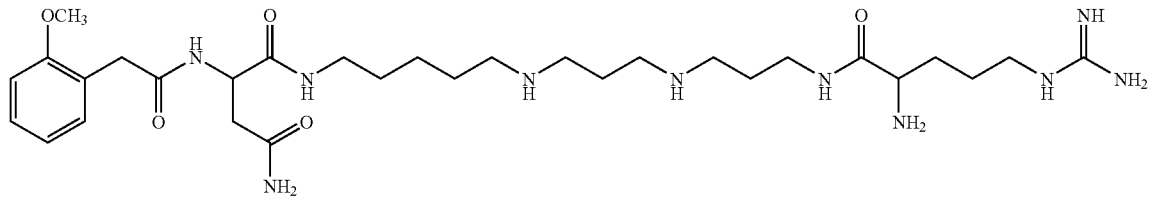

Compound 6

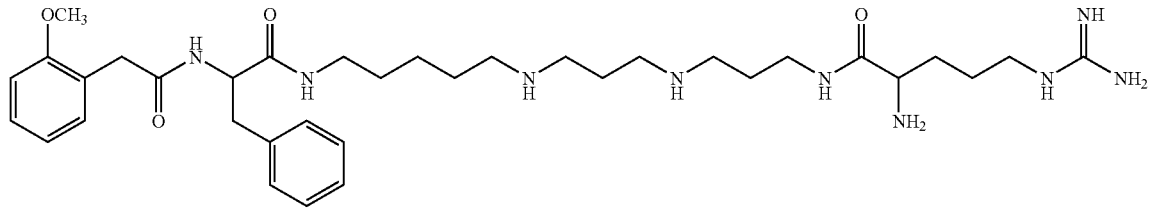

Compound 7

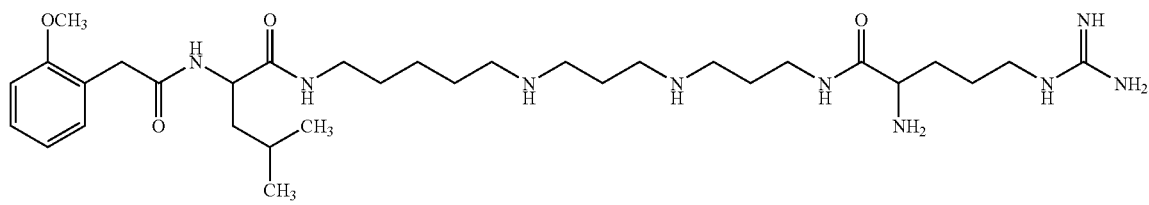

-continued
Compound 8
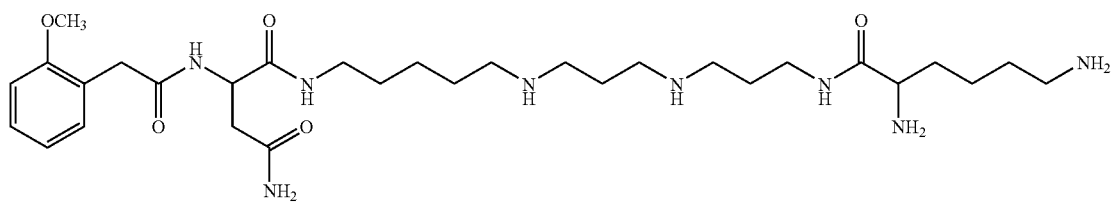
Compound 9
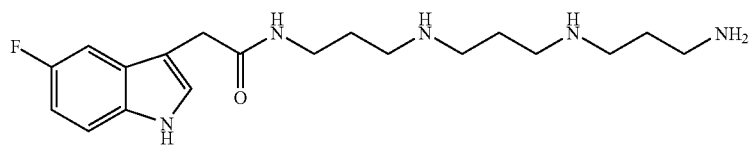
Compound 10
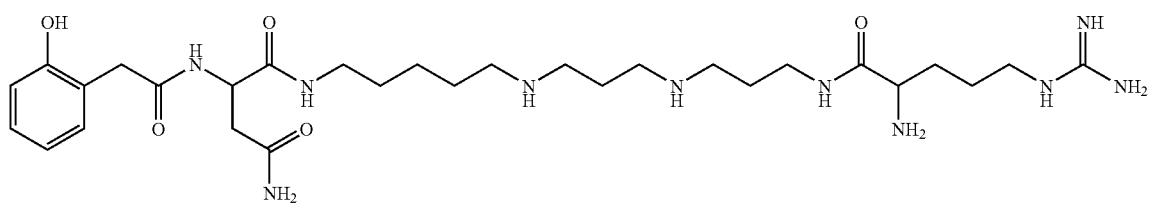
Compound 11
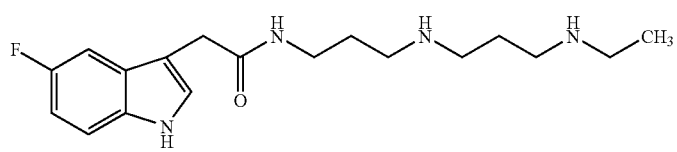
Compound 12
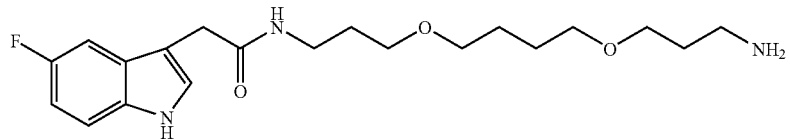
Compound 13
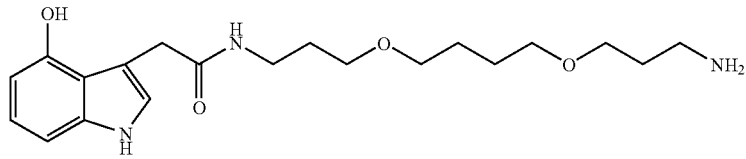
Compound 14
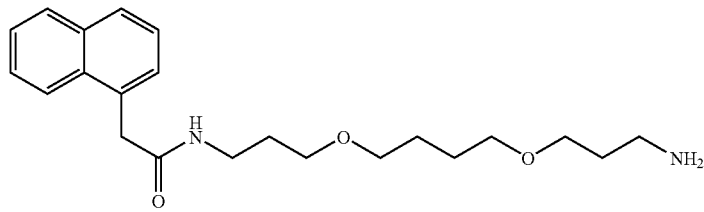
Compound 15
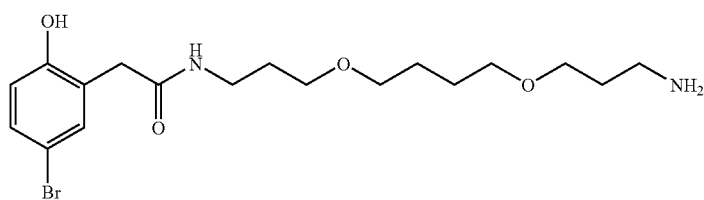

-continued

Compound 16

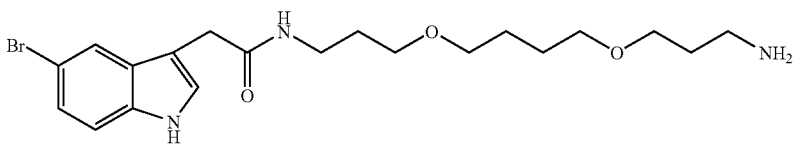

Compound 17

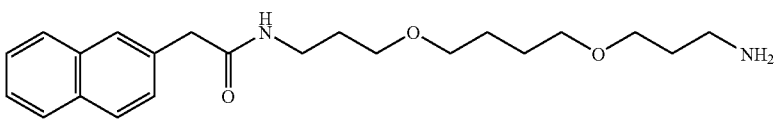

Compound 18

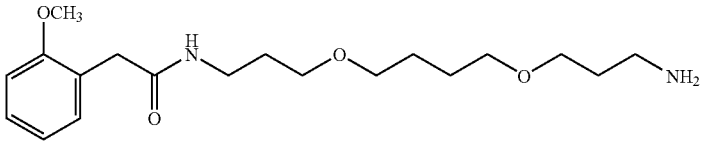

Applicant has also determined (see Example 23 below) that simplified arylalkylamines (see below) are potent, non-competitive antagunists of the NMDA receptor-ionophore complex. The simplified arylalkylamines are distinct from the arylalkylamines exelmplified by Compounds 4–18 as described above. For example, such compounds bind to the site labeled by [$^3$H]MK-801 at concentrations ranging approximately 1 to 400-fold higher than those which antagonize NMDA receptor-mediated function. Such simplified arylalkylamines possess one or more of the following additional biological properties: significant neuroprotectant activity, significant anticonvulsant activity, significant analgesic activity, no PCP-like stereotypic behavior in rodents (hyperexcitability and head weaving) at effective neuroprotectant, anticonvulsant and analgesic doses, no generalization to PCP in a PCP discrimination assay at effective neuroprotectant, anticonvulsant and analgesic doses, no neuronal vacuolization at effective neuroprotectant, anticonvulsant and analgesic doses, significantly less potent activity against voltage-sensitive calcium channels, and minimal hypotensive activity at effective neuroprotectant, anticonvulsant and analgesic doses. Such compounds may, however, inhibit the induction of LTP in rat hippocampal slices and may produce motor impairment at neuroprotectant, anticonvulsant and analgesic doses.

One aspect of the invention features a method for treating a patient having a neurological disease or disorder, comprising administering a compound of Formula I:

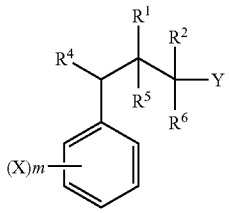

FORMULA I wherein:

$R^1$ and $R^5$ are independently selected from the group consisting of phenyl, benzyl, and phenoxy (each of which is optionally substituted with alkyl, hydroxyalkyl, —OH, —O-alkyl, —O-acyl, —F, —Cl, —Br, —I, —CF$_3$, or —OCF$_3$) —H, alkyl, hydroxyalkyl, —OH, —O-alkyl, and O-acyl;

$R^2$ and $R^6$ are independently selected from the group consisting of —H, alkyl, and hydroxyalkyl; or $R^2$ and $R^6$ together are imino; or $R^1$ and $R^2$ together are —(CH$_2$)$_n$— or —(CH$_2$)$_n$—N(R$^3$)—(CH$_2$)$_n$—;

$R^3$ is independently selected from the group consisting of —H, alkyl, 2-hydroxyethyl and alkylphenyl;

n is an integer from 0 to 6, but at least one n must be greater than 0;

$R^4$ is selected from the group consisting of thiofuran, pyridyl, phenyl, benzyl, phenoxy, and phenylthio (each of which is optionally substituted with alkyl, —F, —Cl, —Br, —I, —CF$_3$, —OH, —OCF$_3$, —O-alkyl, or —O-acyl), —H, alkyl and cycloalkyl;

X is independently selected from the group consisting of phenyl, benzyl, and phenoxy (each of which is optionally substituted with —F, —Cl, —Br, —I, —CF$_3$, alkyl, —OH, —OCF$_3$, —O-alkyl, or —O-acyl) —F, —Cl, —Br, —I CF$_3$, alkyl, —OH, —OCF$_3$, —O-alkyl, and O-acyl;

m is independently an integer from 0 to 5;

Y is —NR$^3$R$^3$, except when $R^1$ and $R^2$ together are —(CH$_2$)$_n$—N(R$^3$)—(CH$_2$)$_n$—, then Y is —H;

and pharmaceutically acceptable salts and complexes thereof, wherein the compound is active at an NMDA receptor.

By "patient" is meant any animal that has a cell with an NMDA receptor. Preferably, the animal is a mammal. Most preferably, the animal is a human.

By "alkyl" is meant a branched or unbranched hydrocarbon chain containing between 1 and 6, preferably between 1 and 4, carbon atoms, such as, e.g., methyl, ethyl, n-propyl, iso-propyl, n-butyl, sec-butyl, iso-butyl, tert-butyl, 2-methylpentyl, cyclopropylmethyl, allyl, and cyclobutylmethyl.

By "lower alkyl" is meant a branched or unbranched hydrocarbon chain containing between 1 and 4 carbon atoms, of which examples are listed herein.

By "hydroxyalkyl" is meant an alkyl group as defined above, substituted with a hydroxyl group.

By "alkylphenyl" is meant an alkyl group as defined above, substituted with a phenyl group.

By "acyl" is meant —C(O)R, where R is H or alkyl as defined above, such as, e.g., formyl, acetyl, propionyl, or butyryl; or, R is —O-alkyl such as in alkyl carbonates or R is N-alkyl such as in alkyl carbamates.

By "cycloalkyl" is meant a branched or unbranched cyclic hydrocarbon chain containing between 3 and 12 carbon atoms.

In preferred aspects of the invention, Y is selected from the group consisting of —NH2 and —NH-methyl;

$R^4$ is thiofuran, pyridyl, phenyl, benzyl, phenoxy, or phenylthio, each of which is optionally substituted with —F, —Cl, —Br, —I, —$CF_3$, alkyl, —OH, —$OCF_3$, —O-alkyl, or —O-acyl;

X is independently selected from the group consisting of meta-fluaro, meta-chloro, ortho-O-lower alkyl, ortho-methyl, ortho-fluoro, ortho-chloro, meta-O-lower alkyl, meta-methyl, ortho-OH, and meta-OH; and either $R^1$, $R^2$, $R^5$, and $R^6$ are —H;

or $R^2$ is methyl, and $R^1$, $R^5$, and $R^6$ are —H;

or $R^1$ is methyl, and $R^2$, $R^5$, and $R^6$ are —H.

In other preferred aspects of the present invention, $R^1$ and $R^5$ are independently selected from the group consisting of —H, lower alkyl, hydroxyalkyl, —OH, —O-alkyl, and —O-acyl;

$R^2$ and $R^6$ are independently selected from the group consisting of —H, lower alkyl, and hydroxyalkyl;

or $R^1$ and $R^2$ together are —$(CH_2)_n$— or —$(CH_2)_n$—N$(R^3)$—, and Y is H;

$R^3$ is independently selected from the group consisting of —H and lower alkyl;

$R^4$ is selected from the group consisting of thiofuran, pyridyl, phenyl, benzyl, phenoxy, and phenylthio (each of which is optionally substituted with lower alkyl, —F, —Cl, —Br, —I, —$CF_3$, —OH, —$OCF_3$, O-alkyl, or —O-acyl), —H, lower alkyl, and cycloalkyl;

X is independently selected from the group consisting of —F, —Cl, —Br, —I, —$CF_3$, lower alkyl, —OH, and —$OCF_3$;

m is independently an integer from 0 to 5;

Y is —$NHR^3$, or hydrogen when $R^1$ and $R^2$ together are —$(CH_2)_n$—N$(R^3)$—, and pharmaceutically acceptable salts and complexes thereof, with the provisos that (a) when $R^1$ and $R^2$ together are —$(CH_2)_n$—N$(R^3)$—, then $R^5$, $R^6$, and Y are hydrogens; and (b) when $R^1$ and $R^2$ together are not $(CH_2)_n$—N$(R^3)$—, then Y is —$NHR^3$.

In one preferred aspect, the invention features a method for treating a patient having a neurological disease or disorder comprising administering a compound of Formula II:

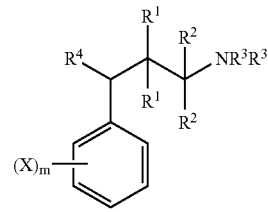

Formula II wherein:

X is independently selected from the group consisting of —H, —Br, —Cl, —F, —I, —$OCF_3$, alkyl, —OH, —$CCF_3$, —O-alkyl, and —O-acyl;

$R^1$ is independently selected from the group consisting of —H, alkyl, hydroxyalkyl, —OH, —O-alkyl, and —O-acyl;

$R^2$ is independently selected from the group consisting of —H, alkyl, and hydroxyalkyl, or both $R^2$s together are imino; $R^3$ is independently selected from the group consisting of —H, alkyl, 2-hydroxyethyl, and alkylphenyl; and m is independently an integer from 0 to 5.

Thus, in this preferred aspect, the compounds include the compound of Formula I, wherein:

X is independently selected from the group consisting of —F, —Cl, —Br, —I, —$CF_3$, alkyl, —OH, —$OCF_3$, —O-alkyl, and —O-acyl;

$R^1$ is selected from the group consisting of —H, alkyl, hydroxyalkyl, —OH, —O-alkyl, and —O-acyl;

$R^2$ and $R^6$ are independently selected from the group consisting of —H, alkyl, and hydroxyalkyl, or $R^2$ and $R^6$ together are imino;

$R^5$ is selected from the group consisting of —H, alkyl, hydroxyalkyl, —OH, —O-alkyl, and —O-acyl;

Y is $NR^3R^3$; and $R^4$ is phenyl, optionally substituted with alkyl, —F, —Cl, —Br, —I, —$CF_3$, —OH, —$OCF_3$, —O-alkyl, or —O-acyl.

In another preferred aspect, the administered compound has the structure of Formula III:

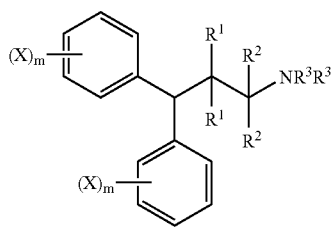

Formula III wherein:

X is independently selected from the group consisting of —H, —Br, —Cl, —F, —I, —$CF_3$, alkyl, —OH, —$OCF_3$, —O-alkyl, and —O-acyl;

$R^1$ is independently selected from the group consisting of —H, alkyl, hydroxyalkyl, —OH, —O-alkyl, and —O-acyl;

$R^2$ is independently selected from the group consisting of —H, alkyl, and hydroxyalkyl, or both $R^2$s together are imino;

$R^3$ is independently selected from the group consisting of —H, alkyl, 2-hydroxyethyl, and alkylphenyl;

$R^4$ is selected from the group consisting of thiofuran, pyridyl, phenyl, benzyl, phenoxy, and phenylthio, (each of which is optionally substituted with (X)m), alkyl, and cycloalkyl; and, m is independently an integer from 0 to 5.

Thus, in the preferred aspect, the compounds include the compound of Formula 1, wherein:

X is independently selected from the group consisting of —F, —Cl, —Br, —I, —$OCF_3$, alkyl, —OH, —$OCF_3$, —O-alkyl, and —O-acyl;

$R^1$ is selected from the group consisting of —H, alkyl, hydroxyalkyl, —OH, —O-alkyl, and —O-acyl;

$R^2$ and $R^6$ are selected from the group consisting of —H, alkyl, and hydroxyalkyl, or $R^2$ and $R^6$ together are imino;

$R^5$ is independently selected from the group consisting of —H, alkyl, hydroxyalkyl, —OH, —O-alkyl, and —O-acyl; and Y is $NR^3R^3$.

In another preferred aspect, the administered compound has the structure of Formulas IV and V.

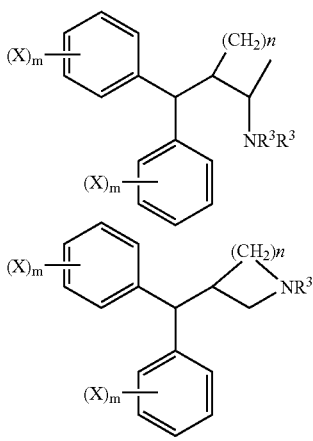

Formula IV

Formula V wherein:

n is an integer from 1 to 6;

X is independently selected from the group consisting of —H, —Br, —Cl, —F, —I —CF3, alkyl, —OH, —OCF$_3$, —O-alkyl, and —O-acyl;

$R^3$ is independently selected from the group consisting of —H, alkyl, 2-hydroxyethyl, and alkylphenyl; and m is independently an integer from 0 to 5.

Thus, in this preferred aspect, the administered compounds include the compound of Formula I, wherein:

$R^3$ is independently selected from the group consisting of —H, and alkyl;

$R^4$ is phenyl, optionally substituted with alkyl, —F, —Cl, —Br, —I, —CF$_3$, —OH, —OCF$_3$, —O-alkyl, or —O-acyl; and R1 and R2 together are —(CH$_2$)$_n$,— or —(CH$_2$)$_n$, —N(R$^3$)—.

In another preferred aspect, the administered compound has the structure of Formulas VI and VII:

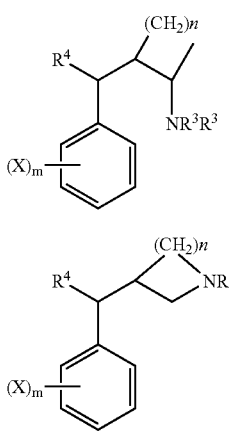

Formula VI

Formula VII wherein:

n is an integer from 1 to 6;

X is independently selected from the group consisting of —H, —Br, —Cl, —F, —I, —CF, alkyl, —OH, —OCF$_3$, —O-alkyl, and —O-acyl;

$R^3$ is independently selected from the group consisting of —H, alkyl, 2-hydroxyethyl, and alkylphenyl;

$R^4$ is selected from the group consisting of thiofuran, pyridyl, phenyl, benzyl, phenoxy, and phenylthio (each of which is optionally substituted with (X)m), alkyl, and cycloalkyl; and m is independently an integer from 0 to 5.

Thus, in this preferred aspect, the administered compounds include the compound of Formula I, wherein:

X is independently selected from the group consisting of —F, —Cl, —Br, —I, CF3, alkyl, —OH, —OCF3, —O-alkyl, and —O-acyl-; and R$_1$ and R$_2$ together are —(CH$_2$)$_n$— or —(CH$_2$)$_n$—N(R$^3$)—.

More preferred aspects are those embodiments in which:

X is independently selected from the group consisting of meta-fluoro, meta-chloro, ortho-O-lower alkyl, ortho-methyl, ortho-fluoro, ortho-chloro, meta-O-lower alkyl, meta-methyl, ortho-OH, and meta-OH;

NH3 is selected from the group consisting of NH, N-methyl, and N-ethyl;

NR$^3$R$^3$ is selected from the group consisting of NH$_2$, NH-methyl, and NH-ethyl;

$R^1$ is selected from the group consisting of —H and methyl;

$R^2$ is selected from-the group consisting of —H and methyl; and $R^4$ is selected from the group consisting of phenyl, benzyl, and phenoxy, each of which is optionally substituted with alkyl, —F, —Cl, —Br, —F, —CF$_3$, —OH, —OCF$_3$, —O-alkyl, or —O-acyl.

Especially preferred aspects are those embodiments in which:

X is meta-fluoro;

each $R^1$ and $R^2$ is —H;

NR$^3$ is selected from the group consisting of NH and N-methyl;

NR$^3$R$^3$ is selected from the group consisting of NH$_2$ and NH-methyl; and $R^4$ is selected from the group consisting of phenyl, benzyl, and phenoxy, each of which is optionally substituted with alkyl, —F, —Cl, —Br, —I, —CF$_3$, —OH, —OCF$_3$, —O-alkyl, or —O-acyl.

In a further aspect, the invention features a method for treating a patient having a neurological disease or disorder comprising administering the compounds of Formula VIII:

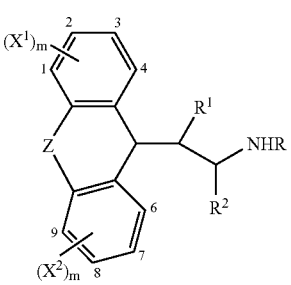

FORMULA VIII wherein:

Z is selected from the group consisting of —CH$_2$CH$_2$—, —CH$_2$CH(CH$_3$)—, —CH=CH—, —O—CH$_2$—, S—CH$_2$—, —O—, and —S—;

$X^1$ and $X^2$ are independently selected from the group consisting of —F, —Cl, —CH$_{31}$ —OH, and lower O-alkyl in the 1-, 3-, 7-, or 9-substituent positions;

m is independently an integer from 0 to 2;

—NHR is selected from the group consisting of —NH$_2$, —NHCH$_3$, and —NHC$_2$H$_5$;

R$^1$ is selected from the group consisting of —H, alkyl, hydroxyalkyl, —OH, —O-alkyl, and —O-acyl, and R$^2$ is selected from the group consisting of —H, alkyl, hydroxyalkyl, and pharmaceutically acceptable salts and complexes thereof, wherein the compound is active at an NMDA receptor.

Especially preferred aspects are those embodiments in which:

Z is —CH$_2$CH$_2$—;

X$^1$ or X$^2$ is —F, or both X$^1$ and X$^2$ are —F;

either R$^1$ or R$^2$ is methyl or both R$^1$ and R$^2$ are —H; and

—NHR is selected from the group consisting of —NH$_2$ or —NHCH$_3$.

In other preferred embodiments, the invention features-a method for treating a patient having a neurological disease or disorder comprising administering the compounds of Formula IX:

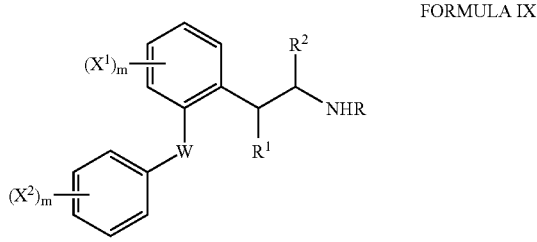

FORMULA IX wherein:

W is selected from the group consisting of —CH$_2$—, —O—, and —S—;

X$^1$ and X$^2$ are independently selected from the group consisting of —F, —Cl, —CH$_3$, —OH, and lower O-alkyl;

m is independently an integer from 0 to 2;

—NHR is selected from the group consisting of —NH$_2$, —NHCH$_3$, and —NHC$_2$H$_5$;

R$^1$ is selected from the group consisting of —H, alkyl, hydroxyalkyl, —OH, —O-alkyl, and —O-acyl; and R$^2$ is selected from the group consisting of —H, alkyl, hydroxyalkyl, and pharmaceutically acceptable salts and complexes thereof, wherein the compound is active at an NMDA receptor.

In preferred aspects, the administered compound is selected from the group consisting of Compound 128, 129, 130, 131, 132, 200, 201, 202, 203, 204, 205, 206, 207, 208, 209, 210, 211, 212, 213, 214, and 215.

In preferred embodiments, the methods of treatment include administration of a compound selected from Compounds 19 through 215, or pharmaceutically acceptable salts and complexes thereof. Preferably, the compound has an IC$_{50}$≦10 μM at an NMDA receptor, more preferably ≦2.5 μM, and most preferably ≦0.5 μM at an NMDA receptor.

In further preferred embodiments, the methods of treatment include administration of a compound selected from the group consisting of Compound 19, 20, 21, 22, 23, 24, 25, 27, 28, 29, 30, 31, 32, 33, 34, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 75, 76, 77, 78, 79, 81, 82, 83, 84, 85, 86, 87, 88, 89, 90, 91, 92, 93, 94, 95, 96, 97, 98, 100, 101, 102, 103, 105, 106, 107, 108, 109, 111, 114, 115, 116, 117, 118, 119, 120, 121, 122, 123, 124, 125, 126, 127, 128, 1–29, 130, 131, 132, 133, 134, 135, 136, 137, 138 (potential prodrug), 139, 141, 142, 143, 144, 145, 146, 147, 1–48, 149, and 150, and pharmaceutically acceptable salts and complexes thereof. These compounds have an IC$_{50}$≦10 μm at an NMDA receptor.

In more preferred embodiments, the methods of treatment include administration of a compound selected from the group consisting of Compound 19, 20, 21, 22, 23, 24, 25, 27, 28, 29, 30, 31, 32, 33, 34, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 69, 70, 75, 76, 81, 82, 83, 85, 86, 87, 88, 89, 90, 91, 92, 93, 94, 95, 96, 97, 100, 101, 102, 103, 105, 106, 108, 109, 111, 115, 118, 119, 120, 121, 122, 125, 126, 127, 128, 129, 130, 131, 132, 133, 135, 136, 137, 138 (potential prodrug), 139, 142, 144, 145, 146, 147, 148, 149, and 150, and pharmaceutically acceptable salts and complexes thereof. These compounds have an IC$_{50}$≦2.5 μM at an NMDA receptor.

In other embodiments, the compound is selected from the group consisting of Compound 54, 55, 56, 57, 58, 59, 60, 61, 62, 63, 64, 65, 66, 69, 76, 82, 83, 88, 89, 90, 92, 93, 94, 95, 96, 101, 102, 103, 105, 109, 111, 115, 118, 119, 120, 121, 122, 125, 126, 127, 129, 130, 131, 135, 136, 137, 138, 139, 142, 144, 145, 148, 149, and 150, and pharmaceutically acceptable salts and complexes thereof.

In particularly preferred embodiments, the methods of treatment include administration of a compound selected from the group consisting of Compound 19, 20, 21, 22, 23, 24, 25, 27, 28, 30, 31, 32, 33, 38, 39, 43, 44, 46, 47, 49, 50, 52, 53, 54, 55, 56, 57, 58, 59, 60, 61, 62, 63, 64, 65, 66, 69, 82, 83, 89, 90, 91, 93, 94, 95, 96, 97, 103, 111, 118, 119, 120, 122, 126, 135, 136, 137, 138 (potential prodrug), 142, 144, 145, 147, 148, 149, and 150, and pharmaceutically acceptable salts and complexes thereof. These compounds have an IC$_{50}$≦0.5 μM at an NMDA receptor.

In more preferred embodiments, the methods of treatment include administration of a compound selected from the group consisting of Compound 20, 24, 25, 33, 50, 60, 66, 69, 103, 111, 118, 119, 120, 122, 136, 137, 138 (potential prodrug), 142, 144, 145, 148, 149, and 150, and pharmaceutically acceptable salts and complexes thereof.

In particularly preferred embodiments, the methods of treatment include administration of a compound selected from the group consisting of Compound 20, 33, 50, 60, 119, and 144, and pharmaceutically acceptable salts and complexes thereof.

In other particularly preferred embodiments, the methods of treatment include administration of a compound selected from the group consisting of Compound 33, 50, 60, 119, and 144, and pharmaceutically acceptable salts and complexes thereof.

In preferred aspects, the invention provides a method for treating a patient having a neurological disease or disorder, comprising administering a compound which is selected from the group consisting of Compound 156, 157, 158, 159, 160, 161, 162, 163, 164, 165, 166, 167, 168, 169, 170, 171, 181, 182, 183, 184, 185, 186, 187, and pharmaceutically acceptable salts and complexes thereof. These compounds have an IC$_{50}$≦10 μM at an NMDA receptor.

In further preferred aspects, the invention provides a method for treating a patient having a neurological disease or disorder, comprising administering a compound which is selected from the group consisting of Compound 157, 158, 159, 163, 164, 166, 167, 168, 169, 170, 171, 181, 185, 186, and pharmaceutically acceptable salts and complexes thereof. These compounds have an IC$_{50}$≦10μM at an NMDA receptor.

In other more preferred aspects, the invention provides a method for treating a patient having a neurological disease or disorder, comprising administering a compound which is selected from the group consisting of Compound 156, 157, 158, 159, 161, 162, 163, 164, 165, 166, 167, 168, 169, 170, 171, 181, 183, 184, 185, 186, 187, and pharmaceutically acceptable salts and complexes thereof. These compounds have an $IC_{50} \leq 2.5$ µM at an NMDA receptor.

In further preferred aspects, the invention provides a method for treating a patient having a neurological disease or disorder, comprising administering a compound which is selected from the group consisting of Compound 157, 158, 159, 163, 164, 166, 167, 168, 169, 170, 171, 181, 185, 186, and pharmaceutically acceptable salts and complexes thereof. These compounds have an $IC_{50} \leq 2.5$ µM at an NMDA receptor.

In other particularly preferred aspects, the invention provides a method for treating a patient having a neurological disease or disorder, comprising administering a compound which is selected from the group consisting of Compound 156, 157, 158, 159, 161, 163, 164, 165, 167, 168, 169, 170, 171, 181, 186 and pharmaceutically acceptable salts and complexes thereof. These compounds have an $IC_{50} \leq 0.5$ µM at an NMDA receptor.

In further preferred aspects, the invention provides a method for treating a patient having a neurological disease or disorder, comprising administering a compound which is selected from the group consisting of Compound 157, 158, 159, 163, 164, 167, 168, 169, 170, 171, 181, 186 and pharmaceutically acceptable salts and complexes thereof. These compounds have an $IC_{50} \leq 0.5$ µM at an NMDA receptor.

In other preferred aspects, the invention provides a method for treating a patient having a neurological disease or disorder comprising of administering a compound selected from the group consisting of Compounds 151–215, and pharmaceutically acceptable salts and complexes thereof.

In more preferred aspects, the invention provides a method for treating a patient having a neurological disease or disorder comprising administering a compound selected from the group consisting of Compound 151, 152, 153, 154, 155, 157, 158, 159, 163, 164, 166, 167, 168, 169, 170, 171, 172, 173, 174, 175, 176, 181, 185, 186, 188, 189, 190, 191, 192, 193, 194, 195, 196, 197, 198, 199, 200, 201, 202, 203, 204, 205, 206, 207, 208, 209, 210, 211, 212, 213, 214, 215 and pharmaceutically acceptable salts and complexes thereof.

The present invention provides simplified arylalkylamines comprising the compounds of Formulas I–IX and all preferred aspects of Formulas I–IX as set out above.

Examples of such simplified arylalkylamines include, but are not limited to, Compounds 19–215, whose structures are provided below. Preferably, the compound has an $IC_{50} \leq 10$ µM at an NMDA receptor. More preferably, the compound has an $IC_{50} \leq 5$ µM, more preferably $\leq 2.5$ µM, and most preferably $\leq 0.5$ µM at an NMDA receptor.

In preferred embodiments, the compound is selected from the group consisting of Compound 21, 22, 23, 24, 25, 26, 27, 28, 29, 33, 34, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 69, 76, 78, 79, 82, 83, 84, 88, 89, 90, 92, 93, 94, 95, 96, 98, 101, 102, 103, 105, 107, 108, 109, 111, 115, 116, 118, 119, 120, 121, 122, 124, 125, 126, 127, 129, 130, 131, 134, 135, 136, 137, 138 (potential prodrug), 139, 141, 142, 143, 144, 145, 148, 149, and 150. These compounds have an $IC_{50} \leq 10$ µM at an NMDA receptor.

In other embodiments, the compound is selected from the group consisting of Compound 54, 55, 56, 57, 58, 59, 60, 61, 62, 63, 64, 65, 66, 69, 76, 82, 83, 88, 89, 90, 92, 93, 94, 95, 96, 101, 102, 103, 105, 109, 111, 115, 118, 119, 120, 121, 122, 125, 126, 127, 129, 130, 131, 135, 136, 137, 138, 139, 142, 144, 145, 148, 149, and 150.

In more preferred embodiments, the compound is selected from the group consisting of Compound 21, 22, 23, 24, 25, 27, 28, 29, 33, 34, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 69, 76, 82, 83, 88, 89, 90, 92, 93, 94, 95, 96, 101, 102, 103, 105, 108, 109, 111, 115, 118, 119, 120, 121, 122, 125, 126, 127, 129, 130, 131, 135, 136, 137, 138 (potential prodrug), 139, 142, 144, 145, 148, 149, and 150. These compounds have an $IC_{50} \leq 2.5$ µM at an NMDA receptor.

In particularly preferred embodiments, the compound is selected from the group consisting of Compound 21, 22, 23, 24, 25, 27, 28, 33, 38, 39, 43, 44, 46, 47, 49, 50, 52, 53, 54, 55, 56, 57, 58, 59, 60, 61, 62, 63, 64, 65, 66, 69, 82, 83, 89, 90, 93, 94, 95, 96, 103, 111, 118, 119, 120, 122, 126, 135, 136, 137, 138 (potential prodrug), 142, 144, 145, 148, 149, and 150. These compounds have an $IC_{50} \leq 0.5$ µM at an NMDA receptor.

In preferred embodiments, the compound is selected from the group consisting of Compound 24, 25, 33, 50, 60, 66, 69, 103, 111, 118, 119, 120, 122, 136, 137, 138, 142, 144, 145, 148, 149, and 150.

In particularly preferred embodiments, the compound is selected from the group consisting of Compound 20, 33, 50, 60, 119, and 144.

In more particularly preferred embodiments, the compound is selected from the group consisting of Compound 33, 50, 60, 119, and 144.

In other preferred aspects, the compound is selected from the group consisting of Compound 151, 152, 153, 154, 155, 157, 158, 159, 163, 164, 166, 167, 168, 169, 170, 171, 172, 173, 174, 175, 176, 181, 185, 186, 188, 189, 190, 191, 192, 193, 194, 195, 196, 197, 198, 199, 200, 201, 202, 203, 204, 205, 206, 207, 208, 209, 210, 211, 212, 213, 214, 215 and pharmaceutically acceptable salts and complexes thereof.

In other preferred aspects, the compound is selected from the group consisting of Compound 157, 158, 159, 163, 164, 166, 167, 168, 169, 170, 171, 181, 185, 186, and pharmaceutically acceptable salts and complexes thereof. These compounds have an $IC_{50} \leq 10$ µM at an NMDA receptor.

In more preferred aspects, the compound is selected from the group consisting of Compound 157, 158, 159, 163, 164, 167, 168, 169, 170, 171, 131, 185, 186, and pharmaceutically acceptable salts and complexes thereof. These compounds have an $IC_{50} \leq 2.5$ µM at an NMDA receptor.

In most preferred aspects, the compound is selected from the group consisting of Compound 157, 158, 159, 163, 164, 167, 168, 169, 170, 171, 181, 186, and pharmaceutically acceptable salts and complexes thereof. These compounds have an $IC_{50} \leq 0.5$ µM at an NMDA receptor.

Excluded from the composition of matter aspect of the present invention are known compounds whose chemical structures are covered by the generic formulae presented above.

Also provided in an aspect of the invention are pharmaceutical compositions useful for treating a patient having a neurological disease or disorder. The pharmaceutical compositions are provided in a pharmaceutically acceptable carrier and appropriate dose. The pharmaceutical compositions may be in the form of pharmaceutically acceptable salts and complexes, as is known to those skilled in the art.

The pharmaceutical compositions comprise the compounds of Formulas I–IX and all preferred aspects of Formulas I–IX as set out above.

Preferred pharmaceutical compositions comprise Compounds 19–215. Preferably, the compound has an $IC_{50} \leq 10$ µM at an NMDA receptor. More preferably the compound has an $IC_{50} \leq 5$ µM, more preferably $\leq 2.5$ µM, and most preferably $\leq 0.5$ µM at an NMDA receptor.

In further preferred embodiments, the pharmaceutical composition comprises a compound selected from the group consisting of Compound 20, 21, 22, 23, 24, 25, 27, 28, 29, 30, 31, 32, 33, 34, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 75, 76, 77, 78, 79, 81, 82, 83, 84, 85, 86, 87, 88, 89, 90, 91, 92, 93, 94, 95, 96, 97, 98, 100, 101, 102, 103, 105, 106, 107, 108, 109, 111, 114, 115, 116, 117, 118, 119, 120, 121, 122, 213, 124, 125, 126, 127, 128, 129, 130, 131, 132, 133, 134, 135, 136, 137, 138, (potential prodrug), 139, 141, 142, 143, 144, 145, 146, 147, 148, 149, and 150. These compounds have an $IC_{50} \leq 10$ µM at an NMDA receptor.

Preferably, the compound is selected from the group consisting of 21, 22, 23, 24, 25, 26, 27, 28, 29, 33, 34, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 69, 76, 78, 79, 82, 83, 84, 88, 89, 90, 92, 93, 94, 95, 96, 98, 101, 102, 103, 105, 107, 108, 109, 111, 115, 116, 118, 119, 120, 121, 122, 124, 125, 126, 127, 129, 130, 131, 134, 135, 136, 137, 138 (potential prodrug), 139, 141, 142, 143, 144, 145, 148, 149, and 150.

In other embodiments, the compound is selected from the group consisting of 54, 55, 56, 57, 58, 59, 60, 61, 62, 63, 64, 65, 66, 69, 76, 82, 83, 88, 89, 90, 92, 93, 94, 95, 96, 101, 102, 103, 105, 109, ill, 115, 118, 119, 120, 121, 122, 125, 126, 127, 129, 130, 131, 135, 136, 137, 138, 139, 142, 144, 145, 148, 149, and 150.

In more preferred embodiments, the pharmaceutical composition comprises a compound selected from the group consisting of Compound 20, 21, 22, 23, 24, 25, 27, 28, 29, 30, 31, 32, 33, 34, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 69, 70, 75, 76, 81, 82, 83, 85, 86, 871 88, 89, 90, 91, 92, 93, 94, 95, 96, 97, 100, 101, 102, 103, 105, 106, 108, 109, 111, 115, 118, 119, 120, 121, 122, 125, 126, 127, 128, 129, 130, 131, 132, 133, 135, 136, 137, 138 (potential prodrug), 139, 142, 144, 145, 146, 148, 149, and 150. These compounds have an $IC_{50} \leq 2.5$ µM at an NMDA receptor.

Preferably, the compound is selected from the group consisting of 21, 22, 23, 24, 25, 27, 28, 29, 33, 34, 37, 38, 39, 40, 41, 42, 43, 44, 45, 46, 47, 48, 49, 50, 51, 52, 53, 54, 55, 56, 57, 53, 59, 60, 61, 62, 63, 64, 65, 66, 69, 76, 82, 83, 88, 89, 90, 92, 93, 94, 95, 96, 101, 102, 103, 105, 108, 109, 111, 115, 118, 119, 120, 121, 122, 125, 126, 127, 129, 130, 131, 135, 136, 137, 138 (potential prodrug), 139, 142, 144, 145, 148, 149, and 150.

In particularly preferred embodiments, the pharmaceutical composition comprises a compound is selected from the group consisting of Compound 20, 21, 22, 23, 24, 25, 27, 28, 30, 31@, 32, 33, 38, 39, 43, 44, 46, 47, 49, 50, 52, 53, 54, 55, 56, 57, 58, 59, 60, 61, 62, 63, 64, 65, 66, 69, 82, 83, 89, 90, 911 93, 94, 95, 96, 97, 103, 111, 118, 119, 120, 122, 126, 135, 136, 137, 138 (potential prodrug), 142, 144, 145, 148, 149, and 150. These compounds leave an $IC_{50} \leq 0.5$ µM at an NMDA receptor.

Preferably, the compound is selected from the group consisting of 21, 22, 23, 24, 25, 27, 28, 33, 38, 39, 43, 44, 46, 47, 49, 50, 52, 53, 54, 55, 56, 57, 58, 59, 60, 61, 62, 63, 64, 65, 66, 69, 82, 83, 89, 90, 93, 94, 95, 96, 103, 111, 118, 119, 120, 122, 126, 135, 136, 137, 138 (potential prodrug), 142, 144, 145, 148, 149, and 150.

In more preferred embodiments, the pharmaceutical composition comprises a compound selected from the group consisting of Compound 20, 24, 25, 33, 50, 60, 66, 69, 103, 111, 118, 119, 120, 122, 136, 137, 138, 142, 144, 145, 148, 149, and 150.

Preferably, the compound is selected from the group consisting of Compound 24, 25, 33, 50, 60, 66, 69, 103, 111, 118, 119, 120, 122, 136, 137, 138, 142, 144, 145, 148, 149, and 150.

In most particularly preferred embodiments, the pharmaceutical composition comprises a compound selected from the group consisting of Compound 20, 33, 50, 60, 119, and 144.

Preferably, the compound is selected from the group consisting of 33, 50, 60, 119, and 144.

In other preferred aspects, the pharmaceutical composition comprises a compound selected from the group consisting of compound 151, 152, 153, 154, 155, 157, 158, 159, 163, 164, 166, 167, 168, 169, 170, 171, 172, 173, 174, 175, 176, 181, 135, 186, 188, 189, 190, 191, 192, 193, 194, 195, 196, 197, 198, 199, 200, 201, 202, 203, 204, 205, 206, 207, 208, 209, 210, 211, 212, 213, 214, 215 and pharmaceutically acceptable salts and complexes thereof, and a pharmaceutically acceptable carrier.

In other preferred aspects the pharmaceutical composition comprises a compound which is selected from the group consisting of Compound 157, 158, 159, 163, 164, 166, 167, 168, 169, 170, 171, 181, 185, 186, and pharmaceutically acceptable salts and complexes thereof, and a pharmaceutically acceptable carrier. These compounds have an $IC_{50} \leq 10$ µM at an NMDA receptor.

In more preferred aspects, the pharmaceutical composition comprises a compound which is selected from the group consisting of Compound 157, 158, 159, 163, 164, 166, 167, 168, 169, 170, 171, 181, 185, 186, and pharmaceutically acceptable salts and complexes thereof, and a pharmaceutically acceptable carrier. These compounds have an $IC_{50} \leq 2.5$ µM at an NMDA receptor.

In most preferred aspects, the pharmaceutical composition comprises a compound which is selected from the group consisting of Compound 157, 158, 159, 163, 164, 167, 168, 169, 170, 171, 181, 186, and pharmaceutically acceptable salts and complexes thereof, and a pharmaceutically acceptable carrier. These compounds have an $IC_{50} \leq 0.5$ µM at an NMDA receptor.

Structural modifications can be made to compounds such as 20 or 60 which do not add materially to the structure-activity relationships (SAR) illustrated here. For example, successful bioisosteric replacement or substitution of optionally substituted phenyl groups, such as those occurring in Compounds 20 or 60, can be accomplished with other lipophilic or semi-polar aromatic (e.g., naphthyl, naphthoxy, benzyl, phenoxy, phenylthio), aliphatic (alkyl, e.g., isopropyl), cycloaliphatic (cycloalkyl, e.g., cyclohexyl), heterocyclic [e.g., pyridyl, furanyl, thiofuranyl (thiophenyl)], or other functional groups or systems, as is well known in the art, will afford clinically useful compounds (structural homologs, analogs, and/or congeners) with similar biopharmaceutical properties and activity at the NMDA receptor (e.g., cf. Compounds 37, 75, 79, 83, 89, 119–122, 125, 126, 128, 130, 132, 137, 144, and 145). For example, such replacements or substitutions have been used to great effect in the development of SAR among other groups of highly clinically and commercially successful synthetic pharmaceutical agents such as the classical H$_I$-antihistamines, anticholinergics (antimuscarinics; e.g., anti-Parkinsonians), antidepressants (including tricyclic compounds), and opioid analgesics [See, Foye et al. (Eds.), *Principles of Medicinal Chemistry*, 4th ed., Lea and Febiger/Williams and Wilkins, Philadelphia, Pa., 1995, pp. 233, 265, 281–282, 340–341, 418–427, and 430; Prous, J. R., *The Year's Drug News, Therapeutic Targets*—1995 Edition, Prous Science Publishers, Barcelona, Spain, 1995, pp. 13, 55–56, 58–59, 74, 89, 144–145, 152, 296297, and 317]. Similarly, bioisosteric replacement or substitution of the methylene or methine groups in the propyl backbone of compounds such as 20 or 60 with, e.g., oxygen, sulfur, or nitrogen, will afford clinically useful NMDA receptor-active compounds with similarly useful biopharmaceutical properties, such as Compound-88 (a modified "classical H$_I$-antihistamine-type" structure), which can be further optimized for activity at the NMDA receptor by preparing, e.g., the corresponding compounds) containing, e.g., (bis)(3-fluorophenyl) group(s), as taught by the present invention. The propyl backbone of compounds such as 20 and 60 may also be modified successfully by the incorporation of ring systems (as in Compounds 102 and 111) and/or unsaturation (e.g., a double bond, as in Compounds 81, 106, 109, and 139) to afford further clinically useful NMDA receptor-active compounds of the present invention (cf. compounds cited above).

In a related aspect, the invention features a method for making a therapeutic agent comprising the steps of screening for said agent by determining whether said agent is active on a receptor-operated calcium channel, and synthesizing said therapeutic agent in an amount sufficient to provide said agent in a therapeutically effective amount to a patient. Said screening may be performed by methods known to those of ordinary skill in the art, and may, for example be performed by the methods set out herein. Those skilled in the art are also familiar with methods used to synthesize therapeutic agents in amounts sufficient to be provided in a therapeutically effective amount.

In a preferred aspect, said receptor-operated calcium channel is an NMDA receptor. In a more preferred aspect, said method further comprises the step of adding a pharmaceutically acceptable carrier to said agent. In a further preferred aspect said therapeutic agent comprises a compound of Formula I, as set out herein. In a further preferred aspect said therapeutic agent comprises a compound of Formula II, III, IV, V, VI, VII, VIII, or IX, as set out herein. In particularly preferred aspects, said therapeutic agent comprises a compound having a structure selected from the group consisting of Formulas I–IX, and all preferred aspects of said formulas as set out herein. In further preferred aspects, said therapeutic agent is selected from the group consisting of Compounds 19–215. In a particularly preferred aspect, said therapeutic agent is provided to a patient having a neurological disease or disorder. In a related aspect, said screening comprises the step of identifying a compound which binds to said receptor-operated calcium channel at a site bound by one of the arylalkylamines Compound 1, Compound 2, and Compound 3.

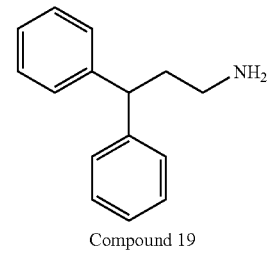

Compound 19

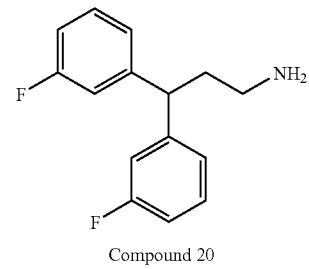

Compound 20

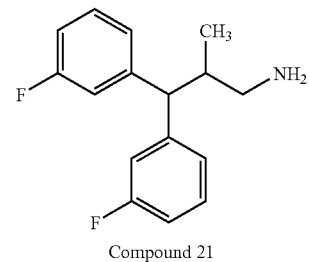

Compound 21

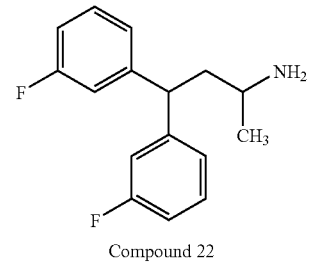

Compound 22

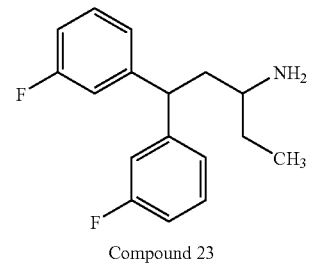

Compound 23

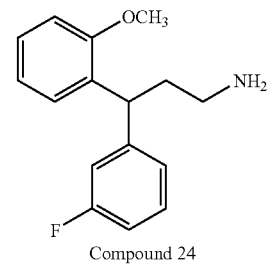

Compound 24

-continued
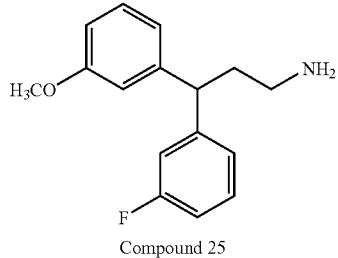
Compound 25
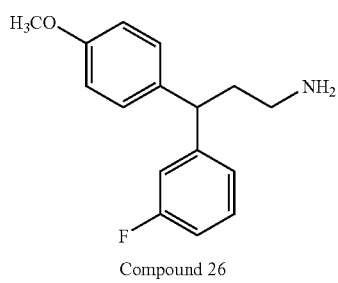
Compound 26
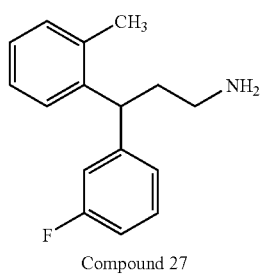
Compound 27
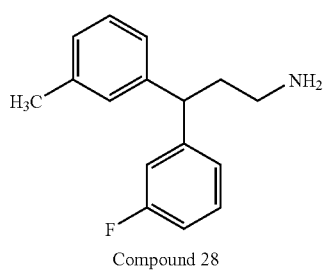
Compound 28
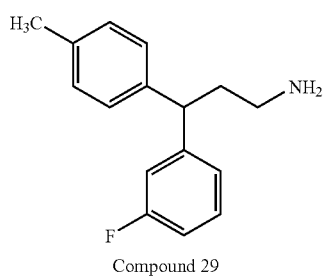
Compound 29
-continued
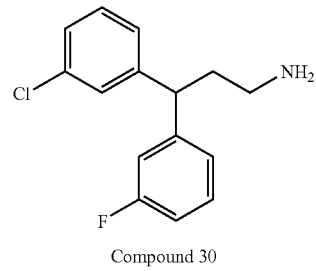
Compound 30
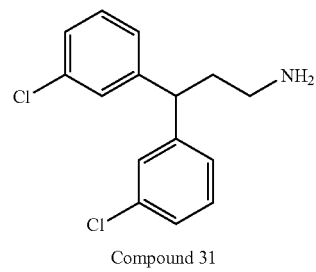
Compound 31
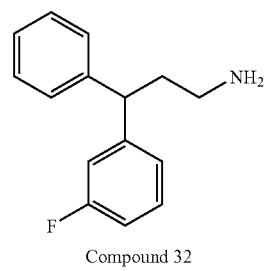
Compound 32
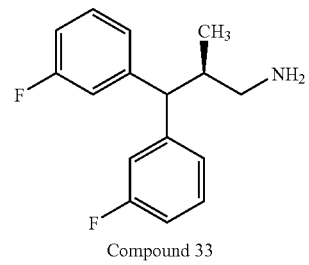
Compound 33
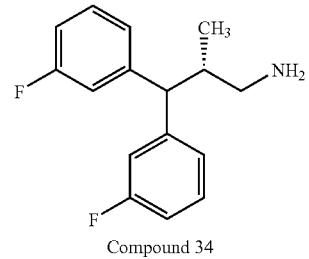
Compound 34
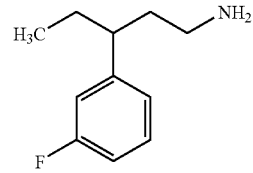
Compound 35

-continued
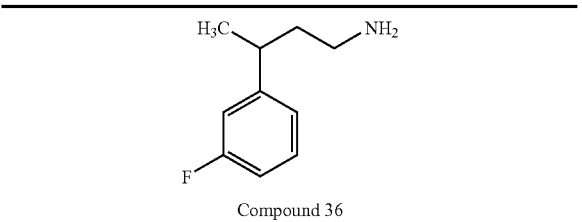
Compound 36
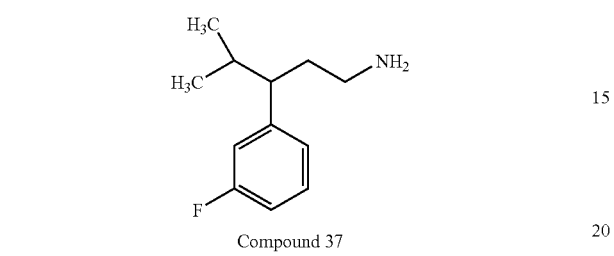
Compound 37
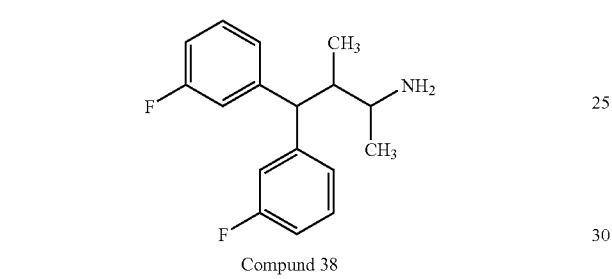
Compund 38
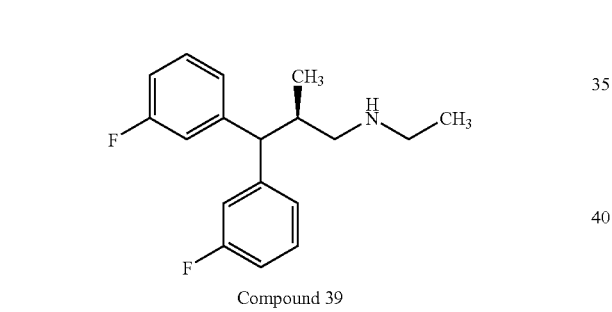
Compound 39
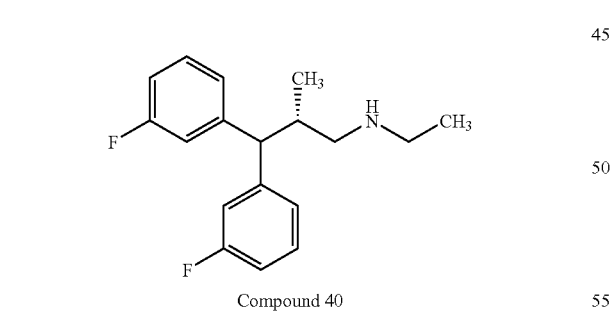
Compound 40
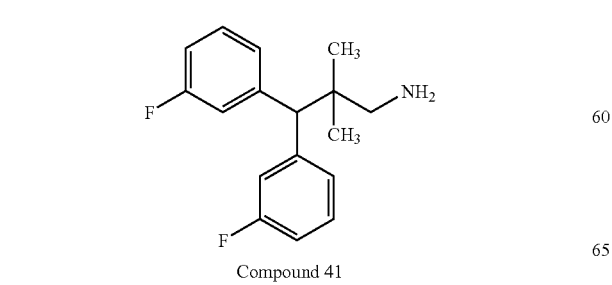
Compound 41
-continued
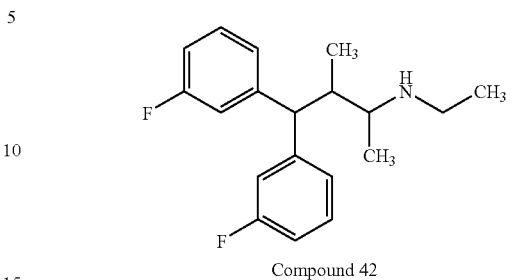
Compound 42
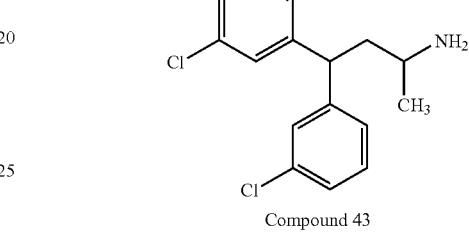
Compound 43
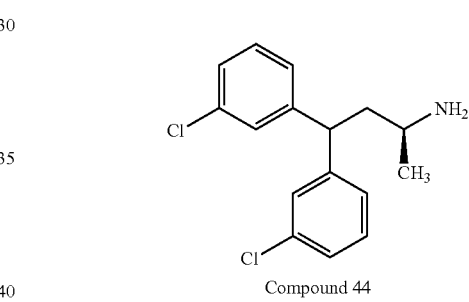
Compound 44
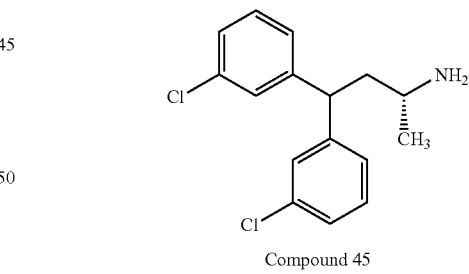
Compound 45
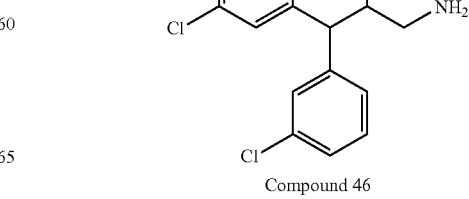
Compound 46

-continued
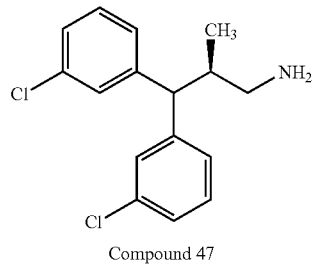
Compound 47
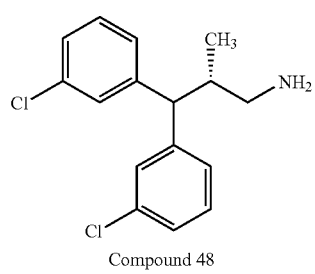
Compound 48
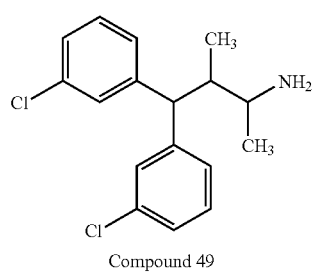
Compound 49
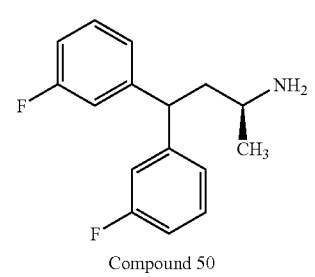
Compound 50
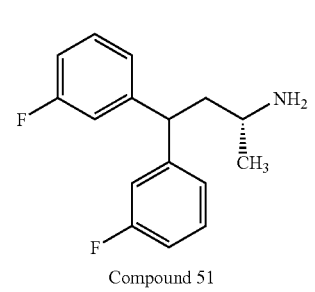
Compound 51
-continued
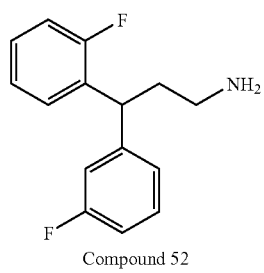
Compound 52
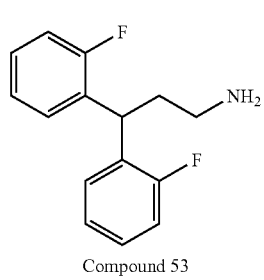
Compound 53
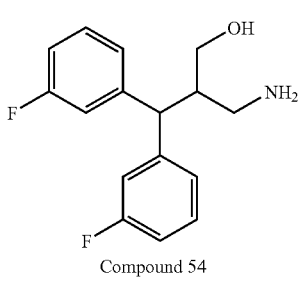
Compound 54
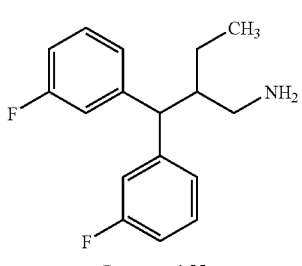
Compound 55
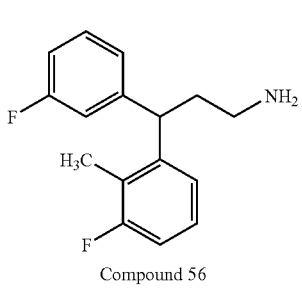
Compound 56

-continued
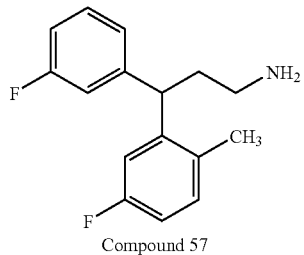
Compound 57
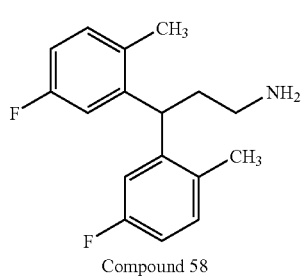
Compound 58
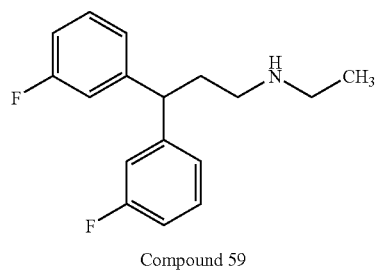
Compound 59
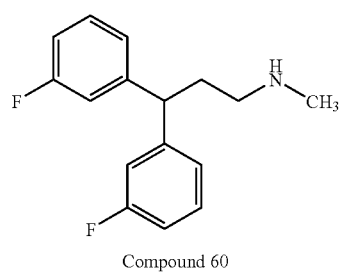
Compound 60
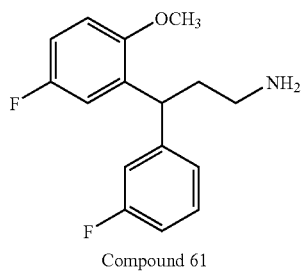
Compound 61
-continued
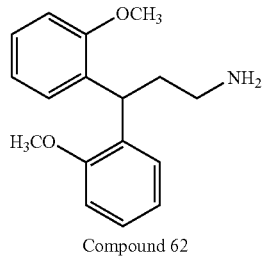
Compound 62
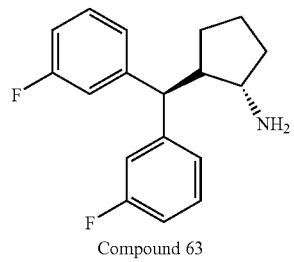
Compound 63
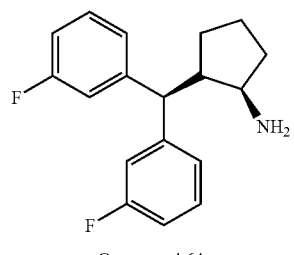
Compound 64
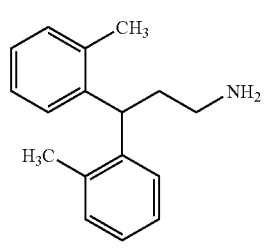
Compound 65
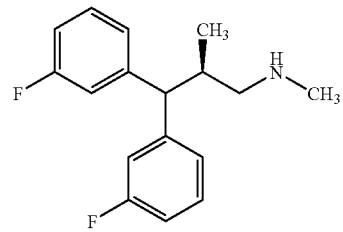
Compound 66
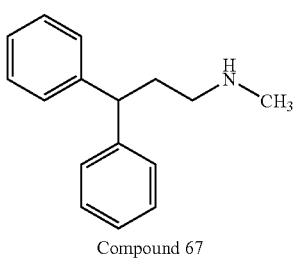
Compound 67

-continued
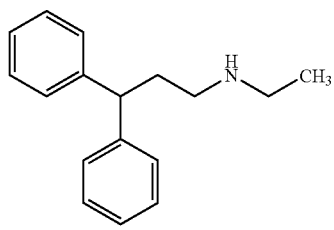
Compound 68
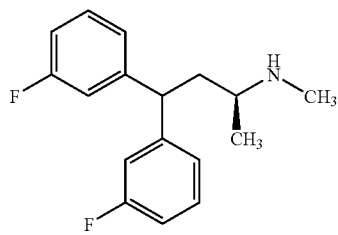
Compound 69
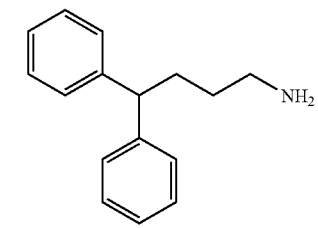
Compound 70
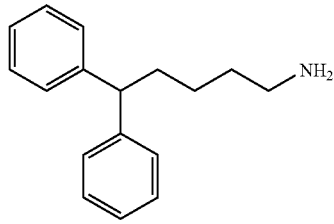
Compound 71
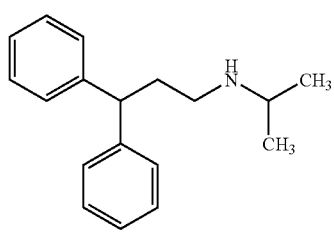
Compound 72
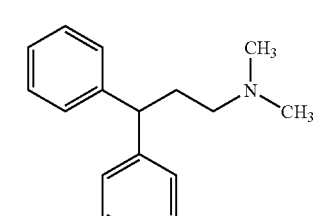
Compound 73
-continued
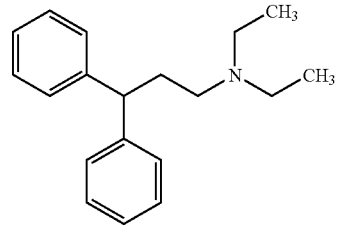
Compound 74
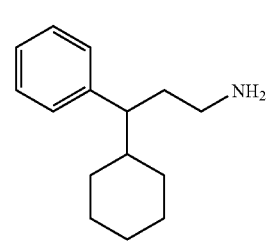
Compound 75
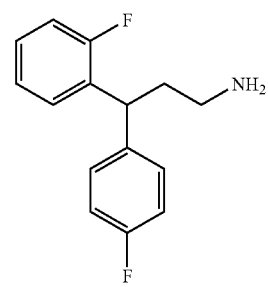
Compound 76
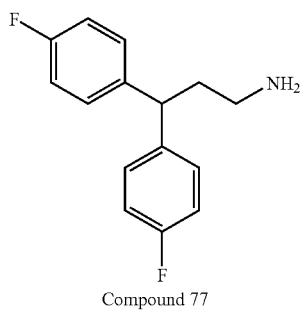
Compound 77
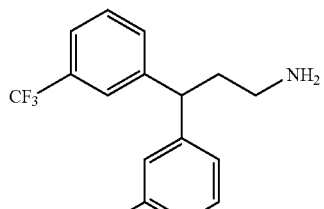
Compound 78

-continued
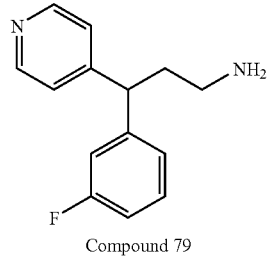
Compound 79
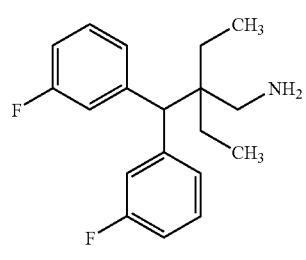
Compound 80
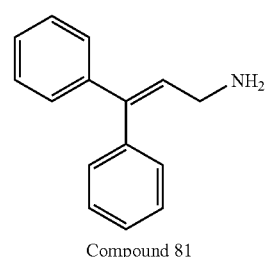
Compound 81
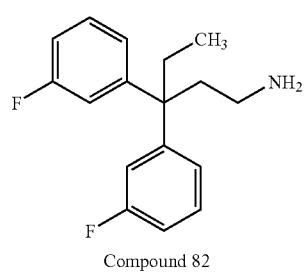
Compound 82
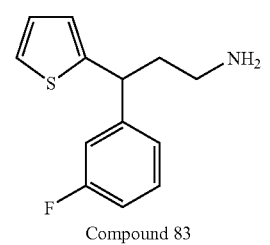
Compound 83
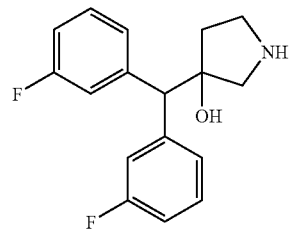
Compound 84
-continued
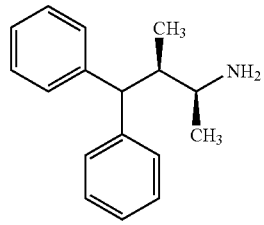
Compound 85
(mixture of 2
compounds)
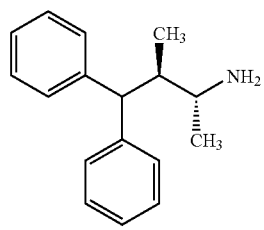
Compound 86
(mixture of 2
compounds)
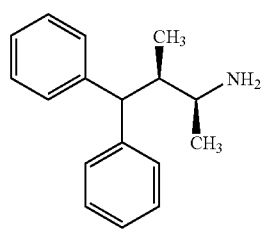
Compound 87
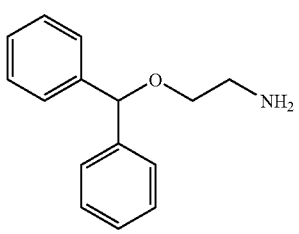
Compound 88

-continued
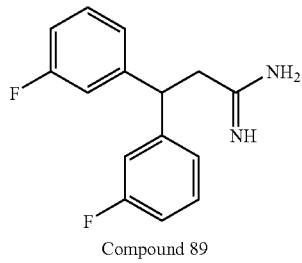
Compound 89
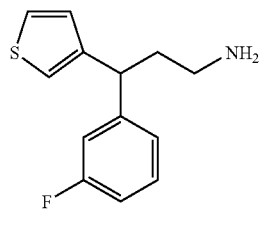
Compound 90
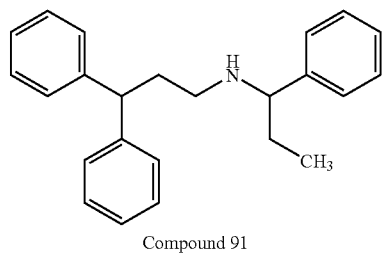
Compound 91
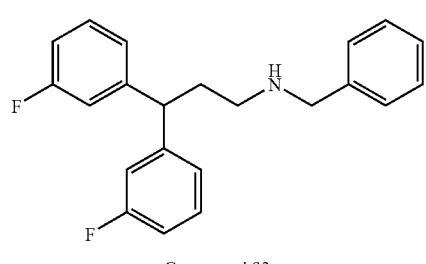
Compound 92
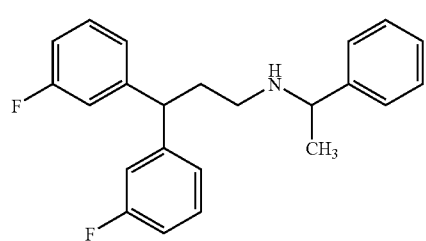
Compound 93
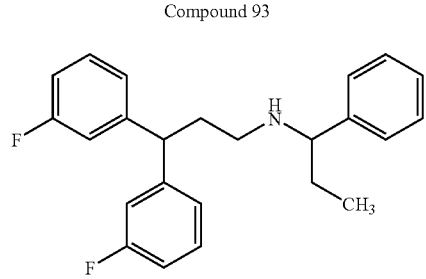
Compound 94
-continued
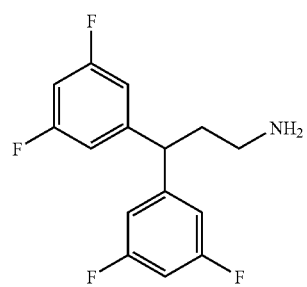
Compound 95
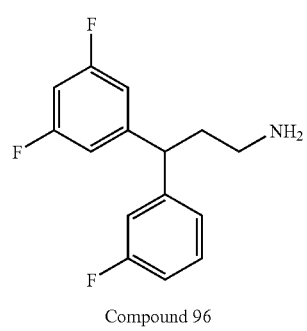
Compound 96
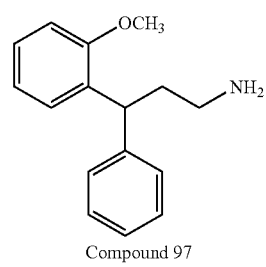
Compound 97
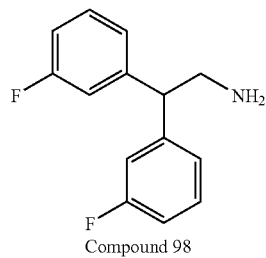
Compound 98
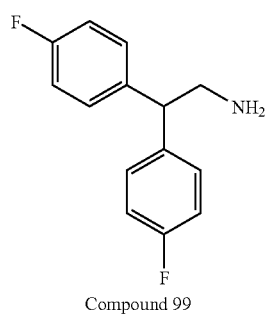
Compound 99

-continued
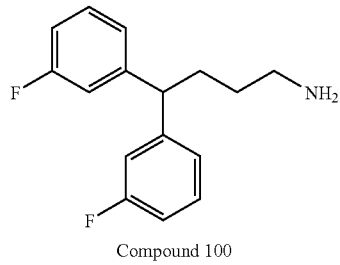
Compound 100
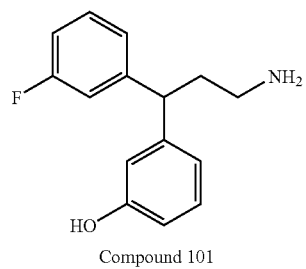
Compound 101
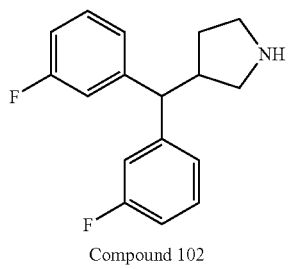
Compound 102
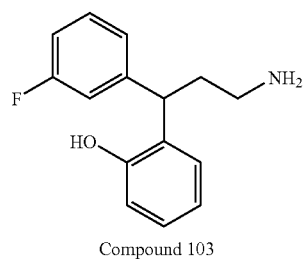
Compound 103
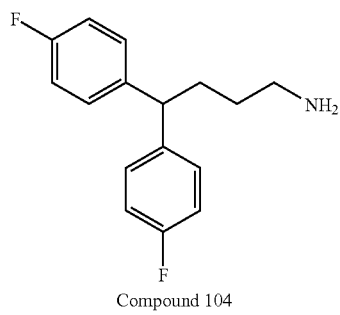
Compound 104
-continued
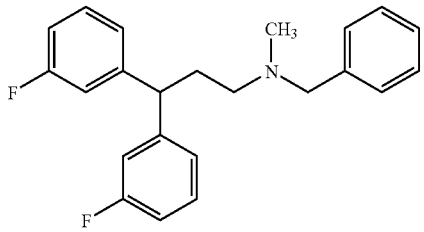
Compound 105
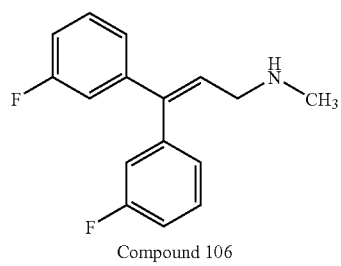
Compound 106
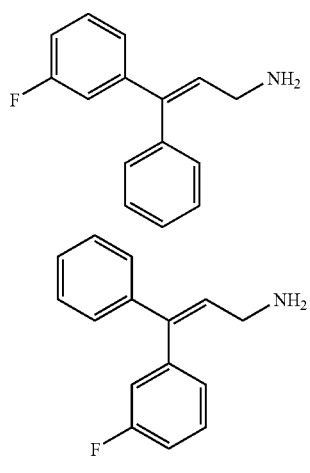
Compound 107
(mixture of 2 compounds)
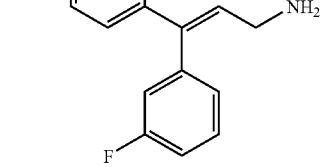
Compound 108
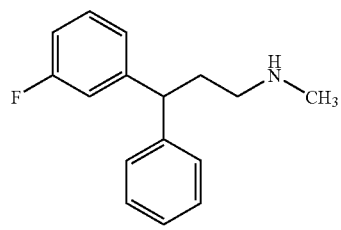
Compound 109

-continued
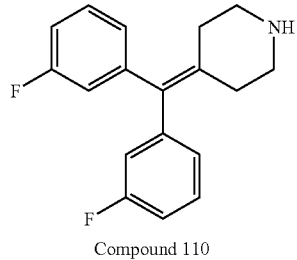
Compound 110
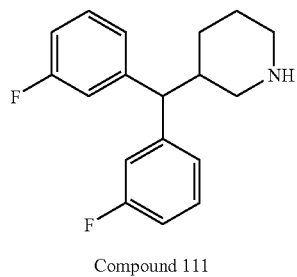
Compound 111
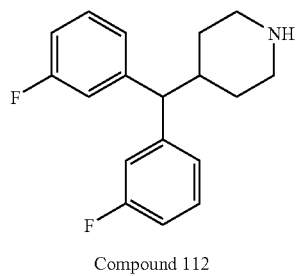
Compound 112
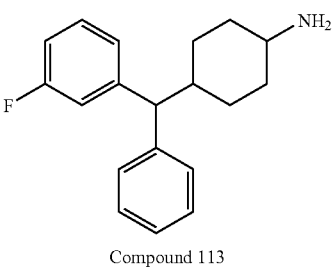
Compound 113
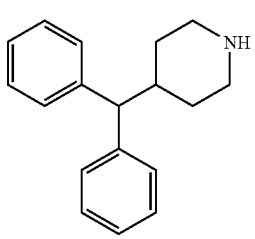
Compound 114
-continued
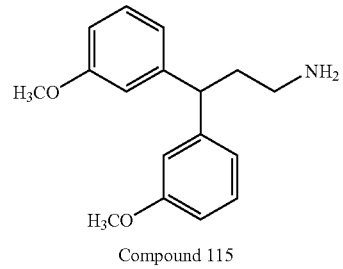
Compound 115
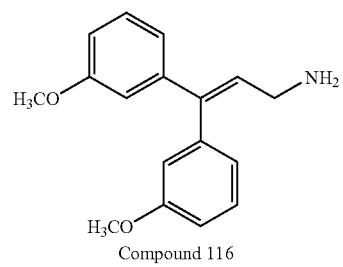
Compound 116
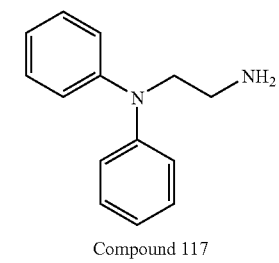
Compound 117
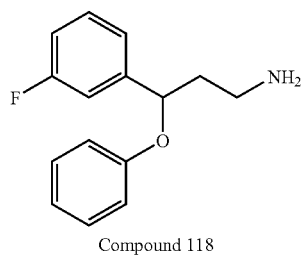
Compound 118
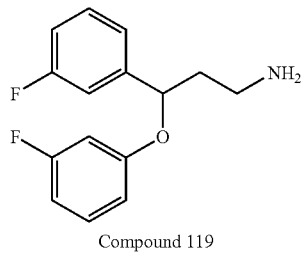
Compound 119
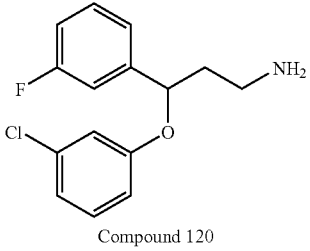
Compound 120

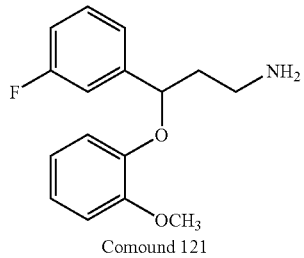
Compound 121
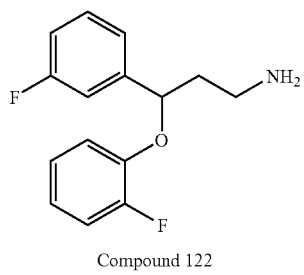
Compound 122
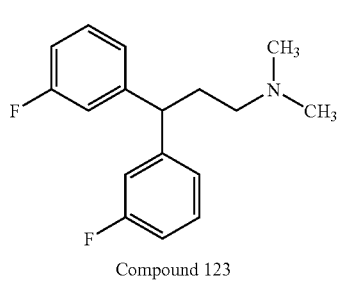
Compound 123
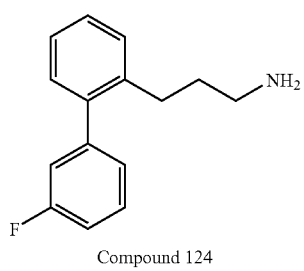
Compound 124
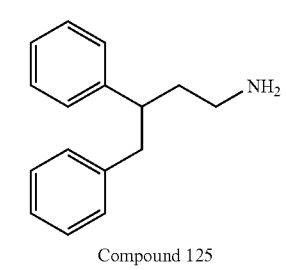
Compound 125
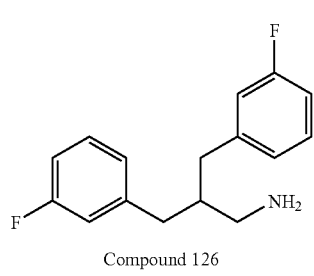
Compound 126
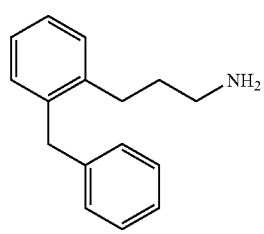
Compound 127
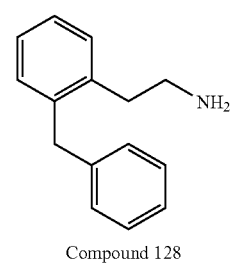
Compound 128
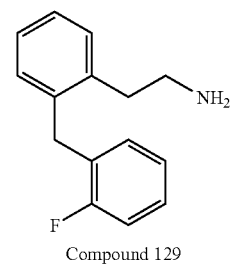
Compound 129
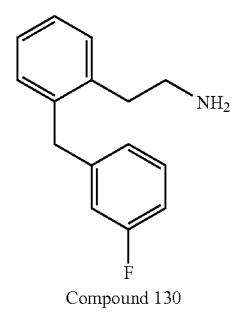
Compound 130
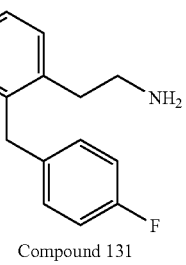
Compound 131

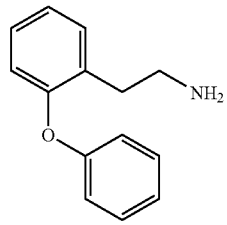
Compound 132
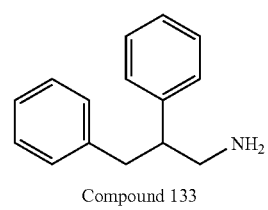
Compound 133
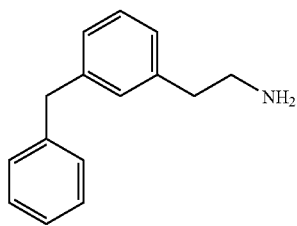
Compound 134
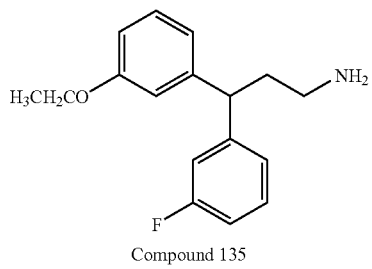
Compound 135
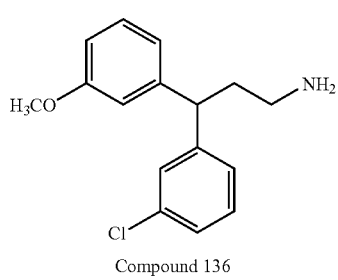
Compound 136
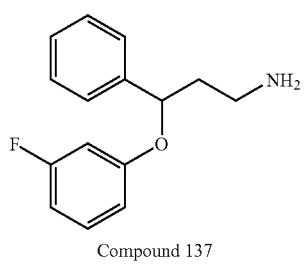
Compound 137
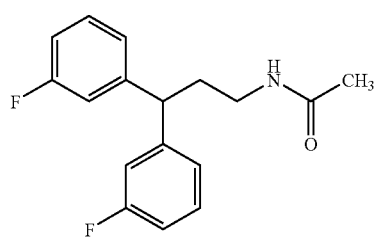
Compound 138
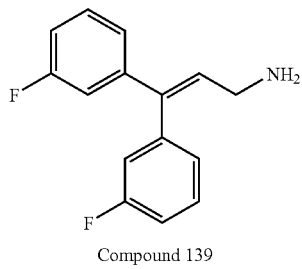
Compound 139
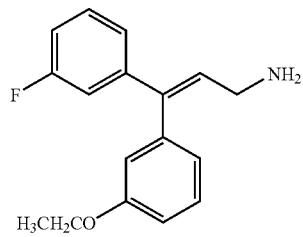
Compound 140
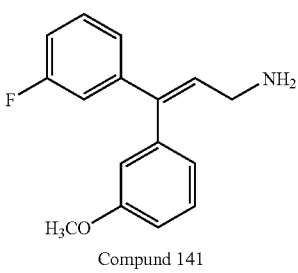
Compound 141
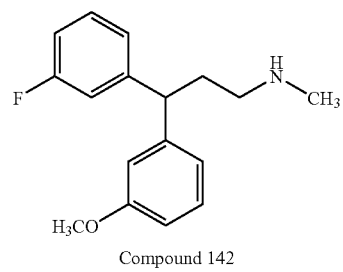
Compound 142

-continued
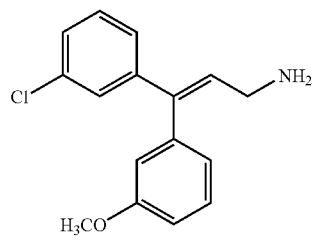
Compound 143
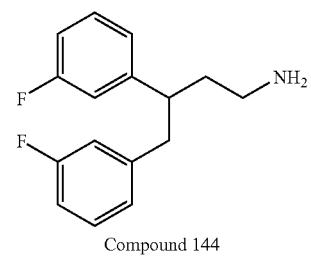
Compound 144
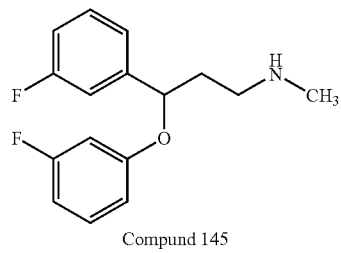
Compund 145
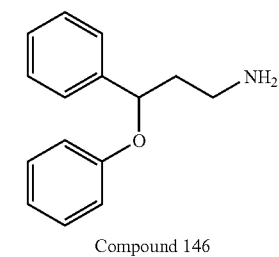
Compound 146
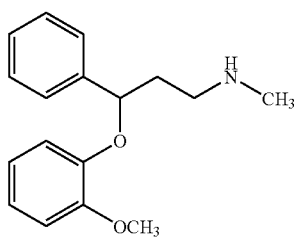
Compound 147
-continued
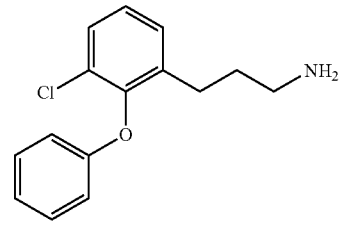
Compound 148
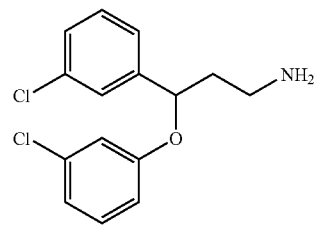
Compound 149
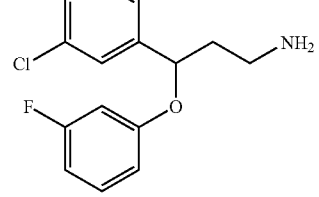
Compound 150
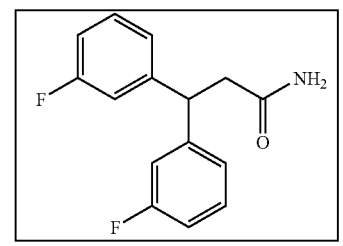
Compound 151
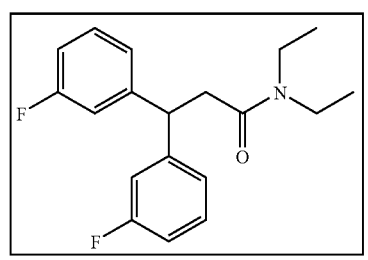
Compound 152
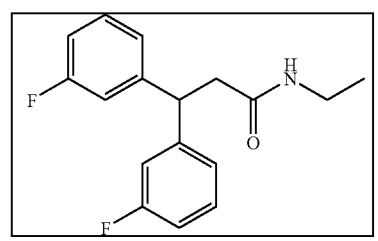
Compound 153

-continued
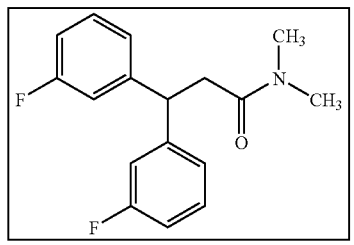
Compound 154
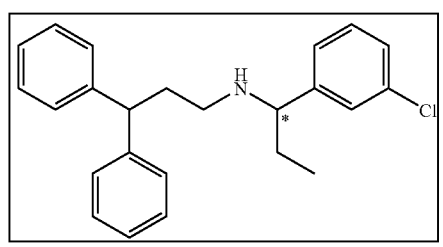
Compound 159
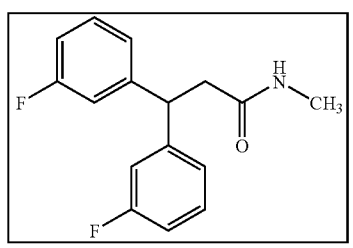
Compound 155
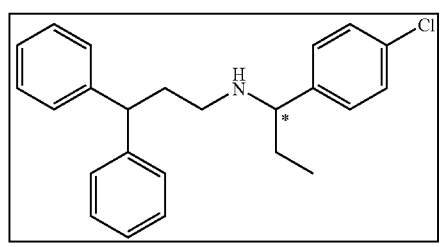
Compound 160
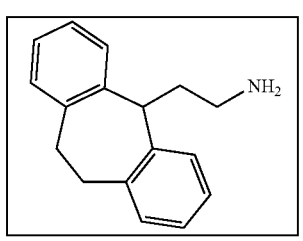
Compound 156
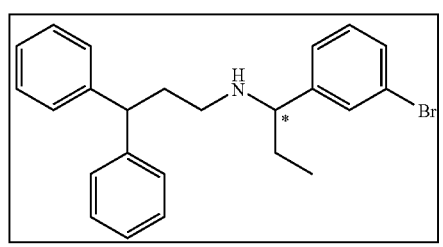
Compound 161
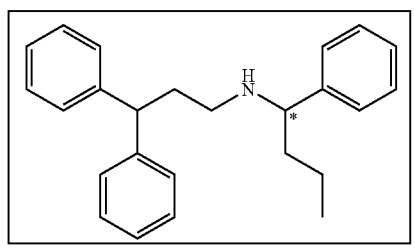
Compound 157
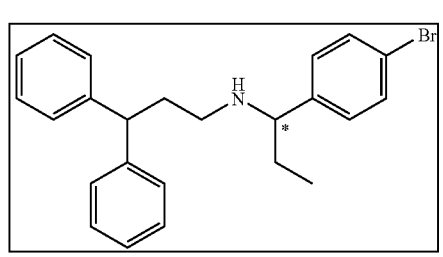
Compound 162
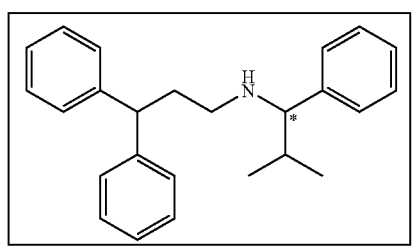
Compound 158
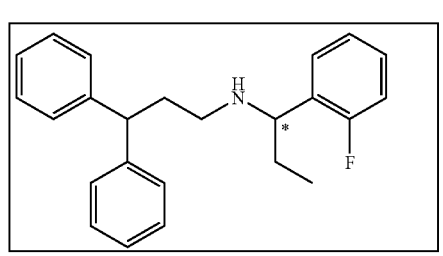
Compound 163

-continued
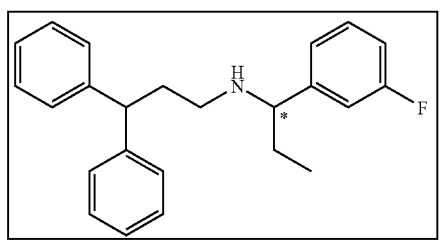
Compound 164
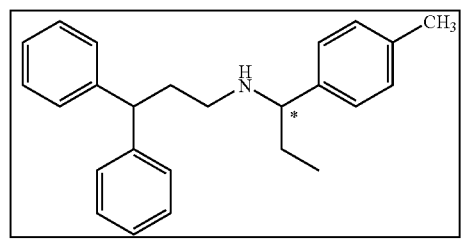
Compound 169
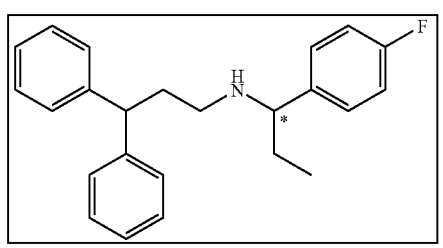
Compound 165
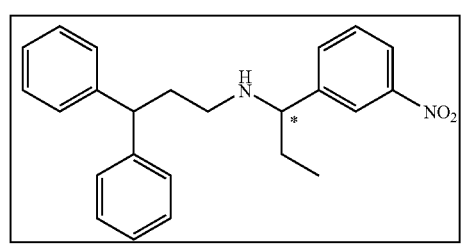
Compound 170
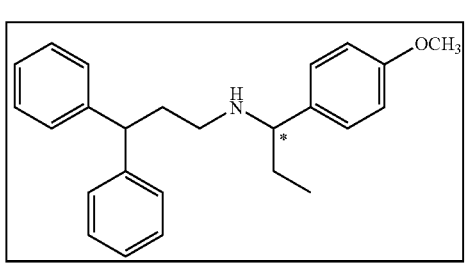
Compound 166
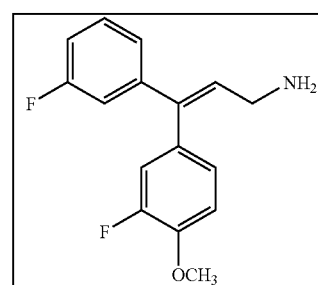
Compound 172
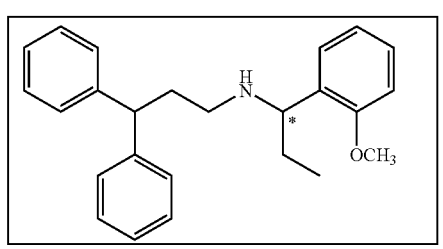
Compound 167
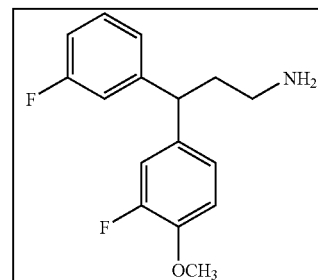
Compound 173
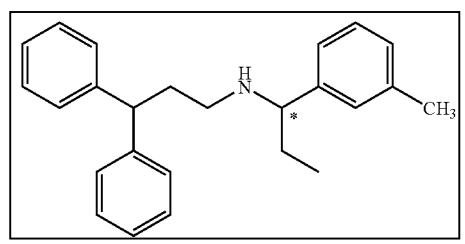
Compound 168
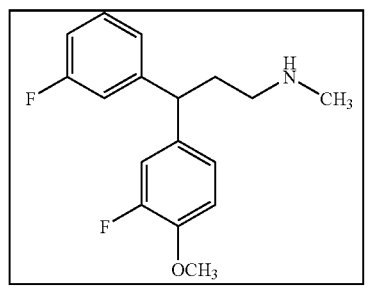
Compound 174

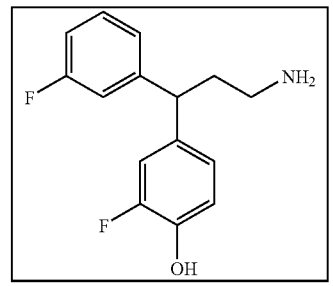
Compound 175
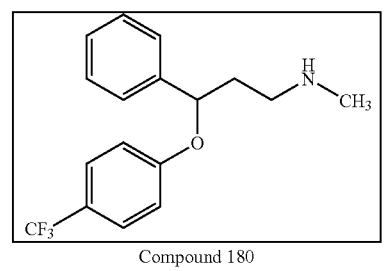
Compound 180
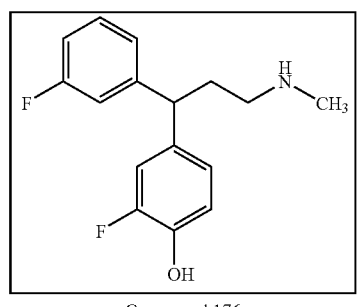
Compound 176
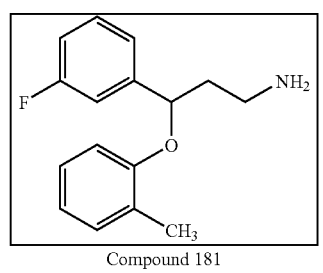
Compound 181
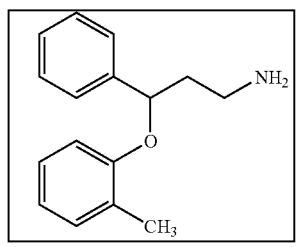
Compound 177
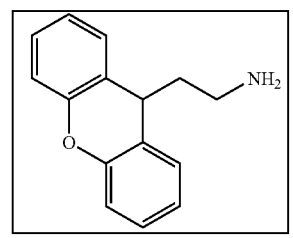
Compound 182
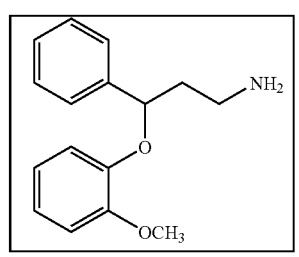
Compound 178
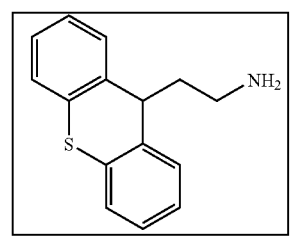
Compound 183
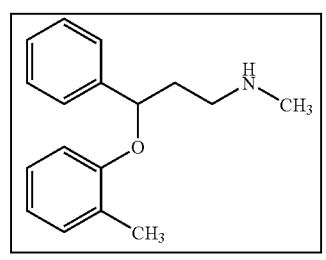
Compound 179
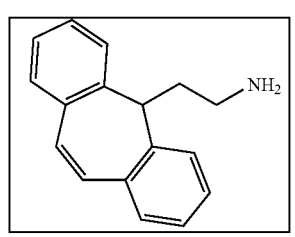
Compound 184

-continued
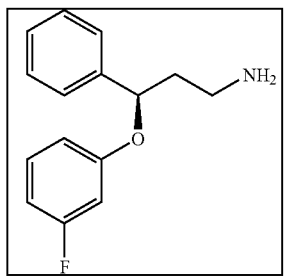
Compound 185
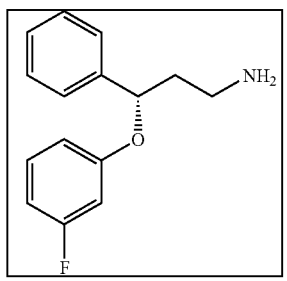
Compound 186
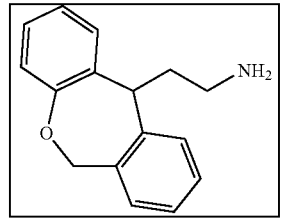
Compound 187
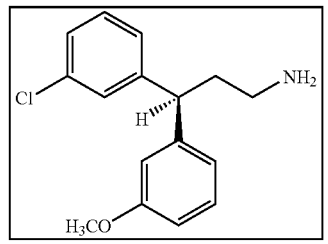
Compound 188
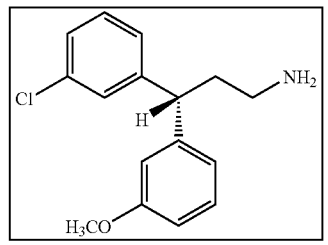
Compound 189
-continued
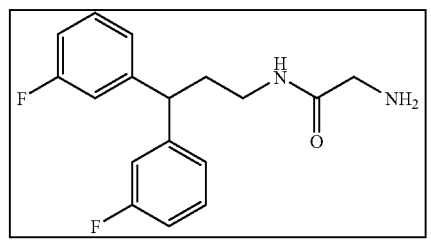
Compound 190
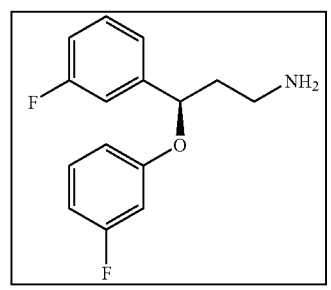
Compound 191
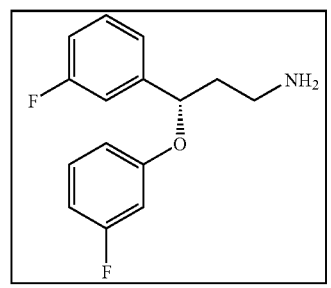
Compound 192
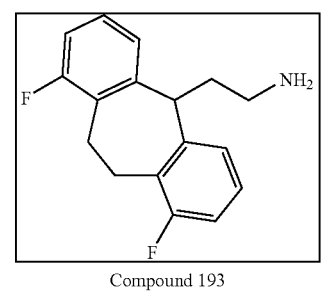
Compound 193
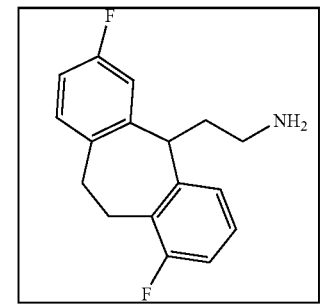
Compound 194

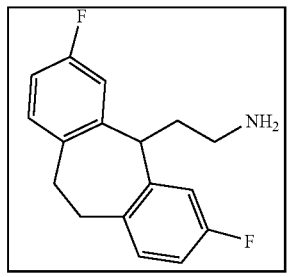
Compound 195
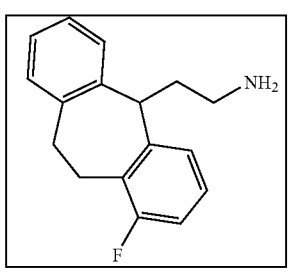
Compound 196
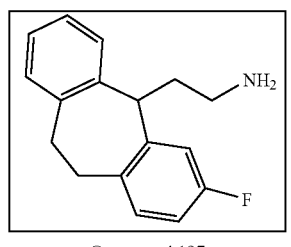
Compound 197
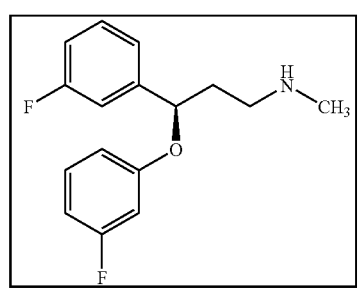
Compound 198
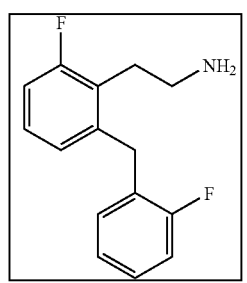
Compound 200
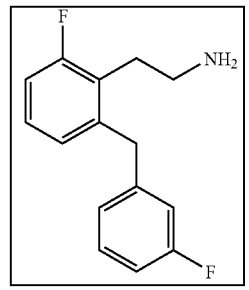
Compound 201
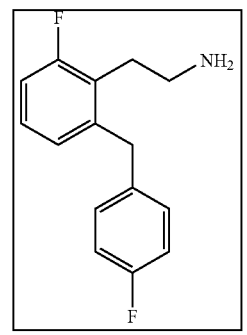
Compound 202
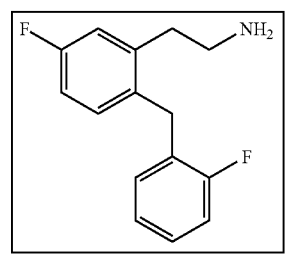
Compound 203
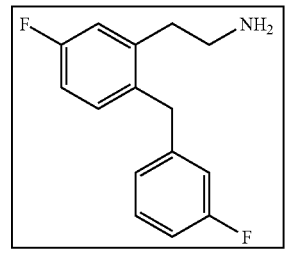
Compound 204
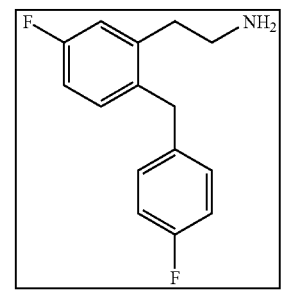
Compound 205

-continued
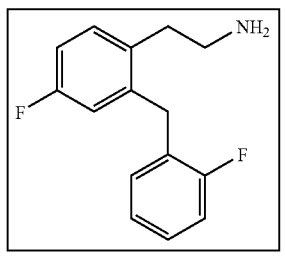
Compound 206
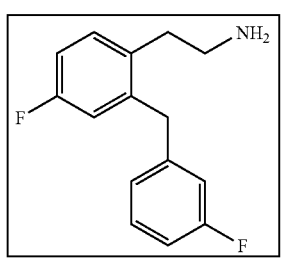
Compound 207
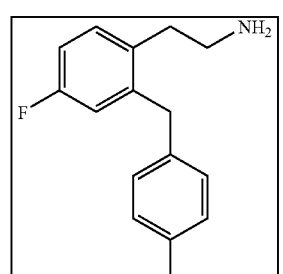
Compound 208
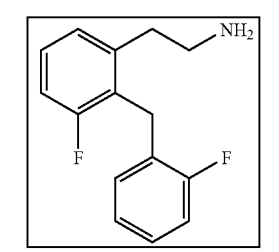
Compound 209
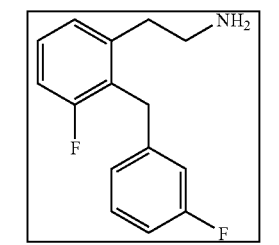
Compound 210
-continued
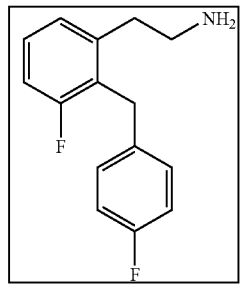
Compound 211
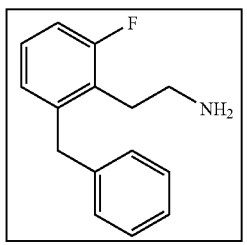
Compound 212
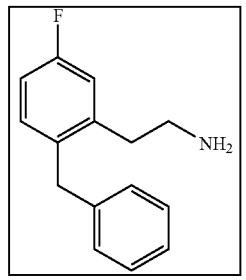
Compound 213
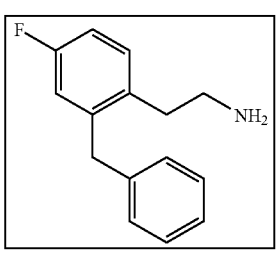
Compound 214
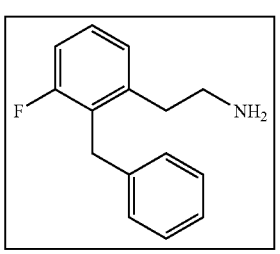
Compound 215
Other features and advantages of the invention will be apparent from the following description of the preferred embodiments thereof, and from the claims.

DESCRIPTION OF THE PREFERRED EMBODIMENTS

The following is a detailed description of the methods and tests by which therapeutically useful compounds can be identified and utilized for the treatment of neurological disorders and diseases. The tests are exemplified by use of Compound 1, Compound 2 or Compound 3, but other compounds which have similar biological activity in these assays can also be used (as discovered) to improve on the tests. Lead compounds such as Compound 1, Compound 2 or Compound 3 can be used for molecular modeling using standard procedures, or existing or novel compounds in natural product libraries can be screened by the methods described below.

One key method is the means by which compounds can be quickly screened with standard radioligand binding techniques (a radiolabeled arylalkylamine binding assay) to identify those which bind at the same site on receptor-operated $Ca^{2+}$ channels as Compound 1, Compound 2 or Compound 3. Data from such radioligand binding studies will also confirm that said compounds do not inhibit [$^3$H] arylalkylamine binding via an action at the known sites on receptor-operated $Ca^{2+}$ channels (such as the glutamate binding site, glycine binding site, MK-801 binding site, $Zn^{2+}$ binding site, $Mg^{2+}$ binding site, sigma binding site, or polyamine binding site on the NMDA receptor-ionophore complex). This screening test allows vast numbers of potentially useful compounds to be identified and screened for activity in the other assays. Those skilled in the art will recognize that other rapid assays for detection of binding to the arylalkylamine site on receptor-operated $Ca^{2+}$ channels can be devised and used in this invention.

Additional testing utilizes electrophysiological (patch clamp) methodology to extend the results obtained with the above-mentioned radioligand binding assay. Such results will confirm that compounds binding to the arylalkylamine site are functional, noncompetitive antagonists of receptor-operated $Ca^{2+}$ channels with the following properties in common with the arylalkylamines themselves: open-channel block manifested as use-dependent block, and voltage-dependent onset and reversal from block. Such results will also confirm that said compounds do not have their primary activity at the previously described sites on receptor-operated $Ca^{2+}$ channels (such as the glutamate binding site, glycine binding site, MK-801 binding site, $Zn^{2+}$ binding site, $Mg^{2+}$ binding site, sigma binding site, or polyamin binding site on the NMDA receptor-ionophore complex).

In addition, recombinant DNA technology can be used to make such testing even more rapid. For example, using standard procedures, the gene(s) encoding the novel arylalkylamine binding site (i.e., receptor) can be identified and cloned. This can be accomplished in one of several ways. For example, an arylalkylamine affinity column can be prepared, and solubilized membranes from cells or tissues containing the arylalkylamine receptor passed over the column. The receptor molecules bind to the column and are thus isolated. Partial amino acid sequence information is then obtained which allows for the isolation of the gene encoding the receptor. Alternatively, CDNA expression libraries are prepared and subtractions of the library are tested for their ability to impart arylalkylamine receptors on cells which do not normally express such receptors (e.g., CHO cells, mouse L cells, HEK 293 cells, or Xenopus oocytes). In this way, the library fraction containing the clone encoding the receptor is identified. Sequential subfractionation of active library fractions and assay eventually results in a single clone encoding the arylalkylamine receptor. Similarly, hybrid-arrest or hybrid-depletion cloning can be used. Xenopus oocytes are injected with MRNA from a appropriate tissue or cell source (e.g., human brain tissue). Expression of the arylalkylamine receptor is detected as, for example, an NMDA- or glutamate-stimulated influx of calcium which can be blocked by Compound 1, Compound 2 or Compound 3. CDNA clones are tested for their ability to block expression of this receptor when CDNA or CRNA are hybridized to the mRNA of choice, prior to injection into Xenopus oocytes. The clone responsible for this effect is then isolated by the process described above. Once the receptor gene is isolated, standard techniques are used to identify the polypeptide or portion(s) thereof which is(are) sufficient for binding arylalkylamines (the arylalkylamine binding domain[s]). Further, using standard procedures, the entire receptor or arylalkylamine binding domain(s) can be expressed by recombinant technology. Said receptor or binding domain(s) can be isolated and used as a biochemical reagent such that, rather than using a competitive assay exemplified below, a simple direct binding assay can be used. That is, a screen is set up for compounds which bind at the novel arylalkylamine receptor. In this way large numbers of compounds can be simultaneously screened, e.g., by passage through a column containing the novel arylalkylamine receptor or arylalkylamine binding domain, and analysis performed on compounds which bind to the column.

Additional testing utilizes the combination of molecular biological techniques (expression of cloned NMDA, AMPA or nicotinic cholinergic receptors) and patch clamp electrophysiological techniques. Specifically, arylalkyl-amine analogs can be rapidly screened for potency at cloned and expressed subunits of the above-mentioned receptor-ionophore complexes. Site-directed mutagenesis can be utilized in an effort to identify which amino acid residues may be important in determining arylalkylamine potency.

Assays for Potent and Selective Antagonists of Receptor-Operated Calcium Channels in the Mammalian CNS Desired properties of a drug include: high affinity and selectivity for receptor-operated $Ca^{2+}$ channels, such as those present in NMDA, AMPA and nicotinic cholinergic receptor-ionophore complexes (compared to responses mediated via other neurotransmitter receptors, neurotransmitter receptor-operated ion channels, or voltage-dependent ion channels) and a noncompetitive antagonism of said receptor-operated $Ca^{2+}$ channels.

The NMDA receptor-ionophore complex is utilized as an example of a receptor-operated Ca 2, channel. Activation of the NMDA receptor opens a cation-selective channel that allows the influx of extracellular $Ca^{2+}$ and $Na^+$, resulting in increases in [$Ca^{2+}$] and depolarization of the cell membrane. Measurements of [$Ca^{2+}$], were used as primary assays for detecting the activity of arylalkylamine compounds on NMDA receptors. Purified arylalkylamines, synthetic arylalkylamines, and synthetic analogs of arylalkylamines were examined for activity in in vitro assays capable of measuring glutamate receptor activity. Selected for detailed study were the arylalkylamines present in the venom of various spider species. The arylalkylamines present in these venoms are structurally distinct but have the basic structure of the class represented by Compounds 1 through 3. Other more simplified synthetic analogs generally consist of suitably substituted aromatic chromophobic groups attached to an alkyl (poly)amine moiety (see Compounds 19 through 215 below).

A primary assay that provides a functional index of glutamate receptor activity and that allows high-throughput screening was developed. Primary cultures of rat cerebellar granule cells loaded with the fluorimetric indicator fura-2 were used to measure changes in $[Ca^{2+}]_i$ elicited by NMDA and its coagonist glycine. This assay provides an extremely sensitive and precise index of NNDA receptor activity. Increases in $[Ca^{2+}]_i$ evoked by NMDA are dependent on the presence of glycine, and are blocked by extracellular $Mg^{2+}$ or antagonists acting at the glutamate, glycine, or MK-801 binding sites. Increases in $[Ca^{2+}]$ elicited by NMDA/glycine are readily distinguished from those resulting from depolarization by their refractoriness to inhibition by blockers of voltage-sensitive $Ca^{2+}$, channels. The fidelity with which measurements of $Ca^{2+}$], corroborate results obtained by electrophysiological and ligand-binding studies suggests that such measurements mirror closely activation of the NMDA receptor-ionophore complex.

EXAMPLE 1

Potent Noncompetitive Inhibition of NMDA Receptor Function

Preferential inhibitory effects of arylalkylamines on NMDA receptor-mediated increases in $[Ca^{2+}]_i$ in cultured rat cerebellar granulescells were measured. Increases in $[Ca^{2+}]_i$ were elicited by the addition of NMDA/glycine (50 µM/1 µM) in the presence or absence of different concentrations of each test compound. The $IC_{50}$ values were derived for each test compound using from 2 to 8 separate experiments per test compound, and the standard error level was less than 10% of the mean value for each compound.

All of the arylalkylamines tested blocked increases in $[Ca^{2+}]_i$ in cerebellar granule cells elicited by NMDA/glycine. Certain arylalkylamines similar in structure to Compound 1 or Compound 2 were nearly as potent as MK-801 ($IC_{50}=34$ nM) which is the most potent compound in the literature known to preferentially block NMDA receptors. Compound 3 had an $IC_{50}=2$ nM, that is, 17-fold more potent than MK-801. Many of the arylalkylamines tested were more potent than competitive antagonists such as APS ($IC_{50}=15$ µM). The inhibitory effects of the arylalkylamines were not overcome by increasing the concentrations of NMDA or glycine. That is, no change was observed in the $EC_{50}$ for either NMDA or glycine. The arylalkylamines are thus noncompetitive antagonists at the NMDA receptor-ionophore complex, and act neither at the glutamate nor the glycine binding sites.

EXAMPLE 2

Activity Against Kainate and AMPA Receptor Function

Measurements of $[Ca^{2+}]_i$ in cerebellar granule cells can also be used to monitor activation of the native kainate or AMPA receptors present in this tissue. Although the increases in $[Ca^{2+}]_i$ evoked by these agonists are of a lesser magnitude than those evoked by NMDA/glycine, such responses are robust and can be used to precisely assess the specificity of action of arylalkylamines on pharmacologically defined glutamate receptor subtypes. Comparative measurements of $[Ca^{2+}]_i$ revealed a clear distinction in the receptor selectivity of the arylalkylamines. Some, like JSTX-3 (Joro Spider toxin from the spider Nephila clavata), were more potent antagonists of responses elicited by kainate (100 µM) or AMPA (30 µM). On the other hand, arylalkylamines within the two structural classes defined by Compound 1 and by Compound 2 were found to inhibit preferentially responses evoked by NMDA (showing about a 100-fold difference in potency). Thus, arylalkylamines such as Compound 1 and Compound 2 are potent and selective inhibitors of NMDA receptor-mediated responses in cerebellar granule cells.

EXAMPLE 3

Patch Clamp Electrophysiology Studies

Patch clamp electrophysiological studies on isolated cortical or hippocampal neurons from adult rat brain have provided additional insight into the mechanism of action of Compound 1, Compound 2 and Compound 3. These studies revealed potent and selective inhibitory effects of arylalkylamines on responses mediated by NMDA receptors. Thus, compounds such as Compound 1 blocked responses to NMDA at nanomolar concentrations without affecting the responses to kainate. These results, which show selective inhibitory effects of the arylalkylamines in cortical and hippocampal neurons, indicate that the arylalkylamines target NMDA receptors in different regions within the mammalian CNS. Moreover, it was found that the inhibitory effects of these compounds were use- and voltage-dependent. This strongly suggests that these compounds are blocking the open channel and, by this action, behave as noncompetitive NMDA receptor antagonists. Importantly, however, the arylalkylamines could be distinguished from both $Mg^{2+}$ and MK-801, especially with respect to the voltage-dependence of their onset of action and reversibility of effect.

EXAMPLE 4

Radioligand Binding Assays

Radioligand binding studies have demonstrated that arylalkylamines such as Compound 1 and Compound 2 have a unique site of action. Although they act like MK-801 in some respects (noncompetitive open-channel blockade, discussed above), they fail to displace [$^3$H]MK-801 binding at concentrations that completely block NMDA receptor-mediated responses. Assays such as these also demonstrate that the arylalkylamines do not bind with high affinity to the known MK-801, $Mg^{2+}$ or polyamine binding sites on the NMDA receptor-ionophore complex. Neither do the arylalkylamines bind directly to either the glutamate, glycine or sigma binding sites at concentrations that block NMDA receptor-mediated responses. [$^3$H] Compound 2 was synthesized as a radioligand for use in binding studies to further explore the mechanism of action of Compound 2 and particularly for use in a high-throughput screen to assess the activity of other analogs and to detect new lead structures. A similar approach was taken for [$^3$H] COMPOUND 5. It is clear that compounds like Compound 1 and Compound 2 target a site on the NMDA receptor-ionophore complex for which no other known compounds presently exist. The novel site of action of the arylalkylamines at the molecular level translates into pronounced therapeutic advantages at the behavioral level. As described below, the arylalkylamines possess a quite different behavioral profile from other noncompetitive antagonists of the NMDA receptor.

EXAMPLE 5

Synaptic Transmission Studies

The above findings demonstrate that certain arylalkylamines, specifically those related in structure to Compound 1 and Compound 2, act through a novel mechanism and site of action to potently and selectively inhibit NMDA receptor-mediated responses on neurons from several different brain areas. To further assess the selective inhibitory actions of the arylalkylamines, their effects on synaptic transmission mediated by NMDA or AMPA receptors were assessed.

Glutamate-mediated transmission at synapses of Schaffer collateral fibers and CAl pyramidal cells was measured in slices of rat brain containing the hippocampus. This assay measures electrophysiologically the postsynaptic depolarization caused by the presynaptic release of glutamate, and can readily distinguish synaptic transmission mediated by NMDA or AMPA receptors. Arylalkylamines like Compound 1, Compound 2 and Compound 3 were again found to exert preferential inhibitory effects on NMDA receptor-mediated responses, and depressed responses mediated by AMPA receptors only at much higher concentrations. For example, Compound 1 had an $IC_{50}$ for the NMDA receptor-mediated response of 20 µM, but an $IC_{50}$ for the AMPA receptor-mediated response of 647 µM. These results show that arylalkylamines can selectively inhibit synaptic transmission mediated by NMDA receptors. Other naturally occurring arylalkylamines present in the venom of Agelenopsis aperta likewise exert potent and selective inhibitory effects on NMDA receptor-mediated responses in the rat hippocampus.

In the aggregate, then, the results of these various studies are complementary and together identify a structurally novel class of compounds with potent and selective inhibitory activity on NMDA receptors in the mammalian CNS. Additionally, these compounds target a unique site on the NMDA receptor-ionophore complex. Compound 1, Compound 2 and Compound 3 were selected for additional study in a variety of in vitro and in vivo assays that model therapeutically important endpoints.

Neuroprotectant Activity

Desired properties of a neuroprotectant drug include the following. (1) The drug can be administered by oral or injectable routes (i.e., it is not significantly broken down in the stomach, intestine or vascular system and thus reaches the tissues to be treated in a therapeutically effective amount). Such drugs are easily tested in rodents to determine their bioavailability. (2) The drug exhibits neuroprotectant activity, (i.e., efficacy) when given after an ischemic insult (stroke, asphyxia) or traumatic injury (head trauma, spinal cord injury). (3) The drug is devoid of or has minimal side effects such as impairment of cognition, disruption of motor performance, sedation or hyperexcitability, neuronal vacuolization, cardiovascular activity, PCP-like abuse potential, or PCP-like psychotomimetic activity.

Although glutamate is the physiological synaptic transmitter, chronic exposure to glutamate leads to neuronal cell death. Much of the neurodegeneration caused by glutamate appears to be mediated by NMDA receptors and results directly from chronically elevated levels of cytosolic $Ca^{2+}$. There is now extensive experimental support for the view that NMDA and AMPA receptors play a major role in mediating the neuronal degeneration following a stroke and other ischemic/hypoxic events (Choi, Glutamate neurotoxicity and diseases of the nervous system. Neuron 1: 623, 1988). Most of this evidence is based on the ability of competitive or noncompetitive antagonists of the NMDA or AMPA receptor to effectively block neuronal cell death in both in vitro and in vivo models of stroke. Compound 1, Compound 2 and Compound 4 were therefore examined for neuroprotectant effects in standard assays designed to detect such activity.

EXAMPLE 6

Cortical Neuron Protection

To assess the in vitro neuroprotectant effect of arylalkylamines, mouse cortical neurons grown in culture were exposed for 5 minutes to NMDA, and cell death after 24 hours was monitored by measuring the release of lactate dehydrogenase (LDH), a cytoplasmic enzyme that is released from dying cells (Choi et al., Glutamate neurotoxicity in cortical cell culture. J. Neurosci. 7: 357, 1987). Exposure to NMDA killed about 80% of the cortical neurons. Compound 1 or Compound 2, included along with NMDA, prevented cell death with $IC_{50}$ values of 70 µM and 30 µM, respectively. The effective concentrations of the arylalkylamines are higher than those of other noncompetitive NMDA receptor antagonists, but similar to those of competitive antagonists. The effective concentrations of NMDA receptor antagonists vary depending on the particular experimental conditions and the type of cell studied 'cortical, hippocampal, striatal). This neuroprotectant effect likely results from the ability of these compounds to block the influx of extracellular $Ca^{2+}$ triggered by the NMDA receptor.

More rigorous testing to determine potential therapeutic efficacy involved in vivo stroke models. In these models, the blood supply is temporarily blocked by clamping the main arteries to the brain. Two in vivo models of this sort were used to determine the ability of Compound 1, Compound 2 and Compound 4 to prevent neuronal cell loss.

EXAMPLE 7

Bilateral Carotid Artery Occlusion

The first assay was the bilateral common carotid artery occlusion model of forebrain ischemia performed in the gerbil (Karpiak et al., Animal models for the study of drugs in ischemic stroke. Ann. Rev. Pharmacol. Toxicol. 29: 403, 1989; Ginsberg and Busto, Rodent models of cerebral ischemia. Stroke 20: 1627, 1989). Blood flow to the brain was interrupted for 7 minutes by clamping the carotid arteries. The test compounds were administered as a single dose given intraperitoneally (i.p.) 30 minutes after reinstating blood flow. During the course of these experiments, the core body temperature of the animals was maintained at 37° C. to prevent any hypothermic reaction. It has been shown that many NMDA receptor antagonists cause hypothermia and this effect can account for much of the protective effect of these compounds. The brains were examined for neuronal cell death 4 days later by silver staining sections of the brain and quantifying death by morphometric analysis. Compound 2 (20 mg/kg) significantly (p<0.05) protected against neuronal cell death in all areas of the brain examined (region CAl of hippocampus, striatum and neocortex). Doses as low as 1 mg/kg afforded complete (>98%) protection of the striatum. The degree of protection is comparable to that achieved with similar doses of the noncompetitive NMDA antagonist, MK-801.

In subsequent experiments, Compound 1 (10 mg/kg) produced a 23% reduction in the amount of neuronal death in region CA1 of the gerbil hippocampus measured at 7 days post-ischemia, while Compound 4 (10 mg/kg) provided 90% protection.

EXAMPLE 8

Middle Cerebral Artery Occlusion

The middle cerebral artery model of stroke performed in the rat (Karpiak et al., Animal models for the study of drugs in ischemic stroke. *Ann. Rev. Pharmacol. Toxicol.* 29: 403, 1989; Ginsberg and Busto, Rodent models of cerebral ischemia. Stroke 20: 1627, 1989) is different from the gerbil model because it results in a more restricted brain infarct, and thereby approximates a different kind of stroke—(focal thrombotic stroke). In the first study using this stroke model, one cerebral artery was permanently occluded by surgical ligation. The test compounds were administered 30 minutes after the occlusion by a single intraperitoneal (i.p.) injection. During the course of these experiments, the core body temperature of the animals was maintained at 37° C. to prevent any hypothermic reaction. Brains were assessed histologically for neuronal cell loss 24 hours later. Infarct volumes were calculated using the area of histological pallor from 10 slides and integrating the distance between each successive section. A single dose (30 mg/kg) of Compound 1 was found to significantly ($p<0.05$) protect against neuronal cell loss equally as well as a maximally effective dose (10 mg/kg) of MK-801 (approximately 15% protection). Preliminary studies with Compound 2 (20 mg/kg) indicated a similar trend.

In the second study of focal cerebral ischemia in the rat, the middle cerebral artery was permanently occluded by passing a small piece of suture thread through the carotid artery to the region of the middle cerebral artery. Core body temperature was maintained at 37° C. Compound 4, 10 mg/kg i.p. administered immediately after the onset of the ischemic event, produced a statistically significant reduction in the volume of the brain infarct (20%) recorded 24 hr later.

In a third model of focal cerebral ischemia in the rat, an ischemic infarct was produced by a photothrombotic method using the dye Rose Bengal. Compound 4, 10 mg/kg i.p. administered 30 min after the ischemic event, produced a 20% reduction in the volume of the infarct, similar to that seen with the noncompetitive NMDA receptor antagonist, MK-801.

In a fourth model of focal cerebral ischemia in the rat, the middle cerebral artery was temporarily occluded by passing a small piece of suture thread through the carotid artery to the region of the middle cerebral artery. The suture thread was withdrawn after an ischemic period of 2 hr. Core body temperature was maintained at 37° C. Compound 4 administered at 10 mg/kg i.p. immediately after the onset of the ischemic event, produced a statistically significant reduction in the volume of the brain infarct (37%) recorded 72 hr later.

Several important features of the lead compounds emerge from these in vivo results. First, and most importantly, Compound 1, Compound 2 and Compound 4 demonstrate neuroprotectant effects in several different in vivo models of stroke. The gerbil assay is a model for transient global cerebral ischemia and hypoxia such as cardiac arrest or perinatal hypoxia. The rat assays are models of permanent and temporary focal cerebral ischemia. The finding that Compound 1 and Compound 4 are neuroprotective in the permanent focal stroke models is surprising because the accessibility of the drug to the site of infarction is limited to the penumbral region which generally is not large. Nonetheless, Compound 1 and Compound 4-significantly ($p<0.05$) limited the extent of damage. Second, the compounds are effective when administered after the ischemic event. This is important because there is believed to be a "window of opportunity" following an infarct during which drugs may effectively halt necrotic damage. How long this time is in humans has not been defined precisely, and will likely vary depending upon the type of infarct. The essential observation, however, is that these compounds can prevent the spread of neuronal cell death once the degenerative process has commenced. Finally, Compounds 1, 2, and 4 are effective when administered parenterally, demonstrating that they penetrate the blood-brain barrier.

Anticonvulsant Activity

Desired properties of an anticonvulsant drug include: the drug can be administered by oral or injectable routes, the drug exhibits effective anticonvulsant activity against several seizure types, including, but not limited to, simple partial seizures, complex partial' seizures, status epilepticus, and trauma-induced seizures such as occur following head injury, including head surgery; and the drug is devoid of or has minimal side effects such as impairment of cognition, disruption of motor performance, sedation or hyperexcitability, neuronal vacuolization, cardiovascular activity, PCP-like abuse potential, or PCP-like psychotomimetic activity.

Glutamate is the major excitatory transmitter in the brain, and thus may play a major role in seizure activity, and contribute to the pathogenesis of epilepsy. Much of the evidence favoring a major role for glutamate receptors in epilepsy derives from pharmacological studies demonstrating that glutamate receptor agonists elicit seizures, and that NMDA and AMPA receptor antagonists are effective anticonvulsants when administered in vivo. There are numerous in vivo models involving different kinds of seizures and behavioral effects that are relevant for clinically distinct forms of epilepsy. It is thus prudent to test for effects in several models, because it may be an oversimplification to suppose that the same mechanism underlies all forms of seizure activity.

EXAMPLE 9

Convulsant Blocking Activity

In initial studies, the ability of arylalkylamines to block seizures induced by kainate, picrotoxin or bicuculline were examined. Each of these convulsants acts through a different mechanism and seizures elicited by kainate are qualitatively different from those elicited by picrotoxin or bicuculline. In these experiments, a fraction of Agelenopsis aperta venom containing several arylalkylamine toxins was administered intravenously (iv) 5 min before picrotoxin or bicuculline, and 5 min after kainate administration. The arylalkylamines diminished the seizures induced by all three of these agents. The effects of picrotoxin or bicuculline were so severe that all 19 control animals died within 25 minutes. In contrast, there were no deaths in the 9 animals pretreated with the arylalkylamines. In fact, only about half the animals treated with the arylalkylamines showed any convulsions at all and those symptoms abated within an hour. These results demonstrate clear anticonvulsant effects of arylalkylamines and prompted further studies using purified arylalkylamines and their analogs.

EXAMPLE 10

Seizure Stimuli

Three different seizure-inducing test paradigms were used initially in this second group of studies and arylalkylamines such as Compound 1 proved to be effective anticonvulsants in two such paradigms. The first two models used DBA/2 mice which are prone to audiogenic seizures. Seizures were elicited by sound (bell tone at 109 dBs) or the intraperitoneal (ip) administration of NMDA (56 mg/kg). The test substances were administered 15–30 min before the convulsant stimulus. The number of clonic seizures was recorded for 1 min following the audiogenic stimulus or for 15 min following the administration of NMDA. Compound 1, Compound 2, and several other arylalkylamines such as Compound 3 and Compound 4 depressed seizures evoked by either stimulus. For example, Compound 2 had an $ED_{50}$ of 0.13 mg/kg s.c. for audiogenic stimulus and 0.083 mg/kg s.c. for NMDA stimulus. Similarly, the $EC_{50}$ for Compound 4 in the audiogenic seizure model (0.08 mg/kg) approached that for MK-801 (0.02 mg/kg). In contrast, neither Compound 1 nor Compound 2 was effective at doses up to 50 mg/kg s.c. in reducing seizures in CF-1 mice elicited by i.p. NMDA.

In a second independent series of experiments, Compound 1 and Compound 4 were found to prevent seizures induced by sound in another genetically susceptible mouse model of reflex epilepsy (Frings mice) following intraperitoneal injection with $IC_{50}$ values of 14.3 mg/kg and –15 mg/kg, respectively. These compounds were considerably more potent against audiogenic seizures in Frings mice following intracerebro-ventricular (i.c.v.) injection, with $IC_{50}$ values of 0.63 µg (Compound 1) and 4.77 µg (Compound 4). Compound 1 was also found to be effective against seizures elicited by maximal electroshock in CF1 mice at a dose of 4 µg i.c.v.

In further studies using the genetically susceptible mouse model of reflex epilepsy (Frings mice), Compound 9, Compound 12 and Compound 14, administered by i.c.v. injection, prevented sound-induced seizures with $IC_{50}$ values of 4.77 µg, 12.2 µg and 13.9 µg, respectively.

These collective findings demonstrate that arylalkylamines such as Compound 1, Compound 2 and Compound 4 are effective in preventing epileptic (audiogenic) and nonepileptic (chemoconvulsant) seizures. This generalized pattern of activity suggests that arylalkylamines are clinically useful in controlling seizure activity. In addition, the potency of Compound 1, Compound 2 and especially Compound 4 in in vivo models of seizure activity shows that these compounds can have the therapeutically relevant effects when administrated parenterally in low doses, and are especially potent when administered directly into the cerebral ventricles.

Analgesic Activity

Desired properties of an analgesic drug include: the drug can be administered by oral or injectable routes, the drug exhibits analgesic activity, the drug is devoid of or has minimal side effects such as impairment of cognition, disruption of motor performance, sedation or hyperexcitability, neuronal vacuolization, cardiovascular activity, PCP-like abuse potential, or PCP-like psychotomimetic activity.

Glutamate and NMDA receptor-mediated responses may play a role in certain kinds of pain perception (Dickenson, A cure for wind up: NMDA receptor antagonists as potential analgesics. *Trends Pharmacol. Sci.* 11: 302, 1990). The possible analgesic effects of Compound 1, Compound 2, Compound 3 and Compound 4 were therefore examined.

EXAMPLE 11

Writing Response Test

In the first series of experiments, the animals were administered an unpleasant stimulus (2-phenyl-1,4-benzoquinone, PBQ) which elicits a writhing response (abdominal stretching). Typically, the number of writhes occurring in a 5 min observation period is recorded. Classic analgesic drugs, such as morphine, are effective at decreasing the number of PBQ-elicited writhes (100% block of the writhing response at 4 mg/kg i.p.). Nonsteroidal anti-inflammatory agents are likewise effective in this model. Compound 1 (2 mg/kg), Compound 2 (2 mg/kg) and Compound 3 (I mg/kg) depressed the writhing response by greater than 95% when administered s.c. or i.p. 30 minutes before PBQ. These results demonstrate that Compound 1, Compound 2 and Compound 3 alleviate visceral pain.

In a similar series of studies, Compound 1 and Compound 4 were found to inhibit acetic acid-induced writhing in mice following i.p. injection with $IC5_0$ values of 10 mg/kg and 1 mg/kg, respectively.

EXAMPLE 12

Hot Plate Test

Compound 1 was tested for analgesic activity in an additional assay. in this model of analgesic activity, mice were administered test substances s.c. 30 min before being placed on a hot plate (50° C.). The time taken to lick the feet or jump off the plate is an index of analgesic activity, and effective analgesics increase the latency to licking or jumping. morphine (5.6 mg/kg) increased the latency to jump by 765%. Compound 1 was likewise effective in this assay and, at doses of 4 and 32 mg/kg, increased the latency to foot licking by 136% and the latency to jumping by 360%, respectively.

It is noteworthy that the analgesic effects of Compound 1 in the hot plate assay were not accompanied by a decreased performance in the inverted grid assay (see below). This shows that the increase in the latency to jump off the hot plate does not simply reflect impaired motor capabilities. Together, these data suggest that Compound 1 possesses significant analgesic activity.

In a later series of experiments, Compound 1 and Compound 4 were demonstrated to possess significant analgesic activity in rats when administered by the intrathecal (i.th.) route. In these experiments, a 52° C. hot plate was used as the nociceptive stimulus. Compound 1 (0.3–3 nmol) and Compound 4 (0.3–3 nmol) produced dose- and time-dependent antinociceptive effects; these arylalkylamines were similar to morphine (0.3–3 nmol) in terms of potency and efficacy. The NMDA receptor antagonist, MK-801, on the other hand, was ineffective in this assay (3–30 nmol).

EXAMPLE 13

Tail Flick Test

In this standard assay, the thermal nociceptive stimulus was 52° C. warm water with the latency to tail flick or withdrawal taken as the endpoint. Compound 1 (0.3–3 nmol) and Compound 4 (0.3–3 nmol) produced a dose- and time-dependent analgesic effect following i.th. administration. These arylalkylamines were similar to morphine (0.3–3 nmol) in terms of potency and efficacy. The NMDA receptor antagonist, MK-801, on the other hand, was ineffective in this assay (3–30 nmol).

EXAMPLE 14

Formalin Test

Male Sprague-Dawley rats were habituated to an observation chamber for at least 1 hr before receiving an injection of dilute formalin (5%) in a volume of 50 μl into the left rear paw. Behavioral responses were monitored immediately after s.c. injection of formalin into the dorsal surface of the paw by counting the number of flinches exhibited by the animal. Behaviors were monitored for at least 50 min after formalin injection and were recorded as early phase responses (O-10 min post-formalin) and late phase responses (20 50 min post-formalin). Compounds were injected intrathecally (i.th.) 10 min prior to formalin (pretreatment) or 10. min after formalin (post-treatment) in a volume of 5 μl.

Intraplantal administration of formalin produced a typical biphasic response of flinching behavior, commonly described as the early and late phase responses. Intrathecal administration of Compound 1 (0.3–10 nmol) or Compound 4 (0.3–10 nmol) given as pretreatment to formalin effectively inhibited both early- and late-phase flinching behaviors. This effect of pretreatment with the arylalkylamines was similar to that seen with pretreatment with morphine (I-10 nmol) or MK-801 (1–30 nmol).

Compound 1 (0.3–10 nmol i.th.) administered after the formalin produced some inhibition of late-phase flinching, though significance was achieved only at the 10 nmol dose. Compound 4 (0.3–10 nmol i.th.) administered after the formalin produced significant inhibition of late-phase flinching, with significance achieved at the 3 and 10 nmol doses. This analgesic profile of activity of the arylalkylamines is similar to that seen with post-formalin administration of morphine (1–10 nmol); post-formalin administration of MK-801 (1–30 nmol), however, failed to affect late-phase flinching.

Taken together, the results obtained with the hot plate, tail flick and formalin assays demonstrate that arylalkylamines such as Compound 1 and Compound 4 have significant analgesic activity in several rodent models of acute pain. The formalin assay additionally demonstrates that arylalkylamines are effective in an animal model of chronic pain. Importantly, the arylalkylamines possess significant analgesic activity when administered after the formalin stimulus. This profile of activity clearly distinguishes the arylalkylamines from standard NMDA receptor antagonists such as MK-801.

Side Effects of Arylalkylamines

Given the important role NMDA receptors play in diverse brain functions, it is not surprising to find that antagonists of this receptor are typically associated with certain unwelcome side effects. In fact, it is this property that provides the major obstacle to developing therapies that target NMDA receptors. The principal side effects, which characterize both competitive and noncompetitive antagonists, are a PCP-like psychotomimetic activity, impairment of motor performance, sedation or hyperexcitability, impairment of cognitive abilities, neuronal vacuolization, or cardiovascular effects (Willetts et al., The behavioral pharmacology of NMDA receptor antagonists. *Trends Pharmacol. Sci.* 11: 423, 1990; Olney et al., Pathological changes induced in cerebrocortical neurons by phencyclidine and related drugs. *Science* 244: 1360, 1989). The psychotomimetic effect associated with inhibition of NMDA receptor-mediated responses is epitomized in the response to phencyclidine (PCP) or "angel dust" which acts at the MK-801 binding site. Impairment of cognitive ability is associated with the important role .that NMDA receptors normally play in learning and memory.

Relatively less is known concerning the side effect profile of AMPA receptor antagonists. However, it is becoming clear that such compounds also elicit motor impairment, ataxia and profound sedation.

The activity of arylalkylamines was examined in animal models that index motor impairment, sedation and-psychotomimetic activity as well as both in vitro and in vivo models of learning and memory.

(a) PCP-Like Psychotomimetic Activity

In rodents, both competitive and noncompetitive antagonists of the NMDA receptor produce a PCP-like stereotypic behavior characterized by hyperactivity, head-weaving, and ataxia (Willetts et al., The behavioral pharmacology of NMDA receptor antagonists. *Trends Pharmacol. Sci.* 11: 423, 1990; Snell and Johnson, In: *Excitatory Amino Acids in Health and Disease*, John Wiley & Sons, p. 261, 1988). We investigated whether the arylalkylamines would elicit such behaviors. In addition, we investigated whether the arylalkylamines would substitute for PCP in rats trained to discriminate PCP from saline (Willetts et al., The behavioral pharmacology of NMDA receptor antagonists. *Trends Pharmacol. Sci.* 11: 423, 1990), and whether the arylalkylamines would elicit a PCP-like neuronal vacuolization (Olney et al., Pathological changes induced in cerebrocortical neurons by phencyclidine and related drugs. Science 244: 1360, 1989).

EXAMPLE 15

Locomotor Activity

The first assay simply monitors locomotor activity during the first hour following peripheral (s.c. or i.p.) administration of test substance. Mice received a dose of Compound 1 15 min before being placed into activity chambers. Activity was quantified by counting the number of breaks in a phototube grid in a 60 min period. In this assay, MK-801 (0.25 mg/kg p.o.) causes a 2- to 3-fold increase in locomotor activity. However, Compound 1, even when tested at 32 mg/kg s.c., did not elicit hyperactivity and, in fact, tended to depress it. This result, using a purified arylalkylamine in mice, complements earlier results obtained in rats where the entire arylalkylamine-containing fraction from Agelenopsis aperta, when injected intravenously, did not elicit a PCP-like behavioral syndrome but seemed to produce a mild sedative effect.

EXAMPLE 16

Motor Impairment

In the first assay for generalized motor impairment, Compound I was examined in the inverted grid assay. In this assay, animals are placed on a wire-holed grid suspended from a rotating metal bar which can be inverted. The animals are then scored for their ability to climb to the top or hang on to the grid. Animals with severe motor impairment fall off the grid. This assay provides an index of "behavioral disruption" that may result from ataxia, loss of the righting reflex, sedation, or muscle relaxation. In these tests, Compound 1, administered at 32 mg/kg s.c., did not lessen the ability of DBA/2 mice to right themselves when the grid was inverted (p>0.05). Compound 2 was likewise without effect (p>0.05) on motor performance in DBA/2 mice when administered at a dose of 20 mg/kg s.c. These doses are considerably higher than those required to prevent sound-induced seizures in DBA/2 mice (see Example 10 above).

The second assay of acute motor impairment was the rotorod assay. In this assay, Frings and CF1 mice were injected with test compound and placed on a knurled rod which rotated at a speed of 6 rpm. The ability of the mice to maintain equilibrium for long periods of time was determined; those mice that were unable to maintain equilibrium on the rotorod for 1 min in each of 3 trials were considered impaired. Compound 1 produced acute motor impairment in Frings mice with a TD, (that dose which produced motor toxicity in 50% of the test animals) of 16.8 mg/kg i.p. This dose is similar to that which prevents sound-induced seizures in Frings mice (see Example 10 above). There is a much clearer separation between effective and toxic doses of Compound 1 in Frings mice, however, when the Compound is administered i.c.v. In this case, no apparent motor toxicity was evident until the dose of Compound 1 exceeded 1.56 μg i.c.v. (>2 times the $ED_{50}$ of 0.63 μg). Finally, motor impairment in @—F1 mice was noted with Compound 1 following i.c.v. administration of 4 μg.

Compound 4, Compound 9, Compound 12 and Compound 14 were administered to Frings mice by i.c.v. injection, and acute motor impairment was measured. The $TD_{50}$ values for Compounds 4, 9, 12 and 14 were 8–16 μg, 14.8 μg, 30.2 μg and 30.8 μg, respectively. These $TD_{50}$ values were 2–3 times higher than the effective $IC_{50}$ values for anticonvulsant potency (see Example 10 above); a clear separation between effective and toxic doses was noted.

EXAMPLE 17

PCP Discrimination

In this assay, rats who have been trained to lever press for food reinforcement must select which of two levers in their cages is correct. The only stimulus they have for selecting the correct lever is their ability to detect whether @hey received a PCP or vehicle injection. After about two months of training, rats become very good at discriminating PCP from vehicle injections and can then be tested with other drugs to determine if they are discriminated as PCP. When tested in this procedure, other drugs which are known to produce a PCP-like intoxication substitute for PCP. These drugs include various PCP analogs such as ketamine and the noncompetitive NMDA receptor antagonist, MK-801.

Compound 1 (1–30 mg/kg i.p.) did not substitute for PCP, and thus was completely devoid of PCP-like discriminative stimulus effects. At 30 mg/kg i.p., only 1 of the 7 animals tested responded at all on either level. It is thus clear that a behaviorally effective dosage range of Compound 1 was evaluated. As the ability of test compounds to produce PCP-like effects in rats is believed to be predictive of their ability to produce PCP-like psychotomimetic activity and abuse liability in humans, these results strongly suggest that the arylalkylamines such as Compound 1 will lack such deleterious side effects in man.

EXAMPLE 18

The administration of compounds such as PCP and MK-801 to rats produces a neurotoxic effect termed neuronal vacuolization. Following a single dose of such compounds, vacuoles are found in particular central neurons, especially those in the cingulate cortex and retrosplenial cortex. No such vacuolization was present in rats treated with Compound I at the single high dose of 100 mg/kg i.p.

Taken together, the results on locomotor activity, motor impairment, PCP discrimination and neuronal vacuolization strongly suggest that arylalkylamines will be devoid of PCP-like side effects in man.

(b) Cognitive Impairment

One of the major reasons for postulating a role of NMDA receptors in memory and learning derives from cellular studies on long-term potentiation (LTP) in the rat hippocampus. LTP is a long-lasting increase in the magnitude of synaptic responses produced by brief yet intense synaptic stimulation. Since the discovery of this phenomenon, it has become the preeminent cellular model of learning in the vertebrate brain (Teyler and Discenna, Long-term potentiation. *Annu. Rev. Neurosci.* 10:131, 1987). Transmission at synapses formed by Schaffer collaterals onto CA1 pyramidal cells is mediated by NMDA and AMPA receptors. Following a brief tetanizing stimulus, the magnitude of the population spike (a measure of synaptic transmission) is greatly increased and remains so for hours. It has been shown that all known competitive and noncompetitive antagonists of NMDA receptors block LTP in the rat hippocampus, whereas antagonists of non-NMDA receptors are without effect (Collingridge and Davis, In: *The NMDA Receptor,* IRL Press. p. 123, 1989). This supports a role of NMDA receptors in memory and learning.

EXAMPLE 19

LTP Assay

The effects of selected arylalkylamines and literature standards were examined for effects on LTP in slices of rat hippocampus. As anticipated, all the conventional competitive (AP5 and AP7) and noncompetitive (MK-801 and ifenprodil) NMDA receptor antagonists inhibited the induction of LTP in the hippocampus. Slices of rat hippocampus were superfused for 30–60 min with a test compound before delivering a tetanizing stimulus consisting of 3 trains, separated by 500 msec, of 100 Hz for 1 sec each. The response amplitude was monitored for an additional 15 minutes post-tetanus. The tetanizing stimulus caused a mean 95% increase in the amplitude of the synaptic response. The induction of LTP was significantly blocked (p<0.05) by competitive (AP5, AP7) or noncompetitive (MK-801, ifenprodil) NMDA receptor antagonists. Quite surprisingly, none of the arylalkylamines tested (Compound 1, Compound 2, Compound 3 and others) blocked the induction of LTP (p>0.05), even when used at high concentrations (100–300 μM) that caused some inhibition of the control response.

These results highlight yet another unique and important feature of arylalkylamines. Arylalkylamines are the first, and at present the only, class of compounds shown to be selective and potent antagonists of the NMDA receptor that do not block the induction of LTP. This likely reflects the novel mechanism and site of action of arylalkylamines and suggests that drugs which target the novel site on the NMDA receptor will similarly lack effects on LTP As LTP is the primary cellular model for learning and memory in the mammalian CNS, it additionally suggests that such drugs will lack deleterious effects on cognitive performance.

EXAMPLE 20

Learning Tests

Preliminary experiments using one of the more potent synthetic arylalkylamine analogs, Compound 3, in an in vivo learning paradigm demonstrate that these drugs lack effects on cognitive performance. In this test, rats were trained to alternate turning in a T maze for a food reward. MK-801 was included for comparison. Test compounds were administered i.p. 15 min before testing. Control animals made the correct choice about 80% of the time. Increasing doses of MK-801 progressively decreased the number of correct choices and this decrement in behavior was accompanied by hyperactivity. In contrast, Compound 3 did not impair the ability of the animals to make the correct choices ($p > 0.05$). At the highest doses tested, Compound 3 caused some decrease in locomotor activity, exactly the opposite effect observed with MK-801.

Although MK-801 decreased learning performance in parallel with increases in locomotor activity, other studies using different paradigms in rodents and primates have shown a clear dissociation between the effects on learning and locomotion. Thus, both competitive and noncompetitive NMDA receptor antagonists impair learning at doses which do not cause any overt change in motor behavior. This demonstrates that conventional NMDA receptor antagonists impair learning independently of other side effects. The results of the T-maze assay demonstrate that Compound 3, and other arylalkylamines, do not impair learning even at doses that cause some decrease in locomotor activity.

One additional observation emerged from these learning tests. The animals, first response on the second day of testing was random and was therefore not dependent on the last response of the previous day's testing. Control animals thus correctly made the first choice about 50% of the time. MK-801 has no effect on this first choice. However, animals administered Compound 3 on the previous day made the first choice correctly considerably more often. Unlike control animals then, the animals treated with Compound 3 behaved as if they remembered the last choice of the previous day.

In a second series of experiments, the effect of Compound 4 on learning in the Morris water maze task was evaluated. In this test, a hidden platform was placed in a fixed location in a circular steel tank, and submerged 2 cm below the surface of the water. Each rat was given 3 trials per day with a 10 min intertrial interval for 5 days. A trial was initiated by placing the rat in the water, nose facing the wall of the tank, at one of three predetermined starting locations. The order of the start location was varied daily. Learning was measured as a decrease in time required to swim to the platform. If an animal failed to locate the platform within 60 sec after the start of the trial, the rat was hand-guided to it. The animals remained on the platform for 10 sec before being removed from the tank. Ten min after the last training trial on day 5, the animals received a probe test. The platform was removed for this 1 trial task and the animals were allowed to swim for 60 sec to assess the spatial bias for the platform location. Two measures were recorded from this task: latency to first crossing the area where the platform had been, and total number of crossings. A total of 5 injections of Compound 4 were given to each rat. In the first series of experiments, Compound 4 was administered at 10 mg/kg i.p. daily for 5 days. This treatment regimen impaired learning; however, these animals experienced significant weight loss and unusual behavioral signs ("shivering," motor impairment, difficulty in swimming) with repeated dosing of Compound 4. In a subsequent study, six animals received 1 mg/kg i.p. for the first 4 days of training, while two animals received 5 mg/kg i.p. during this period. on the last day of training, both groups received 10 mg/kg. Neither the 1 mg/kg nor the 5 mg/kg animals showed any impairment in learning the location of the hidden platform, nor did the final 10 mg/kg dose produce any impairment in the ability of the animal to perform the already learned task.

The results of these learning tasks are encouraging. They suggest that arylalkylamines lack the learning and memory deficits that typify other NMDA receptor antagonists. In fact, there is a suggestion that the arylalkylamines may even be nootropic (memory enhancers).

(c) Cardiovascular Effects

In vivo studies with certain arylalkylamines revealed a hypotensive effect of these compounds, especially at high doses. On the basis of these results, a systematic study of the effects of arylalkylamines on cardiovascular function was performed.

EXAMPLE 21

$Ca^{2+}$ Channel Inhibition

We have discovered that some of the arylalkylamines are quite potent inhibitors of voltage-sensitive $Ca^{2+}$, channels, specifically those sensitive to inhibition by dihydropyridines (L-type channels). Such effects on vascular smooth muscle would be expected to dilate blood vessels and cause a drop in blood pressure, thus producing hypotension.

The ability of arylalkylamines to inhibit dihydropyridine-sensitive $Ca^{2+}$ channels was examined in cerebellar granule cells and a rat aortic smooth muscle cell line, $A_7r5$ cells. In cerebellar granule cells, Compound 2 inhibited depolarization-induced increases in $[Ca^{2+}]_I$ at concentrations 100-fold higher than those required to block responses to NMDA ($IC_{50}$ values of 24 µM and 161 nM, respectively). Overall, we have observed a wide range of potencies against voltage-sensitive $Ca^{2+}$ channels that does not correlate with potency against NMDA receptors. This strongly suggests that further structure-activity work based on chemical modification of the arylalkylamine molecule will lead to the development of compounds that are very potent NMDA antagonists with low potency against voltage-sensitive $Ca^{2+}$ channels. Indeed, Compound 1 (with an $IC_{50}$ of 102 nM against NMDA receptor-mediated responses in cerebellar granule cells) is a relatively poor inhibitor of voltage-sensitive $Ca^{2+}$ channels in cerebellar granule cells ($IC_{50=257}$ µM) and is virtually without effect on voltage-sensitive $Ca^{2+}$ influx in $A_7r5$ cells ($IC_{50}=808$ µM).

Arylalkylamines are not, however, indiscriminate blockers of voltage-sensitive $Ca^{2+}$ channels. They do not, for example, affect voltage-sensitive $Ca^{2+}$ channels in cerebellar Purkinje cells (P-type channels) or those channels thought to be involved in neurotransmitter release (N-channels). The arylalkylamines that do block voltage-sensitive $Ca^{2+}$ channels appear to target specifically L-type $Ca^{2+}$ channels. Moreover, as mentioned above, there is a high degree of structural specificity in this effect. For example, one arylalkylamine is 57 times more potent than another arylalkylamine in blocking $Ca^{2+}$ influx through L-type channels, where the only structural difference between the compounds is the presence or absence of a hydroxyl group.

EXAMPLE 22

In Vivo Cardiovascular Studies

The arylalkylamines Compound 1 and Compound 2 produce moderate drops (20–40 mm Hg) in mean arterial blood pressure (MABP) in anesthetized rats at doses which are effective in the in vivo stroke models (10–30 mg/kg s.c.). The hypotensive effect of Compound 4 has been evaluated in greater detail. Compound 4 elicited a marked drop (40 mm Hg) in mean arterial pressure which persisted for approximately 90–120 min when administered at the dose of 10 mg/kg i.p.; it was in this same group of rats that Compound 4 afforded significant neuroprotection in the suture model of middle cerebral artery occlusion (see Example 8 above). Similar results were obtained in the rat study in which Compound 4 demonstrated neuroprotectant activity in the Rose Bengal photothrombotic model of focal ischemic stroke (see Example 8 above). Further studies using the pithed rat preparation strongly suggest that the hypotensive activity of Compound 4 is a peripherally mediated effect. The hypotension and bradycardia produced by Compound 4 was maintained in rats pretreated with atropine, suggesting that these effects are not mediated by a cholinergic mechanism. Similarly, Compound 4 elicited hypotension and bradycardia in chemically sympathectomized rats (pretreated with a ganglionic blocker), suggesting that these effects are not mediated via the sympathetic nervous system.

On the basis of these findings, it is anticipated that chemical efforts will minimize the cardiovascular side effects by (1) enhancing the uptake of arylalkylamine into the brain such that lower doses are required for neuroprotection, and (2) increasing the selectivity (potency ratio) of arylalkylamines for receptor-operated $Ca^{2+}$ channels over voltage-sensitive $Ca^{2+}$ channels.

EXAMPLE 23

Biological Activity of Compound 19 and Analogs

Compounds 19–215 had high potencies against NMDA-induced increases in $[Ca^{2+}]_I$ rat cerebellar granule cells grown in culture (Table 1). The inhibitory effect of Compound 19 on responses to NMDA was noncompetitive. Compounds 19–215 inhibited [$^3$H]MK-801 binding in membranes prepared from rat hippocampal and cortical tissue (Table 1).

Compound 19 possessed the following additional biological activities: significant ($p<0.05$ compared to control) anticonvulsant activity against maximal electroshock-induced seizures in mice following i.p. administration ($ED_{50}=26.4$ mg/kg and $TD_{50}$ (rotorod)=43.8 mg/kg); significant anticonvulsant activity against maximal electroshock-induced seizures in mice following oral (p.o.) administration ($ED_{50}=35$ mg/kg), but with motor impairment at 30 mg/kg; significant analgesic activity in the hot-plate and PBQ-induced writhing assays at 16 mg/kg i.p.; no PCP-like stereotypic behavior (hyperexcitability and head weaving) at 30 mg/kg i.p. in rats; no generalization to PCP in the PCP discrimination assay in rats at doses up to the behaviorally active dose of 30 mg/kg i.p. Compound 19 was significantly less potent in antagonizing increases in $[Ca^{2+}]_I$ elicited by depolarizing concentrations of KC1 in rat cerebellar granule cells ($IC_{50}=10.2$ μM), and was without effect on blood pressure when administered s.c. in rats at doses up to 100 mg/kg. Compound 19, however, did block the induction of LTP in rat hippocampal slices when tested at 100 μM.

Compound 20 possessed the following additional biological activities: significant anticonvulsant activity against maximal electroshock-induced seizures in mice following i.p. administration (ED50=20.1 mg/kg and $TD_{50}$ (rotorod)=20.6 mg/kg); no significant anticonvulsant activity against maximal electroshock-induced seizures in mice following oral (p.o.) administration at doses up to 30 mg/kg, but with motor impairment at 30 mg/kg; significant anticonvulsant activity against sound-induced seizures in a genetically susceptible mouse model of reflex epilepsy (Frings mice) following i.p. ($ED_{50}=2.1$ mg/kg and $TD_{50}=19.9$ mg/kg) and oral ($ED_{50}=9.7$ mg/kg and $TD_{50}=21.8$ mg/kg) administration; significant anticonvulsant activity against maximal electroshock-induced seizures in rats following oral administration with an $ED_{50}$ value of 33.64 mg/kg and an $TD_{50}$ value of 55.87 mg/kg; an increase in seizure threshold as indexed by the i.v. Metrazol test in mice at the dose of 10 mg/kg i.p.; significant neuroprotectant activity in a rat model of temporary focal ischemia (a 51% reduction in the infarct volume following the administration of two doses of 1 mg/kg i.p., the first given immediately after middle cerebral artery occlusion and the second given 6 hr later; a 43% reduction in the infarct volume following the administration of two doses of 1 mg/kg i.p., the first given 2 hr after middle cerebral artery occlusion (i.e., at the time of reperfusion) and the second given 6 hr later); significant neuroprotectant activity (a 24% reduction in the infarct volume) in a rat model of permanent focal ischemia following the administration of 1 mg/kg i.p. at 30 min and again 4 hr post-occlusion; significant neuroprotectant activity (a 50% reduction in the infarct volume) in a rat photothrombotic model of focal ischemia following tie administration of 10 mg/kg i.p. at 15 min, 3 hr, and again 6 hr post-occlusion; no significant analgesic activity at the dose of 25 mg/kg i.p. in the rat 52° C. hot plate test or the rat 48° C. tail flick test; significant analgesic activity, not blocked by the opiate receptor antagonist naloxone, in the rat formalin test at the dose of 10 mg/kg i.p.; significant analgesic activity, not blocked by naloxone, against acetic acid-induced abdominal writhing in mice at the dose of 10 mg/kg i.p.; no generalization to PCP in the PCP discrimination assay in rats at doses up to the behaviorally active dose of 10 mg/kg i.p.; no neuronal vacuolization in rats when administered at doses of 10 and 30 mg/kg i.p.; no significant cardiovascular activity in anesthetized rats at doses up to 15 μmoles/kg i.v. or 10 mg/kg i.p.; no significant cardiovascular activity in conscious beagle dogs at doses of 0.3 or 1 mg/kg i.v. (60 sec bolus injection); transient increases in mean arterial pressure and heart rate in conscious beagle dogs at the dose of 3 mg/kg i.v., with larger magnitude and longer duration effects seen at the dose of 10 mg/kg i.v. (60 sec bolus injection); increased motor activity, agitation and anxiousness, slight tremors, licking of the mouth, whining, and urination in conscious beagle dogs at the dose of 3 mg/kg i.v. (60 sec bolus injection); dilated pupils, whole body tremors, incoordination, licking of the mouth, salivation, panting, rapid blinking of the eyes, whining, anxiousness, seizures, and death in conscious beagle dogs at the dose of 10 mg/kg i.v. sec bolus injection); no behavioral effects in conscious male NMRI mice at the doses of 2 and 4 mg/kg i.p.; excitation and increased reactivity to touch in conscious male NMRI mice at the dose of 8 mg/kg i.p.; excitation, Straub tail, tremor, stereotypies, hypothermia, and mydriasis in conscious male NMRI mice at the doses of 16 and 32 mg/kg i.p.; convulsions and death in conscious male NMRI mice at the dose of 64 mg/kg i.p.; convulsions and death in conscious male NMRI mice at the doses of 128 and 256 mg/kg i.p.; no behavioral effects in conscious male Wistar rats at the dose of 2 mg/kg i.v.; excitation, stereotypies, increased reactivity to touch, increased muscle tone, and tremor in conscious male wistar rats at doses ranging from 4 to 16 mg/kg i.v.; Straub tail, convulsions, and death in conscious male wistar rats at the dose of 32 mg/kg i.v.

Compound 21 possessed the following additional biological activities: significant anticonvulsant activity against sound-induced seizures in a genetically susceptible mouse model of reflex epilepsy (Frings mice) following i.p. administration ($ED_{50}$=3.41 mg/kg and $TD_{50}$ (motor impairment)= 15.3 mg/kg).

Compound 33 (an enantiomer of Compound 21) possessed the following additional biological activities:significant anticonvulsant activity against sound-induced seizures in a genetically susceptible mouse model of reflex epilepsy (Frings mice) following i.p. administration ($ED_{50}$=4.6 mg/kg and $TD_{50}$ (motor impairment)=27.8 mg/kg); significant anticonvulsant activity against maximal electroshock-induced seizures in rats following oral administration at the dose of 25 mg/kg, with no motor toxicity apparent at this dose; significant neuroprotectant activity in a rat model of focal ischemic stroke following i.p. administration of 2 mg/kg 30 min prior to vessel occlusion and 2 mg/kg 3 hr post-occlusion; no significant analgesic activity at the dose of 25 mg/kg i.p. in the rat 52° C. hot plate test or the rat 48° C. tail flick test; significant analgesic activity in a rat model of chronic neuropathic pain following i.th. administration of doses ranging from 15 to 80 µg; significant analgesic activity in a rat model of chronic neuropathic pain following i.p. administration of doses of 3–10 mg/kg; no neuronal vacuolization when administered to rats at the dose of 30 mg/kg i.p.; no significant cardiovascular activity in anesthetized rats at doses up to 3 mg/kg i.v.; no significant cardiovascular activity in conscious beagle dogs at the dose of 0.3 mg/kg i.v. (60 sec bolus injection); transient increases in mean arterial pressure in conscious beagle dogs at the dose of 1 mg/kg i.v., with larger magnitude and longer duration effects seen at the doses of 3 and 10 mg/kg i.v. (60 sec bolus injection); a transient increase in heart rate in conscious beagle dogs at the dose of 10 mg/kg i.v. (60 sec bolus injection); licking of the mouth in conscious beagle dogs at the dose of 3 mg/kg i.v. (60 sec bolus injection); dilated pupils, whole body tremors, incoordination, licking of the mouth, salivation, and panting in conscious beagle dogs at the dose of 10 mg/kg i.v. (60 sec bolus injection); no significant drug-induced changes in the ECG in conscious beagle dogs at doses up to 10 mg/kg i.v. (60 sec bolus injection); no behavioral effects in conscious male NMRI mice at the doses of 2 and 4 mg/kg i.p.; excitation, increased reactivity to touch, and hypothermia in conscious male NMRI mice at the dose of 8 mg/kg i.p.; excitation, Straub tail, tremor, jumping, stereotypies, hypothermia, and mydriasis in conscious male NMRI mice at the doses of 16 and 32 mg/kg i.p.; convulsions in conscious male NMRI mice at the dose of 64 mg/kg i.p.; convulsions and death in conscious male NMRI mice at the doses of 128 and 256 mg/kg i.p.

Compound 34 (an enantiomer of Compound 21) possessed the following additional biological activities: significant anticonvulsant activity against sound-induced seizures in a genetically susceptible mouse model of reflex epilepsy (Frings mice) following i.p. administration ($ED_{50}$=22 mg/kg and $TD_{50}$ (motor impairment) between 10 and 15 mg/kg); hyperthermia in conscious male NMRI mice at the dose of 2 mg/kg i.p.; no behavioral effects in conscious male NMRI mice at the dose of 4 mg/kg i.p.; excitation, increased reactivity to touch, and hypothermia in conscious male NMRI mice at the dose of 8 mg/kg i.p.; excitation, Straub tail, tremor, jumping, stereotypies, hypothermia, and mydriasis in conscious male NMRI mice at the doses of 16 and 32 mg/kg i.p.; convulsions in conscious male NMRI mice at the dose of 64 mg/kg i.p.; convulsions and death in conscious male NMRI mice at the doses of 128 and 256 mg/kg i.p.

Compound 22 possessed the following additional biological activities: significant anticonvulsant activity against sound-induced seizures in a genetically susceptible mouse model of reflex epilepsy (Frings mice) following i.p. ($ED_{50}$=4.9 mg/kg and $TD_{50}$, (inverted grid)=26.8 mg/kg) and oral ($ED_{50}$=5.1 mg/kg and $LD_{50}$–18.3 mg/kg) administration; and no significant cardiovascular activity in anesthetized rats at doses up to 15 µmoles/kg (4.47 mg/kg) i.v.

Compound 50 (an enantiomer of Compound 22) possessed the following additional biological activities: significant anticonvulsant activity against sound-induced seizures in a genetically susceptible mouse model of reflex epilepsy (Frings mice) following i.p. administration ($ED_{50}$=2.7 mg/kg and $TD_{50}$ (motor impairment)=17.4 mg/kg); significant anticonvulsant activity against sound-induced seizures in a genetically susceptible mouse model of reflex epilepsy (Frings mice) following p.o. administration ($ED_{50}$=9.0 mg/kg and $TD_{50}$ (motor impairment)=18.9 mg/kg); significant anticonvulsant activity against maximal electroshock-induced seizures in rats following oral administration with $ED_{50}$=28 mg/kg and $TD_{50}$=20 mg/kg; significant neuroprotectant activity in a rat model of focal ischemic stroke following i.p. administration of 2 mg/kg 30 min prior to vessel occlusion and 2 mg/kg 3 hr post-occlusion; no significant analgesic activity at the dose of 25 mg/kg i.p. in the rat 52° C. hot plate test or the rat 48° C. tail flick test; and no significant cardiovascular activity in anesthetized rats at doses up to 5 mg/kg i.v.

Compound 51 (an enantiomer of Compound 22) possessed the following additional biological activities: significant anticonvulsant activity against sound-induced seizures in a genetically susceptible mouse model of reflex epilepsy (Frings mice) i.p. administration ($ED_{50}$=9.1 mg/kg and $TD_{50}$, (motor impairment)=13.6 mg/kg).

Compound 24 possessed the following additional biological activities: significant anticonvulsant activity against sound-induced seizures in a genetically susceptible mouse model of reflex epilepsy (Frings mice) following i.p. administration ($ED_{50}$=5 mg/kg and $TD_{50}$ (motor impairment)=16 mg/kg); significant anticonvulsant activity against maximal electroshock-induced seizures in rats following oral administration with $ED_{50}$=46 mg/kg and $TD_{50}$=51 mg/kg; no significant neuroprotectant activity in a rat model of focal ischemic stroke following i.p. administration of 2 mg/kg 30 min prior to vessel occlusion and 2 mg/kg 3 hr post-occlusion; and no significant cardiovascular activity in anesthetized rats at doses up to 10 mg/kg i.v.

Compound 25 possessed the following additional biological activities: significant anticonvulsant activity against maximal electroshock-induced seizures in mice following i.p. administration with an $ED_{50}$=mg/kg and a $TD_{50}$=32.18 mg/kg; significant anticonvulsant activity against maximal electroshock-induced seizures in rats following oral administration with an ED50=46.43 mg/kg and a TD., between 163 and 326 mg/kg.

Compound 31 possessed the following additional biological activities: significant anticonvulsant activity against sound-induced seizures in a genetically susceptible mouse model of reflex epilepsy (Frings mice) following i.p. administration ($ED_{50}$=6 mg/kg and $TD_{50}$ (motor impairment) between 10 and 20 mg/kg).

Compound 46 possessed the following additional biological activities: significant anticonvulsant activity against sound-induced seizures in a genetically susceptible mouse model of reflex epilepsy (Frings mice) following i.p. administration ($ED_{50}$=25 mg/kg and $TD_{50}$ (motor impairment) between 18 and 21 mg/kg); and no significant neuroprotectant activity in a rat model of focal ischemic stroke following i.p. administration of 2 mg/kg 30 min prior to vessel occlusion and 2 mg/kg 3 hr post-occlusion.

Compound 57 possessed the following additional biological activities: significant anticonvulsant activity against sound-induced seizures in a genetically susceptible mouse model of reflex epilepsy (Frings mice) following i.p. administration ($ED_{50}$=1 mg/kg and $TD_{50}$ (motor impairment) between 6 and 8 mg/kg).

Compound 58 possessed the following additional biological activities: significant anticonvulsant activity against sound-induced seizures in a genetically susceptible mouse model of reflex epilepsy (Frings mice) following i.p. administration ($ED_{50}$=0.9 mg/kg and $TD_{50}$ (motor impairment)= 14.5 mg/kg); no significant neuroprotectant activity in a rat model of focal ischemic stroke following i.p. administration of 2 mg/kg 30 min prior to vessel occlusion and 2 mg/kg 3 hr post-occlusion; and no significant cardiovascular activity in anesthetized rats at doses up to 2 mg/kg i.v.

Compound 59 possessed the following additional biological activities: significant anticonvulsant activity against sound-induced seizures in a genetically susceptible mouse model of reflex epilepsy (Frings mice) following i.p. administration ($ED_{50}$=2.7 mg/kg and $TD_{50}$ (motor impairment)= 7.8 mg/kg); a reduction in seizure threshold as indexed by the i.v. Metrazol test in mice at the dose of 11.7 mg/kg i.p.; no significant neuroprotectant activity in a rat model of focal ischemic stroke following i.p. administration of 2 mg/kg 30 min prior to vessel occlusion and 2 mg/kg 3 hr post-occlusion; and no significant cardiovascular activity in anesthetized rats at doses up to 10 mg/kg i.v.

Compound 60 possessed the following additional biological activities: significant anticonvulsant activity against sound-induced seizures in a genetically susceptible mouse model of reflex epilepsy (Frings mice) following i.p. administration ($ED_{50}$=4.4 mg/kg and $TD_{50}$ (motor impairment)= 9.2 mg/kg); significant anticonvulsant activity against sound-induced seizures in a genetically susceptible mouse model of reflex epilepsy (Frings mice) following oral administration ($ED_{50}$=10 mg/kg and $TD_{50}$ (motor impairment)= 25.6 mg/kg); significant anticonvulsant activity against maximal electroshock-induced seizures in mice following i.p. administration ($ED_{50}$=8.17 mg/kg and $TD_{50}$ (rotorod)= 17.30 mg/kg); no effect on seizure threshold as indexed by the i.v. Metrazol test in mice at the doses of 1 and 4 mg/kg i.p.; a reduction in seizure threshold as indexed by the i.v. Metrazol test in mice at the doses of 8 and 17 mg/kg i.p.; significant neuroprotectant activity in a rat model of temporary focal ischemic stroke following i.p. administration of 2 mg/kg 30 min prior to vessel occlusion and 2 mg/kg 3 hr post-occlusion; significant neuroprotectant activity in a rat model of temporary focal ischemic stroke following i.p. or i.v. administration of 1 mg/kg 2 hr and again 8 hr post-occlusion; significant neuroprotectant activity in a rat model of temporary focal ischemic stroke following i.v. administration of 1 mg/kg 2 hr post-occlusion; no significant neuroprotectant activity in a rat photothrombotic model of focal ischemia following the administration of 10 mg/kg i.p. at 15 min, 3 hr, and again 6 hr post-occlusion; no neuronal vacuolization when administered at doses of 20 mg/kg i.p. or 10 mg/kg i.v.; no significant cardiovascular activity in conscious beagle dogs at the dose of 0.3 mg/kg i.v. (60 sec bolus injection); transient increases in mean arterial pressure in conscious beagle dogs at the doses of 1 and 3 mg/kg i.v., with larger magnitude and longer duration effects seen at the dose of 10 mg/kg i.v. (60 sec bolus injection); transient increases in heart rate in conscious beagle dogs at the doses of 3 and 10 mg/kg i.v. (60 sec bolus injection), no significant changes in the ECG in conscious beagle dogs at doses ranging from 0.3 to 10 mg/kg i.v. (60 sec bolus injection); no significant behavioral effects in conscious beagle dogs at the doses of 0.3 and 1 mg/kg i.v. (60 sec bolus injection); a slight increase in respiratory rate in conscious beagle dogs at the dose of 0.3 mg/kg i.v. (60 sec bolus injection); dilated pupils, whole body tremors, salivation, and urination in conscious beagle dogs at the dose of 10 mg/kg i.v. (60 sec bolus injection); no significant behavioral effects in conscious male Wistar rats at doses up to 4 mg/kg i.v.; excitation, stereotypies, increased reactivity to touch, increased muscle tone, and tremor in conscious male Wistar rats at the dose of 8 mg/kg i.v.; Straub tail, convulsions, and death in Unconscious male Wistar rats at the dose of 16 mg/kg i.v.

Compound 119 possessed the following additional biological activities: significant anticonvulsant activity against sound-induced seizures in a genetically susceptible mouse model of reflex epilepsy (Frings mice) following i.p. administration with an $ED_{50}$=7.0 mg/kg and $TD_{50}$ (motor impairment)=26.3 mg/kg.

Compound 120 possessed the following additional biological activities: significant anticonvulsant activity against sound-induced seizures in a genetically susceptible mouse model of reflex epilepsy (Frings mice) following i.p. administration with an $ED_{50}$=4.77 mg/kg and $TD_{50}$ (motor impairment) between 20 and 30 mg/kg.

Compound 122 possessed the following additional biological activities: significant anticonvulsant activity against sound-induced seizures in a genetically susceptible mouse model of reflect epilepsy (Frings mice) following i.p. administration with an $ED_{50}$=4.7 mg/kg and $TD_{50}$ (motor impairment)=15.3 mg/kg.

Compound 138 possessed the following additional biological activities: significant anticonvulsant activity against maximal electroshock-induced seizures in mice following i.p. administration with an $ED_{50}$=51.9 mg/kg and $TD_{50}$ (motor impairment)=100.7 mg/kg.

Compound 151 possessed the following additional biological activities: significant anticonvulsant activity against maximal electroshock-induced seizures in mice following i.p. administration with an $ED_{50}$=36.5 mg/kg and $TD_{50}$ (motor impairment)=108.4 mg/kg; a significant increase in seizure threshold as indexed by the i.v. Metrazol test in mice at the doses of 36.5 and 108 mg/kg i.p.

Compound 156 possessed the following additional biological activates: significant anticonvulsant activity against sound-induced seizures in a genetically susceptible mouse model of reflex epilepsy (Frings mice) following i.p. administration with an $ED_{50}$=5.0 mg/kg and $TD_{50}$ (motor impairment)=17.4 mg/kg.

Taken together, the results obtained with these simplified synthetic arylalkylamines suggest that such simplified molecules do not interact specifically with the arylalkylamine binding site on receptor-operated $Ca^{2+}$ channels as do Compounds 1, 2 and 3. Specifically, Compounds 19–215 bind to the site labeled by [$^3$H]MK-801 at concentrations ranging approximately 1 to 400-fold higher than those which antagonize the function of the NMDA receptor-ionophore complex. The fact that Compounds 19–215 at therapeutic doses do not generally produce PCP-like stereotypic behavior, substitute for PCP in drug discrimination assays, or elicit neuronal vacuolization suggests, however, that such compounds might be useful either as lead compounds or drug candidates for neurological disorders and diseases. It has been reported that compounds which bind with low affinity (relative to MK-801) to the site labeled by [$^3$H]MK-801 might possess therapeutic utility and possess a more favorable side effect profile than that possessed by a high affinity antagonist such as MK-801 itself (Rogawski, Therapeutic potential of excitatory amino acid antagonists: channel blockers and 2,3-benzo-diazepines. *Trends Pharmacol. Sci.* 14: 325, 1993). The low affinity of certain compounds within the group of Compounds 19–215 (relative to MK-801) for the site labeled by [$^3$H]MK-801 may place these compounds into this general class of low affinity noncompetitive antagonists.

Identification of a Novel Modulatory Site on Receptor-Operated Calcium Channels

Having identified arylalkylamines which have. therapeutically useful properties as defined above, compounds can now be identified which act at the critical arylalkylamine binding site on receptor-operated $Ca^{2+}$ channels, such as those present within NMDA, AMPA and nicotinic cholinergic receptor-ionophore complexes.

Examples of suitable tests now follow:

EXAMPLE 24

Radioligand Binding in Rat Cortex or Cerebellum.

The following assay can be utilized as a high throughput assay to screen product libraries (e.g., natural product libraries and compound files at major pharmaceutical companies) to identify new classes of compounds with activity at this unique arylalkylamine site. These new classes of compounds are then utilized as chemical lead structures for a drug development program targeting the arylalkylamine binding site on receptor-operated $Ca^{2+}$ channels. The compounds identified by this assay offer a novel therapeutic approach to treatment of neurological disorders or diseases. Examples of such compounds include those provided in the generic chemical formulae above. Routine experiments can be performed to identify those compounds having the desired activities.

Rat brain membranes are prepared according to the method of Williams et al. (Effects of polyamines on the binding of [$^3$H]MK-801 to the NMDA receptor: Pharmacological evidence for the existence of a polyamine recognition site. *Molec. Pharmacol.* 36: 575, 1989) with the following alterations: Male Sprague-Dawley rats (Harlan Laboratories) weighing 100–200 g are sacrificed by decapitation. The cortex or cerebellum from 20 rats are cleaned and dissected. The resulting brain tissue is homogenized at 4° C. with a polytron homogenizer at the lowest setting in 300 ml 0.32 M sucrose containing 5 µM K-EDTA (pH 7.0). The homogenate is centrifuged for 10 min at 1,000 ×g and the supernatant removed and centrifuged at 30,000 ×g for 30 minutes. The resulting pellet is resuspended in 250 ml 5 µM K-EDTA (pH 7.0) stirred on ice for 15 min, and then centrifuged at 30,000 ×g for 30 minutes. The pellet is resuspended in 300 ml 5 µM K-EDTA (pH 7.0) and incubated at 32° C. for 30 min. The suspension is then centrifuged at 100,000 ×g for 30 min. Membranes are washed by resuspension in 500 ml 5 µM K-EDTA (pH 7.0), incubated at 32° C. for 30 min, and centrifuged at 100,000 ×g for 30 minutes. The wash procedure, including the 30 min incubation, is repeated. The final pellet is resuspended in 60 ml 5 µM K-EDTA (pH 7.0) and stored in aliquots at −80° C. The extensive washing procedure utilized in this assay was designed in an effort to minimize the concentrations of glutamate and glycine (co-agonists at the NMDA receptor-ionophore complex) present in the membrane preparation.

To perform a binding assay with [$^3$H]arylalkylamine, aliquots of SPMs (Synaptic Plasma Membranes) are thawed, resuspended in 30 mls of 30 µM EPPS/1 mM K-EDTA, pH 7.0, and centrifuged at 100,000 ×g for 30 minutes. SPMs are resuspended in buffer A (30 µM EPPS/1 µM K-EDTA, pH 7.0). The [$^3$H]larylalkylamine is added to this reaction mixture. Binding assays are carried out in polypropylene test tubes. The final incubation volume is 500 µl. Nonspecific binding is determined in the presence of 100 µM nonradioactive arylalkylamine. Duplicate samples are incubated at 0° C. for 1 hour. Assays are terminated by the addition of 3 ml of ice-cold buffer A, followed by filtration over glass-fiber filters (Schleicher & Schuell No. 30) that are presoaked in 0.33% polyethyleneimine (PEI). The filters are washed with another 3×3 ml of buffer A, and radioactivity is determined by scintillation counting at an efficiency of 35–40% for $^3$H.

In order to validate the above assay, the following experiments are also performed:

(a) The amount of nonspecific binding of the [$^3$H]arylalkylamine to the filters is determined by passing 500 µl of buffer A containing various concentrations of [$^3$H]Hlarylalkylamine through the 10 presoaked glass-fiber filters. The filters are washed with another 4×3 ml of buffer A, and radioactivity bound to the filters is determined by scintillation counting at an efficiency of 35–40% for $^3$H. In filters that are not pretreated with 0.33% PEI, it was found that 87% of the $^3$H-ligand was bound to the filter. Presoaking with 0.33% PEI reduces the nonspecific binding to 0.5–1.0% of the total ligand added.

(b) A saturation curve is constructed by resuspending SPMs in buffer A. The assay buffer (500 µl) contains 60 µg of protein. Concentrations of [$^3$H]larylalkylamine are used, ranging from 1.0 nM to 400 µM in half-log units. A saturation curve is constructed from the data, and an apparent $K_D$ value and $B_{max}$ value determined by Scatchard analysis (Scatchard, The attractions of proteins for small molecules and ions. *Ann. N.Y. Acad. Sci.* 51: 660, 1949). The cooperativity of binding of the [$^3$H]arylalkylamine is determined by the construction of a Hill plot (Hill, A new mathematical treatment of changes of ionic concentrations in muscle and nerve under the action of electric currents, with a theory to their mode of excitation. *J. Physiol.* 40: 190, 1910).

(c) The dependence of binding on protein (receptor) concentration is determined by resuspending SPMs in buffer A. The assay buffer (500 µl) contains a concentration of [$^3$H]arylalkylamine equal to its $K_D$ value and increasing concentrations of protein. The specific binding of [$^3$H]arylalkylamine should be linearly related to the amount of protein (receptor) present.

(d) The time course of ligand-receptor binding is determined by resuspending SPMs in buffer A. The assay buffer (500 µl) contains a concentration of [$^3$H]arylalkylamine equal to its $K_D$ value and 100 µg of protein. Duplicate samples are incubated at 0° C. for varying lengths of time;

the time at which equilibrium is reached is determined, and this time point is routinely used in all subsequent assays.

(e) The pharmacology of the binding site can be analyzed by competition experiments. In such experiments, the concentration of [$^3$H]arylalkylamine and the amount of protein are kept constant, while the concentration of test (competing) drug is varied. This assay allows for the determination of an $IC_{50}$ and an apparent $K_D$ for the competing drug (Cheng and Prusoff, Relationship between the inhibition constant ($K_i$) and the concentration of inhibitor which causes 50 percent inhibition ($IC_{50}$) of an enzymatic reaction. *J. Biochem. Pharmacol.* 22: 3099, 1973). The cooperativity of binding of the competing drug is determined by Hill plot analysis.

Specific binding Of the [$^3$H]arylalkylamine represents binding to a novel site on receptor-operated $Ca^{2+}$ channels such as those present within NMDA-, AMPA and nicotinic cholinergic receptor-ionophore complexes. As such, other arylalkylamines should compete with the binding of [$^3$H] arylalkylamine in a competitive fashion, and their potencies in this assay should correlate with their inhibitory potencies in a functional assay of receptor-operated $Ca^{2+}$ channel antagonism (e.g., inhibition of NMDA receptor-induced increases in $[Ca^{2+}]_i$ in cultures of rat cerebellar granule cells). Conversely, compounds which have activity at the other known sites on receptor-operated Ca 2, channels (e.g., MK-801, $Mg^{2+}$, polyamines) should not displace ($^3$H]arylalkylamine binding in a competitive manner. Rather, complex allosteric modulation of [$^3$H]arylalkylamine binding, indicative of noncompetitive interactions, might be expected to occur. In preliminary experiments, MK-801 did not displace [$^3$H]arylalkylamine binding at concentrations up to 100 µM.

(f) Studies to estimate the dissociation kinetics are performed by measuring the binding of [$^3$H]arylalkylamine after it is allowed to come to equilibrium (see (d) above), and a large excess of nonradioactive competing drug is added to the reaction mixture. Binding of the [$^3$H]arylalkylamine is then assayed at various time intervals. With this assay, the association and dissociation rates of binding of the [$^3$H] arylalkylamine are determined (Titeler, *Multiple Dopamine Receptors: Receptor Binding Studies in Dopamine Pharmacology*. Marcel Dekker, Inc., New York, 1983). Additional experiments involve varying the reaction temperature (0° C. to 37° C.) in order to understand the temperature dependence of this parameter.

EXAMPLE 25

Radioligand Binding in Cerebellar Granule Cells

Primary cultures of cerebellar granule neurons are obtained from 8-day-old rats and plated onto squares of Aclar plastic coated with poly-L-lysine. The plastic squares are placed in 24-well culture plates, and approximately $7.5 \times 10^5$ granule cells are added to each well. Cultures are maintained in Eagles' medium (HyClone Laboratories) containing 25 µM KC1, 10% fetal calf serum (HyClone Laboratories), 2 µM glutamine, 100 µg/ml gentamicin, 50 U/ml penicillin, and 50 µg/ml streptomycin at 37° C. in a humid atmosphere of 5% $CO_2$ in air for 24 hr before the addition of cytosine arabinoside (10 µM, final). No changes of culture medium are made until the cells are used for receptor binding studies 6–8 days after plating.

To perform a binding assay with [$^3$H]arylalkylamine, the reaction mixture consists of 200 µl of buffer A (20 µM K-HEPES, 1 µM K-EDTA, pH 7.0) in each well of the 24-well plate. The [$^3$H]arylalkylamine is added to this reaction mixture. Nonspecific binding is determined in the presence of 100 µM nonradioactive arylalkylamine. Triplicate samples are incubated at 0° C. for 1 hour. Assays are terminated by manually scraping the cells off the Aclar squares and placing them into polypropylene test tubes. The membranes prepared from whole cells in this manner are suspended in 10 ml of ice-cold buffer A, and filtered over glass-fiber filters (Schleicher & Schuell No. 30) that are presoaked in 0.33% PEI. The filters are washed with another 3×3 ml of buffer A, and radioactivity on the filters is determined by scintillation counting at an efficiency of 35–40% for $^3$H. The assay may be terminated by centrifugation rather than filtration in order to minimize nonspecific binding.

Specific experiments to characterize and validate the assay are performed essentially as above, except that cells are used in place of membranes for the initial binding. The binding assay allows for the determination of an $IC_{50}$ value and an apparent $K_D$. for the competing drug as described by Scatchard analysis (The attractions of proteins for small molecules and ions. *Ann. N.Y. Acad. Sci.* 51: 660, 1949). Cooperativity of binding of the competing drug is determined by Hill plot analysis (A new mathematical treatment of changes of ionic concentrations in muscle and nerve under the action of electric currents, with a theory to their mode of excitation. *J. Physiol.* 40: 190, 1910). The specific binding of the [$^3$H]arylalkylamine represents binding to a novel site on receptor-operated calcium channels.

EXAMPLE 26

Recombinant Receptor Binding Assay

The following is one example of a rapid screening assay for useful compounds of this invention. In this assay, a CDNA or gene clone encoding the arylalkylamine binding site (receptor) from a suitable organism such as a human is obtained using standard procedures. Distinct fragments of the clone are expressed in an appropriate expression vector to produce the smallest polypeptide(s) obtainable from the receptor which retain the ability to bind Compound 1, Compound 2 or Compound 3. In this way, the polypeptide(s) which includes the novel arylalkylamine receptor for these compounds can be identified. Such experiments can be facilitated by utilizing a stably transfected mammalian cell line (e.g., HEK 293 cells) expressing the arylalkylamine receptor.

Alternatively, the arylalkylamine receptor can be chemically reacted with chemically modified Compound 1, Compound 2 or Compound 3 in such a way that amino acid residues of the arylalkylamine receptor which contact (or are adjacent to) the selected compound are modified and thereby identifiable. The fragments of the arylalkylamine receptor containing those amino acids which are determined to interact with Compound 1, Compound 2 or Compound 3 and are sufficient for binding to said molecules, can then be recombinantly expressed, as described above, using a standard expression vector(s).

The recombinant polypeptide(s) having the desired binding properties can be bound to a solid phase support using standard chemical procedures. This solid phase, or affinity matrix, may then be contacted with Compound 1, Compound 2 or Compound 3 to demonstrate that those compounds can bind to the column, and to identify conditions by which the compounds may be removed from the solid phase. This procedure may then be repeated using a large library of compounds to determine those compounds which are able to bind to the affinity matrix, and then can be released in a manner similar to Compound 1, Compound 2 or Compound 3. However, alternative binding and release conditions may be utilized in order to obtain compounds capable of binding under conditions distinct from those used for arylalkylamine binding (e.g., conditions which better mimic physiological conditions encountered especially in pathological states). Those compounds which do bind can thus be selected from a very large collection of compounds present in a liquid medium or extract.

Once compounds able to bind to the arylalkylamine binding polypeptide(s) described above are identified, those compounds can then be readily tested in the various assays described above to -determine whether they, or simple derivatives thereof, are useful compounds for therapeutic treatment of neurological disorders and diseases described above.

In an alternate method, native arylalkylamine receptor can be bound to a column or other solid phase support. Those compounds which are not competed off by reagents which bind other sites on the receptor can then be identified. Such compounds define novel binding sites on the receptor. Compounds which are competed off by other known compounds thus bind to known sites, or bind to novel sites which overlap known binding sites. Regardless, such compounds may be structurally distinct from known compounds and thus may define novel chemical classes of agonists or antagonist which may be useful as therapeutics. In summary, a competition assay can be used to identify useful compounds of this invention.

EXAMPLE 27

Patch-Clamp Electrophysiology Assay

The following assay is performed for selected compounds identified in the above-mentioned radioligand binding assays as interacting in a highly potent and competitive fashion at the novel arylalkylamine binding site on receptor-operated $Ca^{2+}$ channels, such as those present in NMDA-, AMPA- or nicotinic cholinergic receptor-ionophore complexes. This patch-clamp assay provides additional relevant data about the site and mechanism of action of said previously selected compounds. Specifically, the following pharmacological and physiological properties of the compounds interacting at the arylalkylamine binding site are determined, utilizing the NMDA receptor-ionophore complex as an example of receptor-operated $Ca^{2+}$ channels, potency and efficacy at blocking NMDA receptor-mediated ionic currents, the noncompetitive nature of block with respect to glutamate and glycine, use-dependence of action, voltage-dependence of action, both with respect to onset and reversal of blocking, the kinetics of blocking and unblocking (reversal), and open-channel mechanism of blocking. Such data confirm that the compounds interacting at the arylalkylamine binding site retain the unique biological profile of the arylalkylamines, and do not have their primary activity at the known sites on the NMDA receptor-ionophore complex (glutamate binding site, glycine binding site, MK-801 binding site, $Mg^{2+}$ binding site, $Zn^{2+}$ binding site, sigma binding site, polyamine binding site).

Patch-clamp recordings of mammalian neurons (hippocampal, cortical, cerebellar granule cells) are carried out utilizing standard procedures (Donevan et al., Arcaine blocks N-methyl-D-aspartate receptor responses by an open channel mechanism: whole-cell and single-channel recording studies in cultured hippocampal neurons. *Molec. Pharmacol.* 41: 727, 1992; Rock and Macdonald, Spermine and related polyamines produce a voltage-dependent reduction of NMDA receptor single-channel conductance. *Molec. Pharmacol.* 42: 157, 1992).

Alternatively, patch-clamp experiments can be performed on Xenopus oocytes or on a stably transfected mammalian cell line (e.g., HEK 293 cells) expressing specific subunits of receptor-operated $Ca^{2+}$, channels. In this manner, for example, potency and efficacy at various glutamate receptor subtypes (e.g., NMDAR1, NMDAR2A through NMDAR2D, GluR1 through GluR4) can be determined. Further information regarding the site of action of the arylalkylamines on these glutamate receptor subtypes can be obtained by using site-directed mutagenesis.

EXAMPLE 28

Synthesis of Arylalkylamines

Arylalkylamines such as Compound 1, Compound 2 and Compound 3 are synthesized by standard procedures (Jasys et al., The total synthesis of argiotoxins 636, 659 and 673. *Tetrahedron Lett.* 29: 6223, 1988; Nason et al., Synthesis of neurotoxic Nephila spider venoms: NSTX-3 and JSTX-3. *Tetrahedron Lett.* 30: 2337, 1989). Specific examples of syntheses of arylalkylamine analogs 4–18 are provided in co-pending application U.S. Ser. No. 08/485,038, filed Jun. 7, 1995, and co-pending International Patent Application No. PCT/US94/12293, published as WO95/21612, filed Oct. 26, 1994, hereby incorporated by reference herein in their entirety.

EXAMPLE 29

Synthesis of Simplified Arylalkylamines

Synthesis of Compound 20 was accomplished as follows.

A solution of sodium hydride (1.21 g, 50 mmol) in dimethoxyethane was treated with diethyl cyanomethylphosphonate (8.86 g, 50 mmol) and the reaction stirred 4 hr at room temperature. To this was added 3,3'-difluorobenzophenone (10 g, 46 mmol) in DME. The reaction was stirred 24 hr at room temperature, quenched with $H_2O$, and partitioned between diethyl ether and water. The ether fraction was dried over $Na_2SO_4$, and concentrated. GC/MS of this material showed 90% of the product A and 10% starting benzophenone.

A solution of this material in ethanol with a catalytic amount of $Pd(OH)_2$ was hydrogenated at 55 psi hydrogen for 4 hr at room temperature. The reaction was filtered and the catalyst washed with ethanol (3×). The filtrate and ethanol washes were combined and concentrated. GC/MS of this material showed 90% of the product B and 10% of the starting benzophenone.

A solution of this material in THF was treated with 70 ml 1 M $B_2H_6$ (70 mmol) in THF and refluxed 1 hr. After cooling, the reaction was treated with 6 N HCl (50 ml) and refluxed an additional hour. After cooling, the reaction was basified to pH 14 with 10 N NaOH and equilibrated with ether. The ether layer was removed and washed with 10% HCl (3×). The acidic washes were combined, basified to pH 14 with 10 N NaOH and extracted with dichloromethane (3×). The organic washes were combined, dried over $Na_2SO_4$, and concentrated to yield an oil. GC/MS of this material showed 100% Compound 20. GC/EI-MS ($R_t$=7.11 min) m/z (relative intensity) 247 ($M^+$,31), 230 (100), 215

(30), 201 (52), 183 (63), 134 (23), 121 (16), 101 (21), 95 (15), 77 (15). This material in diethyl ether was filtered and treated with 35 ml 1 M HCl in ether. The precipitate was collected, dried, and recrystallized from water-ethanol to afford 1.045 g of Compound 20, as the hydrochloride salt. $^1$H-NMR (CDCl$_3$) d 8.28 (3H, br s), 7.28–7.17 (2 H, m), 7.02–6.86 (6 H, m), 4.11 (1H, t, J=8 Hz), 2.89 (2H, br t, J=8 Hz), 2.48 (2H, br t, J=7 Hz); $^{13}$C-NMR (CDCl$_3$) d 164.6, 161.3, 144.8, 144.7, 130.4, 130.3, 123.3, 123.2, 114.7, 114.5, 114.1, 113.8, 47.4, 38.4, 32.7.

Synthesis of Compound 21, Compound 33 and Compound 34 was accomplished as follows.

A 100 ml round-bottomed flask equipped with stir bar, septa, and argon source was charged with Compound 1 (2.43 g, 10 mmol) in 30 ml THF. The solution was cooled to −78° C. and treated dropwise with 11 ml lithium bis(trimethylsilyl) amide (1M in THF) (11 mmol). The reaction was stirred at −78° C. for 30 min and treated dropwise with excess iodomethane (3.1 ml, 50 mmol). The reaction was stirred 30 min at −58° C. GC/EI-MS analysis of an aliquot from the reaction showed consumption of the starting nitrile 1. The reaction was quenched with water, diluted with diethyl ether and transferred to a separatory funnel. The ether layer was washed with 10% HCl (3×), brine (1×), dried with anhydrous MgSO$_4$, and concentrated to a brown oil. This material was distilled (Kugelrohr, 100° C.) at reduced pressure to afford 1.5 g of a clear oil. GC/EI-MS of this material showed it to contain the desired product 2, ($R_f$=7.35 min) m/z (rel. int.) 257 (M$^+$, 3), 203 (100), 183 (59), 170 (5), 133 (4), 109 (3); $^1$H-NMR (CDCl$_3$) d 7.4–6.9 (8H, m), 4.01 (1H, d, J=10 Hz), 3.38 (1H, dq, J=7, 10 Hz), 1.32 (3H, d, J=7 Hz); $^{13}$C-NMR (CDCl$_3$) d 19.4, 30.5, 54.2, 114.5, 114.6, 114.7, 114.9, 115.0, 115.3, 123.3, 123.4, 123.6, 123.7, 130.5, 130.6, 131.7.

Product 3 was synthesized by the catalytic reduction of 2 using Raney nickel in 95:5 EtOH:aqueous sodium hydroxide (2 Eq.) under 60 psi hydrogen. GC/EI-MS ($R_f$=7.25 min) m/z (rel. int.) 261 (M$^+$, 20), 244 (35), 229 (16), 215 (17), 201 (80), 183 (100), 133 (42), 115 (27), 109 (47), 95 (20); $^1$H-NMR (CDCl$_3$) d 7.3–6.8 (8H, m), 3.62 (1H, d, J=10 Hz), 2.70 (1H, M), 2.40 (2H, m), 1.73 (2H, m), 0.91 (3H, d, J=7 Hz). Note that product 3 in this reaction sequence corresponds to Compound 21.

Product 2 in 10% IPA-hexane (100 mg/ml) was chromatographed, in 500 μM aliquots, through Chiral Cel OD (2.0×25 cm) using 10% IPA-hexane at 10 ml/min measuring optical density at 254 nm. This afforded the two optically pure enantiomers 4 and 5 (as determined by analytical chiral HPLC; Note, the stereochemistry of these two compounds has not been assigned at this time). These two compounds were identical in their GC/EI-MS and $^1$H-NMR spectra as product 2 (data above).

Each of the enantiomers 4 and 5 was reduced separately using dimethyl sulfideborane complex in the following manner. A solution of compound (4 or 5) in THF was heated to reflux and treated with excess (2 Eq.) 1M (in THF) dimethyl sulfideborane complex and the reaction refluxed 30 min. After this time the reaction was cooled to 0° C. and treated with 6 N HCl. The reaction was set to reflux 30 min. After this time the reaction was transferred to a separatory funnel, basified to pH>12 with 10N NaOH, and the product (6 or 7) extracted into ether. The ether layer was washed with brine, dried over anhydrous MgSO$_4$ and concentrated to an oil. The product was purified by prep-TLC using 5% methanol-chlorform. Each of the individual enantiomers (6 and 7) were found to be identical in their GC/EI-MS and $^1$H-NMR spectra as product 3 (data above). Note that products 6 and 7 in this scheme correspond to Compounds 33 and 34. Compound 33.HCl: mp=260–270° C. (dec), $[^{OC}]_{365}26$=+6.6 (c 1.0 in EtOH), $[OC]_D26$=+0.4 (c 1.0 in EtOH). Compound 34.HCl: $[^{OC}]_{365}23$=−6.1 (c 1.0 in EtOH), $[^{OC}]_D23$=+0.1 (c 1.0 in EtOH). Compound 33.HI: The free base of Compound 33 was dissolved in EtOH and 47% hydriodic acid (1.1 equivt.) was added. The solvent was evaporated under vacuum and the resulting solid hydroiodide was recrystallized twice from heptane/EtOAc by slow evaporation: mp=195–197° C. The absolute configuration of compound 33.HI was determined to be R by single-crystal (monoclinic

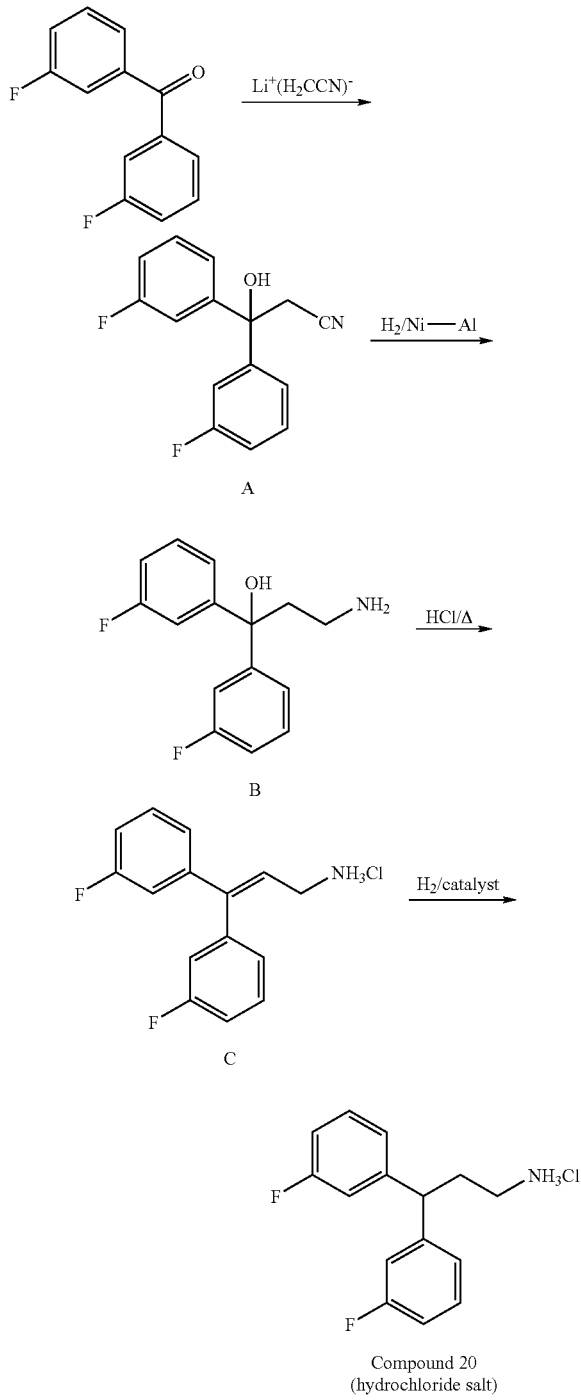

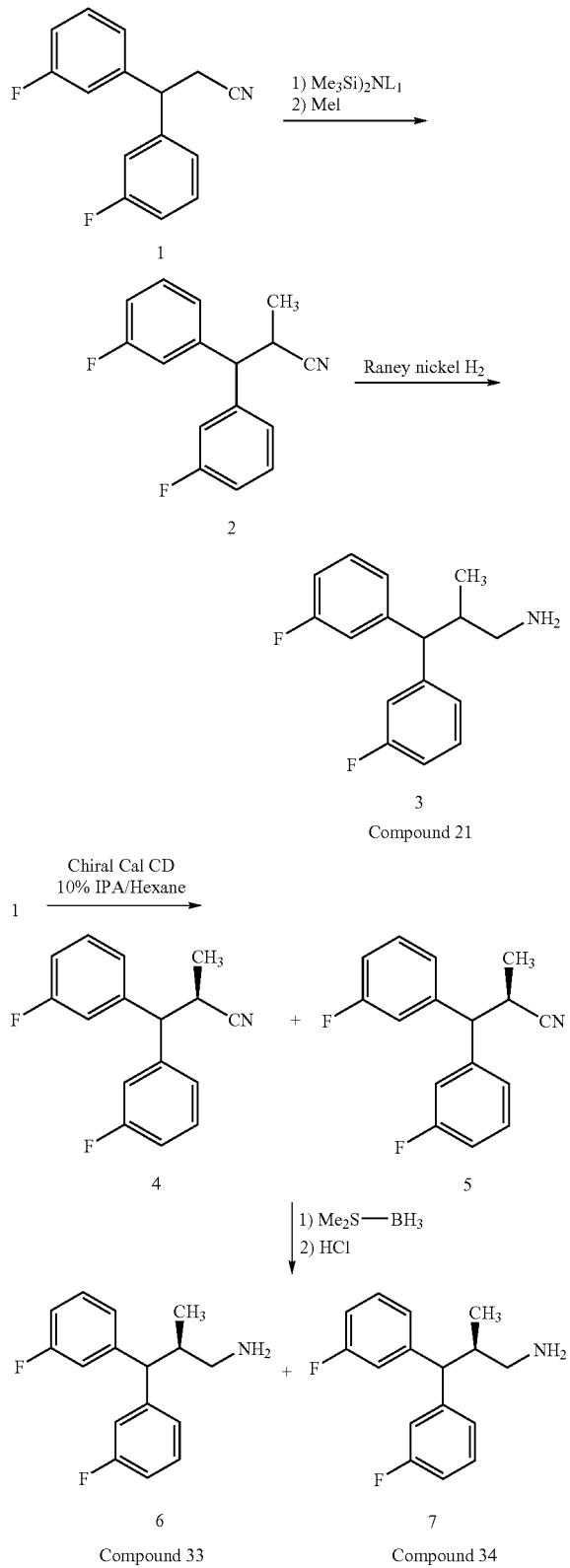

Synthesis of Compound 22 was accomplished as described below. Compound 23 was synthesized in a similar manner.

Triethyl phosphonoacetate (17.2 g, 76.8 mmol) was slowly added to a suspension of sodium hydride (3.07 g, 76.8 mmol) in N,N-dimethylformamide (350 ml). After 15 minutes 3,3'-difluorobenzophenone (15.2 g, 69.8 mmol) was added to the solution and stirred an additional 18 hr. The reaction mixture was quenched with water and partitioned between water and ether. The combined organic layers were washed with brine and dried over anhydrous magnesium sulfate. The solvent was evaporated in vacuo to give 19.7 g of ethyl 3,3-bis(3-fluorophenyl)acrylate as a yellow oil.

To a solution of ethyl 3,3-bis(3-fluorophenyl)-acrylate (19.7 g, 68.4 mmol) in 200 ml of ethanol was added palladium hydroxide on carbon (3.5 g). The mixture was shaken under 60 psi of hydrogen for 3 hours, then filtered and evaporated in vacuo to give 19.5 g of product A as a colorless oil.

The ethyl ester A (19.2 g) was hydrolyzed by stirring for 6 days with 50 ml of 10 N sodium hydroxide. The reaction mixture was then diluted with 50 ml of water and acidified to pH 0 with concentrated HCl. The aqueous mixture was extracted 3 times with ether and the ether extracts dried over magnesium sulfate and evaporated to give 3,3-bis(3-fluorophenyl) propionic acid as a white powder.

3,3-Bis(3-fluorophenyl)priopionic acid (13 g, 49.6 mmol) was dissolved in 50 ml (685 mmol) of thionyl chloride and stirred overnight at room temperature. The excess thionyl chloride was removed in vacuo on a rotary evaporator to give 13.7 g of product B as a yellow oil.

To acid chloride B (13.7 g, 49 mmol) dissolved in 100 ml of dry THF was added iron(III) acetylacetonate (0.52 g, 1.47 mmol). Methylmagnesium chloride (16.3 ml, 49 mmol) was then added over a period of 1 hr by syringe pump. The reaction was stirred for an additional hour, then quenched by pouring into ether/5% HCl. The ether layer was separated, washed with 5% HCl and saturated NaCl, and dried over sodium sulfate. The solvent was evaporated in vacuo to give 4,4-bis(3-fluorophenyl)-2-butanone as a yellow oil. The crude oil was purified on silica gel using heptane/ethyl acetate as the elutant.

To 4,4-bis(3-fluorophenyl)-2-butanone (5.7 g, 21.9 mmol) in 25 ml of ethanol was added pyridine (1.91 g, 24.1 mmol) and methoxylamine hydrochloride (2.01 g, 24.1 mmol). The reaction was stirred overnight at room temperature, then poured into ether/5% HCl. The ether layer was separated, washed with 5% HCl and saturated NaCl, and dried over sodium sulfate. The solvent was evaporated in vacuo to give 6.26 g of the 0-methyl oxime of 4,4-bis(3-fluorophenyl)-2-butanone. To sodium borohydride (4.1 g, 108.3 mmol) in 15 ml of THF was slowly added zirconium tetrachloride (6.31 g, 27.1 mmol). This mixture was stirred for 15 min, then the oxime (6.26 g, 21.7 mmol) in 6 ml of THF was added over 5 min. After 3 hours of stirring at room temperature, the reaction was worked up by slowly adding 50 μM sodium hydroxide followed by ether. The aqueous layer was extracted 4 times with ether, and the combined ether extracts were dried over sodium sulfate. The solvent was evaporated in vacuo to give 5.3 g of Compound 22.

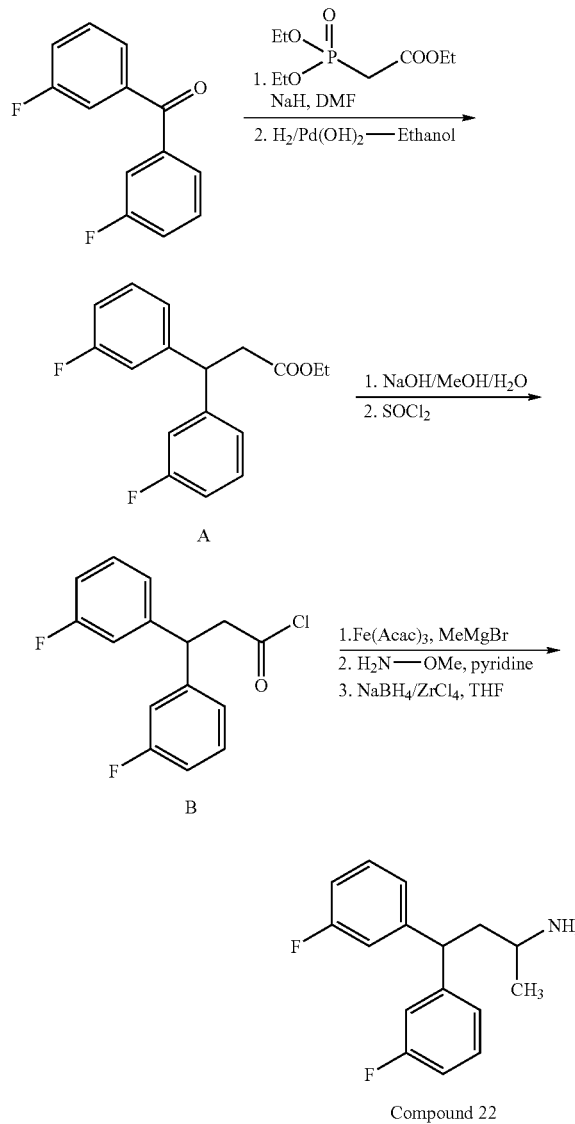

Compound 22

Synthesis of Compound 24 was accomplished as described below. Compounds 25–29, 52–53, 65, 76–78, 83, 90, 96–97, 115, and 135–136 were prepared in a similar manner.

A suspension of magnesium turnings (0.95 g, 39.2 mmol) in 150 ml anhydrous diethyl ether was treated with 1-bromo-3-fluorobenzene 6.83 g, 39.2 mmol) dropwise via syringe. After 1.5 hr the solution was transferred via cannula to a flask containing o-anisaldehyde (5.0 g, 36.7 mmol) in 100 ml anhydrous diethyl ether at 0° C. and stirred 2 hr. The reaction mixture was quenched with water and partitioned between water and ether. The combined organic layers were washed with brine and dried over anhydrous magnesium sulfate to afford 7.90 g (93% yield) of product A.

Pyridinium dichromate (16.0 g, 42.5 mmol) was added to a solution of the alcohol A (7.90 g, 34.0 mmol) in dichloromethane (100 ml), and the reaction was stirred 12 hr. Diethyl ether (300 ml) was added to the reaction mixture and the black solution was filtered through a silica gel plug (30 cm) and washed with an additional 500 ml ether. After evaporation of the solvent in vacuo, the solid was recrystallized from acetone to give 7.45 g (95% yield) of product B.

Diethyl cyanomethylphosphonate (7.0 g, 39.5 mmol) was slowly added to a suspension of sodium hydride (1.58 g, 39.5 mmol) in 100 ml N,N-dimethylformamide. After 30 minutes the ketone 3 was added to the solution and stirred an additional 2 hr. The reaction mixture was quenched with water, and partitioned between water and ether. The combined organic layers were washed with brine and dried over anhydrous magnesium sulfate. The solvent was evaporated in vacuo to give a pale yellow oil.

In a glass bomb, the oil was dissolved in 100 ml ethanol and 20 ml 10N NAOH. A catalytic amount of Raney Nickel suspended in water (ca. 15 mol percent) was added to the solution. The reaction mixture was shaken under 60 psi $H_2$ for 12 hr on a Parr Hydrogenator. After filtering off excess Raney Nickel, the solution was extracted with chloroform. The combined organic layers were washed with brine and dried over anhydrous magnesium sulfate. After filtration, the oil was run through a silica gel column in chloroform and methanol. The solvent was evaporated in vacuo to give a pale yellow oil. GC/EI-MS ($R_t$=8.10 min) mlz (rel. intensity) 259 (100), 242 (44), 213 (48), 183 (42), 136 (50), 109 (94), 91 (60), 77 (25). The oil was then acidified with hydrogen chloride in diethyl ether. Evaporation of the ether afforded a pale yellow solid that was recrystallized in hot acetonitrile to afford 3.45 g (42.1% yield) white needles of Compound 24, as the hydrochloride salt.

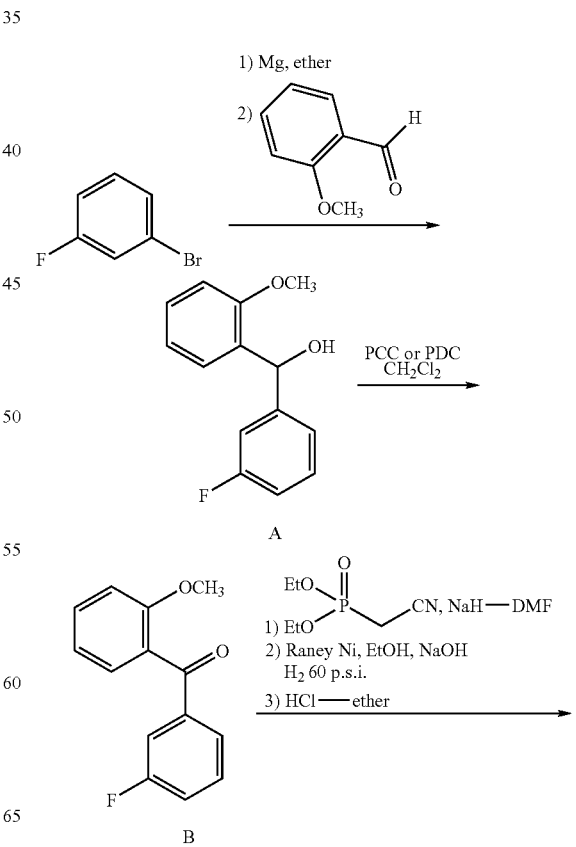

-continued

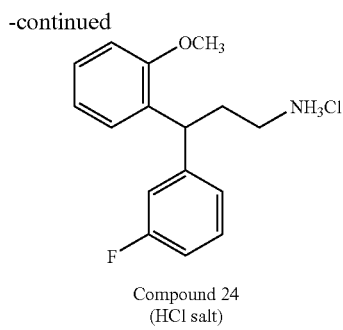

Compound 24
(HCl salt)

Compounds 101 and 103 were synthesized from Compounds 25 and 24, respectively, by cleavage of their 0-methyl ethers with borane tr4-bromide in the normal manner.

Synthesis of Compound 30 was accomplished as described below. Compound 31 was prepared in a similar manner.

A suspension containing magnesium turnings (0.95 g, 39.1 mmol) in 150 ml anhydrous diethyl ether was treated with 1-bromo-3-fluorobenzene (6.85 g, 39.1 mmol) dropwise via syringe. After 1.5 hr the solution was transferred via cannula to a flask containing 3-chlorobenzaldehyde (5.0 g, 35.6 mmol) in 100 ml anhydrous diethyl ether at 0° C. and stirred 2 hr. The reaction mixture was quenched with water and partitioned between water and ether. The combined organic layers were washed with brine and dried over anhydrous magnesium sulfate to afford 8.40 g (>99% yield) of product A.

Pyridinium chlorochromate (15.0 g, 39.8 mmol) was added to a solution of the alcohol A (8.40 g, 35.5 mmol) in 100 ml dichloromethane and stirred 18 hr. Diethyl ether (300 ml) was added to the reaction mixture and the black solution was filtered through a silica gel plug (30 cm), and washed with an additional 500 ml ether. After evaporation of the solvent the solid was recrystallized from acetone to give 6.31 g (76% yield) of product B.

Diethyl cyanomethylphosphonate (5.2 g, 29.6 mmol) was slowly added to a suspension of sodium hydride (1.2 g, 29.6 mmol) in N,N-dimethylformamide (100 ml). After 30 minutes the ketone B was added to the solution and stirred an additional 6 hr. The reaction mixture was quenched with water and partitioned between water and ether. The combined organic layers were washed with brine and dried over anhydrous magnesium sulfate. The solvent was evaporated in vacuo to give a yellow oil.

In a glass bomb, the oil was dissolved in ethanol (100 ml) and 10N NaOH (20 ml). A catalytic amount of rhodium suspended on alumina (ca. 35 mol percent) was added to the solution. The reaction mixture was shaken under 60 psi $H_2$ for 24 hr on a Parr Hydrogenator. After filtering off excess catalyst, the solution was extracted with chloroform. The combined organic layers were washed with brine and dried over anhydrous magnesium sulfate. After filtration and evaporation of the solvent in vacuo, the oil was taken up in tetrahydrofuran (100 ml). Diborane (23.4 ml, 1.0 M) was added and the solution was refluxed for 1.5 hr. The solvent was evaporated in vacuo and 6N HCl (50 ml) was added carefully. The solution was refluxed for 1 hr. After cooling, the mixture was basified with 10N NaOH to pH 14 and partitioned between dichloromethane and water. The combined organic layers were dried over anhydrous magnesium sulfate and filtered. After evaporation of the solvent, the yellow oil was run through a silica gel column in chloroform and methanol. The solvent was evaporated in vacuo to give a yellow oil. GC/EI-MS ($R_t$=8.15 min) m/z (rel. intensity) 263 (17), 246 (21), 211 (84), 196 (33), 183 (100), 165 (19), 133 (19). The oil was then acidified with hydrogen chloride in diethyl ether. Evaporation of the ether afforded 0.96 g of a white solid, Compound 30, as the hydrochloride salt.

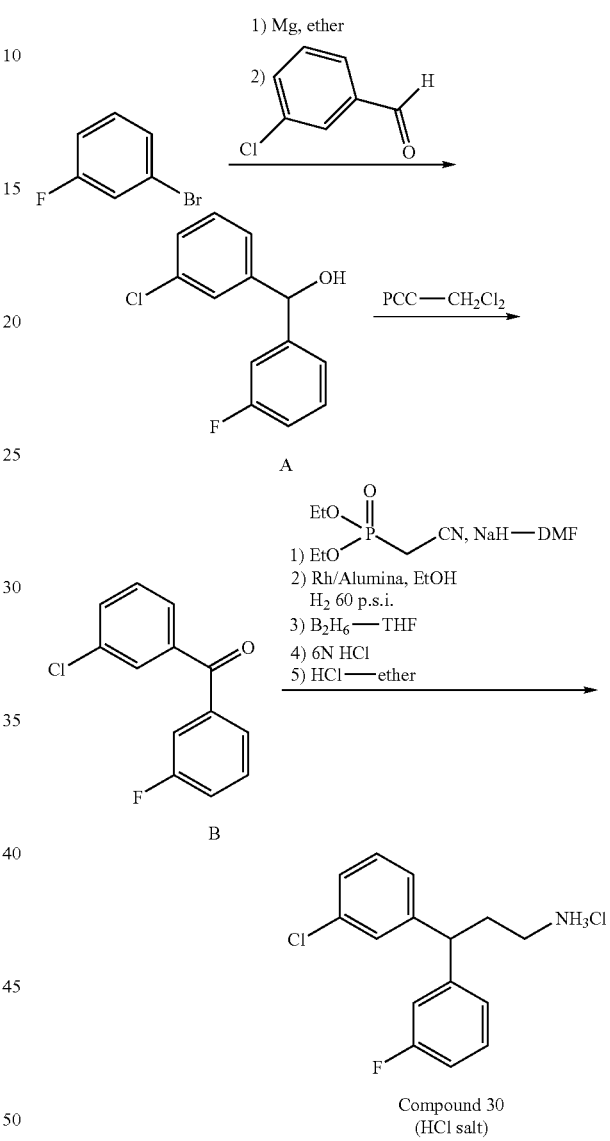

Compound 30
(HCl salt)

Synthesis of Compound 35 was accomplished as described below. Compounds 36–37 were prepared in a similar manner.

A solution of 3-fluorobenzaldehyde (3.0 g, 24.2 mmol) at 0° C. in 150 ml diethyl ether was treated with 3.0 M ethyl magnesium chloride (12.7 ml, 25.4 mmol) in tetrahydofuran (THF) via syringe. After 4 hr, the reaction mixture was quenched with water and partitioned between water and ether. The combined organic layers were washed with brine and dried over anyhydrous magnesium sulfate to afford 4.25 g of product A.

Pyridinium chlorochromate (6.53 g, 30.3 mmol) was added to a solution of A in dichloromethane (100 ml) and stirred 18 hr. Diethyl ether (300 ml) was added to the reaction mixture and the black solution was filtered through a silica gel plug (30 cm) and washed with an additional 500 ml ether. After evaporation of the solvent the solid was recrystallized from acetone to give 3.05 g of product B. The solvent was evaporated in vacuo to give a pale yellow oil.

Diethyl cyanometliylphosphonate (4.7 g, 26.4 mmol) was slowly added to a suspension of sodium hydride (1.1 g, 26.4 mmol) in 100 ml N,N-dimethylformamide. After 30 minutes the ketone B was added to the solution and stirred an additional 6 hr. The reaction mixture was quenched with water and partitioned between water and ether. The combined organic layers were washed with brine and dried over anhydrous magnesium sulfate. The solvent was evaporated in vacuo to give a yellow oil.

In a glass bomb, the oil was dissolved in 100 ml ethanol and 20 ml 10N NaCH. A catalytic amount of Raney Nickel suspended in water (ca. 15 mol percent) was added to the solution. The reaction mixture was shaken under 60 psi $H_2$ for 24 hr on a Parr Hydrogenator. After filtering off excess catalyst, the solution was extracted with chloroform. The combined organic layers were washed with brine and dried over anhydrous magnesium sulfate. After filtration, the oil was run through a silica gel column in chloroform and methanol. The solvent was evaporated in vacuo to give a pale yellow oil. GC/EI-MS ($R_t$=3.45 min) m/z (rel. intensity) 167 (4), 150 (63), 135 (58), 109 (100), 96 (53), 75 (48). The oil was then acidified with hydrogen chloride in diethyl ether. Evaporation of the ether left a pale yellow solid that was recrystallized in hot acetonitrile to afford 2.2 g of Compound 35, as the hydrochloride salt.

Synthesis of Compound 38 was accomplished as described below.

To a solution of 3,3-bis(3-fluorophenyl)-propionitrile (1.5 g, 6.17 mmol) in 250 ml of THF at −70° C. was added butyl lithium (4.25 ml in hexanes, 6.8 mmol) by syringe over 5 minutes. The solution was stirred for 5 min then methyl iodide (1.75 g, 12.3 mmol) was added over 1 min. The reaction mixture was then allowed to warm up to room temperature and worked up by diluting with ether and washing with 5% HCl and water. The ether layer was dried over sodium sulfate and evaporated to give 1.5 g of time methylated nitrile as a yellow oil.

To the 3,3-bis(3-fluorophenyl) 2-methyl-propionitrile (1.46 g, 5.7 mmol) in 50 ml of dichloromethane at 0° C. was added diisobutylaluminum hydride (1.02 ml, 5.7 mmol) by syringe over a 10 min period. The reaction was stirred for 30 min at 0° C. followed by 2 additional hours at room temperature. The reaction was worked up by adding 200 ml of 10% HCl and stirring at 40° C. for 30 min followed by extraction of the product with dichloromethane. The organic layer was dried over sodium sulfate and evaporated to give 1.36 g of the product A.

To a solution of the aldehyde A (1–36 g, 5.23 mmol) in 40 ml of ether at 0° C. was added methylmagnesium bromide (5.23 ml in ether, 5.23 mmol). The reaction was stirred for 3 hr at room temperature, and then quenched with dilute HCl. The ether layer was separated, dried over sodium sulfate and evaporated to give 1.48 g of 4,4-bis(3-fluorophenyl) -3-methylbutan-2-ol.

To a solution of the alcohol (1.4 g, 5.07 mmol) in 300 ml of dichloromethane was added pyridinium chlorochromate 1.2 g, 5.58 mmol), and the mixture was stirred overnight. The reaction was then diluted with 100 ml of ether and filtered through a silica plug. The solvent was evaporated to give 1.39 g of product B.

The ketone B (1.3 g, 4.9 mmol) was added to a solution of methoxylamine hydrochloride (0.45 g, 5.3B mmol) and pyridine (0.44 mL, 5.38 mmol) in 30 ml of ethanol, and stirred overnight. The ethanol was then evaporated, and the residue taken up in ether and 10% HCl. The ether layer was separated, washed once with 10% HCl, dried over sodium sulfate and evaporated to give 1.4 g of the O-methyl oxime.

To a suspension of sodium borohydride (0.87 g, 23.1 mmol) in 5 ml of THF was added zirconium tetrachloride (1.35 g, 5.8 mmol), and the solution was stirred for 15 min followed by the addition of another 5 ml of THF. The 0-methyl oxime (1.4 g, 4.6 mmol) in 5 ml of THF was then added, and the mixture stirred overnight. The THF was removed by evaporation in vacuo, and the residue treated with 10% sodium hydroxide. After the bubbling ceased ether was added and the layers separated. The aqueous layer was extracted four times with ether, and the combined ether extracts were dried over sodium sulfate. The ether was evaporated to give 1.25 g of Compound 38.

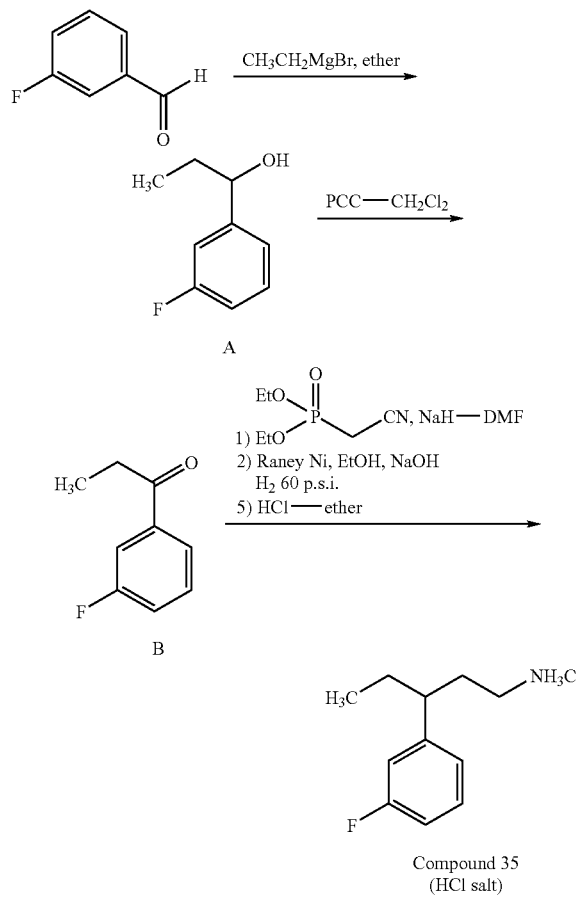

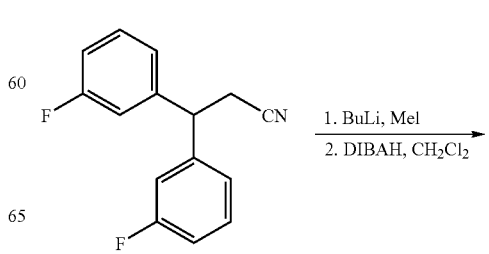

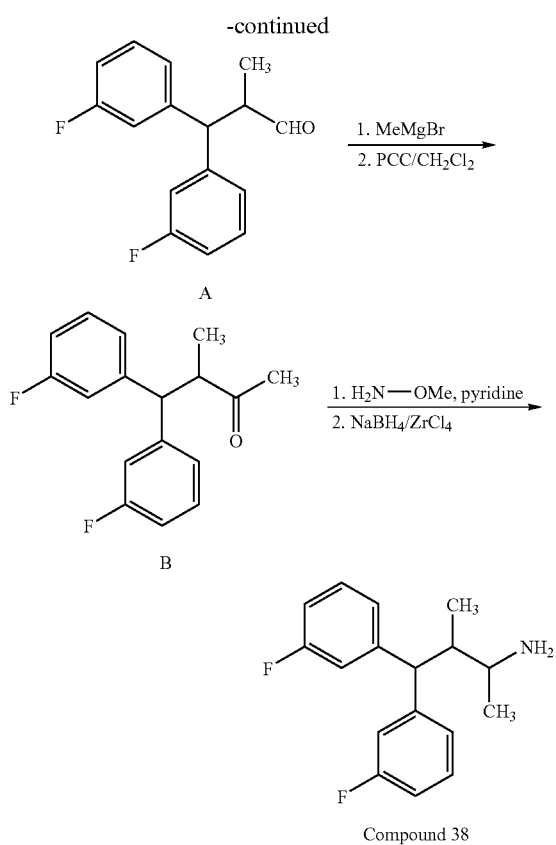

Compound 32 and Compounds 39–53 were synthesized according to standard procedures as described above.

Compounds 107, 116, 139, and 143 were prepared as synthetic intermediates used in the preparation of Compounds 32, 115, 20, and 25, respectively.

Compound 50 was also prepared using the chiral synthesis described below.

To an ice-cold solution of N-benzyl-(S)-a-methylbenzylamine (18.0 g, 85.2 mmol) in THF (75 ml) was added butyl lithium (2.5 M in hexane; 37.5 ml, 93.8 mmol) via a syringe over a period of 10 min at such a rate as to keep the reaction temperature below 10° C. during the addition. The reaction was then stirred at 0° C. for 15 min. The reaction was cooled to −78° C. in a dry ice/isopropanol bath and then a solution of benzyl crotonate (15.0 g, 85.2 mmol) in THF (100 ml) was added dropwise over a period of 45 min. The reaction was stirred at −78° C. for 15 min, and then saturated NH$_4$Cl (50 ml) was added. The reaction mixture was then quickly transferred to a separatory funnel containing saturated NaCl (500 ml) and ether (200 ml). The layers were separated and the aqueous layer extracted with ether (200 ml). The combined organic layers were dried, evaporated, and chromatographed on silica gel (50 mm×30 cm) (hexane-ethyl acetate [20:1]) to yield 21.0 g, 63.7% of product A. $^1$H-NMR showed that the diastereoselectivity of the reaction is >90%.

A mixture of magnesium (2.58 g, 106 mmol), THF (200 ml), and 1-bromo-3-fluorobenzene (18.60 g, 106.3 mmol) was refluxed for 45 min. While still under reflux, product A (16.45 g, 42.45 mmol) was added via syringe with THF (25 ml) over a 2 min period. The reaction was refluxed for 1 hr, and then allowed to cool to room temperature. Saturated NH$_4$Cl(aq., 200 ml) was added. The reaction mixture was then transferred to a separatory funnel containing saturated NaCl(aq) (500 ml) and diethyl ether (200 ml). The layers were separated and the aqueous layer extracted with ether (200 ml). The combined organic layers were dried over sodium sulfate and evaporated to give 21.41 g of product B as a yellow liquid.

Product B (20.02 g, 42.45 mmol, theoretical) was dissolved in acetic acid (120 ml) and sulfuric acid (30 ml). The reaction was stirred at 90° C. for 1 hr. The acetic acid was rotary evaporated giving a brown sludge. This material was placed in an ice bath and cold water (400 ml) was added. The product immediately precipitated. To the reaction was slowly added 10 N NaOH (150 ml) to neutral pH. Diethyl ether (200 ml) was added to this mixture. The mixture was shaken until there was no undissolved material. The ether layer was separated, washed with water 2×100 ml), dried over sodium sulfate, and rotary evaporated yielding 13.14 g (68.2% based on ester) of a thick brown oil. This oil was taken up in ether and converted to the hydrochloride salt with hydrogen chloride in diethyl ether to give product C. as a yellow-white solid.

Product C (7.17 g, 14.6 mmol) was taken up in absolute ethanol (200 ml). Pearlman's catalyst (Pd(OH)$_2$/C; 2.00 g) was added. The reaction was shaken under 70 psi hydrogen gas at 70° C. for 20 hr, and the reaction mixture was filtered through Celite. The filtrate was rotary evaporated to give 3.54 g of a light yellow glass. This material was taken up in diethyl ether (100 ml) and was basified with 1 N NaOH (25 ml). The ether layer was washed with water (1×25 ml), dried over sodium sulfate, and rotary evaporated to give 2.45 g of a light yellow oil. This material was Kugelrohr distilled (90–100° C., 1 mm Hg) to give 1.17 g of a colorless liquid. This material was taken up in diethyl ether and converted to the hydrochloride salt with ethereal hydrogen chloride. After rotary evaporation, the salt was recrystallized from 0.12 N HCl (200 mg/ml). The crystals were filtered off and were washed with cold 0.12 N HCl yielding 0.77 g (18%) of Compound 50 as silvery white crystals (as the hydrochloride salt).

Compound 51 was synthesized in a similar manner to Compound 50 utilizing N-benzyl-(R)-α-methylbenzylamine as a chiral starting material.

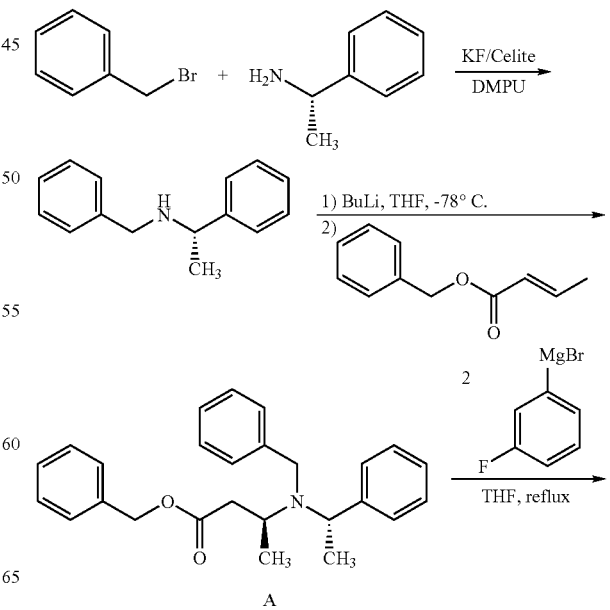

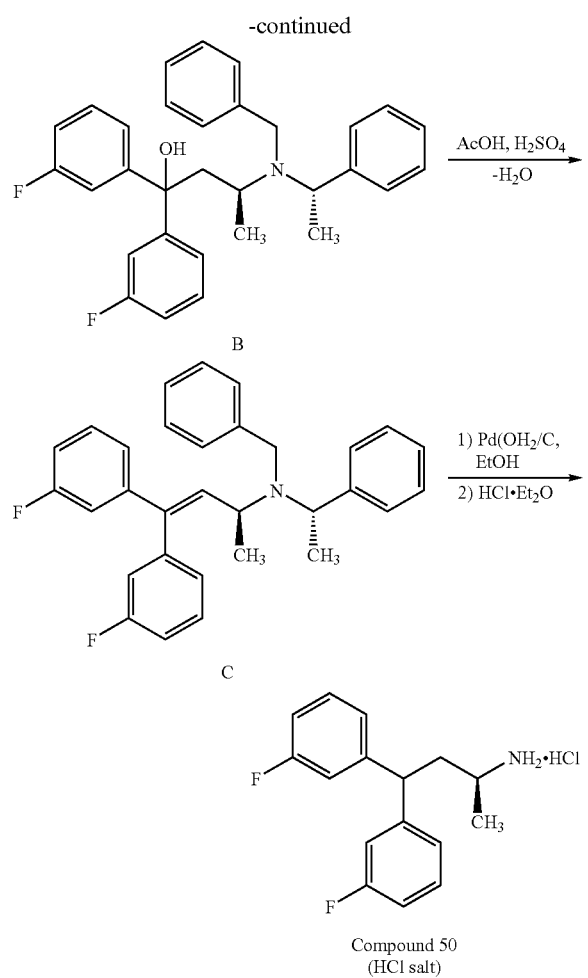

Compound 50
(HCl salt)

Synthesis of Compound 54 was accomplished as described below.

To a solution of 3,3'-difluorobenzophenone (5 g, 22.9 mmol) and methyl cyanoacetate (3.4 g, 34.4 mmol) in 15 ml of ether was added titanium isopropoxide (16.9 ml, 57.25 mmol). This solution was stirred for 6 days at room temperature then quenched with 0.5 mol of HCl in 300 ml of water. The mixture was diluted with 100 ml of ether, and the layers separated. The ether layer was washed with 5% HCl and saturated brine, then dried over sodium sulfate. The solvents were evaporated in vacuo to give 8 g of product A.

Compound A was dissolved in 50 ml of isopropanol, followed by the addition of a small amount of bromocresol green. Sodium cyanoborohydride (1.52 g, 24.2 mmol) was added all at once followed immediately with the dropwise addition of concentrated HCl, added at such a rate as to keep the solution yellow. After hours the reaction was worked up by partitioning between ether and water. The ether layer was . washed with water and saturated brine, dried over sodium sulfate, and concentrated to give the product B.

To a solution of lithium aluminum hydride (30.4 ml, 30.4 mmol) in THF was added product B (1 g, 3.04 mmol) in 2 ml of THF over a period of 30 seconds. This solution was stirred overnight at room temperature, then quenched with the addition of 20 ml of ethyl acetate. The solvents were then removed in vacuo, and the resulting oil was dissolved in aqueous HCl and acetonitrile. The product was then purified on a C-18 column with a gradient of 0.1% HCl to acetonitrile to give 82 mg of Compound 54, as the hydrochloride salt. EI-MS m/z (relative intensity) 277 ($M^+$, 100), 260 (2.4), 242 (8.6), 229 (28), 215 (11.7), 204 (16), 183 (12), 133 (9.5), 124 (14), 109 (6.8), 30 (22).

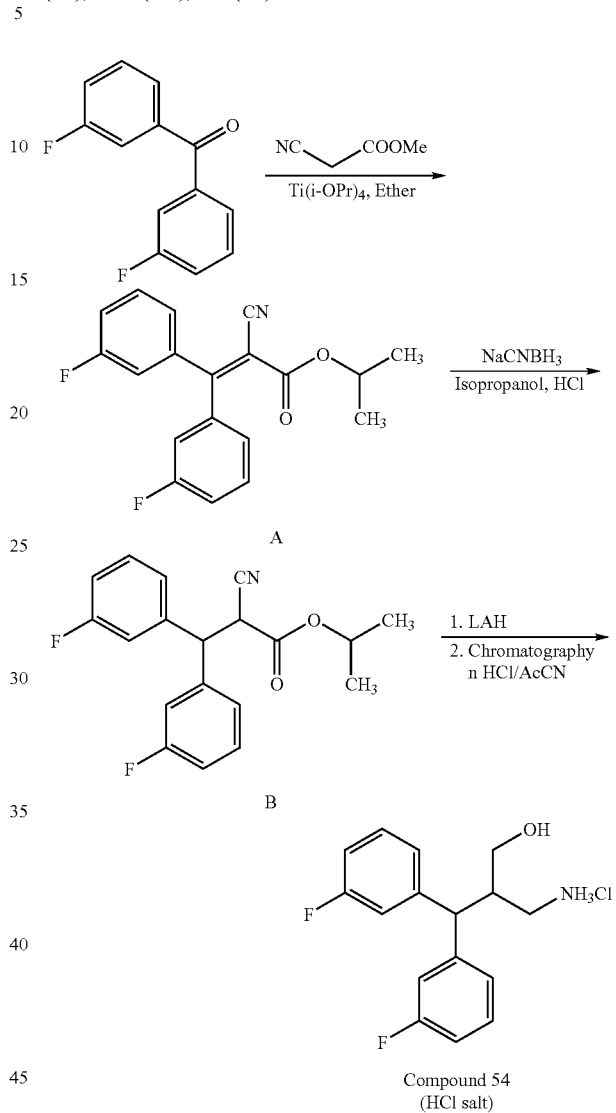

Compound 54
(HCl salt)

Compound 55 was synthesized analogously to Compound 21 except that ethyl iodide was used in the alkylation step. GC/EI-MS ($R_t$=7.43 min) m/z (relative intensity) 275 ($M^+$, 100), 258 (66), 229 (63), 204 (57) 201 (72), 183 (84), 134 (57), 124 (68), 109 (98), 72 (72).

The synthesis of Compound 56 was accomplished as follows.

The alcohol A was synthesized from 3-fluorobromobenzene and 3-fluoro-2-methylbenzaldehyde as described for product A Ln the synthesis of Compound 24.

The alcohol A (8.4 g, 36.2 mmol) was stirred with manganese dioxide (12.6 g, 144.8 mmol) in 100 ml of dichloromethane for 4 days. The reaction mixture was then diluted with ether and filtered through a 0.2 micron teflon membrane filter. The filtrate was concentrated to give 7.6 g of the ketone B.

The substituted acrylonitrile C was synthesized as described for product A in the Compound 20 synthesis.

To the nitrile C (4 g, 15.7 mmol) in 240 ml of ethanol was added 2 g of 10% palladium dihydroxide on carbon. This mixture was hydrogenated at 60–40 psi for 3 days. The reaction mixture was then filtered and concentrated. The resulting oil was dissolved in chloroform and chromatographed on silica.gel (30% methanol/5% isopropylamine in chloroform) to give the amine. This amine was dissolved in aqueous HCl/acetonitrile and purified via HPLC on C-18 (10% acetonitrile/0.1% HCl to 50% acetonitrile/0.1% HCl over 60 min) then lyophilized to give 800 mg of Compound 56, as the hydrochloride salt. GC/EI-MS ($R_t$=7.39 min) m/z (relative intensity) 261 ($M^+$, 64), 244 (56), 229 (57), 215 (100), 203 (53), 183 (21), 133 (39), 122 (31), 109 (32).

The synthesis of Compound 57 was accomplished as follows.

To a solution of 5-fluoro-2-methylbenzonitrile (5 g, 37 mmol) in 50 ml of THF was added 3-fluorophenylmagnesium bromide (46 ml, 40 mmol) and copper (I) cyanide (0.27 g, 0.8 mmol). this solution was refluxed for 4 hours, then poured into ether/20% HCl and stirred for a further 2 hours. The layers were separated, and the ether layer washed with water and saturated brine. The solution was dried over sodium sulfate and concentrated. The crude oil was purified on silica (hexane to 50% dichloromethane in hexane over 60 min) to give 6.7 g of the ketone A.

The ketone A was converted to Compound 57 as described for Compound 56. GC/EI-MS ($R_t$=7.35 min) m/z (relative intensity) 261 ($M^+$, 52), 244, (41), 229 (67), 215 (100), 203 (42), 201 (42), 183 (21), 133 (45), 122 (28), 109 (26).

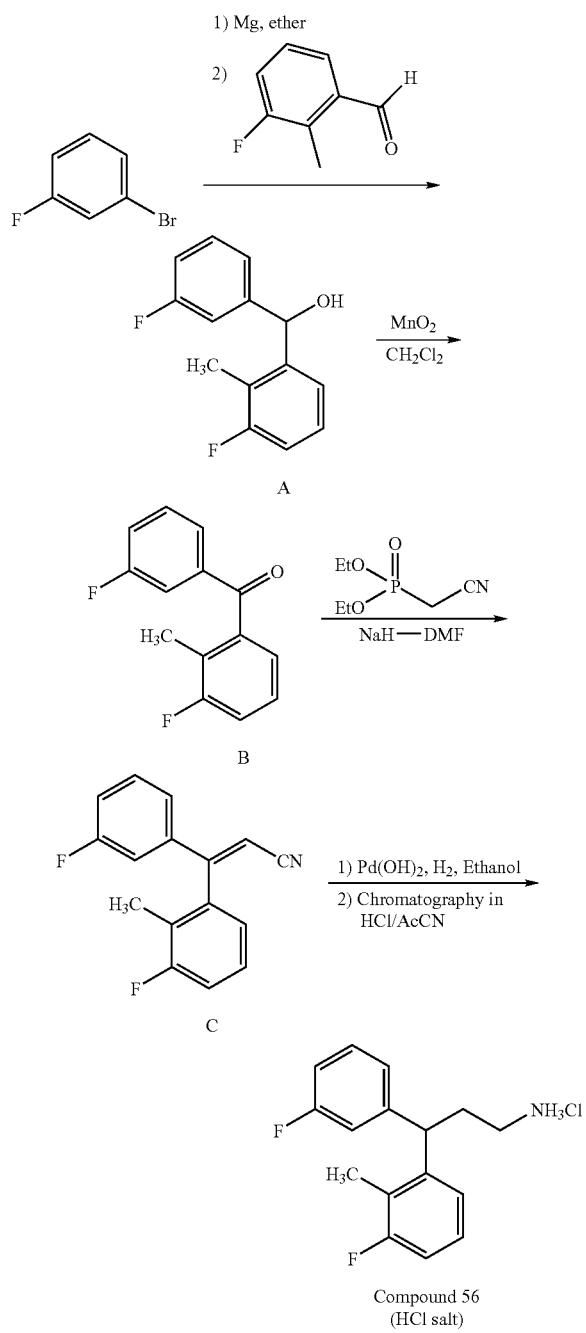

Compound 56
(HCl salt)

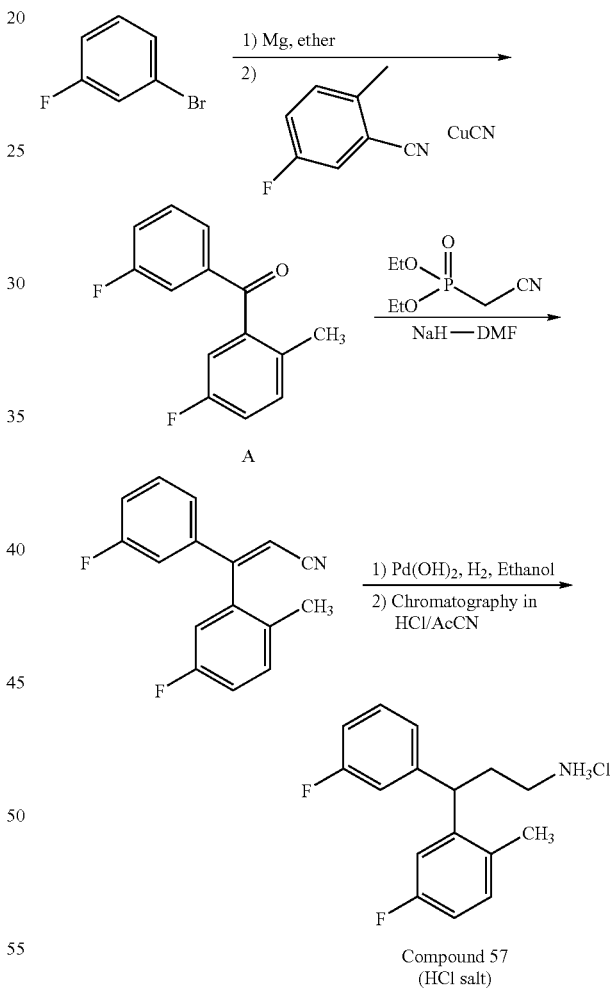

Compound 57
(HCl salt)

The synthesis of Compound 58 was accomplished as follows.

To a solution of 5-fluoro-2-methylbenzoyl chloride (2.24 g, 13 mmol) in 10 ml of dry THF was added iron III acetylacetonate (0.16 g, 0.44 mmol). The solution was cooled to 0° C., and a THF solution of 5-fluoro-2-methylphenylmagnesium bromide (20 ml, 15.5 mmol) was added by syringe over a period of 30 min. The reaction was stirred for another 30 min, then poured slowly into ether/5% HCl.

The ether layer was separated, washed with saturated brine, dried over sodium sulfate, and concentrated to give 3.2 g of ketone A.

Dry THF (30 ml)-was cooled to −78° C. followed by the addition of butyl lithium (5.85 ml, 14.6 mmol, 2.5 M solution in hexanes). Acetonitrile (0.76 ml, 14.62 mmol) was then added over a period of 2 min, then allowed to stir at −78° C. for 15 min. To this solution was added ketone A (3 g, 12.2 mmol) in 5 ml of THF. The solution was stirred for 30 min at −78° C. then allowed to warm to room temperature and stirred overnight. The reaction mixture was partitioned between ether and 5% HCl. The ether layer was separated, washed with saturated brine, dried over sodium sulfate, and concentrated to give 2.2 g of the nitrile B.

The nitrile B (1 g, 3.48 mmol) was dissolved in 30 ml of ethanol and 3 ml of 10 N sodium hydroxide. To this solution was added 1 g of a 5% aqueous slurry of Raney nickel, and the mixture was hydrogenated at 60 psi for 20 hours. The reaction was filtered and concentrated to a white solid. This residue was taken up in ether/water and the ether layer separated. The ether solution was dried over sodium sulfate and concentrated to give 0.96 g of the hydroxyamine C.

The hydroxyamine C (0.96 g, 3.3 mmol) was taken up in concentrated HCl and heated to 700° C. which caused brief solution, and then precipitation of the alkene D. The alkene was collected by filtration and dissolved in 30 ml of ethanol and 1 ml of conc. HCl. Palladium dihydroxide on carbon (0.4 g) was added to the solution, and the mixture hydrogenated at 60 psi for hours. The product was isolated by filtering off the catalyst and evaporating the solvent. The residue was dissolved in 0.1% HCl and acetonitrile, and purified on C-18 (15% acetonitrile/0.1% HCl to acetonitrile) to give 0.6 g of Compound 58, as the hydrochloride salt. GC/EI-MS ($R_t$=7.82 min) m/z (relative intensity) 275 ($M^+$, 100), 258 (20) 243 (74), 229 (38), 214 (65) 201 (31), 196 (32), 183 (20), 148 (35), 138 (42), 133 (48), 122 (69), 109 (41).

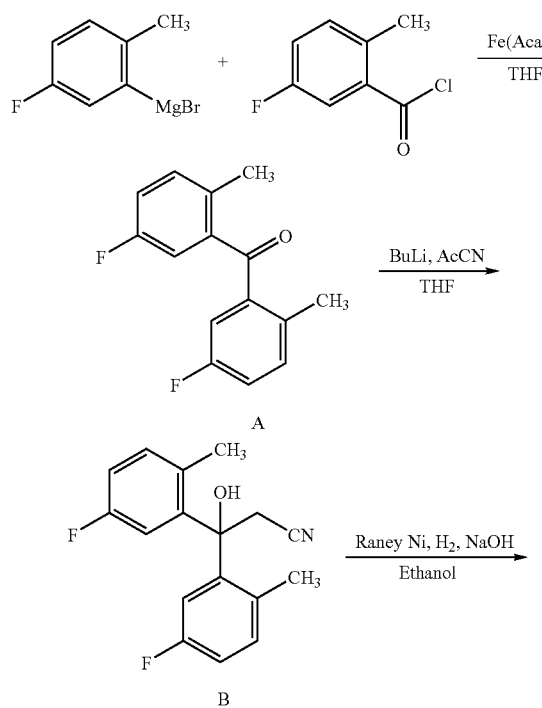

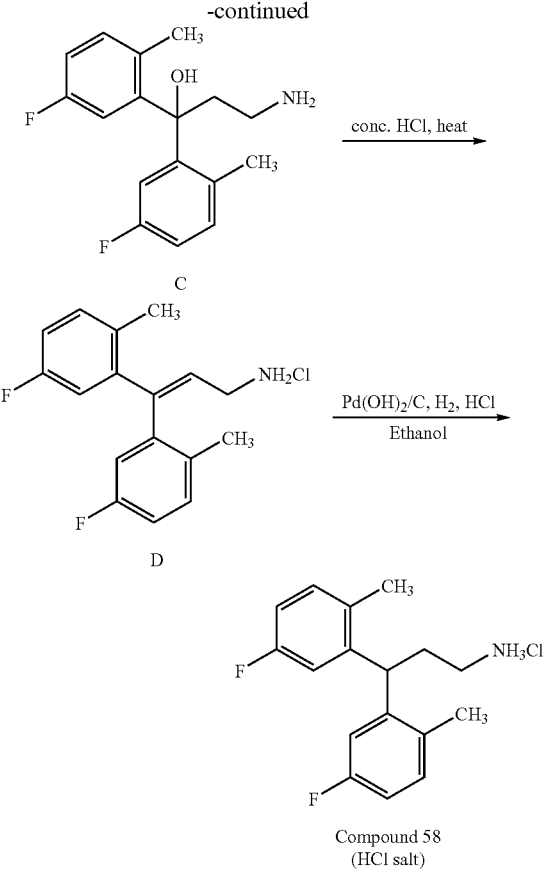

Compound 58
(HCl salt)

Synthesis of Compound 59 was accomplished as follows.

Compound 20 (2.0 g, 7.05 mmol) was dissolved in abs. EtOH (200 ml) and cooled to 5–10° C. in an ice bath. Acetaldehyde (0.395 ml, 7.05 mmol, cooled to −4° C.) was added followed by nickel-aluminum alloy (200 mg, Fluka Chemika), and the reaction was hydrogenated on a Parr apparatus at 50 psi for 2 hr. GC/MS showed 75% yield of the product and 2% of the N,N-diethyl side-reaction product. The reaction mixture was filtered through diatomaceous earth and the filtrate was evaporated under reduced pressure. The crude product was dissolved in isopropanol (5 ml)/ether (60 ml)/ethereal HCl (1 M), and then hexane (5 ml) was added to the cloud point. The cloudy mixture was filtered through paper, then hexane 10 ml was added to the cloud point, and the solution was filtered again. The filtrate was stoppered and the product was allowed to crystallize at room temperature. The crystals were collected and dried to provide 0.325 g (14.8% yield) of Compound 59, as the hydrochloride salt (colorless needles).

The synthesis of Compound 60 was accomplished as follows. Compounds 66, 69, 108, 123, 142, and 145 can be synthesized in a similar manner starting from Compounds 33, 50, 32, 60, 25 and 119, respectively.

Compound 20 (as the free base) (1.0 g, 4.0 mmol) was refluxed in ethyl formate (150 ml) for 2 hr. The solvent was then removed under reduced pressure to provide 1.1 g, 99% yield of formamide A as a colorless oil. GC/MS showed the product to be 100.0% pure and was used in the following step without further purification.

The formamide A (1.1 g, 4.0 mmol) was dissolved in dry THF (100 ml) and heated to reflux (no condenser). Borane-methyl sulfide complex (1.2 ml, 12 mmol, 10.5 M) was added dropwise over a period of 3 min to the refluxing solution. Reflux was maintained for approximately 15 min, open to the air, until the reaction volume was reduced to approximately 30 ml. The reaction was then cooled in an ice bath, and ice (5 g, small pieces) was carefully added followed by H$_2$O (25 ml) and conc. HCl (25 ml). The acidic solution was refluxed for 30 min. The reaction mixture was then cooled in an ice bath, basified with NaOH (10N), extracted with ether (3×100 ml), dried (Na$_2$SO$_4$, anhydrous) and evaporated under reduced pressure. The crude product was dissolved in ether (10 ml)/hexane (50 ml) and ethereal HCL (1 M) was added dropwise to precipitate the hydrochloride salt. The salt was collected and recrystallized from isopropanol (3 ml)/ether (40 ml) to provide 0.5 g of Compound 60, as the hydrochloride salt.

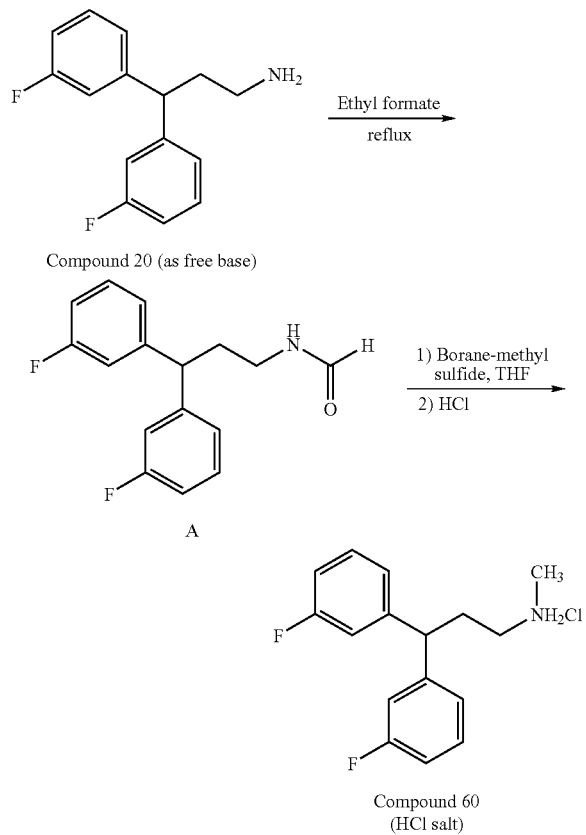

Compound 20 (as free base)

Ethyl formate
reflux

A

1) Borane-methyl sulfide, THF
2) HCl

Compound 60
(HCl salt)

Alternatively, Compound 60 was synthesized from commercially available starting materials in the following four step reaction sequence. The first intermediate in this synthetic route, ethyl-N-benzyl-N-methyl-3-aminopropionate, was prepared by conjugate addition of N-benzylmethylamine to ethyl acrylate. The ester functionality of the first intermediate was then reacted with two equivalents of Grignard reagent (prepared from 1-bromo-3-fluorobenzene) to provide N-benzyl-N-methyl-3-hydroxy-3(bis-3-fluorophenyl) propylamine. The Grignard reaction product was then dehydrated in a mixture of 6N HCl/acetic acid to yield N-benzyl-N-methyl-3-(bis-3-fluorophenyl)-2-propenamine. Catalytic hydrogenation of this material as its hydrochloride salt in ethanol over Pearlman's catalyst [Pd(OH)$_2$/C] provided, after, recrystallization from ethyl acetate, colorless, needles of Compound 60 as the hydrochloride salt.

In a 500-mL, 3-necked flask equipped with thermometer, reflux condenser, and a 125-mL addition funnel [charged with ethyl acrilate (88.3 mL, 81.5 g, 0.815 mol)] was placed N-benzylmethylamine (100 mL, 94.0 g, 0.776 mol). The ethyl acrylate was added dropwise to the stirring reaction mixture over a period of 80 min. After stirring for 18 h at room temperature, the product was vacuum distilled and the fraction containing product was collected at 78–95° C. (0.12–0.25 mm Hg), (138 g, 80% yield): Bp 78–95° C. (0.12–0.25 mm Hg); TLC, R$_f$ 0.23 [hexane-EtOAc (5:1)], R$_f$=0.57 [MeOH—CHCl$_3$ (100:5)] GC, t$_R$=6.06 min; MS, 221 (M$^+$), 206 (M-CH$_3$), 192 (M-C$_2$H$_5$), 176 (M-OC$_2$H$_5$), 144 (M-C$_6$H$_5$), 134 [CH$_2$N(CH$_3$) CH$_2$Ph] 120 [N(CH$_3$) CH$_2$Ph], 91 (C$_7$H$_7$), 77 (C$_6$H$_5$), 42 (CH$_2$CH$_2$N); $^1$H NMR (free base, CDCl$_3$) d 1.25 ppm (t, J=7.1, 3H, CH$_2$CH$_3$), 2.20 (s, 3H, NCH$_3$), 2.5I (t, J=7.3, 2H, COCH$_2$), 2.74 (t, J=7.2, 2H, CH$_2$N), 3.51 (s, 2H, NCH$_2$Ph), 4.13 (q, J=7.1,. 2H, OCH$_2$CH$_3$), 7.18–7.35 (m, 5H, ArH); $^{13}$C NMR (free base, CDCl$_3$) d 15.2 (CH$_2$CH$_3$), 34.0 (COCH$_2$), 42.9 (NCH$_3$), 53.8 (NCH$_2$), 61.4 (OCH$_2$CH$_3$), 63.1 (CH$_2$Ph), 128.0 (CH), 129.2 (CH), 130.0 (CH), 139.9 (q), 173.7 (q).

In a 5-L, four-necked, round-bottom flask, under nitrogen, were placed Mg [51.5 g, 2.12 mol, turnings, washed with THF (2×300 mL) and THF (2 L). An addition funnel was charged with 1-bromo-3-fluorobenzene (neat, 392.8 g, 2.24 mol). One-twentieth of the bromide was added to the magnesium suspension followed by one crystal of iodine. After initiation of the Grignard reaction the remaining 1-bromo-3-fluorobenzene was then added to the refluxing mixture over a period of 50 min. The reaction was refluxed for an additional 45 min. To the refluxing solution of Grignard reagent was added a solution of ethyl N-benzyl-N-methyl-3-aminopropionate (187.5 g, 0.847 mol) in THF (100 mL) over a period of 20 min. After the ester addition was complete, the reaction was refluxed for 1 h. The reaction was then cooled in an ice bath. Saturated NH$_4$Cl (aq., 400 mL) and H$_2$O (400 mL) were added and the mixture was transferred to a separatory funnel. The organic layer was separated and the aqueous layer was extracted once with THF (400 mL). The combined organic layers were washed with satd. NaCl (2×200 mL, aq.), dried (anh. Na$_2$SO$_4$), filtered through paper, and rotary evaporated vacuum to yield 281.6 g (90%) of crude product as an orange, viscous oil. This material (281.6 g, 0.766 mol) was dissolved in acetonitrile (1.4 L). Concentrated hydrochloric acid (65.0 mL, 0.786 mol, 12N) was added to the stirring filtrate. The crystallizing mixture was then cooled to −20° C. for 17 h. The product was collected, washed with cold acetonitrile (800 mL), and dried to provide a white solid, 235.6 g (69% yield from the ester). For analytical purposes, the hydrochloride salt was further purified by recrystallization from acetonitrile: mp 194–197° C. (uncorr.); TLC, R$_f$=0.23 (hexane-EtOAc (5:1)], R$_f$=0.85 [MeOH—CHCl$_3$ (100:5], R$_f$=0.72 [MeOH—CHCl$_3$ (100:3)]; GC, t$_R$=10.93 min; MS, 367 (M$^+$), 272 (M-C$_6$H$_4$F), 258 (M-CH$_2$Ph-H$_2$O), 219 [(C$_6$H$_4$F)$_2$ CH], 148 [CH$_2$CH$_2$N(CH$_3$)CH$_2$Ph], 134 [CH$_2$N (CH$_3$ CH$_2$Ph], 91 (C$_7$H$_7$, 42 (CH$_2$CH$_2$N); $^1$H NMR (free base, CDCl$_3$) d 2.18 (s, 3H, NCH$_3$), 2.41 (m, 2H, CHCH$_2$), 2.58 (m, 2H, CH$_2$N), 3.42 (s, 2H, CH$_2$PH), 6.86 (dt, J$_1$=8.5, J$_2$=1.8, 2H, Ar—H), 7.18–7.30 (m, 10H, Ar—H), 8.33 (bs, 1H, OH); $^{13}$C NMR (free base, CDCl$_3$) d 35.6 (CHCH$_2$), 41.5 (CH$_3$, NCH$_3$), 54.3 (CH$_2$, CH$_2$N), 62.6 (CH$_2$,CH$_2$Ph), 113.1 (d, J=23, CH, Ar—C$_{5,5'}$), 113.5 (d, J=23, CH), 121.2 (d, J=3, CH), 127.5 (CH), 128.5 (CH), 129.2 (CH), 129.5 (CH), 129.6 (CH), 137.0 (q), 150.2 (q), 162.8 (d, J=243, q, Ar—C$_{3,3'}$).

In a 5-L, 3-necked reaction vessel, equipped with an overhead mechanical stirrer, reflux condenser, and thermometer, was placed N-benzyl-N-methyl-3-hydroxy-3-bis (3-fluorophenyl) propylamine hydrochloride (225.4 g, 0.559 mol), 6N HCl (1392 mL) and glacial HOAc (464 mL). The suspension was heated in a water bath (80–85° C.) and stirred for 18 h. After 18 h of heating, the reaction mixture was cooled in an ice/MeOH bath. Ethyl acetate (500 mL) was added to the cooled reaction mixture. NAOH (10N, 1.7 L) was then added to the cooled mixture over a period of 25 min at such a rate as to keep the temperature below 40° C. The mixture was transferred to a 6-L separatory funnel. The organic layer was separated and the aqueous layer was extracted with ethyl acetate (2×500 mL). The combined organic layers were washed with satd. NaCl (2×100 mL, aq.), dried $Na_2SO_4$ (250 g), rotary evaporated, and then dried under vacuum to provide 185.6 g (95% yield) of the free base as a fluid, brownish-colored oil.

The material above was stirred with hexane (1.5 L). The resulting solution was filtered through paper. 4M HCl in dioxane (146 mL) was added dropwise with stirring to the filtrate over a period of 5 min. The semi-translucent solvent was then decanted away from the light-yellow colored, semisolid precipitate. The crude hydrochloride salt was dissolved in refluxing ethyl acetate (600 mL) and was filtered. The filtrate was then thoroughly cooled in an ice bath, and hexane (110 mL) was slowly added, with vigorous stirring. After cooling in an ice bath for 2 h, the entire flask filled with a white crystalline solid. This material was collected on a filter funnel, washed with ice-cold hexane/ethyl acetate E(1:41, 400mL], and dried to yield 128.7 g, 59.7% of a white solid. On standing the mother liquor precipitated another 14.8 g of an off-white solid. Total yield 128.7 g+14.8 g=143.5 (67%). Mp 141–142 ° C. (uncorr.); TLC, $R_f$=0.20 [hexane-EtOAc (5:1)], $R_f$=0.75 [MeOH—$CHCl_3$ (100:5)], $R_f$=0.49 [MeOH—$CHCl_3$ (100:3)]; GC, $t_R$=10.40 min; MS, 349 ($M^+$), 330, 301, 281, 258 (M-$CH_2Ph$), 240, 229 [M-N($CH_3$)$CH_2Ph$], 201, 183, 146, 133, 109, 91 ($CH_2C_6H_5$), 65, 42 ($CH_2NHCH_3$); $^1H$ NMR (free base, $CDCl_3$) d 2.20 ppm (s, 3H, N$CH_3$), 3.08 (d, J=6.8, 2H, $CH_2$N), 3.47 (d, J<1, 2H, $CH_2$Ph), 6.29 (t, J=6.8, 1H, CH), 6.85–7.04 (m, 6H, ArH), 7.19–7.35 (m, 7H, ArH).

N-Benzyl-N-methyl-3-bis(3-fluorophenyl)allylamine hydrochloride (120.0 g, 0.311 mol) was dissolved in abs. EtOH (1250 mL). Pd(OH)$_2$/charcoal (10.0 g, ~20% Pd, Fluka Chemical) was added. The reaction mixture was stirred under a steady flow of hydrogen gas for 18 h at 25° C. (atmospheric pressure). The mixture was then filtered through Celite®/fritted glass, the catalyst was washed with ETOH (2×50 mL), and the solvent was removed under reduced pressure to yield 95.4 g, 103% of crude product. This material was dissolved in refluxing ethyl acetate (300 mL) with vigorous stirring and filtered. The flask was allowed to stand for 2 h at 25° C., during which time the hydrochloride salt began to crystallize as needles. The flask was then cooled, the product was collected, washed with ice-cold ethyl acetate (20 mL), and dried to yield 73.7 g, 80%, of Compound 60 as a white, crystalline solid. Mp 129–130° C.; UV/Vis, e=2.1×$10^3$ L $mol^{-1}$ $cm^{-1}$ (264 nm, EtOH, 25° C., linear range: 0.05–0.20 mg/mL); TLC, $R_f$=0.00 [hexane-EtOAc (5:1)], $R_f$=0.07 [MeOH—$CHCl_3$ (100:5)], $R_f$=0.19 [MeOH—$CHCl_3$—$NH_4OH$ (100:5:1)]; GC, $t_R$=7.45 min; MS, 261 ($M^+$), 229, 215, 201, 183, 164, 150, 138, 122, 101, 83, 75, 57, 42, [$CH_2NHCH_3$], $^1H$ NMR (HCl salt, $CDl_3$ +1 gtt MeOD) δ 2.56 (m, 2H, N$CH_2$), 2.60 (s, 3H, NC$H_3$) 2.85 (t, J=8.0, 2H, CH$CH_2$) 4.11 (t, J=8.0, 1H, CH), 6.87–6.98 (m, 4H, ArH), 7.06 (d, J=7.7, 2H, $Ar_{2,2'}$,H), 7.25 (dd, $J_1$=6, $J_2$=8, ArH); $^{13}C$ NMR (HCl salt, $CDCl_3$ +1 gt MeOD) δ 30.9 ($CH_2$, CH$CH_2$), 32.7 ($CH_3$, N$CH_3$), 47.6 (CH, $CHCH_2$), 47.8 ($CH_2$, $CH_2$N), 113.9 (J=21, $ArC_{2,2'}$ or $ArC_{4,4'}$), 114.5 (d, J=22, $ArC_{2,2'}$ or $ArC_{4,4'}$), 123.2 (d, J=3, Ar—$C_{6,6'}$), 130.3 (d, J=9, Ar—$C_{5,5'}$), 144.7 (d, J=7, Ar—$C_{1,1'}$), 162.9 (d, J=245, Ar—$C_{3,3'}$); IR: KBr pellet ($cm^{-1}$), 3436.9, 2963.4, 2778.5, 2453.7, 1610.6, 1589.3, 1487.0, 1445.3, 1246.0, 764.5; solubility: 2 g/mL ($H_2O$), 1 g/mL (ETOH); anal. calcd. for $C_{16}H_{17}NF_2$-HCl Karl Fischer: 0.26 $H_2O$): C, 64.37; H, 6.11; N, 4.69. found: C, 64.14; H, 6.13; N, 4.69.

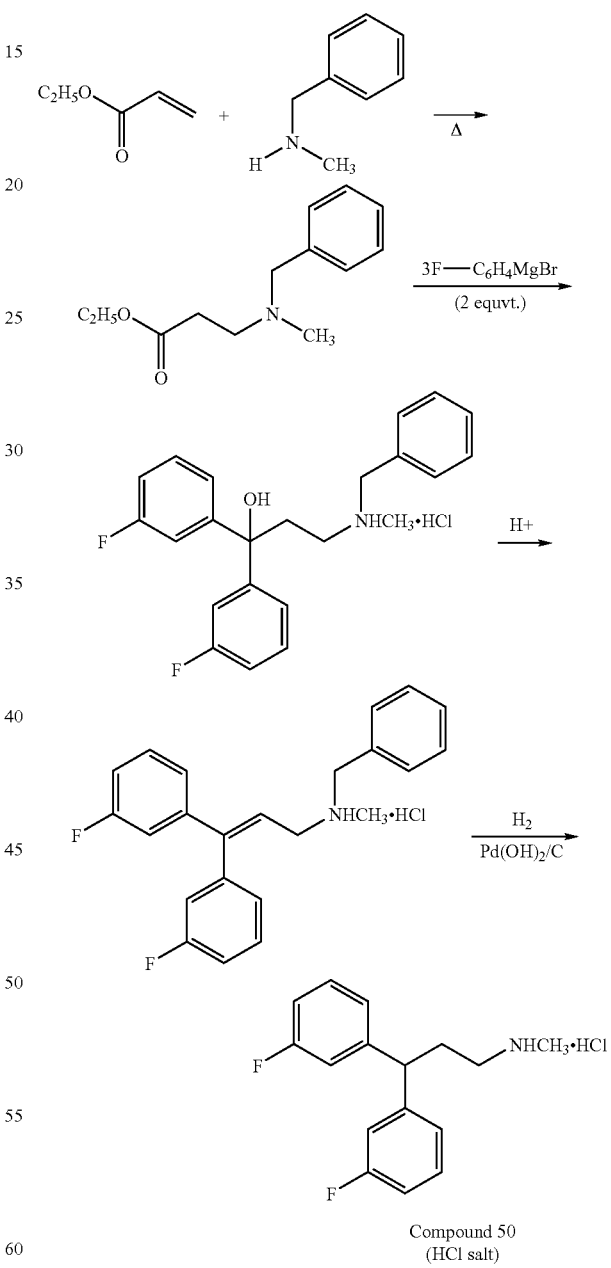

Compound 50
(HCl salt)

Compound 105 was prepared by selective reduction of its corresponding alkene by catalytic hydrogenation over Pd/C.

Compound 61 was prepared from 2-bromo-4-fluoroanisole and 3-fluorobenzaldehyde as described for Compound 24. GC/EI-MS ($R_t$=9.22 min) m/z (relative intensity) 277

(M+, 74), 260 (46), 245 (35), 231 (44), 229 (34), 217 (24), 203 (28), 201 (31), 183 (28), 154 (24), 133 (19), 109 (100).

Compound 62 was prepared from 2-bromoanisole and 2-methoxybenzaldehyde as described for Compound 24. GC/EI-MS (R$_t$=9.30 min) m/z (relative intensity) 271 (M+, 100), 254 (17), 240 (23), 225 (40), 223 (45), 207 (22), 181 (32), 165 (31), 136 (48), 121 (98), 91 (83).

The synthesis of Compound 63 was accomplished as follows.

Alcohol A was obtained from 3-fluorobenzaldehyde as described for product A of the Compound 24 synthesis.

To alcohol A (10.275 g, 47 mmol) in 200 ml of ethanol was added 1.6 g of 10% Pd/C and 1 ml of concentrated HCl. This mixture was hydrogenated for 3 hr at 60 psi, then filtered and concentrated to give the diphenylmethane B.

Product-B (2.01 g, 9.86 mmol) was dissolved in 20 ml of THF and cooled to −78° C. Butyl lithium (4.4 ml, 10.8 mmol, 2.5 M in hexanes) was added slowly by syringe, and then the reaction stirred for another 30 min at −78° C. To this orange solution was added cyclopentene oxide (0.9 ml, 10.3 mmol). The reaction was allowed to stir 3 hours while warming slowly to room temperature. The reaction was quenched with 150 ml of 10% HCl and extracted 3 times with ether. The ether layer was dried over sodium sulfate and concentrated to give 2.5 g of the alcohol C.

To the alcohol C (1 g, 3.5 mmol) in 10 ml of dry THF was added triphenylphosphine (1.37 g, 5.2 mmol) in 5 ml of THF and p-nitrobenzoic acid (0.87 g, 5.2 mmol) in 5 ml of THF. This solution was cooled to 0° C. followed by the addition of DEAD (0.82 ml, 5.2 mmol), and allowed to stir overnight. The reaction was partitioned between water and ether. The ether was removed in vacuo and the resulting oil was chromatographed on silica gel in hexane/ethyl acetate to yield 365 mg of the cis-ester. This ester was hydrolyzed in methanol with potassium carbonate by stirring overnight. After removal of the methanol, the residue was taken up in ether, washed with water, dried over sodium sulfate and concentrated to give 250 mg of the cis alcohol D.

To the alcohol D (0.25 g, 0.9 mmol) in 5 ml of dry THF was added triphenylphosphine (342 mg, 1.3 mmol) in 5 ml of THF and phthalimide (191.3 mg, 1.3 mmol) in 5 ml of THF. This solution was cooled to 0° C. followed by the addition of DEAD (0.205 ml, 1.3 mmol), and allowed to stir overnight. The reaction was partitioned between water and ether. The ether was removed in vacuo and the resulting oil was chromatographed on silica gel in hexane/ethyl acetate to yield 100 mg of the phthalimide E.

To a solution of the phthalimide E (100 mg) in 20 ml of ethanol was added 8.8 mg of hydrazine hydrate. The solution was refluxed for 5 hours then stirred at room temperature overnight. The reaction was worked up by adding 1 ml of conc. HCl and filtering off the white solid. The resulting solution was concentrated to dryness and the solid taken up in ether and aqueous sodium hydroxide. The ether layer was dried over sodium sulfate and concentrated to a white solid. This was taken up in a small amount of ether and treated with 10 drops of 1M HCl in ether. After stirring overnight, the white solid was collected by filtration and dried to give 50 mg of Compound 63, as the hydrochloride salt. GC/EI-MS (R$_t$=9.22 min) m/z (relative intensity) 287 (M+, 45), 270 (12), 201 (63), 183 (81), 133 (38) 109 (43), 83 (44), 56 (100), 43 (37).

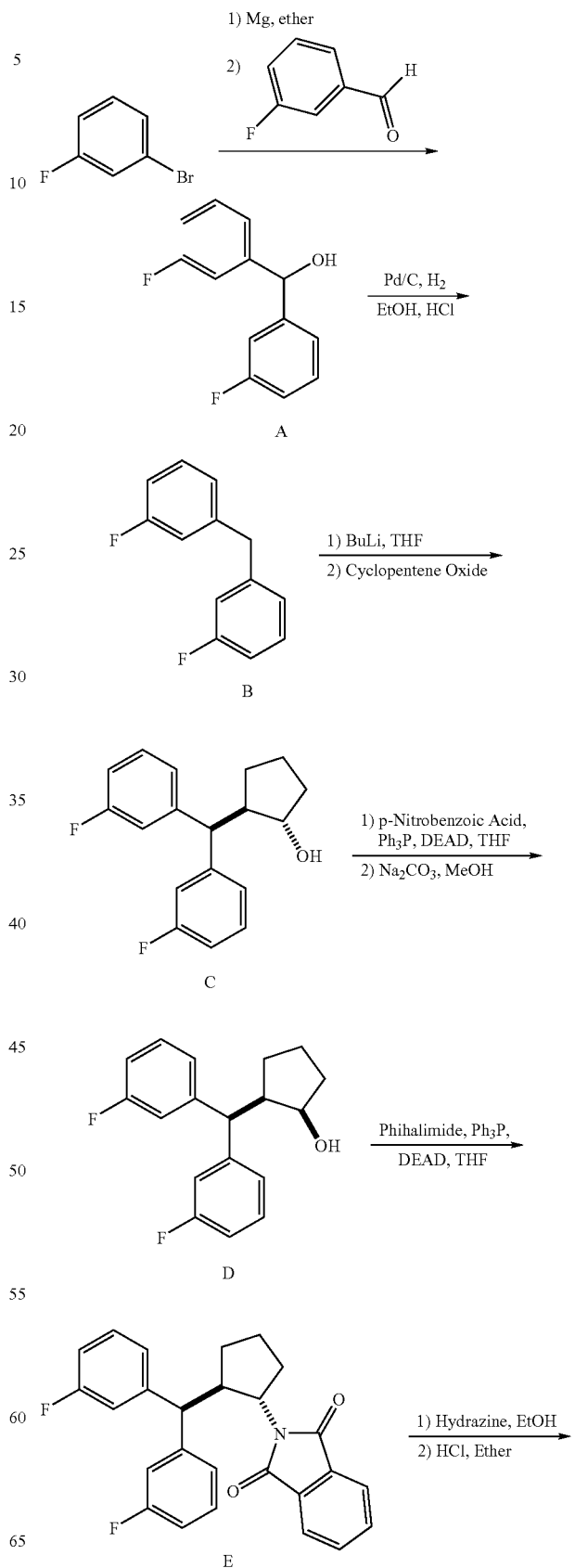

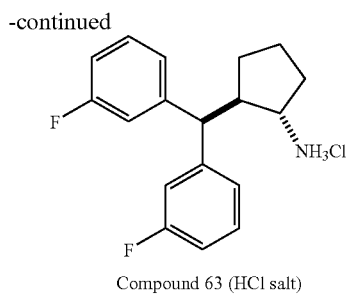

Compound 63 (HCl salt)

The synthesis of Compound 64 was done as described for Compound 63 except that the inversion step (product C to D) was omitted in order to obtain the cis amine as the final product. GC/EI-MS ($R_t$=8.28 min) m/z (relative intensity) 287 (M+, 15), 270 (4), 201 (13), 183 (15), 133.(11), 109 (16), 84 (43), 56 (100), 43 (32).

The synthesis of Compound 65 was accomplished as follows.

The ketone A was synthesized similarly to ketone B in the Compound 24 synthesis using 2-methylphenylmagnesium bromide and 2-methylbenzaldehyde as starting materials. This ketone was converted to the final product using the procedure outlined for Compound 58. GC/EI-MS ($R_t$=7.84 min) m/z (relative intensity) 239 (M+, 88), 222 (14), 207 (100), 193 (46), 178 (71), 165 (60), 130 (39), 120 (40), 115 (51), 104 (40),91 (38), 77 (21).

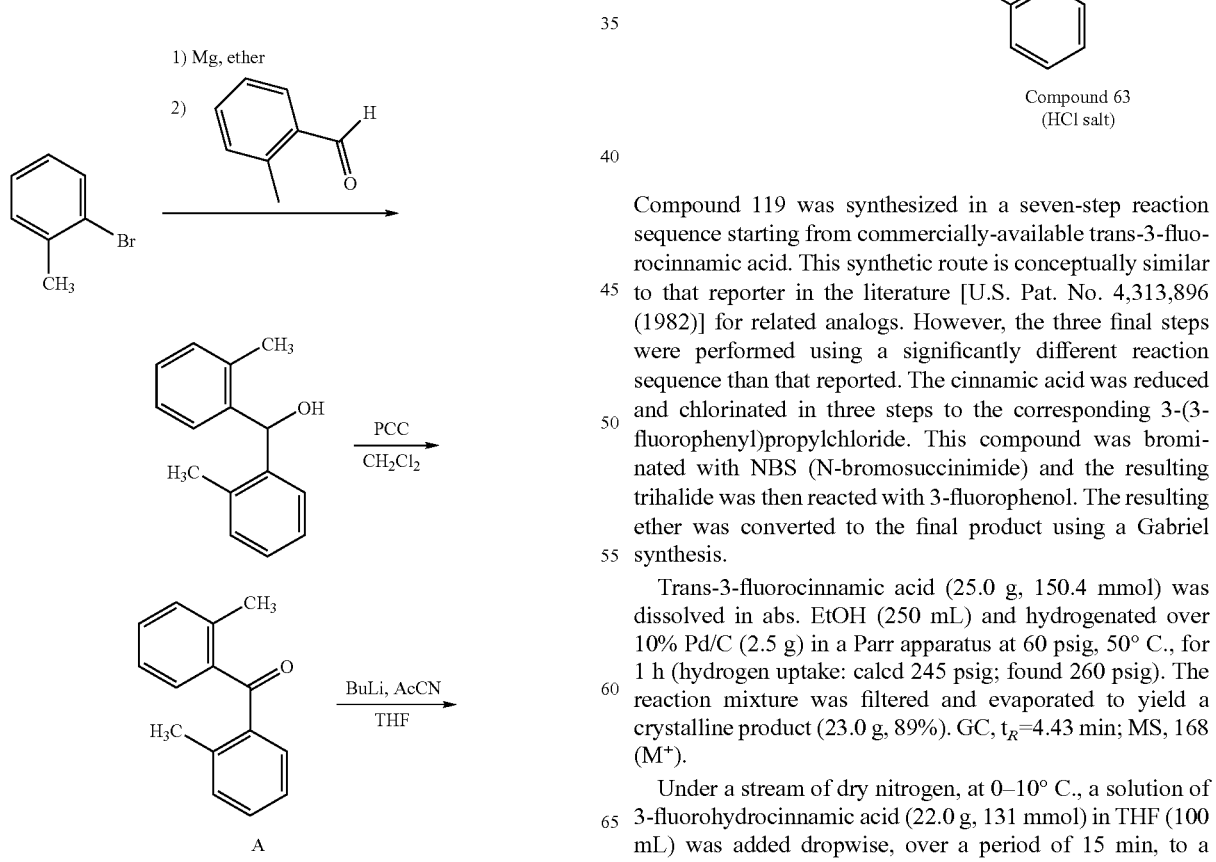

Compound 63 (HCl salt)

Compound 119 was synthesized in a seven-step reaction sequence starting from commercially-available trans-3-fluorocinnamic acid. This synthetic route is conceptually similar to that reporter in the literature [U.S. Pat. No. 4,313,896 (1982)] for related analogs. However, the three final steps were performed using a significantly different reaction sequence than that reported. The cinnamic acid was reduced and chlorinated in three steps to the corresponding 3-(3-fluorophenyl)propylchloride. This compound was brominated with NBS (N-bromosuccinimide) and the resulting trihalide was then reacted with 3-fluorophenol. The resulting ether was converted to the final product using a Gabriel synthesis.

Trans-3-fluorocinnamic acid (25.0 g, 150.4 mmol) was dissolved in abs. EtOH (250 mL) and hydrogenated over 10% Pd/C (2.5 g) in a Parr apparatus at 60 psig, 50° C., for 1 h (hydrogen uptake: calcd 245 psig; found 260 psig). The reaction mixture was filtered and evaporated to yield a crystalline product (23.0 g, 89%). GC, $t_R$=4.43 min; MS, 168 (M+).

Under a stream of dry nitrogen, at 0–10° C., a solution of 3-fluorohydrocinnamic acid (22.0 g, 131 mmol) in THF (100 mL) was added dropwise, over a period of 15 min, to a suspension of LiAlH$_4$, (4.23 g, 111 mmol) in THF (200 mL).

The reaction was heated to reflux for a period of 1 h and then worked-up according to Fieser & Fieser's Reagents for Organic Synthesis (Vol. 1, 1967) to provide a white solid (20.1 g, 99%). GC, $t_R$=3.74 min; MS, 154 (M$^+$).

A solution of 3-(3-fluorophenyl)-1-propanol (15.0 g, 97.4 mmol) and triphenylphosphine (36.0 g, 137.3 mmol) in CCl$_4$, (150 mL) was refluxed for 19 h. Additional P(C$_6$H$_5$)$_3$ (3×3.0 g, 3×11.4 mmol) was added periodically over a period of 24 h. The resulting precipitate was removed by filtration and the solids were washed with hexane. The filtrate was evaporated under vacuum and the residue was suspended in hexane (200 mL) and then filtered. Evaporation of the filtrate provided 16.0 g (95.1%) of crude product which was purification by silica gel flash chromatography, elution with hexane, to provide 14.7 g (87%) of a colorless liquid. GC, $t_R$=3.63 min; MS, 172/174 (M$^+$).

A solution of the above chloride (12.0 g, 69.5 mmol), N-bromosuccinimide (17.3 g, 97.2 mmol), and dibenzoyl peroxide (0.06 g) in CCl$_4$, (75 mL) was refluxed for 1 h. The reaction mixture was then cooled in an ice bath, filtered, and the solids were washed with hexane. The filtrate was evaporated to provide 17.9 g (100%) of product. GC, $t_R$=5.21 min; MS, 251/253 (M$^+$).

A mixture of 3-bromo-3-(3-fludrophenyl) -1-propylchloride (4.0 g, 15.9 mmol), 3-fluorophenol (1.98 g, 17.7 mmol), and K$_2$CO$_3$ (2.65 g, 19.2 mmol) suspended in acetone (80 mL) was refluxed for 15 h. The volatiles were then removed under vacuum and the resulting residue was suspended in a mixture of hexane (200 mL) and NaOH (0.1N, 100 mL). The layers were separated and the organic layer washed, 1.0N NaOH (100 mL) and H$_2$O (100 mL), dried (anh. Na$_2$SO$_4$), and evaporated in vacuo. The resulting residue was chromatographed on silica gel, elution with hexane followed by hexane/EtOAc [100:1 ] then [40:1] to provide 1.64 g (37%) of product as a colorless oil. GC, $t_R$=7.28 min; MS, 282/283 (M$^+$); TLC r$_f$=0.3, hexane/EtOAc [40:1].

A solution of 3-(3-fluorophenyl)-3-(3-fluorophenoxy)-1-propylchloride (1.52 g, 5.38 mmol) and potassium phthalate (1.20 g, 6.48 mmol) was heated to 90° C. in DMF (30 mL) for a period of 2 h in a nitrogen atmosphere. The reaction mixture was then cooled and poured into H$^2$O (100 mL). The resulting solution was extracted with Et$_2$O (2×100 mL). The organic extract was washed, sat. NaCl (100 mL) and H$_2$O (2×100 mL), dried (anh. Na$_2$SO$_4$), and evaporated under vacuum to provide 2.17 g of crude product. The material was chromatographed on silica gel, elution with hexane/EtOAc (40:1) and then [20:1] to provide after evaporation 1.81 g (86%) of product as a glass.

A solution of N-phthaloyl-3-(3-fluorophenyl)-3-(fluorophenoxy)-1-propylamine (1.74 g, 4.42 mmol) and anh. hydrazine (1.43 g, 44.6 mmol) in abs. EtOH (30 mL) was refluxed for 1 h. The reaction was cooled and evaporated under vacuum. The resulting material was suspended in Et$_2$O (75 mL) and washed with 0.2N NaOH (2×25 mL). The organic layer was dried (anh. Na$_2$SO$_4$), and evaporated under vacuum to provide 1.04 g (89.3%) which was purified by reverse-phase chromatography [Vydac Prep. C18; 264 nm; 50 mL/min; gradient elution ACN/0.1% HCl aq., 10%–50% over 20 min; r$_t$=17.4 min], to yield 0.89 g (67%) of Compound 119 as a hygroscopic hydrochloride salt.

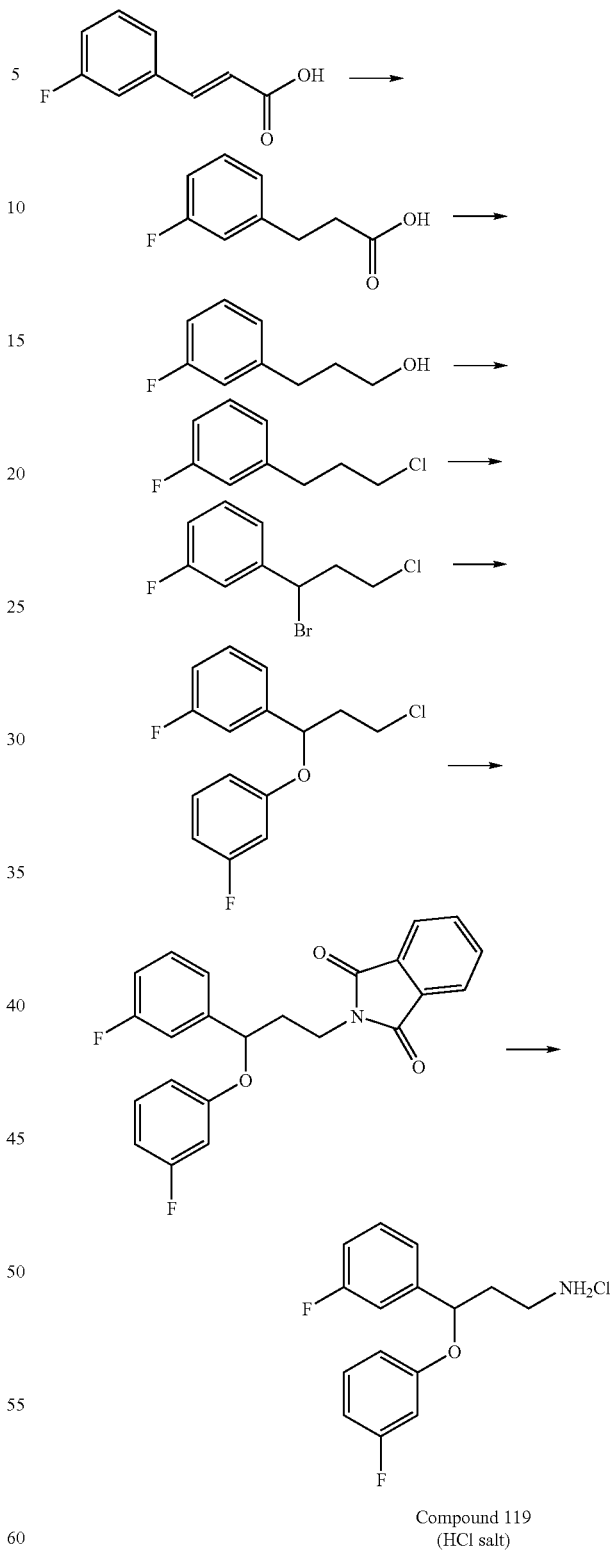

Compound 119
(HCl salt)

Compounds 118, 120–122 and 137 were prepared in a manner similar to the procedures used for the preparation of Compound 119.

Compound 113 was synthesized from commercially available 4,4-diphenylcyclohexenone in three steps. First, the alkene in the starting material was reduced by means of catalytic hydrogenation. Methoxylamine formation followed by reduction using standard procedures.

The synthesis of Compounds 188 and 189 was accomplished as follows.

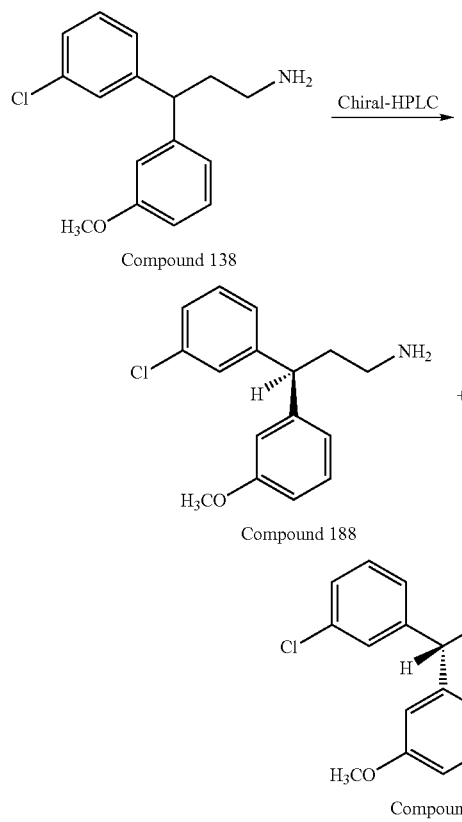

Compound 138

Compound 188

Compound 189

Compounds 188 and 189

The enantiomers of Compound 136 were separated by analytical chiral HPLC. Aliquots (20 μg) were injected onto a Chiralcel-OD-R (Chiral Technologies, Inc., Exton, Pa.) reversed-phase HPLC column (0.46×250 mm) using the following conditions: gradient elution, 40%–70% ACN (60–30% 0.5N KTFA) over 30 min; flow rate, 1 mL/min; detector, 264 nm. Two identically-sized peaks were collected at 21.0 and 24.4 min. GC/MS analysis of the two samples indicate that both materials have identical GC retention times as well as identical mass spectra.

The synthesis of Compound 151 was accomplished as follows.

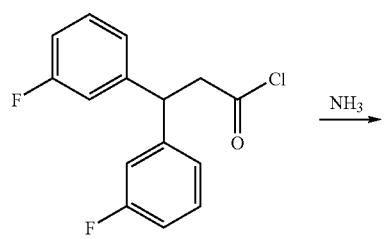

-continued

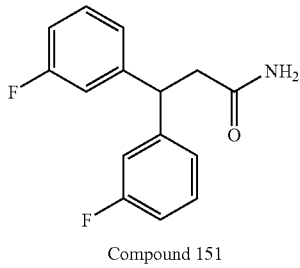

Compound 151

3,3-Bis(3-fluorophenyl)propanamide (Compound 151)

A solution of liquid anh. ammonia (10 mL) in CH$_2$Cl$_2$ (50 mL) at −78° C. was treated with a solution of 3,3-bis(3-fluorophenyl)propionyl chloride (2.19 g, 7.81 mmol) in CH$_2$Cl$_2$ (25 mL). The reaction was then stirred at ambient temperature for 15 min and was then diluted with diethyl ether (500 mL), washed three times with 10% HCl, three times with 1N NaOH, and finally once with H$_2$O. The organic layer was dried (anh. Na$_2$SO$_4$) and evaporated to give the primary amide as a white solid (2.01 g, 98%).

The synthesis of Compound 156 was accomplished as follows.

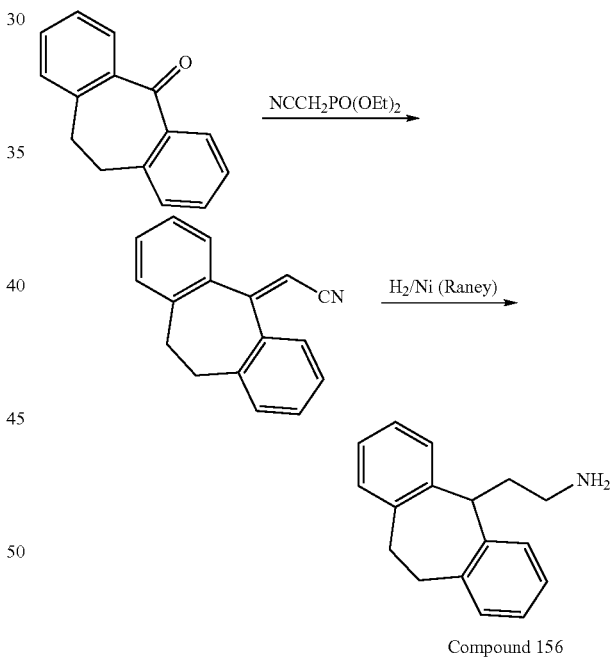

Compound 156

5-Cyanomethylidino-10,11-dihydrodibenzo[a,d]cycloheptene

To a solution of diethyl cyanomethylphosphonate (9.66 g, 54.5 mmol) in dry N,N-dimethylformamide (DMF, 40 mL) was added NaH (60% dispersion, 2.20 g, 55.0 mmol) over a period of 2 min. The reaction was stirred for 10 min and then a solution of dibenzosuberone (10.3 g, 49.6 mmol) in dry DMF (10 mL) was added over a period of 2 min. The reaction was stirred at 80° C. for 4 h under N$_2$. Water (200 mL) was added and the reaction mixture was extracted with Et$_2$O (2×100 mL). The combined organic layers were rotary evaporated to less than 50 mL. The resulting crystals were collected and washed with cold Et$_2$O (2×50 mL) to yield 7.48 g (65.3%).

5-(2-Aminoethyl)-5H-10,11-dihydrodibenzo[a,d]cycloheptene hydrochloride (Compound 156)

5-Cyanomethylidino-10, 11-dihydrodibenzo[a,d]cycloheptene was dissolved in EtOH (100 mL). 1N NaOH (10 mL) and Raney® nickel (aq. suspension, 0.50 g) were added. The reaction mixture was shaken under 60 psig H$^2$ at 50° C. for 22 h, and was then filtered through Celite®. The filtrate was rotary evaporated and the residue was dissolved in Et$_2$O (100 mL), washed with satd. aq. NaCl (50 mL) and H$_2$O (50 mL). The Et$_2$O layer was dried (anh. Na$_2$SO$_4$) and rotary evaporated to give the crude product (850 mg) as a colorless oil. This oil was dissolved in EtOAc (5 mL) and filtered. 1.0M HCl (5 mL) in Et$_2$O was added to the filtrate and a white, crystalline solid precipitated. This material was recrystallized from EtOH (5 mL)-Et$_2$O (12 mL) to yield 600 mg (50.7%) of product as a white powder.

The synthesis of Compound 167 was accomplished as follows.

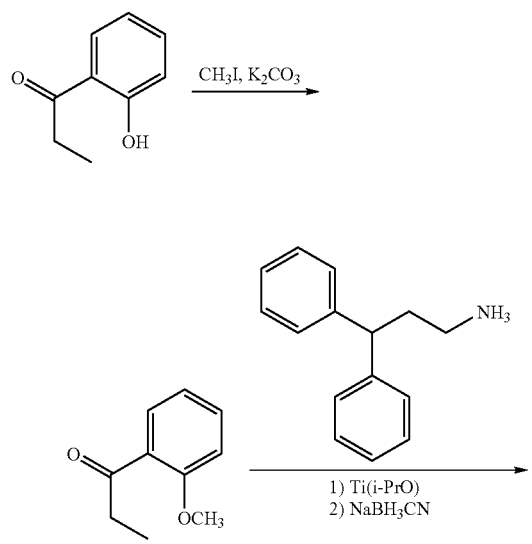

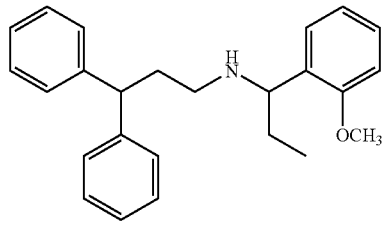

Compound 167

2-Methoxypropiophenone

A mixture of 2-hydroxypropiophenone (3.00 g, 20.0 mmol), iodomethane (3.40 g, 24.0 mmol), and K$_2$CO$_3$ (granular, anh.; 13.8 g, 99.9 mmol) was refluxed in acetone (75 mL) for 18 h. The reaction mixture was cooled to room temperature and the inorganic salts were removed by filtration. The filtrate was evaporated under vacuum to give an oil which was subsequently dissolved in diethyl ether (200 mL) and then washed with 0.1N NaOH (3×50 mL) followed by H$_2$O (50 mL). The organic layer was dried (anh. Na$_2$SO$_4$), filtered, and evaporated to an orange oil (3.17 g, 96.9%). This material was used in the following step without further purification. TLC, R$_f$ 0.55 (1% MeOH:1% IPA:CHCl$_3$); GC, tr 4.58 min; MS, m/z 164 (M+1).

(R,S)-N-1-(2-methoxyphenylpropyl)-3,3-diphenylpropylamine (Compound 167)

A solution of 2-methoxypropiophenone (0.848 g, 5.17 mmol), 3,3-diphenylpropylamine (1.00 g, 4.70 mmol), and titanium(IV) isopropoxide [Ti(OCH(CH$_3$)$_2$)$_4$; (1.76 mL, 5.88 mmol, 1.25 equiev)] was stirred at room temperature for 6 h. EtOH (2 mL) was then added, followed by sodium cyanoborohydride (0.295 g, 4.70 mmol) in portions over a period of 10 min, and the reaction was then stirred for 18 h. The reaction mixture was then poured into diethyl ether (200 mL) and the resulting suspension was centrifuged to remove the titanium precipitate. The supernatant was collected and the pellet was rinsed with diethyl ether (200 mL). The combined organic washings were evaporated under vacuum to give a crude oil which was chromatographed on silica gel (elution with 4% MeOH—CH$_2$Cl$_2$) to provide 647 mg (38%) of product. The material was then dissolved in diethyl ether (50 mL), filtered, and excess ethereal HCl was added to precipitate the hydrochloride salt (125 mg, 7.4%) as a white solid; TLC, R$_f$ 0.25 (4% MeOH—CH$_2$Cl$_2$); GC, t$_r$=11.2 min; MS, m/z 359 (M+). The synthesis of Compounds 172–176 was accomplished as follows.

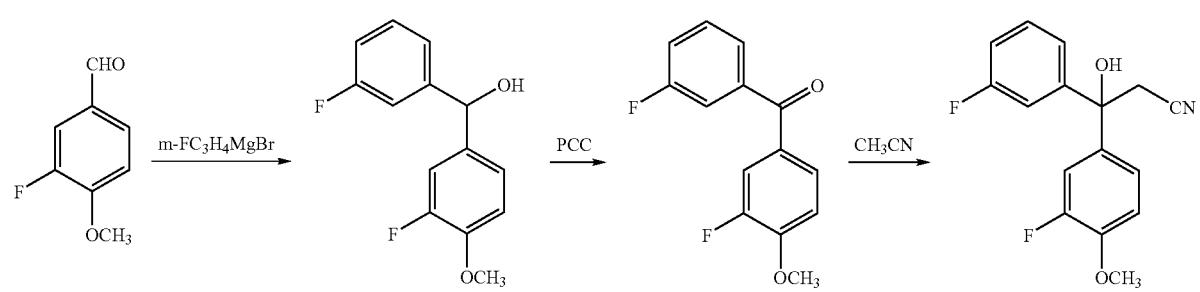

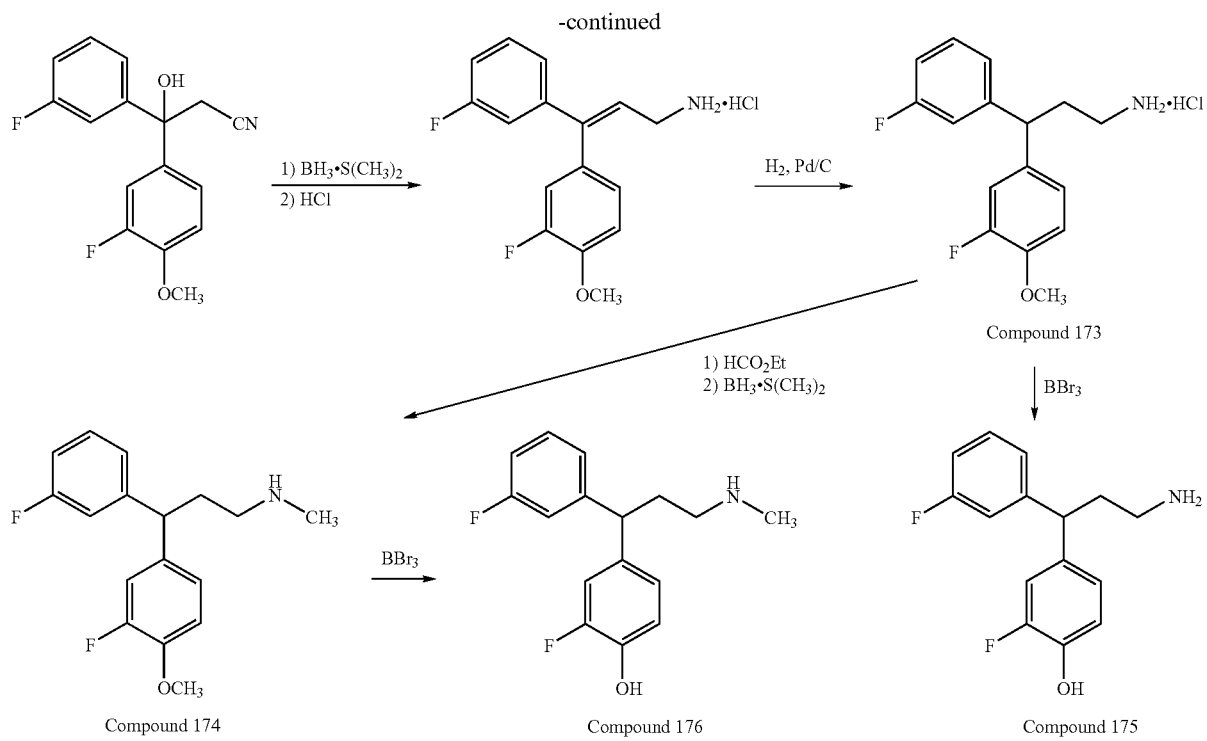

R,S)-3,3'-Difluoro-4-methoxybenzhydrol

A mixture of Mg° turnings (2.45 g, 101 mmol), 1-bromo-3-fluorobenzene (17.6 g, 100 mmol), and dry THF (200 mL) was carefully heated to reflux for 30 min. While still refluxing, 3-fluoro-p-anisaldehyde (15.3 g, 99.3 mmol) in THF (100 mL) was added over a period of 5 min. The reaction temperature was maintained for 30 min. cooled to room temperature, and then the reaction was quenched with satd. aq. NH$_4$Cl (200 mL). The organic layer was separated, washed with satd. aq. NaCl (2×200 mL), dried (anh. Na$_2$SO$_4$) and rotary evaporated to yield 23.5 g (94.4%) of product as an orange-brown oil.

3,3'-Difluoro-4-methoxybenzophenone

Pyridinium chlorochromate (22.3 g, 103 mmol) was added to a solution of 3,3'-difluoro-4-methoxybenzhydrol (23.5 g, 93.8 mmol) in CH$_2$—Cl$_2$ (300 mL) and the reaction mixture was stirred for 16 h. Diethyl ether (500 mL) was added and the reaction mixture was filtered through Celite. The filtrate was rotary evaporated and the resulting oil was flash chromatographed (gradient elution-of hexanes to 1:1 hex-EtOAc). The TLC-pure fractions were rotary evaporated to yield 1.58 g of a white solid. The rest of the impure fractions containing product were combined and rotary evaporated to the point where crystals began to form. Additional hexane (300 mL) was added and the crystallizing solution was allowed to stand. The resulting crystals were collected and washed with hexanes (2×50 mL) to yield 6.81 g of product. The two batches were combined to afford a total yield of 8.39 g (36.1%).

(R,S)-α-Cyanomethyl-3,3'-difluoro-4-methoxybenzhydrol

To dry THF (100 mL) was added butyllithium (2.6M in heptane; 16.0 mL, 41.6 mmol) at −78° C. Acetonitrile (2.20 mL, 42.1 mmol) was added over a period of 1 min and the reaction was stirred at −78° C. under N$_2$ for 30 min. A solution of 3,3'-difluoro-4-methoxybenzophenone (8.38 g, 33.8 mmol) in anh. THF (50 mL) was added to the reaction over a period of 5 min and the solution was stirred at −78° C. for 30 min. The cold bath was removed and the reaction was allowed to warm for 30 min. Satd. aq. NH$_4$C$_1$ (100 mL) was added to quench the reaction. The THF layer was separated, washed with satd. aq. NaCl (2×25 mL), dried (anh. Na$_2$SO$_4$), rotary evaporated, and dried under vacuum to yield 10.1 g (103%) of product as a yellow oil.

(E)- and (Z)-3-(3-Fluoro-4-methoxy)-3-(3-fluorophenyl)allylamine hydrochloride (Compound 172)

(R,S)-α-Cyanomethyl-3,3'-difluoro-4-methoxybenzhydrol (9.77 g, 33.8 mmol) was dissolved in dry THF (200 mL) and heated to boiling (no condenser). Under a stream of nitrogen, borane-dimethyl sulfide complex (BH$_3$ S(CH$_3$)$_2$, 10.1M; 16.8 mL, 170 mmol) was added carefully over a period of 2 min to the boiling solution. Boiling was then maintained for 15 min until most of the THF was gone. The reaction mixture was then cooled in an ice bath. Ice (10 g) was carefully added, followed by H$_2$O (50 mL). The reaction was then heated to near boiling and 12.1N HCl (100 mL) was added. The reaction was boiled (no condenser) for 30 min and was then cooled in an ice bath, basified with 10N NaOH (100 mL) and extracted twice with Et$_2$O (200 mL, 100 mL). The combined ether layers were washed with 1N NaOH (50 mL) and H$_2$O (50 mL) dried (anh. Na$_2$SO$_4$), and rotary evaporated. The resulting oil was flash chromatographed (CHCl$_3$; 1:100 MeOH—CHCl$_3$; 1:10 MeOH—CHCl$_3$) through flash silica gel to afford 6.83 g of a yellow oil. This oil was dissolved EtOH (2 mL) and Et$_2$O (10 ML). 1.0 HCl in Et$_2$O (27 ML) was added and the solution was rotary evaporated to yield 7.10 g (67.5%) of product as a solid, yellow foam.

(R,S)-3-(3-Fluoro-4-methoxy)-3-(3-fluorophenyl) propylamine maleate (Compound 173)

The mixture of (E)- and (Z)-3-(3-fluoro-4-methoxy)-3-(3-fluorophenyl)-allylamine hydrochlorides (7.10 g, 22.8 mmol) was dissolved in ETOH (200 mL) and a suspension of palladium on charcoal (10% Pd; 0.71 g) in H₂O (3.5 mL) was added. The reaction mixture was then shaken under 60 psig H₂ for 18 h and subsequently filtered through Celite. The filtrate was rotary evaporated, the residue was dissolved in EtOAc (25 mL) and Et₂O (100 mL), and was basified with sat. aq. NaHCO₃ (25 mL). The organic layer was separated, dried (anh. Na₂SO₄), and rotary evaporated to yield 6.28 g of an oil. This oil and maleic acid (2.59 g) were dissolved into hot EtOAc (100 mL). Diethyl ether (70 mL) was added and crystals soon began to form. The crystals were collected and dried to yield 2.45 g (27.3%) of a white powder. The combined filtrate and washings afforded more crystalline product out upon standing. The second crop was filtered, washed with 1:1 EtOAc-Et₂O (2×25 mL) and Et₂O (1×25 mL), and dried to provide 3.69 g (41.2%) of a white powder. The total yield was thus 6.14 g (68.5%).

(R,S)-3-(3-Fluoro-4-methoxy)-3-(3-fluorophenyl) propyl-formamide (R,S)-3-(3-Fluoro-4-methoxy)-3-(3- fluorophenyl)propyl amine maleate (3.12 g, 7.93 mmol) was free-based in a mixture of EtOAc (25 mL), Et₂O (100 mL), and satd. aq. NaHCO₃ (25 mL). The organic layer was separated, dried (anh. Na₂SO₄), and rotary evaporated. A solution of the amine in ethyl formate (75 mL, 930 mmol) was refluxed for 17 h. The reaction solution was rotary evaporated to yield 2.38 g (98.3%) of formamide as a light-orange, viscous oil.

(R,S)-N-Methyl-3-(3-fluoro-4-methoxy)-3-(3-fluorophenyl)propyl amine maleate (Compound 174)

(R,S)-3-(3-Fluoro-4-methoxy)-3-(3-fluorophenyl)propyl formamide (2.27, 7.43 mmol) in THF (100 mL) was heated to boiling (no condenser). Borane-dimethyl sulfide complex (10.1M; 2.30 mL, 23.2 mmol) was added carefully over a period of 2 min to the boiling solution. Boiling was then maintained for 15 min. The reaction was then cooled in an ice bath. Ice (10 g) was carefully added, followed by H₂O (30 mL), followed by 12.1N HCl (50 mL). The reaction was then boiled (no condenser) for 30 min. The reaction was subsequently cooled in an ice bath, basified with 10n NaOH (50 mL), and extracted with Et₂O (200 mL). The ether layer was washed with satd. aq. NaCl (100. mL), dried (anh. Na₂SO₄), and rotary evaporated to yield 2.03 g of a yellow oil. This material was purified by RP-HPLC (20–60% acetonitrile-0.1% aq. HCl over 20 min). The collected fractions were frozen and lyophilized to yield 1.28 g of a white solid. The free-base of the purified amine was dissolved in EtOAc. Maleic acid (305 mg) was added and the mixture was heated until everything had dissolved. The product was crystallized by adding Et₂O (5 ML). The crystals were filtered and washed with 1:1 EtOAc-Et₂O (10 ML) followed by Et₂O (10 mL) to yield 967 mg of product as a white, finely crystalline solid. (R,S)-3-(3-Fluoro-4-hydroxy)-3-(3-fluorophenyl) propylamine maleate (Compound 175)

(R,S)-3-(3-Fluoro-4-methoxy)-3-(3-fluorophenyl)propylamine maleate (2.45 g, 6.23 mmol) was free-based in the normal manner and dissolved in CH₂Cl₂ (25 mL). The resulting solution was cooled to −78° C. Under N₂ flow, boron tribromide (1-OM in CH₂Cl₂; 15 mL, 15 mmol) was added over a period of 5 min. The cold bath was removed and the reaction mixture was allowed to warm to room temperature. After 30 min at 25° C., the reaction was hydrolyzed with 12.1N HCl 10 mL). The aqueous layer was neutralized (pH 7) by the careful addition of 10n NaOH (14 mL). Satd. aq. NaHCO₃ (50 mL) was added along with Et₂O (100 mL) and EtOAc (20 mL). This mixture was shaken vigorously and the organic layer was separated. The aqueous layer was extracted with EtOAc (20 mL). The combined organic layers were dried (anh. Na₂SO₄) and rotary evaporated. The resulting oil was dissolved in EtOH, 1.0M HCl in Et₂O (7 mL) was added, and the solution was rotary evaporated. This material was then purified by RP-HPLC [20–60% acetonitrile-0.1% HCl (aq.) over 20 min]. The collected fractions were frozen and lyophilized, affording 716 mg of a white solid. The free-base of the purified amine (315 mg) was dissolved in EtOAc. Maleic acid (138 mg) was added and the mixture was heated until everything dissolved. The EtOAc was rotary evaporated to give a hard glass which was dissolved in MeOH (5 mL). Water (100 mL) was then added and the solution was subsequently frozen and lyophilized. The above procedure yielded 445 mg of product as a white solid.

(R,S)-N-Methyl-3-(3-fluoro-4-hydroxy)-3-(3-fluorophenyl) propyl amine hydrochloride (Compound 176)

A solution of (R,S)-N-methyl-3-(3-fluoro-4-methoxy)-3-(3-fluorophenyl)propylamine (703 mg, 2.41 mmol) in CH₂Cl₂ (10 mL) was cooled to −78° C. Under nitrogen, boron tribromide (1.0M in CH₂Cl₂; 6.0 mL, 6.0 mmol) was added over a period of 5 min. The cooling bath was then removed and the reaction was allowed to warm to room temperature. After 1 h, the reaction was quenched with 12.1N HCl (5 mL). The aqueous layer was then neutralized (pH 7) by the careful addition of 10N NaOH (~7 mL). Satd. aq. NaHCO₃ (25 mL) was added along with Et₂O (50 mL), EtOAc (15 mL), and CHCl₃ (5 mL). This mixture was shaken vigorously, and the organic layer was separated, dried (anh. Na₂SO₄), and filtered through paper. The crude product was then purified by RP-HPLC (20–60% acetonitrile-0.1% aq. HCl gradient over 20 min). The fractions were frozen and lyophilized to afford 602 mg of product as a white solid.

The synthesis of Compound 185 was accomplished as follows.

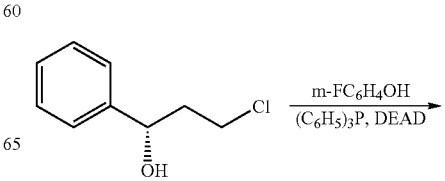

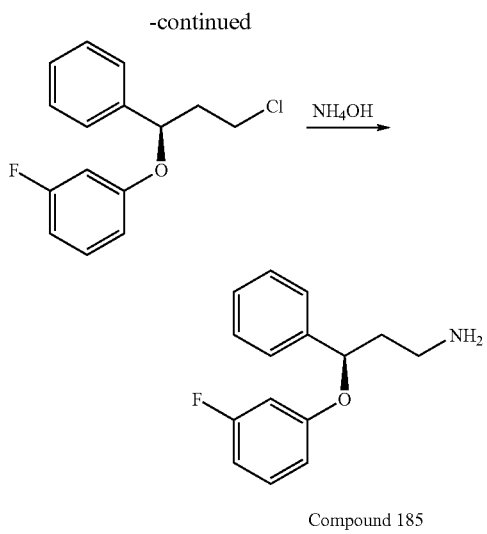

Compound 185

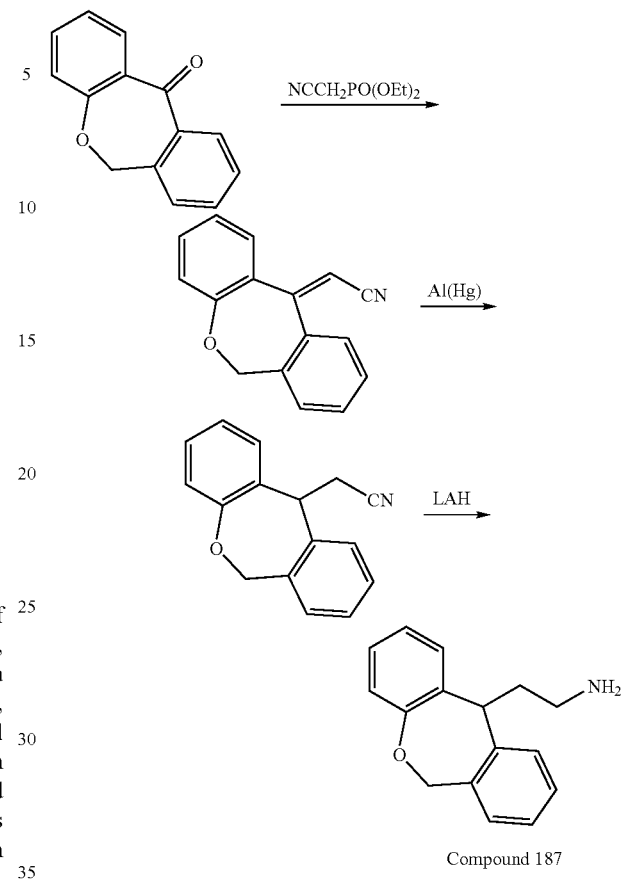

Compound 187

(R)-3-(3-Fluorophenoxy)-3-phenylpropylchloride

Following a similar procedure for the chiral synthesis of fluoxetine [Srebnik, M. et al., *J. Org. Chem.* 25 53(13), 2916–20 (1988), hereby incorporated by reference herein], a solution of (S)-(−)3-chloro-1-phenyl-1-propanol (4.00 g, 23.4 mmol), 3-fluorophenol (2.63 g, 23.4 mmol), and diethyl azodicarboxylate (4.00 g, 23.4 mmol) were dissolved in THF (200 mL). The mixture was cooled to 0° C. and triphenylphosphine (6.77 g, 25.8 mmol, 1.1 equiv) was added slowly over 10 min. The reaction mixture was then stirred at room temperature for 18 h. The THF was subsequently evaporated under vacuum to afford a gel which was washed with pentane (3×50 mL). The pentane washings were filtered and the filtrate was evaporated under vacuum to give a clear oil. This oil was dissolved in diethyl ether (150 mL) and washed with 1% HCl-satd. NaCl (25 mL), 0.1N NaOH-satd. NaCl (2×25 mL), and finally $H_2O$ (2×25 mL). The organic layer was then dried (anh. $Na_2SO_4$), filtered, and evaporated to dryness under vacuum to give an orange oil. The crude product was chromatographed on silica gel (25×180 mm, gravity column), elution with 40:1 hexane-EtOAc, to provide 971 mg (15.7%) of product as a colorless oil.

(R)-3-(3-Fluorophenoxy)-3-phenylpropylamine (Compound 185)

A solution of (R)-3-(3-fluorophenoxy)-3-phenylpropyl chloride (0.971 g, 3.96 mmol), conc. $NH_4OH$ (30 mL), and EtOH (20 mL) were shaken at 90° C. on a Parr apparatus (50–90 psig) for 18 h. The mixture was then evaporated under vacuum and the residue was dissolved in $Et_2O$ (100 mL) and washed with $H_2O$ (2×25 mL). The organic layer was dried (anh. $Na_2SO_4$), filtered, and evaporated under vacuum to provide a yellow oil. This material was then dissolved in EtOAc (50 mL) and filtered. A solution of 30 maleic acid (0.272 g, 2.6 mmol, 0.93 equiv) dissolved in hot EtOAc (5 mL) was added to precipitate the maleate salt (519 mg, 53.5%) as a white solid: TLC $R_f$ 0.25 (1% MeOH—$CHCl_3$); GC, $t_r$ 7.37 min; MS, m/z 245 (M+). The synthesis of Compound 187 was accomplished as follows.

11-Cyanomethylene-10,11-dihydrodibenzo[b,c]oxepine

To a solution of diethyl cyanomethylphosphonate (5.06 g, 28.6 mmol) in dry DMF (15 mL) was added NaH (60% mineral oil dispersion; 1.14 g, 28.5 mmol) over a period of 2 min. The reaction was stirred for 10 min and then a solution of 6,11-dihydrodibenzo[b,c]oxepin-11-one [Kurokawa M. et al., *Chem, Pharm, Bull.* 39(10), 2564–2573 (1991), hereby incorporated by reference herein] (4.00 g, 19.0 mmol) in dry DMF (5 mL) was added. The reaction mixture was stirred under argon for 21 h. Water (100 mL) was then added and the product was extracted with EtOAc (2×50 mL). The combined organic layers were washed with satd. aq. NaCl (2×50 mL), dried (anh. $Na_2SO_4$), and rotary evaporated. The resulting solid was recrystallized from hot EtOAc (10 mL) hexanes(40 mL) to provide 2.43 g (54.7%) of product.

11-Cyanomethyl-11H-10,11-dihydrodibenzo[b,c]oxepine

Following a procedure described in Great Britain Patent 1,129,029 (1968) (*Chem, Abstr.* 70:37664), hereby incorporated by reference herein], for the preparation of aluminum amalgam, Al° granules (2.00 g, 74.1 mmol) were first etched with 0.5N NaOH (100 mL) and then washed with $H_2O$ (100 mL) followed by EtOH 100 mL). A solution of $HgCl_2$ (2.00 g, 7.37 mmol) in $Et_2O$ (100 mL) was added. The reaction mixture was stirred for 5 min and the supernatant was decanted. The solid Al(Hg) amalgam was washed with $H_2O$ (100 mL), EtOH (100 mL), and then $Et_2O$ (100 mL). The amalgam was covered with $Et_2O$ (100 mL) and a solution of 11-cyanomethylene-10,11-dihydrodibenzo[b,c]oxepine (2.00 g, 8.57 mmol) in EtOAc (30 mL) and EtOH (20 mL)

was added. Water (2 mL) was added and the reaction mixture was stirred for 18 h and then filtered. The filtrate was rotary evaporated to yield 1.65 g (81.8%) of product as a white, crystalline solid.

11-(2-Aminoethyl)-11H-10,11-dihydrodibenzo[b,c]oxepine hydrochloride (Compound 187)

To a stirring suspension of lithium aluminum hydride (0.67 g, 18 mmol) in anh. $Et_2O$ (30 mL) was added a solution of 11-cyanomethyl-11H-10,11-dihydrodibenzo[b,c] oxepine (1.65 g, 7.01 mmol) in dry THF (5 mL)/anh. $Et_2O$ (10 mL) over a period of 2 min. The reaction was stirred for 30 min. In the following order, $H_2O$ (0.7 mL), 5N NaOH (0.7 mL), and $H_2O$ (2.1 mL) were added to the reaction mixture. Diethyl ether (30 mL was added and the mixture was filtered. The filtrate was rotary evaporated and the resulting oil was dissolved in ETOH (10 mL) -Et2O (65 mL). 1.0M HCl in $Et_2O$ (10 mL) was added and the solution was allowed to crystallize, giving 1.42 g (73.4%) of the title compound.

Compounds 67–68, 70–75, 79–82, 84–89, 91–95, 98–100, 102, 104–106, 109–114, 117, 124–134, 138, and 140–150 were synthesized by standard procedures known to those skilled in the art, as described above.

Gas Chromatography of Simplified Arylalkylamines

Gas chromatographic and mass spectral data were obtained on a Hewlett-Packard 5890 Series II Gas Chromatograph equipped with a 5971 Series Mass Selective Detector [Ultra-2 Ultra Performance Capillary Column (cross-linked 5% phenyl methyl silicone); column length, 25 m, column i.d., 0.20 mm; The flow rate, 60 mL/min; injector temp., 250° C.; gradient temperature program, 20° C./min from 125 to 325° C. for 10 min, then held constant at 325° C. for 6 min]. Compound 19. (Rt=7.40 min), m/z (rel. int.) 211 (M+,13), 195(16), 194 (100), 193 (73), 180 (8), 179 (33), 178 (19) 168 (24), 167 (50), 166 (23), 165 (72), 164 (8), 153 (10), 152 (31), 117 (13), 116 (38), 115 (26), 106 (14), 104 (14), 103 (24), 102 (8), 91 (11), 78 (14), 77 (29), 63 (9), 51 (17)

Compound 20. (Rt=7.34 min), m/z (rel. int.) 247 (M+,27), 231 (16), 230 (100), 229 (45), 215 (29), 214 (14), 204 (43), 203 (37), 202 (13), 201 (47), 184 (14), 183 (58), 181 (8), 151 (9), 135 (13), 134 (31), 133 (25), 124 (18), 122 (16), 121 (19), 109 (15), 101 (29), 96 (18), 95 (11), 83 (11), 75 (20), 57 (10), 42 (9)

Compound 21. 1(Rt 7.53 min), m/z (rel. int.) 261 (M+,69), 262 (13), 245 (17), 244 (100), 230 (11), 229 (42), 216 (11), 215 (15), 214 (14), 204 (45), 203 (35), 202 (16), 201 (63), 184.(12), 183(61), 148(11), 136 (9), 135 (27), 133 (36), 124 (21), 115(16), 109 (43), 83 (12), 74 (8), 58 (14), 57 (11)

Compound 22. (Rt=7.37 min), m/z (rel. int.) 261 (M+,4), 244 (14), 229 (7), 204 (10), 203 (16), 201 (12), 183 (16), 138 (4), 133 (5), 109 (4), 101 (7), 75 (4), 58 (8), 57(4), 44 (100), 42 (7)

Compound 24.(Rt=8.21 min), m/z (rel. int.) 259 (M+,122), 260 (23), 242 (44), 241 (15), 228 (15), 227 (49), 216 (15), 213 (56), 212 (16), 211 (55), 199 (32), 196 (22), 185 (34), 184 (19), 183 (67), 171 (16), 170 (38), 165 (44), 151 (20), 150 (16), 146 (13), 136 (46), 134 (17), 133 (37), 123 (15), 121 (22), 120 (13), 109 (100), 91 (34), 77 (29), 51 (15)

Compound 25. (Rt=8.49 min), m/z (rel. int.) 259 (M+,39), 243 (16), 242 (95), 241 (25), 227 (27), 217 (15), 216 (100), 215 (27), 212 (13), 211 (50), 201 (14), 200 (11), 199 (15), 196 (15), 185 (20), 184 (19), 183 (50), 171 (24), 170 (28), 165 (15), 146 (10), 136 (11), 134 (12), 133 (23), 121 (21), 77 (9)

Compound 26. (Rt=8.69 min), m/z (rel. int.) 259 (M+,11), 243 (17), 242 (100), 241 (69), 227 (10), 215 (31), 212 (11), 211 (52), 184 (14), 183 (31), 172 (13), 171 (35), 170 (23), 165 (13), 147 (21), 146 (12), 134 (19), 133 (23), 121 (13) 91 (11), 77 (10)

Compound 27. (Rt=8.80 min), m/z (rel. int.) 243 (M+,54), 226 (36), 212 (12), 211 (69), 200 (14), 199 (16), 198 (20), 197 (100), 196 (39), 185 (35), 184 (30), 183 (50), 179 (13), 178 (14), 165 (13), 134 (15), 133 (19), 120 (29), 117 (16), 115 (27),104 (13), 101 (11), 91 (23), 77 (13)

Compound 28. (Rt 8.77 min), m/z (rel. int.) 243 (M+,25), 227 (15), 226 (85), 225(26), 212 (19), 211 (100), 200 (22), 199 (17), 197 (18), 196 (29), 185 (46), 184 (35), 183 (64), 179 (9), 165 (11), 134 (19), 133 (23), 121 (12), 120 (18), 117 (14), 115 (24), 101 (12), 91 (25), 77 (12), 65 (11), 51 (9)

Compound 29. (Rt=7.89 min), m/z (rel. int.) 243 (M+,12), 227 (9), 226 (52), 225 (17), 212 (19), 211 (100), 199 (13), 197 (12), 196 (21), 185 (19), 184 (24), 183 (43), 179 (7), 134 (11), 133 (15), 120 (9), 117 (10), 115 (17), 91 (14)

Compound 30. (Rt=8.36 min), m/z (rel. int.) 263 (M+,21), 246 (26), 220 (13), 212 (17), 211 (100), 197 (10), i96 (25), 185 (43), 184 (30), 183 (69), 181 (9), 165 (12), 133 (18), 115 (14), 101 (15), 75 (15)

Compound 31. (Rt=9.31 min), m/z (rel. int.) 279 (M+,18), 281 (11), 262 (10), 236 (10), 229 (33), 228 (17), 227 (100), 203 (9), 210 (33), 199 (15), 192 (15), 178 (19), 166 (18), 165 (53), 164 (13), 163 (16), 140 (12), 115 (13), 103 (9)

Compound 32. (Rt=7.30 min), m/z (rel. int.) 229 (M+,21), 213 (16), 212 (100), 211 (61), 197 (33), 196 (19), 194 (14), 186 (26), 185 (30), 184 (19), 183 (69), 170 (17), 166 (16) 165 (77), 134 (25), 133 (23), 116 (17), 115 (17), 103 (18), 101 (11), 78 (13), 77 (23), 75 (13), 51 (18), 43 (13), 42 (13)

Compound 33. (Rt 7.56 min), m/z (rel. int.) 261 (M+,68), 245 (18), 244 (100), 229 (43), 215 (16), 214 (15), 204 (57), 203 (43), 202 (15), 201 (64), 184 (14), 183 (73), 148 (16), 136 (13), 135 (46), 133 (60), 124 (51), 115 (27), 111 (14), 109 (96), 107 (16), 96 (14), 83 (27), 75 (20), 58 (96), 57 (33), 56 (23), 41 (35)

Compound 34. (Rt=7.39 min), m/z (rel. int.) 261 (M+, 72), 262 (14), 245 (18), 244 (100), 229 (42), 216 (9), 215 (15), 214 (14), 204 (52), 203 (38), 202 (14), 201 (54), 184 (12), 183 (62), 181 (10), 148 (13), 136 (9), 135 (31), 133 (40), 124 (30), 115 (18), 109 (57), 107 (9), 83 (13), 58 (21), 57 (11)

Compound 35. (Rt=4.45 min), m/z (rel. int.) 181 (M+,8), 165 (10), 164 (76), 138 (48) 136 (11), 135 (63), 133 (12), 123 (22), 122 (22), 121 (11), 110 (21), 109 (100), 101 (13), 96 (27), 83 (14), 75 (11), 56 (15), 45 (21), 44 (40), 42 (9), 41 (15)

Compound 37. (Rt=4.87 min), m/z (rel. int.) 196 (M+,4), 195 (17), 178 (76), 163 (20), 152 (41), 150 (22), 137 (12), 136 (29), 135 (60), 133 (19), 124 (13), 123 (20), 122 (49), 121 (17), 110 (78), 109 (100), 101 (17), 96 (29), 83 (17), 75 (12), 56 (29), 55 (12), 45 (53), 44 (45), 43 (39), 41 (30)

Compound 38. (Rt=7.68 min), m/z (rel. int.) 275 (M+,0.1), 203 (5), 201 (6), 183 (8), 135 (4), 133 (4), 109 (8), 71 (3), 45 (3), 44 (100), 42 (4)

Compound 39. (Rt=7.67 min), m/z (rel. int.) 289 (M+,6), 203 (3), 201 (5), 183 (6), 135 (2), 133 (3), 109 (7), 85 (3), 70 (3), 59 (4), 58 (100)

Compound 40. (Rt=7.63 min), m/z (rel. int.) 289 (M+,19), 203 (6), 201 (13), 183 (17), 152 (5), 135 (6), 133 (8), 109 (15), 85 (5), 70 (4), 58 (100)

Compound 41. (Rt=7.93 min), m/z (rel. int.) 275 (M+,23), 258 (20), 203 (27), 202 (14), 201 (52), 184 (9), 183 (59), 181 (10), 150 (11), 149 (18), 147 (11), 135 (24), 134 (14), 133 (40), 124(12), 123 (19), 109 (76), 107 (9), 103 (10), 83 (15), 75 (10), 72 (100), 71 (12), 57 (18), 56 (21), 55 (41)

Compound 43. (Rt=9.18 min), m/z (rel.int.) 293 (M+,11), 276 (10), 243 (11), 241 (31), 236 (11), 235 (16), 201 (18), 199 (22), 179 (11), 178 (25), 176 (10), 166 (16), 165 (70), 164 (19), 163 (24), 103 (9), 102 (9), 75 (11), 44 (100), 43 (11), 42 (15)

Compound 46. (Rt=9.34 min), m/z (rel. int.) 293 (M+,46), 295 (28), 276 (16), 243 (24), 242 (15), 241 (75), 237 (12), 236 (18), 201 (33), 199 (31), 178 (26), 176 (13), 166 (31), 165 (100), 164 (32), 163 (43), 152 (11), 151 (13), 149 (12), 140 (30), 139 (11), 129 (12), 127 (20), 125 (31), 117 (26), 116 (26), 115 (64), 91 (12), 89 (17), 77 (13), 75 (22), 63 (14), 58 (51), 57 (15), 56 (19), 41 (19)

Compound 50. (Rt=7.37 min), m/z (rel. int.) 261 (M+,2), 244 (9), 229 (4), 204 (7), 203 (11), 201 (8), 183 (11), 101 (5), 58 (7), 44 (100), 42 (7)

Compound 51. (Rt=7.30 min), m/z (rel. int.) 261 (M+,5), 244 (20), 229 (9), 204 (14), 203 (23), 202 (6), 201 (20), 183 (27), 133 (7), 121 (6), 101 (9), 75 (6), 58 (7), 44 (100), 43 (6), 42 (11)

Compound 52. (Rt=7.24 min), m/z (rel. int.) 247 (M+,56), 231 (13), 230 (81), 229 (47), 216 (12), 215 (32), 214 (16), 204 (29), 203 (31), 202 (16), 201 (63), 196 (21), 184 (20), 183 (100), 182 (11), 181 (15), 170 (13), 151 (13), 150 (11), 135 (13), 134 (29), 133 (25), 124 (14), 122 (20), 121 (21), 109 (13), 101 (27), 96 (21), 75 (23), 43 (14), 42 (15)

Compound 53. (Rt=7.21 min), m/z (rel. int.) 247 (M+,98), 248 (17), 231 (13), 230 (84), 229 (56), 215 (38), 214 (16), 203 (33), 202 (16), 201 (68), 196 (26), 184 (16), 183 (100), 181 (15), 151 (21), 150(15), 135 (14), 134 (35), 133 (24), 124 (19), 122 (23), 121 (25), 111 (13), 101(31), 96 (19), 75 (19)

Compound 55. (Rt 7.86 min) m/z (rel. int.) 275 (M+,98), 276 (20), 258 (59), 229 (58), 216 (31), 215 (22), 214 (19), 204 (49), 203 (41), 202 (21), 201 (82), 184 (18), 183 (100), 181 (14), 150 (21), 135 (33), 133 (55), 124 (41), 115 (13), 109 (90), 101 (15), 83 (20), 75 (16), 72 (23), 57 (13), 56 (24)

Compound 56. (Rt=7.79 min), m/z (rel. int.) 261 (M+,67), 262 (12), 244 (54), 229 (56), 218 (27), 217 (16), 216 (19), 215 (100), 214 (45), 203 (50), 202 (32), 201 (51), 197 (16), 196 (26), 183 (24), 138 (17), 135 (20), 134 (17), 133 (39), 122 (26), 121 (13), 109 (30), 101 (17), 96 (14), 83 (16), 75(13)

Compound 57. (Rt=7. 65 min) m/z (rel. int.) 261 (M+, 62) 244 (50), 229 (50), 218 (24), 217 (13), 216 (18), 215 (100), 214 (36), 203 (42), 202 (19), 201 (33), 197 (14), 196 (19), 183 (17), 138 (19), 135 (16), 134 (12), 133 (29), 122 (29), 109 (25), 101 (13)

Compound 58. (Rt=8.15 min), m/z (rel. int.) 275 (M+,134), 276 (26), 258 (23), 244 (19), 243 (100), 232 (25), 229 (53), 217 (51), 216 (23), 215 (67), 214 (97), 201 (44), 197 (21), 196 (43), 183 (23), 148 (38), 147 (21), 138 (46), 135 (46), 134 (18), 133 (64), 125 (25), 123 (28), 122 (81), 115 (27), 109 (54), 107 (17), 83 (27), 44 (19), 43 (19)

Compound 59. (Rt=7.61 min), m/z (rel. int.) 275 (M+,27), 204 (8), 203 (10), 201 (19), 183 (25), 109 (8), 101 (7), 58 (100), 57 (8), 56 (8), 44 (9)

Compound 60. (Rt=7. 34 min), m/z (rel. int.) 261 (M+, 55) 262 (10), 204 (16), 203 (15), 201 (31), 183 (35), 133 (11), 122 (11), 121(10), 109 (9), 101 (16), 96 (11), 75 (10), 57 (9), 44 (100), 42 (11)

Compound 61. (Rt=8.07 min), m/z (rel. int.) 277 (M+,68) 278 (13), 260 (31), 246 (11), 245 (25), 234 (12), 231 (32), 229 (26), 217 (20), 203 (23), 201 (24), 188 (12), 183 (22), 154 (24), 151(15), 150(10), 133 (18), 124 (10), 109 (100), 95 (11), 44 (14)

Compound 62. (Rt=8.93 min), m/z (rel. int.) 271 (M+,115), 272 (22), 254 (16), 239 (22), 225 (36), 223 (40), 181 (33), 165 (34), 153 (13), 152 (24), 136 (39), 132 (13), 131 (16), 123 (20), 122 (13), 121 (89), 119 (13), 115 (23), 105 (17), 91 (100), 77 (22)

Compound 63. (Rt=8.47 min), m/z (rel. int.) 287 (M+,31), 241 (9), 204 (27), 203 (20), 202 (9), 201 (30), 183 (38), 150 (13), 133 (20), 109 (27), 84 (45), 83 (43), 82 (11), 57 (18), 56 (100), 43 (25)

Compound 64. (Rt=8.57 min), m/z (rel. int.) 287 (M+,63), 288 (13), 270 (14), 242 (16), 241 (17), 215 (17), 214 (18), 204 (35), 203 (27), 202 (18), 201 (70), 183 (86), 150 (18), 147 (16), 146 (17), 135 (16), 133 (45), 109 (45), 84 (31), 83 (38), 82 (13), 75 (15), 57 (21), 56 (100), 43 (44)

Compound 65. (Rt=8.18 min), m/z (rel. int.) 239 (M+,88), 240 (17), 222 (12), 208 (18), 207 (100), 195 (24), 193 (48), 192 (11), 181 (33), 180 (32), 179 (57), 178 (72), 166 (16), 165 (60), 152 (13), 130 (36), 129 (17), 120 (40), 117 (34), 116 (14), 115 (53), 107 (20), 105 (19), 104 (42), 103 (11), 91 (37), 77 (20), 65 (17)

Compound 66. (Rt=7.46 min), m/z (rel. int.) 275 (M+,7), 201 (5), 183 (6), 133 (3), 109 (6), 71 (3), 45 (3), 44 (100), 42 (3)

Compound 67. (Rt=7.56 min), m/z (rel. int.) 225 (M+,24), 194 (8), 193 (12), 179 (6), 168 (10), 167 (12), 166 (6), 165 (20), 152 (9), 120 (8), 116 (6), 115 (7), 103 (7), 77 (8), 51 (5), 44 (100)

Compound 68. (Rt 7.85 min), m/z (rel. int.) 239 (M+,22), 194 (5), 193 (10), 168 (10), 167 (12), 166 (6), 165 (19), 152 (9), 134 (6), 116 (5), 115 (7), 91 (7), 77 (6), 59 (5), 58 (100), 44(8)

Compound 69. (Rt=7.35 min), m/z (rel. int.) 275 (M+,11), 203 (24), 202 (7), 201 (23), 183 (35), 122 (6), 121 (6), 101 (9), 58 (100), 57 (8), 56 (10)

Compound 72. (Rt=7.90 min), m/z (rel. int.) 253 (M+,25), 238 (9), 193 (7), 168 (8), 167 (14), 165 (17), 152 (9), 115 (7), 91 (11), 73 (8), 72 (100), 58 (45), 56 (7), 44 (6), 43 (9), 42 (8)

Compound 73. (Rt=7.29 min), m/z (rel. int.) 239 (M+,9), 240 (2), 167 (2), 165 (5), 152 (2), 115 (2), 77 (2), 59 (5), 58 (100), 44 (3), 42 (5)

Compound 74. (Rt=8.01 min), m/z (rel. int.) 267 (M+,7), 167 (3), 165 (6), 152 (3), 91 (4), 87 (7), 86 (100), 72 (13), 58 (10), 56 (4), 42 (4)

Compound 79. (Rt=7.89 min), m/z (rel. int.) 230 (M+,37), 214 (15), 213 (100), 212 (62), 201 (26), 200 (72), 198 (21), 195 (12), 188 (17), 187 (85), 186 (46), 185 (42), 184 (9), 157 (12), 135 (9), 133 (24), 109 (10), 107 (20), 106 (62), 80 (14), 79 (32), 78 (9), 51 (20)

Compound 81. (Rt=7.40 min), m/z (rel. int.) 209 (M+,89) 210 (14), 208 (100), 193 (17), 192 (56), 191 (42), 189 (12), 178 (20), 166 (11), 165 (45), 152 (12), 132 (86), 131 (10), 130 (53), 117 (22), 115 (48), 106 (22), 105 (10), 104 (12), 103 (16), 91 (16), 77 (22), 51 (15)

Compound 82. (Rt=7.93 min), m/z (rel. int.) 275 (M+,124), 276 (25), 232 (33), 215 (12), 214 (16), 204 (14), 203 (100), 201 (24), 196 (8), 183 (20), 150 (14), 138 (9), 136 (14), 135 (44), 133 (26), 125 (9), 124 (71), 123 (29), 121 (14), 115 (14), 111 (72), 110 (9), 109 (84), 101 (14), 83 (9), 75 (8)

Compound 83. (Rt=7.22 min), m/z (rel. int.) 235 (M+,10), 219 (17), 218 (100), 217 (62), 203 (20), 192 (10), 191 (38), 190 (7), 189 (14), 185 (17), 83 (7), 171 (9), 165 (8), 147 (10), 146 (11), 134 (12), 133 (17), 121 (8), 109 (8), 97 (8), 45 (7)

Compound 85. (Rt=7.73 min), m/z (rel. int.) 239 (M+,7), 222 (15), 179 (8), 178 (9), 168 (16), 167 (33), 166 (12), 165 (43), 161 (9), 152 (20), 146 (17), 129 (7), 120 (15), 118 (7), 117 (19), 115 (25), 91 (25), 77 (7), 72 (9), 44 (100), 42 (6)

Compound 86. (Rt=7.66 min), m/z (rel. int.) 239 (M+,3), 222 (4), 168 (4), 167 (11), 166 (4), 165 (14), 152 (7), 120 (6), 117 (6), 115 (8), 91 (9), 72 (5), 44 (100), 42 (3)

Compound 87. (Rt=7.33 min), m/z (rel. int.) 239 (M+,4), 222 (9), 179 (9), 178 (11), 168 (11), 167 (27), 166 (13), 165 (48), 161 (7), 152 (22), 146 (14), 128 (7), 120 (11), 118 (8), 117 (21), 115 (31), 91 (29), 77 (9), 72 (8), 51 (7), 44 (100), 42 (9)

Compound 88. (Rt=7.4 min), m/z (rel. int.) 227 (M+,0.0), 183 (10), 168 (18), 167 (100), 166 (32), 165 (83), 164 (10), 163 (6), 153 (6), 152 (35), 139 (6), 115 (8), 105 (9), 77 (12), 51 (7), 45 (23)

Compound 89. (Rt=8.74 min), m/z (rel. int.) 260 (M+,220), 261 (39), 259 (89), 242 (18), 203 (17), 202 (16), 201 (61), 183 (58), 165 (100), 150 (20), 148 (25), 138 (24), 137 (61), 122 (73), 121 (31), 111 (47), 101 (23), 96 (16), 75 (16), 44 (17), 43 (29)

Compound 90. (Rt=7.32 min), m/z (rel. int.) 235 (M+,9), 219 (16), 218 (100), 217 (42), 206 (17), 205 (9), 204 (7), 203 (21), 202 (8), 193 (12), 192 (71), 191 (62), 190 (9), 189 (19), 185 (13), 171 (14), 159 (9), 147 (14), 146 (16), 134 (10), 133 (17), 121 (14), 109 (11), 101 (8), 97 (17), 45 (15)

Compound 91. (Rt=10.67 min), m/z (rel. int.) 329 (M+,6), 301 (20), 300 (81), 167 (18), 166 (6), 165 (18), 152 (10), 132 (5), 120 (45), 119 (21), 18 (11), 117 (9), 115 (11), 106 (6), 105 (5), 104 (12), 103 (5), 92 (8), 91 (100), 77 (10), 41 (6)

Compound 92. (Rt=10.37 min), m/z (rel. int.) 337 (M+,30), 338 (7), 204 (7), 203 (7), 201 (7), 183 (10), 133 (6), 121 (8), 120 (70), 106 (6), 92 (9), 91 (100)

Compound 93. (Rt=10.25 min), m/z (rel. int.) 351 (M+,28), 352 (7), 337 (9), 336 (39), 203 (10), 201 (11), 183 (17), 135 (6), 134 (20), 133 (6), 132 (6), 120 (11), 118 (5), 109 (18), 106 (12), 105 (100), 104 (13), 103 (8), 91 (14), 79 (11), 77 (12)

Compound 94. (Rt=10.48 min), m/z (rel. int.) 365 (M+,2), 337 (25), 336 (100), 203 (8), 201 (8), 183 (14), 133 (5), 132 (6), 120 (14), 119 (13), 118 (9), 115 (5), 109 (20), 106 (5), 104 (10), 91 (52)

Compound 95. (Rt=6.68 min), m/z (rel. int.) 283 (M+,59), 284 (11), 267 (11), 266 (71), 265 (19), 251 (24), 250 (9), 241 (14), 240 (100), 239 (48), 237 (30), 232 (10), 220 (17), 219 (65), 199 (9), 152 (12), 151 (18), 142 (20), 140 (13), 139 (20), 127 (22), 119 (24), 114 (12), 101 (10), 63 (10), 44 (9)

Compound 96. (Rt=6.93 min), m/z (rel. int.) 265 (M+,46), 249 (16), 248 (100), 247 (34), 233 (27), 232 (11), 223 (9) 222 (65), 221 (39), 220 (10), 219 (36), 202 (14), 201 (54), 152 (15), 151 (14), 133 (9), 124 (12), 119 (9), 109 (9), 101 (14), 75 (9)

Compound 97. (Rt=8.10 min), m/z (rel. int.) 241 (M+,101), 242 (18), 224(50), 223 (19), 210 (11), 209 (37), 197 (12), 196 (10), 195 (55), 194 (16), 193 (60), 181 (29), 178 (20), 167 (38), 166 (16), 165 (52), 153 (12), 152 (36), 136 (27), 133 (12), 132 (14), 116 (12), 115 (25), 103 (13), 91 (100), 77 (18)

Compound 98. (Rt=6.69 min), m/z (rel. int.) 232 (M+,3), 204 (11), 203 (37), 202 (30), 201 (100), 188 (9), 184 (14), 183 (84), 182 (10), 181 (15), 170(9), 109 (17), 107 (10), 83 (10), 75 (8), 57 (7)

Compound 99. (Rt=6. 75 min), m/z (rel. int. ) 233 (M+, 2), 204 (12), 203 (68), 202 (26), 201 (100), 200 (6), 188 (9), 184 (13), 183 (86), 182 (8), 181 (14), 170 (9), 133 (6), 109(15), 107 (11), 83 (11), 81 (7), 75 (7), 57 (9)

Compound 100. (Rt=7.66 min), m/z (rel. int.) 261 (M+,150), 262 (29), 217 (11), 216 (70), 215 (28), 214 (11), 203 (30), 202 (31), 201 (100), 196 (10), 184 (15), 183 (90), 181 (11), 133 (20), 124 (12), 122 (20), 109 (39), 101 (14), 83 (10), 75 (10), 45 (43)

Compound 101. (Rt=7.72 min), m/z (rel. int.) 245 (M+,20), 229 (16), 228 (100), 227 (36), 213 (21), 211 (22), 202 (57), 201 (30), 199 (21), 183 (50), 181 (14), 171 (15), 170 (26), 165 (12), 152 (21), 134 (19), 133 (35), 122 (28), 120 (19), 120 (13), 119 (12), 109 (20), 107 (20), 106 (18), 101 (15), 94 (15), 91 (20), 77 (18), 74 (15), 65 (20), 63 (14), 55 (14), 51 (15), 44 (27), 43 (17), 42 (14)

Compound 102. (Rt=8.33 min), m/z (rel. int.) 273 (M+,19), 204 (16), 203 (16), 201 (15), 183 (18), 177 (9), 133 (8), 109 (13), 70 (41), 69 (100), 68 (20), 43 (25), 42 (5), 41 (5)

Compound 103. (Rt=8.59 min), m/z (rel. int.) 245 (M+,118), 246 (20), 229 (15), 228 (100), 227 (85), 213 (27), 211 (23), 209 (15), 207 (12), 202 (19), 201 (32), 200 (17), 199 (84), 196 (10), 183 (38), 181 (15), 171 (13), 170 (23), 152 (19), 151 (15), 150 (10), 134 (18), 133 (32), 131 (12), 122 (36), 119 (15), 109 (24), 107 (10), 106 (12), 91 (19), 77 (12)

Compound 104. (Rt=7.72 min), m/z (rel. int.) 261 (M+,94), 262 (17), 217 (15), 216 (92), 215 (18), 204 (12), 203 (86), 202 (25), 201 (100), 184 (10), 183 (69), 148 (12), 133 (13), 122 (8), 109 (26), 101. (9), 83 (8), 45 (33)

Compound 105. (Rt=10.24 min), m/z (rel. int.) 351 (M+,7), 201 (5), 183 (7), 135 (9), 134 (79), 133 (4), 109 (5), 92 (8), 91 (100), 65 (8), 42 (7)

Compound 106. (Rt=7.52 min), m/z (rel. int.) 259 (M+,77), 260 (14), 258 (31), 244 (30), 228 (13), 227 (28), 214 (14), 201 (24), 165 (12), 164 (100), 162 (29), 133 (56), 109 (44), 75 (13), 44 (80), 42 (56)

Compound 107. (Rt=7.45 min), m/z (rel. int.) 227 (M+,101), 228 (16), 226 (100), 211 (22), 210 (68), 209 (49), 207 (13), 196 (22), 184 (15), 183 (62), 150 (50), 148 (31), 133 (44), 132 (53), 130 (45), 117 (15), 115 (29), 106 (14), 77 (18), 75 (13), 51 (14)

Compound 108. (Rt=7.46 min), m/z (rel. int.) 243 (M+,34), 244 (6), 212 (6), 211 (9), 197 (6), 186 (12), 185 (10), 184 (5), 183 (19), 165 (15), 133 (6), 120 (6), 103 (5), 77 (6), 44 (100), 42 (6)

Compound 109. (Rt=8.68 min), m/z (rel. int.) 285 (M+,110), 286 (22), 284 (27), 256 (16), 228 (37), 227 (27), 225 (10), 220 (110), 207 (15), 201 (27), 191 (14), 190 (100), 163 (11), 162 (85), 161 (10), 147 (11), 146 (11), 133 (32), 109 (20), 83 (12), 82 (36)

Compound 110. (Rt=8.66 min), m/z (rel. int.) 285 (M+,91), 286 (16), 284 (100), 243 (16), 227 (26), 225 (11), 221 (10), 220 (17), 214 (12), 207 (15), 201 (23), 147 (25), 146 (16), 133 (17), 109 (20), 42 (15)

Compound 111. (Rt=8.81 min), m/z (rel. int.) 287 (M+,29), 214 (9), 204 (15), 203 (18), 202 (9), 201 (34), 183 (42), 135 (9), 133 (28), 109 (28), 84 (47), 83 (100), 82 (19), 75 (8), 70 (16), 68 (13), 57 (18), 56 (28), 44 (16), 43 (25), 42 (14)

Compound 112. (Rt=8.85 min), m/z (rel. int.) 287 (M+,141), 288 (29), 286 (22), 202 (21), 201 (62), 183 (64), 133 (23), 109 (27), 84 (100), 83 (18), 82 (31), 57 (14), 56 (58), 55 (53), 43 (14), 42 (35)

Compound 113. (Rt=9.08 min), m/z (rel. int.) 251 (M+,27), 180 (38), 179 (36), 178 (39), 174 (15), 173 (100), 166 (11), 165 (53), 158 (12), 152 (10), 132 (9), 115 (28), 91 (31), 82 (18), 77 (16), 56 (45), 51 (9), 43 (23)

Compound 114. (Rt=8.71 min), m/z (rel. int.) 237 (M+,197), 238 (37), 236 (67), 193 (15), 179 (30), 178 (40), 165 (41), 159 (43), 158 (26), 132 (24), 130 (16), 116 (17), 115 (37), 106 (21), 103 (34), 91 (50), 77 (48), 57 (68), 56 (100), 51 (32), 43 (50), 42 (34)

Compound 115. (Rt=9.45 min), m/z (rel. int.) 271 (M+,34), 255 (12), 254 (67), 253 (14), 239 (23), 229 (16), 228 (100), 227 (18), 224 (16), 223 (68), 213 (9), 212 (10), 211 (10), 197 (34), 196 (17), 195 (11), 181 (18), 169 (10), 165 (22), 153 (19), 152 (27), 146 (16), 145 (13), 141 (12), 139 (10), 136 (22), 134 (11), 133 (41), 122 (16), 121 (31), 115 (30), 91 (18), 77 (15), 65 (11), 63 (10), 44 (10)

Compound 116. (Rt=9.50 min), m/z (rel. int.) 269 (M+,41), 268 (32), 254 (8), 253 (21), 252 (100), 251 (14), 238 (23), 237 (18), 221 (10), 209 (9), 178 (8), 165 (19), 162 (22), 160 (19), 152 (18), 147 (11), 146 (8), 145 (18), 139 (9), 130 (11), 115 (10)

Compound 117. (Rt 7.64 min), m/z (rel. int.) 212 (M+,13), 183 (16), 182 (100), 180 (7), 167 (7), 152 (3), 104 (27), 91(7), 78 (4), 77 (41), 51 (13)

Compound 118. (Rt=7.46 min), m/z (rel. int.) 245 (M+,4), 153 (8), 152 (43), 150 (9), 135 (6), 133 (10), 124 (5), 123 (36), 122 (38), 121 (17), 109 (16), 101 (14), 96 (24), 95 (16), 94 (100), 93 (7), 83 (7), 77 (21), 75 (11), 66 (15), 65 (30), 63 (10), 51 (14), 50 (6)

Compound 119. (Rt=7.39 min), m/z (rel. int.) 263 (M+,7), 171 (14), 170 (14), 152 (74), 151 (13), 150 (20), 141 (55), 135 (10), 133 (23), 123 (20), 122 (100), 121 (49), 120 (11), 113 (9), 112 (92), 1ll (9), 109 (41), 107 (12), 103 (13),102 (11), 101 (40), 97 (9), 96 (66), 95 (51), 94 (9), 84 (28), 83 (88), 82(8), 81 (16), 77 (14), 75 (54), 74 (10), 70 (10), 69 (10), 64 (10), 63 (23), 57 (62), 56 (13), 51 (15), 50 (12), 42 (8)

Compound 120. (Rt=8.48 min), m/z (rel. int.) 279 (M+,4), 159 (16), 157 (49), 153 (11), 152 (100), 150 (12), 133 (11), 130 (27), 128 (73), 123 (12), 122 (57), 121 (23), 111 (10), 109 (25), 101 (23), 99 (16), 96 (26), 95 (10), 83 (9), 75 (28), 73 (10), 65 (12), 64 (11), 63 (22), 51 (9), 50 (8)

Compound 121. (Rt=8.30 min), m/z (rel. int.) 275 (M+,2), 152 (15), 125 (8), 124 (100), 122 (14), 121 (7), 109 (35), 96 (7), 95 (10), 81 (14), 77 (9), 65 (7), 52 (11)

Compound 122. (Rt=7.39 min), m/z (rel. int.) 263 (M+,0.1), 170 (12), 152 (66), 151 (10), 150 (18), 141 (68), 135 (10), 133 (19), 123 (16), 122 (76), 121 (39), 112 (100), 111 (18), 109 (36), 107 (11), 103 (11), 102 (9), 101 (33), 96 (56), 95 (32), 92(11), 83 (96), 81 (13), 77 (13), 75 (43), 64 (25), 63 (26), 57 (61), 56 (14), 51 (14), 50 (11)

Compound 123. (Rt=5.88 min), m/z (rel. int.) 275 (M+,46), 276 (9), 202 (8), 201 (30), 183 (28), 133 (8), 109 (9), 101 (9), 71 (9), 59 (12), 58 (100), 44 (8), 42 (26)

Compound 124. (Rt=7.05 min), m/z (rel. int.) 229 (M+,15), 213 (15), 212 (89), 211 (13), 198 (20), 197 (100), 196 (24), 186 (12), 185 (21), 184 (29), 183 (87), 179 (7), 178 (8), 177 (13), 176 (5), 171 (7), 170 (18), 169 (4), 166 (5),165 (20), 152 (5), 133 (7), 75 (4), 63 (4), 57 (9), 56 (4)

Compound 125. (Rt=7.54 min), m/z (rel. int.) 225 (M+,57), 226 (13), 209 (13), 208 (75), 193 (13), 180 (14), 179 (21), 178 (20), 165 (22), 130 (34), 117 (59), 115 (29), 105 (18), 104 (94), 103 (45), 91 (100), 78 (30), 77 (38), 65 (36), 63 (13), 51 (20), 45 (17)

Compound 126. (Rt 7.81 min), m/z (rel. int.) 261 (M+,12), 244 (31), 152 (27), 151 (17), 150 (9), 136 (11), 135 (100), 133 (21), 122 (24), 115 (9), 110 (13), 109 (90), 107 (6), 96 (7), 83 (27), 56 (7)

Compound 127. (Rt=7.93 m/z), m/z (rel. int.) 225 (M+,23), 208 (20), 207 (6), 193 (13), 181 (7), 180 (37), 179 (100), 178 (36), 167 (9), 166 (12), 165 (36), 152 (9), 134 (30), 130 (26), 129 (9), 117 (18), 115 (22), 104 (6), 91 (38), 77 (7), 65 (7)

Compound 128. (Rt 7.42 min), m/z (rel. int.) 211 (M+,83), 212 (15), 194 (36), 193 (18), 182 (62), 181 (20), 180 (17), 179 (53), 178 (60), 176 (11), 167 (57), 166 (44), 165 (100), 152 (24), 120 (39), 116 (12), 115 (28), 104 (22), 103. (15), 91 (46), 89 (16), 78 (10), 77 (20), 65 (15), 63 (12), 51 (12)

Compound 129. (Rt=7.39 min) m/z (rel. int.) 229 (M+,104), 230 (19), 212 (28), 211 (14), 201 (13), 200 (85), 199 (22), 198 (14), 197 (50), 196 (58), 185 (73), 184 (45), 183 (100), 179 (43), 178 (55), 177 (17), 176 (17), 170 (18), 165 (33), 152 (12), 133 (22), 120 (57), 115 (17), 109 (44), 104 (23), 103 (17), 91 (32), 89 (16), 83 (20), 78 (12), 77 (22), 63 (16), 51 (13)

Compound 130. (Rt=7.38 min), m/z (rel. int.) 229 (M+,133) 230 (24), 212 (27), 211 (14), 200 (54), 199 (17), 198 (16), 197 (53), 196 (64), 185 (49), 184 (43), 183 (100), 179 (28), 178 (29), 177 (14), 170 (19), 165 (26), 133 (22), 120 (35), 115 (19), 109 (32), 104 (17), 103 (18), 91 (38), 89 (17), 83 (18), 77 (24), 63 (16)

Compound 131. (Rt=7.40 min), m/z (rel. int.) 229 (M+,146), 230 (26), 212 (48), 211 (23), 200 (51), 199 (17), 198 (16), 197 (61), 196 (70), 185 (50), 184 (43), 183 (100), 179 (28), 178 (28), 170 (20), 165 (23), 133 (21), 120 (35), 115 (20), 109 (59), 104 (25), 103 (17), 91 (27), 89 (17), 83 (22), 77 (22)

Compound 132. (Rt=7.03 min), m/z (rel. int.) 0 (M+,.O), 185 (14), 184 (100), 183 (23), 181 (17), 165 (18), 155 (12), 153 (14), 152 (12), 120 (85), 119 (67), 115 (10), 106 (16), 91 (19), 89 (14), 78 (12), 77 (25), 51 (16)

Compound 133. (Rt=7.09 min), m/z (rel. int.) 211 (M+,13), 195 (16), 194 (100), 181 (27), 180 (70), 179 (31), 178 (28) 166 (25), 165 (40), 152 (9), 120 (14), 119 (14), 118 (102), 115 (10), 104 (26), 103 (53), 102 (12), 91 (62), 89 ('-O), 78 (13), 77 (42), 65 (17), 51 (13)

Compound 134. (Rt=7.45 min), m/z (rel. int.) 211 (M+,14), 183 (15), 182 (100), 181 (14), 179 (13), 178 (18), 167 (27) 166 (18), 165 (46), 152 (10), 115 (8), 104 (8), 103 (6), 91 (29), 89 (7), 78 (5), 77 (7), 65 (7)

Compound 135. (Rt=8.60 min), m/z (rel. int.) 273 (M+,34), 257 (14), 2.56 (76), 231 (16), 230 (100), 228 (18), 227 (57), 213 (14), 211 (37), 202 (30), 201 (40), 199 (26), 184 (13), 183 (50), 151 (12), 171 (17), 170 (20), 152 (15), 150 (19), 134 (15), 133 (31), 122 (14), 121 (29), 109 (16), 107 (13), 106 (17), 91 (12), 65 (12)

Compound 136. (Rt 9.26 min), m/z (rel. int.) 275 (M+,44), 277 (15), 260 (28), 259 (19), 258 (81), 257 (13), 243 (15), 234 (33), 233 (19), 232 (100), 231 (13), 229 (15), 227 (42), 224 (15), 223 (86), 208 (13), 197 (45), 196 (26), 195 (13), 182 (14), 181 (33), 179 (11) 178 (18), 166 (22), 165 (60), 164 (12), 163 (10), 153 (32), 152 (55), 151 (18), 149 (10), 139 (11), 137 (17), 136 (19), 121 (13), 115 (25), 102 (11), 91 (16), 77 (17)

Compound 137. (Rt=7.42 min), m/z (rel. int.) 245 (M+,1), 153 (8) 152 (7), 141 (64), 135 (10), 134 (100), 132 (11), 117 (6), 115 (12), 112 (56), 105 (15), 104 (55), 103 (32), 95 (8), 91 (16), 84 (8), 83 (15), 78 (24), 77 (24), 75 (9), 65 (6), 63 (8), 57 (10), 51 (9)

Compound 138. (Rt=9.24 min), m/z (rel. int.) 289 (M+,77), 290 (16), 230 (20), 229 (21), 215 (15), 203 (22), 201 (32), 183 (36), 134 (10), 133 (13), 124 (10), 121 (9), 109 (10), 101 (10), 73 (100), 43 (23)

Compound 139. (Rt=7.25 min), m/z (rel. int.) 245 (M+,92), 246 (15), 244 (67), 229 (16), 228 (63), 227 (46), 225 (10), 224 (15), 214 (13), 201 (39, 183 (13), 151 (13), 150 (100), 149 (14), 148 (58), 135 (22), 133 (54), 124 (14), 122 (12), 109 (18), 101 (15), 75 (13)

Compound 140a. (Rt=8.64 min), m/z (rel. int.) 271 (M+,72), 272 (14), 270 (37), 255 (21), 254 (100), 242 (19), 227 (14), 226 (63), 225 (50), 199 (19), 197 (30), 196 (25), 183 (32), 176 (27), 170 (20), 150 (44), 148 (34), 146 (14), 133 (32), 131 (14), 121 (11)

Compound 140b. (Rt=8.68 min), m/z (rel. int.) 271 (M+,57), 272 (10), 270 (33), 255 (20), 254 (100), 242 (15), 227 (12), 226 (54), 225 (40), 209 (8), 199 (14), 197 (22), 196 (19), 183 (25), 176 (21), 170 (16), 150 (33), 148 (22), 146 (9), 133 (20), 131 (10)

Compound 141. ($R_t$=8.44 min), m/z (rel. int.) 257 (M+,48), 258 (8), 256 (36), 241 (21), 240 (100), 239 (19), 226 (22), 225 (20), 209 (11), 197 (14), 196 (18), 183 (25), 170 (16), 162 (19), 160 (10), 150 (28), 148 (26), 147 (9), 146 (8), 145 (13), 133 (20), 130 (8), 121 (10)

Compound 142. ($R_t$=8.47 min), m/z (rel. int.) 273 (M+,14), 217 (5), 216 (31), 215 (5), 183 (8), 170 (4), 150 (5), 121 (4), 58 (5), 45 (5), 44 (100)

Compound 143. ($R_t$=9.39 min), m/z (rel. int.) 273 (M+,47), 275 (16), 274 (19), 272 (36), 258 (39), 257 (26), 256 (100), 255 (17), 242 (25), 241 (15), 221 (23), 178 (25), 177 (11), 176 (14), 168 (14), 167 (11), 166 (54), 165 (34), 164 (34), 163 (16), 162 (45), 160 (19), 152 (28), 151 (22), 149 (19), 147 (18), 145 (24), 139 (11), 136 (15), 131 (15), 130(35), 121 (15), 115 (14), 111 (11), 103 (13), 102 (19), 89 (11), 77 (16), 75 (14), 63 (16), 51 (12)

Compound 145. (Rt=7.35 min), m/z (rel. int.) 277 (M+,7), 122 (10), 109 (8), 96 (6), 95 (6), 83 (10), 75 (6), 63 (2), 57 (7), 44 (100), 42 (9).

Compound 148. (Rt=8.43 min), m/z (rel. int.) 261 (M+,3), 170 (14), 169 (5), 168 (44), 153 (4), 151 (4), 140 (6), 139 (4), 138 (15), 132 (6), 125 (7), 123 (40), 115 (6), 103 (24), 102 (8), 101 (5), 95 (7), 94 (100), 89 (5), 77 (22), 75 (6), 66 (S), 65 (16), 63 (7), 51 (10), 50 (4)

Compound 149. (Rt=9.28 min), m/z (rel. int.) 295 (M+,4), 170 (32), 169 (12), 168 (100), 166 (8), 159 (22), 157 (66), 152 (11), 140 (16), 139 (11), 138 (41), 132 (11), 130 (32), 129 (8), 128 (82), 127 (10), 125 (16), 115 (12), 111 (15), 103 (55), 102 (18), 101 (15), 99 (19), 89 (10), 77 (26), 76 (8), 75 (27), 73 (11), 65 (11), 64 (10), 63 (22), 51 (11)

Compound 150. (Rt=8.32 min), m/z (rel int.) 279 (M+,4), 171 (9), 170 (37), 169 (13), 168 (100), 166 (8), 142 (8), 141 (88), 140 (19), 139 (12), 138 (42), 132 (12), 130 (7), 125 (16), 115 (12), 113 (10), 112 (89), 111 (11), 104 (8), 103 (60), 102 (19), 101 (12), 95 (14), 89 (11), 84 (11), 83 (24), 77 (29), 76 (6), 75 (24), 63 (13), 57 (17), 51 (11).

Compound 151. (Rt=7.68 min), m/z (rel. int.) 261 (M+,62), 244 (8), 216 (79), 203 (65), 201 (82), 183 (100), 121 (50), 101 (40), 75 (35), 44 (52).

Compound 152. (Rt=8.097 min), m/z (rel. int.) 42 (34), 43 (10), 44 (42), 56 (13), 57 (10), 58 (72), 71 (6), 72 (74), 73 (14), 74 (14), 75 (14), 86 (15), 95 (9), 96 (10), 100 (42), 101 (31), 114 (90), 115 (8), 120 (10), 121 (20), 122 (9), 123 (7), 138 (10), 149 (9), 164 (7), 170 (8), 181 (7), 183 (100), 184 (15), 188 (8),194 (6), 195 (7), 196 (10), 201 (64), 202 (21), 203 (63), 204 (10), 214 (12), 215 (12), 216 (12), 317 (92), 318 (20).

Compound 153. (Rt=7.88 min), m/z (rel. int.) 42 (7), 43 (8), 44 (32), 46 (16), 72 (24), 75 (11), 86 (21), 95 (8), 96 (9), 101 (20), 109 (14), 121 (30), 122 (14), 123 (6), 139 (6), 149 (10), 170 (6), 181 (6), 183 (59), 184 (9), 188 (6), 194 (11), 195 (7), 196 (10), 201 (51), 202 (17), 203 (56), 204 (8), 214 (10), 215 (18), 216 (52), 217 (13), 289 (100), 290 (20)

Compound 154. (Rt=7.74 min), m/z (rel. int.) 42 (16), 44 (23), 45 (35), 46 (15), 58 (20), 72 (59), 73 (17), 75 (12), 86 (23), 96 (9), 101 (18), 121 (22), 183 (52), 194 (9), 201 (44), 202 (15), 203 (41), 214 (9), 215 (11), 216 (20), 217 (10), 289 (100), 290 (20).

Compound 155. (Rt=7.67 min), m/z (rel. int.) 58 (44), 75 (15), 95 (9), 96 (11), 101 (22), 109 (16), 121 (33), 122 (15), 125 (12), 149 (9), 183 (62), 184 (10), 196 (12), 201 (57), 202 (19), 203 (53), 214 (11), 215 (19), 217 (13), 275 (100), 276 (18)

Compound 156. (Rt=8.93 min), m/z (rel. int.) 237 (M+,11), 220 (41), 219 (30), 219 (30), 206 (7), 205 (39), 204 (5), 194

(28), 193 (100) 192 (21), 191 (31), 190 (9), 189 (17), 179 (15), 178 (50), 177 (5), 176 (5), 165 (20), 152 (7), 128 (5), 116 (7), 115 (39), 91 (11)

Compound 157. (Rt=10.88 min), m/z (rel. int.) 343 (M+,6), 300 (100), 167 (16), 166 (6), 166 (6), 165 (16), 152 (9), 133 (8), 120 (28), 118 (8), 117 (6), 115 (8), 104 (11), 92 (5), 91 (62), 77 (7).

Compound 158. (Rt=10.74 min), m/z (rel. int.) 342 (M+,0.0) 300 (100), 167 (13), 166 (5), 165 (13), 152 (7), 120 (22), 118 (6), 115 (6), 106 (3), 104 (7), 91 (31)

Compound 159. (Rt=11.41 min), m/z (rel. int.) 363 (M+,13), 336 (33), 335 (24), 334 (95), 182 (10), 181 (9), 168 (14), 167 (40), 166 (18), 165 (36), 156 (27), 155 (15), 154 (85), 153 (27), 152 (29), 140 (9), 139 (7), 138 (14), 127 (32), 126 (9), 125 (100), 117 (19), 116 (7), 115 (24), 103 (11), 91 (43), 77 (15), 72 (7), 41 (12).

Compound 160. (Rt=11.48 min.), m/z (rel. int.) 363 (M+,8) 336 (35), 335 (25), 334 (100), 182 (5), 181 (11), 168 (9), 167 (29), 166 (13), 165 (29), 156 (11), 155 (11), 154 (37), 153 (26), 152 (23), 140 (8), 139 (6), 138 (12), 127 (26), 126 (7), 125 (81), 125 (81), 117 (13), 115 (17), 103 (7), 91 (26), 89 (5), 77 (9).

Compound 161. (Rt=11.83 min), m/z (rel. int.) 408 (M+,4), 407 (12), 381 (24), 380 (98), 379 (25), 378 (100), 200 (77), 199 (31), 198 (87), 197 (24), 184 (17), 182 (15), 181 (16), 171 (75), 169 (77), 168 (18), 167 (60), 166 (22), 165 (58), 152 (32), 118 (27), 117 (47), 116 (13), 115 (37), 104 (13), 103 (19), 91 (64), 90 (17), 77 (25)

Compound 162. (Rt=12.02 min), m/z (rel. int.) 408 (M+,3), 380 (100), 379 (25), 378 (99), 200 (40), 199 (32), 198 (48), 197 (30), 184 (18), 182 (16), 181 (23), 171 (83), 169 (85), 168 (16), 167 (49), 166 (18), 165 (50), 152 (28), 119 (11), 118 (32), 117 (46), 116 (12), 115 (34), 104 (11), 103 (17), 91 (63), 90 (16), 89 (10), 77 (23).

Compound 163. (Rt=10.58 min,), m/z (rel. int.) 347 (M+, 14), 318 (100), 181 (5), 168 (6), 167 (24), 166 (17), 165 (26), 152 (16), 150 (6), 139 (8), 138 (66), 137 (23), 137 (23), 136 (10), 124 (6), 122 (13), 117 (8), 115 (14), 110 (8), 109 (100), 103 (6), 91 (22), 77 (7).

Compound 164. (Rt=10.59 min), m/z (rel. int. 347 (M+,14) 318 (100), 181 (5), 178 (5), 168 (7), 167 (27), 166 (17), 165 (28), 152 (16), 150 (6), 139 (8), 138 (70), 137 (18), 136 (11), 122 (14), 117 (6), 115 (13), 110 (7), 109 (79), 103 (6), 91 (20), 91 (20), 77 (6).

Compound 165. (Rt=10.61 min), m/z (rel. int.) 347 (M+,8), 318 (95), 181 (8), 167 (20), 166 (10), 165 (21), 152 (13), 138 (34), 137 (27), 136 (11), 136 (11), 122 (14), 117 (6), 115 (11), 110 (8), 109 (100), 91 (22), 77 (6).

Compound 166. (Rt=11.62 min), m/z (rel. int.) 359 (M+,2), 330 (100), 167 (13), 165 (14), 152 (8), 150 (6), 149 (38), 148 (7), 135 (8), 134 (13), 122 (7), 122 (7), 121 (73), 117 (6), 115 (8), 91 (23), 77 (7)

Compound 167. (Rt=11.18 min) m/z (rel. int.) 359 (M+,4) 330 (100), 136 (0), 121 (6).

Compound 168. (Rt=10.86 min) m/z (rel. int.) 343 (M+,6) 314 (100), 167 (16), 166 (6), 165 (16), 152 (9), 134 (17), 133 (13), 132 (6), 118 (14), 117 (9), 115 (10), 106 (7), 106 (7), 105 (59), 91 (20), 77 (6).

Compound 169. (Rt=10.94 min), m/z (rel . int. 343 (M+,4), 314 (100), 167 (14), 166 (5), 165 (15), 152 (8), 134 (9), 133 (16), 132 (7), 732 (7), 118 (14), 117 (8), 115 (9), 106 (6), 105 (62), 91 (18), 77 (5).

Compound 170. (Rt=12.52 min), m/z (rel. int.) 374 (M+,13), 345 (50), 315 (5), 207 (12), 194 (8), 193 (16), 179 (5), 168 (9), 167 (22), 166 (16), 165 (100), 164 (15), 164 (15), 152 (12), 136 (45), 117 (13), 115 (11), 104 (6), 103 (6), 91 (26), 90 (8), 77 (7).

Compound 171. (Rt=11.16 min), m/z (rel. int.) 341 (M+,14), 182 (8), 181 (53), 168 (6), 167 (18), 167 (18), 166 (8), 165 (21), 152 (11), 144 (8), 132 (18), 131 (100), 129 (10), 128 (5), 120 (12), 118 (5), 117 (9), 116 (10), 115 (15), 106 (5), 104 (9), 103 (9), 91 (48), 77 (10).

Compound 172. (Rt=8.53 min), m/z (rel. int.) 275 (M+,165), 274 (95), 260 (18), 259 (24), 258 (87), 257 (28), 254 (17), 244 (41), 243 (46), 242 (18), 233 (30), 214 (26), 201 (46), 189 (18), 188 (36), 183 (27), 181 (22), 180 (100), 178 (24), 165 (38), 163 (28), 154 (17), 150 (39), 149 (25), 148 (82), 139 (58), 135 (20), 133 (35), 109 (20).

Compound 173. (Rt=8.44 min), m/z (rel. int.) 277 (M+,11), 260 (80), 259 (34), 245 (8), 241 (7), 234 (8), 233 (23), 230(19), 229 (100), 214 (9), 203 (12), 202 (17), 201 (25), 190 (8), 189 (25), 188 (18), 183 (18), 171 (7), 170 (15), 165 (14), 164 (7), 154 (7), 152 (7), 151 (8), 134 (12), 133 (23), 121 (7), 109 (13), 101 (8).

Compound 174. (Rt=8.49 min), m/z (rel. int.) 291 (M+,59), 260 (27), 259 (17), 234 (18), 233 (14), 230 (10), 229 (55), 203 (12), 202 (10), 201 (18), 189 (20), 188 (14), 183 (15), 170 (12), 169 (6), 168 (13), 165 (14), 164 (8), 152 (8), 151 (6), 138 (7), 137 (8), 134 (7), 133 (13), 109 (12), 101 (7) 57 (6), 44 (100), 42 (6).

Compound 175. (Rt=9.64 min), m/z (rel. int.) 303 (M+,8), 123 (47), 109 (6), 96 (7), 95 (40), 85 (26), 84 (100), 82 (7), 75 (9), 68 (4), 56 (25), 55 (29), 43 (9), 42 (16).

Compound 176. (Rt=8.35 min), m/z (rel. int.) 277 (M+,24), 245 (8), 220 (6), 219 (5), 183 (4), 171 (6), 170 (10), 151 (5), 138 (7), 109 (5), 57 (6), 44 (100), 42 (6).

Compound 177. (Rt=7.83 min), m/z (rel. int.) 241 (M+,0.1), 134 (30), 109 (8), 108 (100), 107 (16), 104 (17), 103 (9), 91 (12), 90 (4), 79 (10), 78 (14), 77 (24), 65 (8), 51 (9).

Compound 178. (Rt=8.29 min), m/z (rel. int.) 257 (M+,0.1), 134 (17), 125 (8), 124 (100), 109 (23), 104 (10), 103 (6), 95 (4), 91 (5), 81 (9), 78 (7), 77 (11), 65 (7), 52 (9), 51 (6)

Compound 179. (RC 7.88 min), m/z (rel. int.) 255 (M+,6), 148 (12), 115 (5), 108 (8), 107 (7), 104 (12), 103 (7), 91 (11), 79 (5), 78 (11), 77 (19), 65 (6), 51 (5), 44 (100), 42 (8).

Compound 180. (Rt=7.28 min), m/z (rel. int.) 295 (M+,1), 183 (10), 162 (22), 145 (11), 143 (28), 135 (10), 134 (100), 133 (11), 132 (13), 117 (6), 115 (12), 114 (6), 113 (9), 112 (7), 105 (17), 104 (57), 103 (32), 102 (6), 95 (7), 91 (18), 89 (5), 83 (8), 79 (6), 78 (28), 77 (28), 75 (6), 65 (8), 63 (11), 51 (11)

Compound 181. (Rt=7.7 min), m/z (rel. int.) 259 (M+,3), 137 (16), 135 (5), 122 (15), 121 (6), 109 (15), 108 (100), 107 (18), 96 (7), 91 (5), 79 (7), 78 (5), 77 (17), 65 (5), 51 (5).

Compound 182. (Rt=8.00 min), m/z (rel. int.) 225 (M+,2), 208 (51), 207 (40), 182 (14), 181 (100), 165 (7), 152 (24), 151 (8), 74 (2).

Compound 183. (Rt=8.98 min), m/z (rel. int.) 241 (M+, 7), 224 (33), 223 (46), 199 (6), 198 (15), 197 (100), 178 (6), 165 (28), 152 (13), 150 (2).

Compound 184. (Rt=8.90 min), m/z (rel. int.) 235 (M+,3), 218 (30), 217 (13), 203 (8), 202 (9), 193 (10), 192 (67), 191 (100), 190 (11), 189 (29), 178 (7), 168 (18), 152 (3)

Compound 185. (Rt=7.37 min), m/z (rel. int.) 245 (M+,0.1), 152 (8), 141 (61), 135 (10), 134 (100), 132 (11), 115 (14), 112 (64), 105 (19), 104 (71), 103 (45), 102 (8), 95 (13), 91 (24), 89 (8), 84 (12), 83 (28), 79 (10), 78 (42), 77 (44), 75 (16), 65 (12), 64 (7), 63 (16), 57 (24), 56 (7), 52 (7), 51 (22), 50 (9).

Compound 186. (Rt=7.31 min), m/z (rel. int.) 245 (M+,0.1), 152 (8), 141 (64), 135 (10), 134 (100), 132 (11), 117 (6), 115 (13), 112 (38), 77 (40), 75 (14), 65 (11), 64 (6), 63 (14), 57 (21), 52 (6), 51 (18), 50 (7).

Compound 187. (Rt=8.64 min), m/z (rel. int.) 239 (M+,0.0), 221 (17), 220 (6), 207 (8), 196 (11), 195 (39), 194 (14), 193 (11), 192 (38), 191 (7), 181 (6), 179 (21), 178 (100), 168 (7), 167 (41), 166 (17), 165 (53), 164 (6), 153 (6), 152 (26), 139 (6), 128 (7), 115 (18), 91 (6), 89 (6), 77 (6), 63 (6), 51 (5), 44 (6).

EXAMPLE 30

Biological Properties of Synthesized Arylalkylamines

Compounds synthesized as described in Example 28 and Example 29 were tested for various biological properties detailed in the examples.

TABLE 1

| Compound | $IC_{50}$ ($\mu$M) vs. NMDA[a] | $IC_{50}$ $\mu$M) vs. [3H]MK-801c |
|---|---|---|
| Compound 1 | 0.102 (7) | 126 (4) |
| Compound 2 | 0.192 (4) | not tested |
| Compound 3 | 0.003 (7) | not tested |
| Compound 4 | 0.184 (5) | 89 (1) |
| Compound 5 | 0.102 (1) 0.070 (3)[b] | 15.2 (2) |
| Compound 6 | 0.129 (1) | >100 (1) (0% at 100 $\mu$m)[d] |
| Compound 7 | 0.163 (2) | 129 (1) |
| Compound 8 | 0.099 (2) | 219 (1) |
| Compound 9 | 1.2 (5) | >100 (2) (10% at 100 $\mu$m)[d] |
| Compound 10 | 0.082 (2) | ~80 (1) (57% at 80 $\mu$m)[d] |
| Compound 11 | 4.0 (2) | not tested |
| Compound 12 | 6.0 (11) | 98 (1) |
| Compound 13 | not tested | not tested |
| Compound 14 | 8.8 (2) | ~100 $\mu$m |
| Compound 15 | 4.9 (3) | ~100 $\mu$m |
| Compound 16 | 5.1 (1) | 28.8 (1) |
| Compound 17 | 9.6 (1) | 36.3 (1) |
| Compound 18 | 5.1 (3) | 34 (1) |
| Compound 19 | 0.435 (11) | 2.1 (5) |
| Compound 20 | 0.070 (15) | 0.252 (9) |
| Compound 21 | 0.038 (3) | 0.457 (2) |
| Compound 22 | 0.145 (6) | 3.45 (2) |
| Compound 23 | 0.267 (3) | 5.4 (1) |
| Compound 24 | 0.206 (6) | 0.591 (6) |
| Compound 25 | 0.279 (2) | 0.871 (2) |
| Compound 26 | 27 (2) | 34 (2) |
| Compound 27 | 0.071 (1) | 0.180 (2) |
| Compound 28 | 0.380 (1) | 2.3 (3) |
| Compound 29 | 1.9 (2) | 5.8 (3) |
| Compound 30 | 0.035 (2) | 0.407 (2) |

TABLE 1-continued

| Compound | $IC_{50}$ ($\mu$M) vs. NMDA[a] | $IC_{50}$ $\mu$M) vs. [3H]MK-801c |
|---|---|---|
| Compound 31 | 0.052 (7) | 1.3 (2) |
| Compound 32 | 0.284 (5) | 0.799 (3) |
| Compound 33 | 0.060 (9) | 0.181 (6) |
| Compound 34 | 0.426 (6) | 2.7 (3) |
| Compound 35 | 6.2 (1) | 25.1 (1) |
| Compound 36 | not tested | not tested |
| Compound 37 | 0.944 (2) | 11.1 (2) |
| Compound 38 | 0.407 (2) | 2.3 (2) |
| Compound 39 | 0.251 (1) | 2.9 (3) |
| Compound 40 | 0.933 (1) | 18.1 (3) |
| Compound 41 | 0.724 (1) | 14.0 (3) |
| Compound 42 | not tested | not tested |
| Compound 43 | 0.232 (4) | 7.5 (2) |
| Compound 44 | not tested | not tested |
| Compound 45 | not tested | not tested |
| Compound 46 | 0.013 (3) | 5.2 (2) |
| Compound 47 | not tested | not tested |
| Compound 48 | not tested | not tested |
| Compound 49 | not tested | not tested |
| Compound 50 | 0.089 (6) | 0.762 (4) |
| Compound 51 | 1.1 (4) | 4.5 (2) |
| Compound 52 | 0.102 (3) | 0.380 (2) |
| Compound 53 | 0.217 (3) | 4.2 (2) |
| Compound 54 | 0.036 (4) | 0.046 (3) |
| Compound 55 | 0.035 (3) | 0.153 (2) |
| Compound 56 | 0.218 (4) | 0.955 (2) |
| Compound 57 | 0.028 (4) | 0.063 (2) |
| Compound 58 | 0.028 (2) | 0.203 (3) |
| Compound 59 | 0.272 (2) | 0.453 (3) |
| Compound 60 | 0.416 (11) | 0.641 (9) |
| Compound 61 | 0.134 (4) | 0.324 (2) |
| Compound 62 | 0.177 (5) | 0.617 (1) |
| Compound 63 | 0.093 (6) | 0.245 (3) |
| Compound 64 | 0.309 (3) | 0.851 (2) |
| Compound 65 | 0.167 (3) | 2.0 (1) |
| Compound 66 | 0.236 (4) | 1.2 (2) |
| Compound 67 | 10.95 (2) | 2.9 (1) |
| Compound 68 | 2.9 (1) | not tested |
| Compound 69 | 0.224 (2) | 0.366 (1) |
| Compound 70 | 1.7 (1) | not tested |
| Compound 71 | 6.35 (2) | not tested |
| Compound 72 | 7.4 (1) | not tested |
| Compound 73 | 12.6 (1) | not tested |
| Compound 74 | 27.5 (1) | not tested |
| Compound 75 | 0.94 (2) | not tested |
| Compound 76 | 0.73 (2) | not tested |
| Compound 77 | 5.5 (2) | not tested |
| Compound 78 | 10.2 (1) | not tested |
| Compound 79 | 12.6 (4) | 10.2 (2) |
| Compound 80 | 28 (1) | 182 (1) |
| Compound 81 | 1.4 (1) | 6.1 (2) |
| Compound 82 | 0.106 (5) | 0.794 (1) |
| Compound 83 | 0.341 (4) | 0.794 (1) |
| Compound 84 | 7.9 (2) | 23.4 (1) |
| Compound 85 | 1.2 (3) | 3.5 (1) |
| Compound 86 | 1.2 (3) | 6.0 (1) |
| Compound 87 | 0.657 (4) | 3.0 (1) |
| Compound 88 | 2.5 (3) | 10.6 (2) |
| Compound 89 | 0.240 (3) | 1.2 (2) |
| Compound 90 | 0.270 (4) | 1.4 (2) |
| Compound 91 | 0.162 (3) | 14.1 (2) |
| Compound 92 | 1.3 (3) | 20.2 (2) |
| Compound 93 | 0.486 (3) | 26.9 (2) |
| Compound 94 | 0.248 (4) | 22.6 (2) |
| Compound 95 | 0.311 (3) | 3.0 (2) |
| Compound 96 | 0.187 (5) | 1.1 (2) |
| Compound 97 | 0.410 (3) | 2.6 (1) |
| Compound 98 | 7.9 (1) | 52.5 (2) |
| Compound 99 | >100 (1) | 105 (2) |
| Compound 100 | 0.602 (2) | 3.2 (1) |
| Compound 101 | 0.912 (2) | 2.0 (1) |
| Compound 102 | 1.01 (2) | 3.3 (1) |
| Compound 103 | 0.380 (4) | 0.661 (2) |
| Compound 104 | 7.983 (3) | >10 (1) |
| Compound 105 | 1.03 (1) | >3 (1) |
| Compound 106 | 0.767 (1) | 1.31 (1) |

TABLE 1-continued

| Compound | IC$_{50}$ (μM) vs. NMDA[a] | IC$_{50}$ μM) vs. [3H]MK-801c |
|---|---|---|
| Compound 107 | 2.67 (1) | 3.83 (1) |
| Compound 108 | 1.06 (1) | 0.942 (1) |
| Compound 109 | 1.95 (1) | 1.08 (3) |
| Compound 110 | 42.7 (1) | 13.3 (1) |
| Compound 111 | 0.645 (3) | 0.167 (2) |
| Compound 112 | 28.0 (2) | 21.0 (1) |
| Compound 113 | 13.5 (1) | not tested |
| Compound 114 | 3.4 (1) | not tested |
| Compound 115 | 1.4 (1) | 1.0 (1) |
| Compound 116 | 3.6 (1) | not tested |
| Compound 117 | 19.6 (2) | 6.0 (2) |
| Compound 118 | 0.409 (2) | 0.240 (3) |
| Compound 119 | 0.115 (4) | 0.087 (3) |
| Compound 120 | 0.101 (3) | 0.074 (3) |
| Compound 121 | 0.656 (3) | 0.670 (3) |
| Compound 122 | 0.209 (2) | 0.342 (2) |
| Compound 123 | 9.6 (7) | >3 (2) |
| Compound 124 | 3.5 (1) | 14.3 (3) |
| Compound 125 | 1.7 (1) | 6.7 (2) |
| Compound 126 | 0.398 (3) | 6.0 (1) |
| Compound 127 | 1.2 (3) | 17.5 (2) |
| Compound 128 | 0.646 (4) | 5.5 (1) |
| Compound 129 | 1.26 (2) | not tested |
| Compound 130 | 0.851 (2) | not tested |
| Compound 131 | 1.23 (2) | not tested |
| Compound 132 | 1.3 (1) | 6.4 (1) |
| Compound 133 | 0.760 (1) | 3.0 (1) |
| Compound 134 | 2.5 (1) | >10 (1) |
| Compound 135 | 0.244 (2) | 1.185 (2) |
| Compound 136 | 0.139 (2) | 0.706 (1) |
| Compound 137 | 0.232 (3) | 0.074 (2) |
| Compound 138 | 107 (1) | >100 (1) |
| Compound 139 | 1.97 (2) | 5.6 (2) |
| Compound 140 | 20.8 (1) | not tested |
| Compound 141 | 4.26 (1) | 8.97 (1) |
| Compound 142 | 1.013 (3) | 1.54 (2) |
| Compound 143 | 2.82 (1) | not tested |
| Compound 144 | not tested | not tested |
| Compound 145 | 0.098 (1) | 0.626 (1) |
| Compound 146 | 0.829 (3) | 0.372 (1) |
| Compound 147 | 0.894 (2) | not tested |
| Compound 148 | 0.549 (2) | 0.373 (2) |
| Compound 149 | 0.085 (3) | 0.150 (3) |
| Compound 150 | 0.195 (2) | 0.351 (2) |
| Compound 151 | 54.9 (1) | >100 (1) |
| Compound 152 | not tested | not tested |
| Compound 153 | not tested | not tested |
| Compound 154 | not tested | not tested |
| Compound 155 | not tested | not tested |
| Compound 156 | 0.069 (3) | 0.090 (2) |
| Compound 157 | 0.142 (2) | 23.16 (2) |
| Compound 158 | 0.351 (2) | 39.64 (1) |
| Compound 159 | 0.185 (2) | 10.41 (1) |
| Compound 160 | 7.35 (3) | 48.94 (1) |
| Compound 161 | 0.247 (2) | 5.62 (1) |
| Compound 162 | 1.138 (2) | 76.41 (1) |
| Compound 163 | 0.326 (2) | 10.34 (1) |
| Compound 164 | 0.475 (2) | 18.30 (1) |
| Compound 165 | 0.337 (2) | 171 (1) |
| Compound 166 | 0.619 (2) | 36.7 (1) |
| Compound 167 | 0.080 (2) | 14.5 (1) |
| Compound 168 | 0.092 (2) | 17.4 (1) |
| Compound 169 | 0.298 (2) | 26.7 (1) |
| Compound 170 | 0.238 (2) | 57.0 (1) |
| Compound 171 | 0.310 (3) | 39.6 (1) |
| Compound 172 | 38.0 (1) | 37.3 (1) |
| Compound 173 | 22.9 (1) | 24.1 (1) |
| Compound 174 | not tested | 57.0 (1) |
| Compound 175 | not tested | 5.1 (1) |
| Compound 176 | not tested | 10.0 (1) |
| Compound 177 | not tested | 0.754 (1) |
| Compound 178 | not tested | 1.25 (1) |
| Compound 179 | not tested | 1.67 (1) |
| Compound 180 | <100 (1) | <10 (1) |
| Compound 181 | 0.081 (1) | 0.632 (1) |
| Compound 182 | 2.6 (1) | 7.05 (1) |
| Compound 183 | 0.676 (1) | 5.01 (1) |
| Compound 184 | 1.5 (1) | 1.51 (1) |
| Compound 185 | 0.646 (1) | 0.639 (1) |
| Compound 186 | 0.155 (1) | 0.123 (1) |
| Compound 187 | 1.78 (1) | 2.01 (1) |
| Compound 188 | not tested | not tested |
| Compound 189 | not tested | not tested |
| Compound 190 | not tested | not tested |
| Compound 191 | not tested | not tested |
| Compound 192 | not tested | not tested |
| Compound 193 | not tested | not tested |
| Compound 194 | not tested | not tested |
| Compound 195 | not tested | not tested |
| Compound 196 | not tested | not tested |
| Compound 197 | not tested | not tested |
| Compound 198 | not tested | not tested |
| Compound 199 | not tested | not tested |
| Compound 200 | not tested | not tested |
| Compound 201 | not tested | not tested |
| Compound 202 | not tested | not tested |
| Compound 203 | not tested | not tested |
| Compound 204 | not tested | not tested |
| Compound 205 | not tested | not tested |
| Compound 206 | not tested | not tested |
| Compound 207 | not tested | not tested |
| Compound 208 | not tested | not tested |
| Compound 209 | not tested | not tested |
| Compound 210 | not tested | not tested |
| Compound 211 | not tested | not tested |
| Compound 212 | not tested | not tested |
| Compound 213 | not tested | not tested |
| Compound 214 | not tested | not tested |
| Compound 215 | not tested | not tested |

[a]Inhibition of NMDA/glycine-induced increases in intracellular calcium in cultured rat cerebellar granule cells (RCGC's) (see Example 1). (# in parentheses indicates the number of experiments).
[b]TFA salt.
[c]Inhibition of [3H]MK-801 binding in rat cortical/hippocampal washed membrane preparations (see Example 4).
[d]IC$_{50}$ study incomplete. % inhibition at the stated concentration.

A comparison of the IC$_{50}$ values in the RCGC assay with the IC$_{50}$ values in the [3H]MK-801 binding assay (Table 1) illustrates that the arylalkylamines of the invention inhibit NMDA receptor activity by a mechanism different than that of binding to the MK-801 binding site; the concentration of the compound that inhibits NMDA receptor function is several orders of magnitude less than the concentration that competes at the site labeled by [3H]MK-801. This is not the case, however, with the simplified arylalkylamines exemplified by Compounds 19–215. Such compounds bind to the site labeled by [3H]MK-801 at concentrations ranging approximately 1 to 400-fold higher than those which antagonize NMDA receptor-mediated function in the rat cerebellar granule cell assay.

Some of the simplified arylalkylamines disclosed have structural features similar to portions of other compounds which are utilized as, for example, anticholinergics, antiparkinsonians, antihistamines, antidepressants, calcium channel blockers, coronary vasodilators, opiate analgesics, and antiarrhythmics. However, when certain of these compounds were evaluated for NMDA receptor antagonist potency (Example 1), as can be seen in Table 2, none of the compounds tested, with the exception of (R)- and (S)-fendiline, nisoxetine, and the Eli Lilly compound, had IC$_{50}$ values less than 1 μM. These data are summarized in Table 2.

TABLE 2

| Compound and Therapeutic Utility | Structure | IC$_{50}$ (μM) vs. NMDA[a] |
|---|---|---|
| (R)-fendiline (calcium channel blocker; coronary vasodilator) | 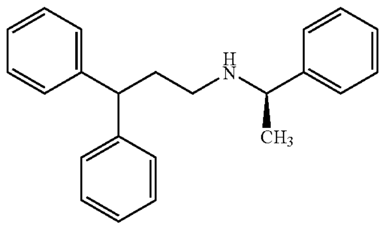 | 0.719 |
| (S)-fendiline (calcium channel blocker; coronary vasodilator) | 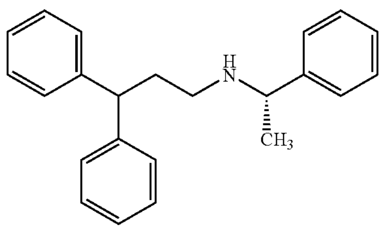 | 0.686 |
| prenylamine (calcium channel blocker; coronary vasodilator) | 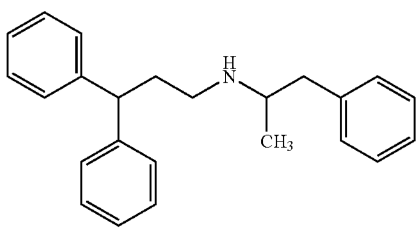 | ~10 |
| pheniramine (antihistamine) | 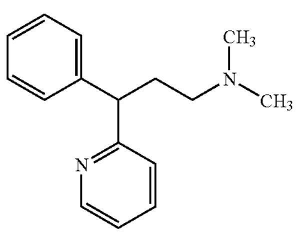 | 22 |
| chlorpheniramine (antihistamine) | 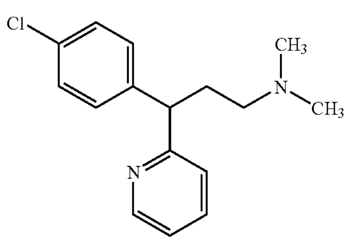 | >100 |
| brompheniramine (antihistamine) | 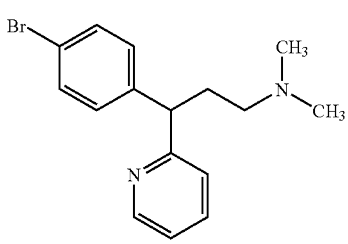 | 138 |

TABLE 2-continued

| Compound and Therapeutic Utility | Structure | IC$_{50}$ (μM) vs. NMDA[a] |
|---|---|---|
| diphenhydramine (antihistamine) | 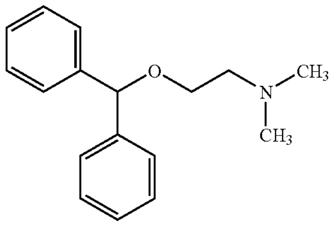 | 26 |
| doxylamine (antihistamine; hypnotic) | 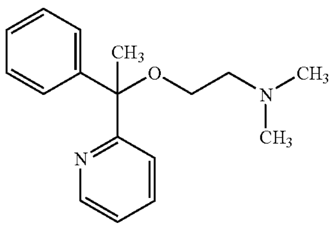 | 62 |
| chlorcyclizine (antihistamine) | 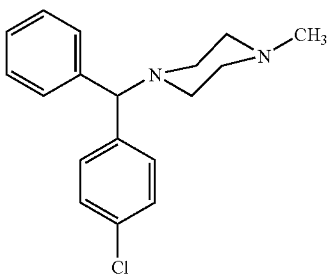 | ~10 |
| cyclizine (antiemetic) | 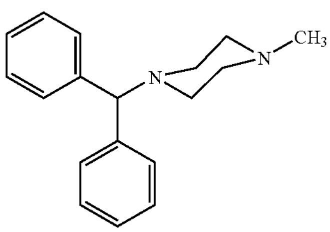 | 28 |
| nor-cyclizine (pharmaceutical intermediate) | 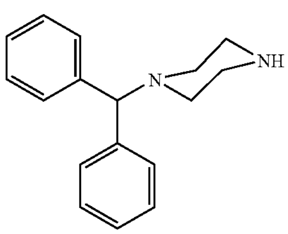 | 23 |
| lidoflazine (calcium channel blocker; coronary vasodilator) | 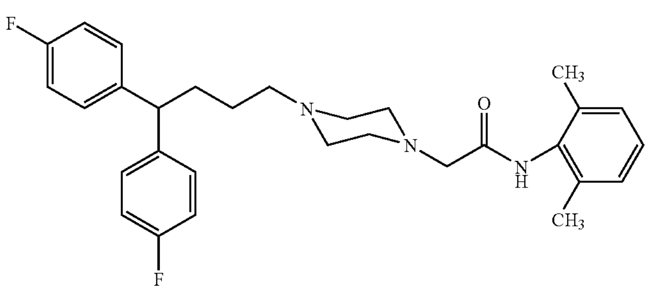 | >30 |

TABLE 2-continued

| Compound and Therapeutic Utility | Structure | IC$_{50}$ (μM) vs. NMDA[a] |
|---|---|---|
| pimozide (antipsychotic) | 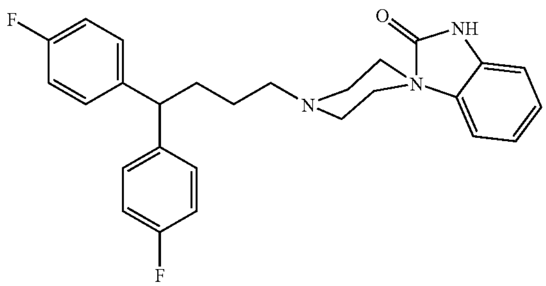 | >10 |
| disopyramide (antiarrhythmic) | 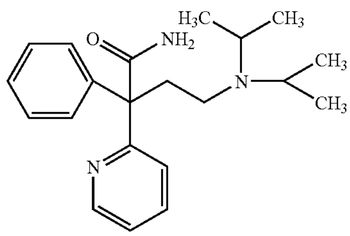 | >100 |
| isopropamide (anticholinergic) | 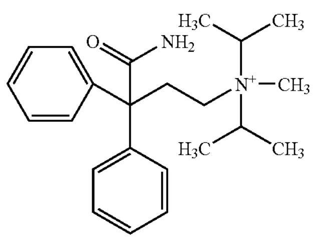 | 87 |
| pridinol (anticholinergic; antiparkinsonian) | 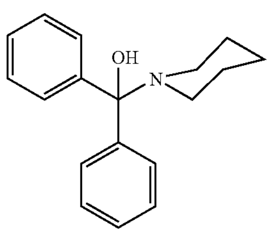 | 10.7 |
| chloropyramine (antihistamine) | 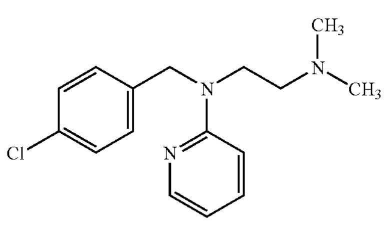 | 76 |
| trihexyphenidyl (anticholinergic; antiparkinsonian) | 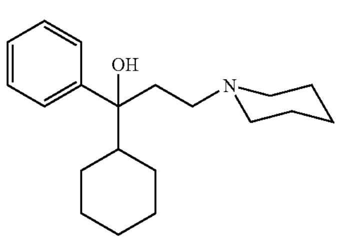 | 5.13 |

TABLE 2-continued

| Compound and Therapeutic Utility | Structure | IC$_{50}$ (μM) vs. NMDA[a] |
| --- | --- | --- |
| fluoxetine (antidepressant) | 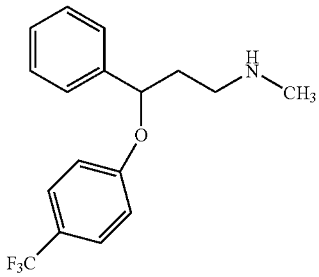 | 3.4 |
| zimeldine (antidepressant) | 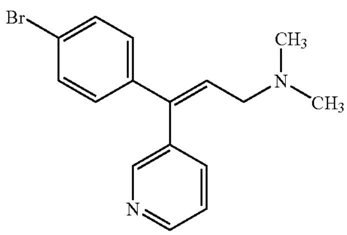 | ≥26 |
| methadone (opiate analgesic) | 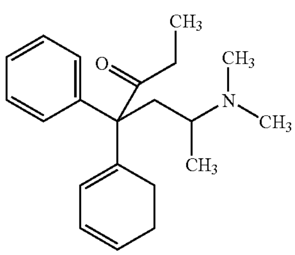 | not tested |
| Astra compound[b] (antidepressant) | 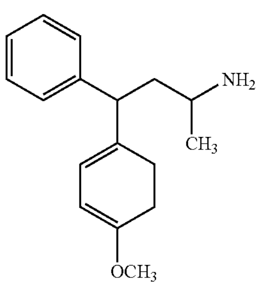 | >30 |
| Nono-Nordisk compound[c] (calcium channel blocker; neuroprotectant) | 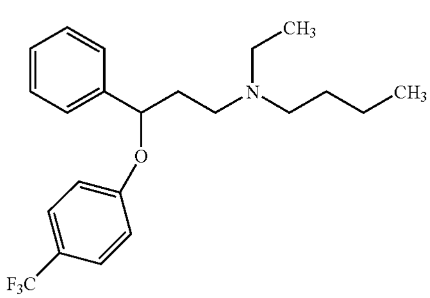 | not tested |

TABLE 2-continued

| Compound and Therapeutic Utility | Structure | IC$_{50}$ (µM) vs. NMDA[a] |
|---|---|---|
| Novo-Nordisk compound[d] (calcium channel blocker; neuroprotectant) | 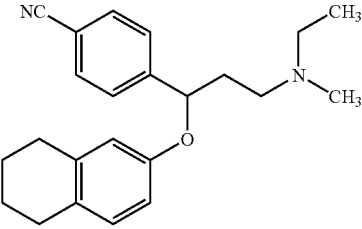 | 28.8 |
| nisoxetine (monoamine uptake inhibitor; antidepressant) | 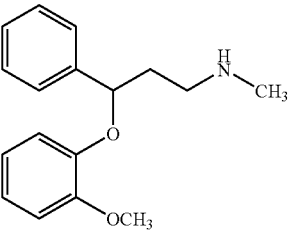 | 0.894 |
| terodiline (calcium channel blocker; anticholinergic; vasodilator) | 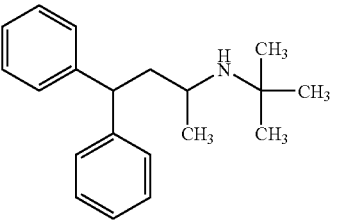 | not tested |
| tomoxetine (monoamine uptake inhibitor; antidepressant) | 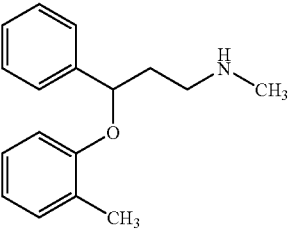 | not tested |
| amitriptyline (serotonin uptake inhibitor; antidepressant) | 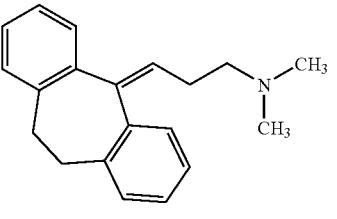 | not tested |
| imipramine (serotonin uptake inhibitor; antidepressant) | 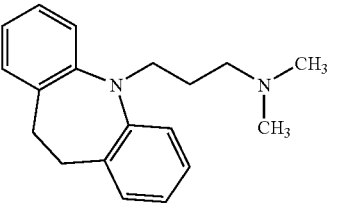 | not tested |

TABLE 2-continued

| Compound and Therapeutic Utility | Structure | IC$_{50}$ (µM) vs. NMDA[a] |
|---|---|---|
| clomipramine (serotonin uptake inhibitor; antidepressant) | 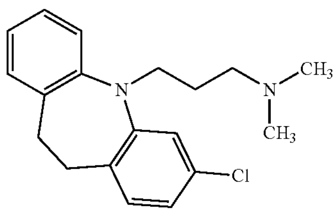 | not tested |
| doxepine (serotonin uptake inhibitor; antidepressant) | 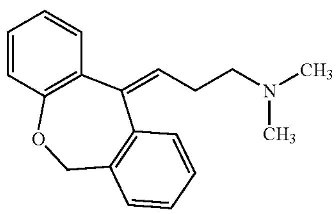 | not tested |
| chlorpromazine dopamine antagonist; neuroleptic) | 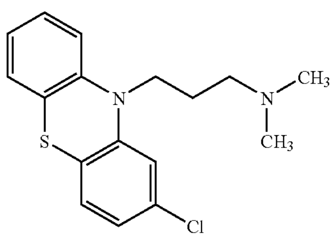 | not tested |
| desipramine (antidepressant) | 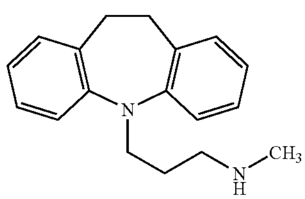 | 2.3 |
| protriptyline (antidepressant) | 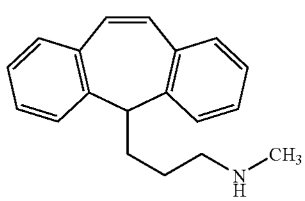 | ≦10 |
| Eli Lilly Compound NMDA receptor antagonist[a] | 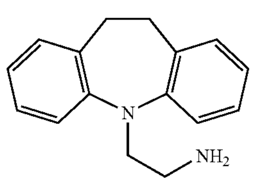 | 0.609 |

[a] Inhibition of NMDA/dlycine-induced increases in intracellular calcium in cultured rat cerebellar granule cells (RCGC, s) (see Example 1).
[b] Disclosed as compound 2 in Table 4 in Marcusson et al., Inhibition of [$^3$H] paroxetine binding by various serotonin uptake inhibitors: structure-activity relationships. Europ. J. Pharmacol. 215: 191–198, 1992.
[c] Disclosed as compound 17 in Jakobsen et al., Aryloxy-phenylpropylamines and their calcium overload blocking compositions and methods of use. U.S. Pat. No. 5,310,756, May 10, 1994.
[d] Disclosed as compound 25 in Jakobsen et al., Aryloxy-phenylpropylamines and their calcium overload blocking compositions and methods of use. U.S. Pat. No. 5,310,756, May 10, 1994.
[e] Disclosed as Compound 1 in McQuaid et al., Inhibition of [$^3$H]-MK801 binding and protection against NMDA-induced lethality in mice by a series of imipramine analogs Res. Comm. in Pathol. and Pharm. 77: 171–178, 1992.

Structure-activity relationship studies were initiated using Compound 19 as the lead structure. An examination of the side chain demonstrated that the propyl side chain was optimal for NMDA receptor antagonist-potency (Table 3). This finding was verified using Compound 20 as the lead structure (Table 3).

TABLE 3

| Compound | Structure | $IC_{50}$ (μM) vs. NMDA[a] |
|---|---|---|
| 2,2-diphenylethylamine | 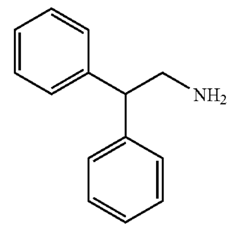 | 24.5 |
| 3,3-diphenylpropylamine (Compound 19) | 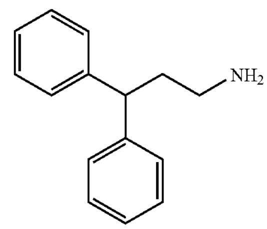 | 0.435 |
| 4,4-diphenylbutylamine (Compound 70) | 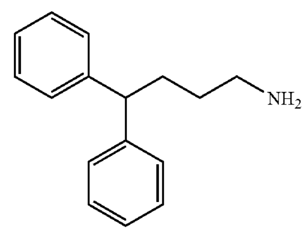 | 1.7 |
| 5,5-diphenylpentylamine (Compound 71) | 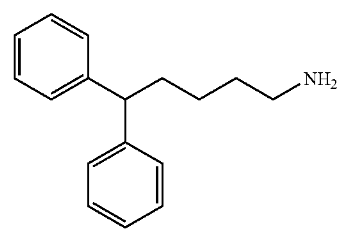 | 6.4 |
| 2,2-bis(3-fluorophenyl)-1-ethylamine (Compound 98) | 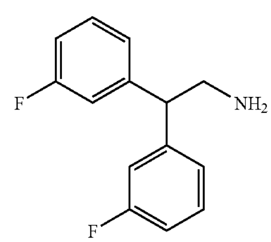 | 7.9 |
| 3,3-bis(3-fluorophenyl)-1-propylamine (Compound 20) | 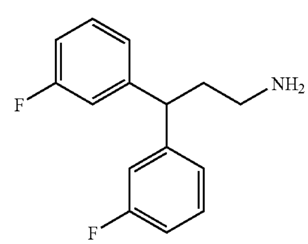 | 0.070 |

TABLE 3-continued

| Compound | Structure | IC$_{50}$ (μM) vs. NMDA[a] |
|---|---|---|
| 4,4-bis(3-fluorophenyl)-1-butylamine (Compound 100) | 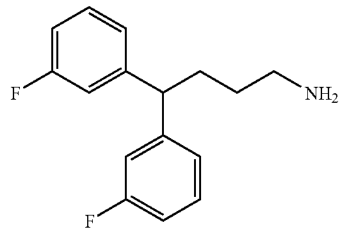 | 0.602 |

[a]Inhibition of NMDA/glycine-induced increases in intracellular calcium in cultured rat cerebellar granule cells (RCGC's) (see Example 1).

Further SAR studies examined the optimal pattern of phenyl ring substitution. Initial studies demonstrated that substitution of a halogen group (fluoro or chloro) at the meta position was optimal for NMDA receptor antagonist potency (Table 4). Increasing the number of fluoro substituents led to an apparent decrease in potency (Table 4).

TABLE 4

| Compound | Structure | IC$_{50}$ (μM) vs. NMDA[a] |
|---|---|---|
| 3,3-diphenyl-1-propylamine (Compound 19) | 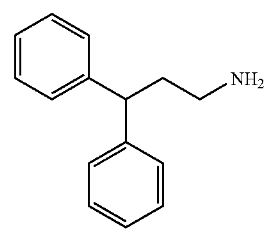 | 0.435 |
| 3-(2-fluorophenyl)-3-(4-fluorophenyl)-1-propylamine (Compound 76) | 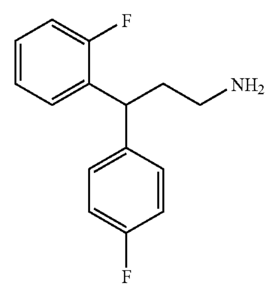 | 0.730 |
| 3,3-bis(4-fluorophenyl)-1-propylamine (Compound 77) | 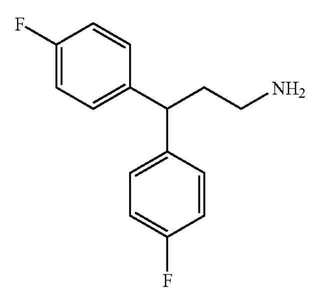 | 5.5 |

TABLE 4-continued

| Compound | Structure | IC$_{50}$ (µM) vs. NMDA[a] |
|---|---|---|
| 3,3-bis(3-fluorophenyl)-1-propylamine (Compound 20) | 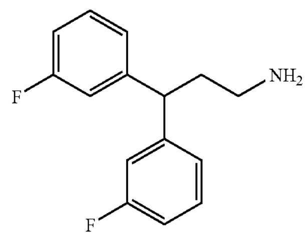 | 0.070 |
| 3-(2-fluorophenyl)-3-(3-fluorophenyl)-1-propylamine (Compound 52) | 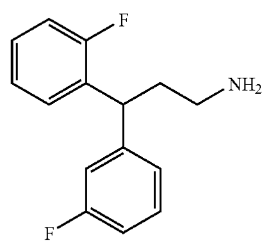 | 0.102 |
| 3,3-bis(2-fluorophenyl)-1-propylamine (Compound 53) | 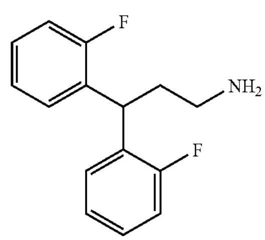 | 0.217 |
| 3,3-bis(3-chlorophenyl)-1-propylamine (Compound 31) | 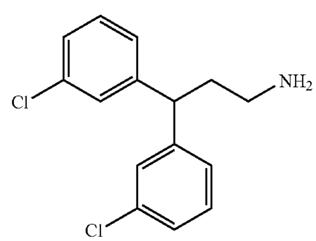 | 0.052 |
| 3-(3-fluorophenyl)-3-(3-chlorophenyl)-1-propylamine (Compound 30) | 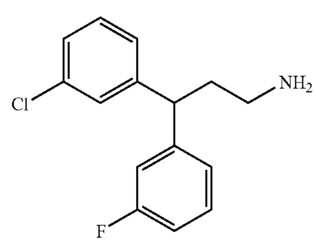 | 0.035 |
| 3-(3-fluorophenyl)-3-phenyl-1-propylamine (Compund 32) | 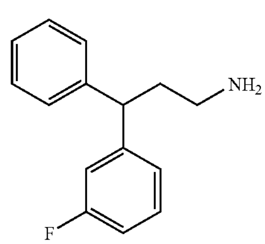 | 0.284 |

TABLE 4-continued

| Compound | Structure | IC$_{50}$ (μM) vs. NMDA[a] |
|---|---|---|
| 3-(3,5-difluorophenyl)-3-(3-fluorophenyl)-1-propylamine (Compund 96) | 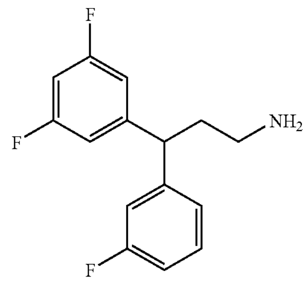 | 0.187 |
| 3,3-bis(3,5,difluorophenyl)-1-propylamine (Compund 97) | 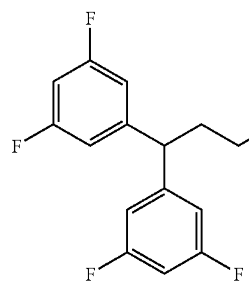 | 0.410 |
| 3,3-bis[3-(trifluoromethyl)phenyl]-1-propylamine (Compound 78) | 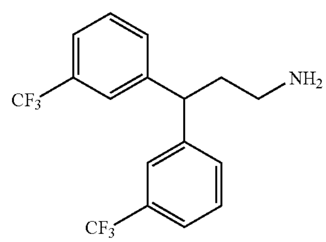 | 10.2 |

[a]Inhibition of NMDA/glycine-induced increases in intracellular calcium in cultured rat cerebellar granule cells (RCGC's) (see Example 1).

Replacement of one of the fluoro groups on one phenyl ring with a methyl, methoxy or hydroxy group led to no change or a decrease in the in vitro NMDA receptor antagonist potency. The ortho position was optimal for this methyl, methoxy or hydroxy group, and the rank order of potency for this substitution was methyl>methoxy>hydroxy (Table 5). Also illustrated in Table 5 are those compounds possessing the 3,3-bis(3-fluorophenyl) moiety with additional methyl or methoxy substitutions on the phenyl rings, often leading to increase in NMDA receptor antagonist potency. Table 5 also illustrates those compounds possessing the 3,3-bis(2-methyphenyl) or 3,3-bis(2-methoxyphenyl) moiety in place of the 3,3-bis(3-fluorophenyl) moiety; these substitutions are acceptable, although a decrease in potency is noted.

TABLE 5

| Compound | Structure | IC$_{50}$ (μM) vs. NMDA[a] |
|---|---|---|
| 3,3-bis(3-fluorophenyl)-1-propylamine (Compound 20) | 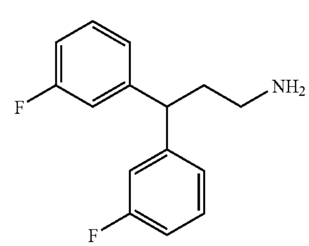 | 0.070 |

TABLE 5-continued

| Compound | Structure | IC$_{50}$ (μM) vs. NMDA[a] |
| --- | --- | --- |
| 3-(3-fluorophenyl)-3-(2-methylphenyl)-1-propylamine (Compound 27) | 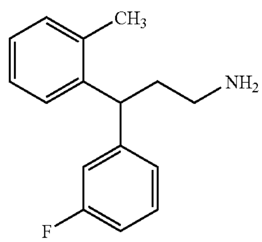 | 0.071 |
| 3-(3-fluorophenyl)-3-(3-methylphenyl)-1-propylamine (Compound 28) | 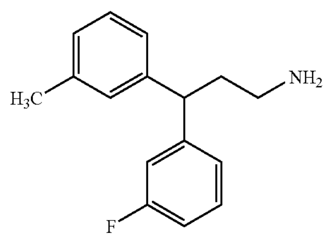 | 0.380 |
| 3-(3-fluorophenyl)-3-(4-methylphenyl)-1-propylamine (Compound 29) | 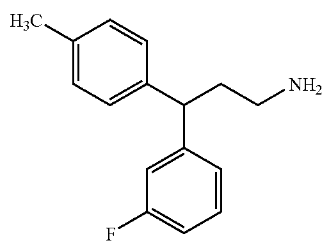 | 1.9 |
| 3-(3-fluorophenyl)-3-(2-methoxyphenyl)-1-propylamine (Compound 24) | 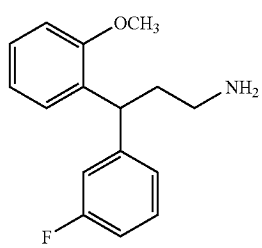 | 0.206 |
| 3-(3-fluorophenyl)-3-(3-methoxyphenyl)-1-propylamine (Compound 25) | 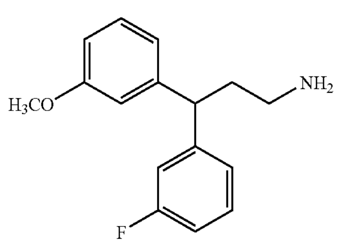 | 0.279 |
| 3-(3-fluorophenyl)-3-(4-methoxyphenyl)-1-propylamine (Compound 26) | | 27 |

TABLE 5-continued

| Compound | Structure | IC$_{50}$ (μM) vs. NMDA[a] |
|---|---|---|
| 3-(2-methoxyphenyl)-3-phenyl-1-propylamine (Compound 97) | 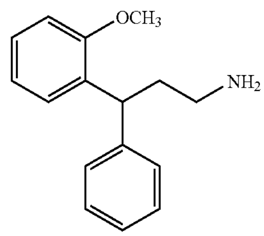 | 0:410 |
| 3-(2-hydroxyphenyl)-3-(3-fluorophenyl)-1-propylamine (Compound 103) | 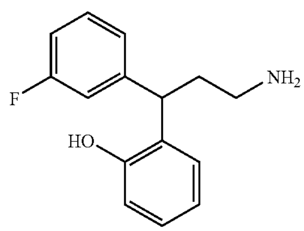 | 0.380 |
| 3-(3-hydroxyphenyl)-3-3-fluorophenyl)-1-propylamine (Compound 101) | 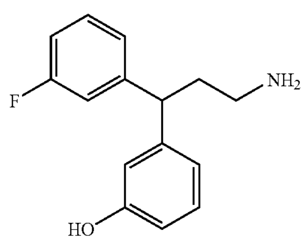 | 0.912 |
| 3-(3-fluorophenyl)-3-(2-methyl-3-fluorophenyl)-1-propylamine (Compound 56) | 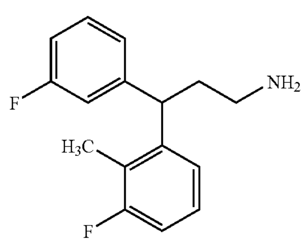 | 0.218 |
| 3-(3-fluorophenyl)-3-(3-fluoro-6-methylphenyl)-1-propylamine (Compound 57) | 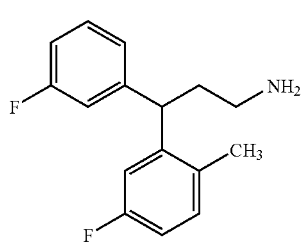 | 0.028 |
| 3,3-bis(3-fluoro-6-methylphenyl)-1-propylamine (Compound 58) | 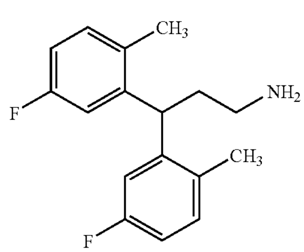 | 0.028 |

TABLE 5-continued

| Compound | Structure | IC$_{50}$ (μM) vs. NMDA[a] |
|---|---|---|
| 3-(3-fluorophenyl)-3-(3-fluoro-6-methoxyphenyl)-1-propylamine (Compound 61) | 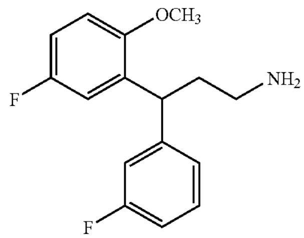 | 0.134 |
| 3,3-bis(2-methylphenyl)-1-propylamine (Compound 65) | 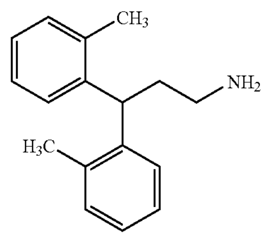 | 0.167 |
| 3,3-bis(2-methoxyphenyl)-1-propylamine (Compound 62) | 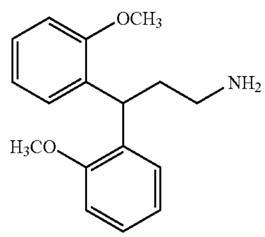 | 0.177 |
| 3,3-bis(3-methoxyphenyl)-1-propylamine (Compound 115) | 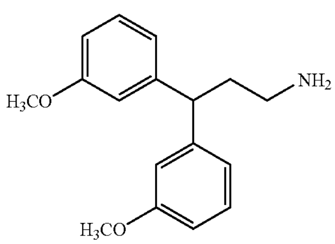 | 1.9 |

[a]Inhibition of NMDA/glycine-induced increases in intracellular calcium in cultured rat cerebellar granule cells (RCGC's) (see Example 1).

The next series of SAR experiments investigated the effect of alkyl chain substitutions (branching patterns) on NMDA receptor antagonist potency in vitro. The addition of a methyl group on either the α or β carbon on the propyl side chain led to a decrease or no change in potency, respectively (Table 6).

TABLE 6

| Compound | Structure | IC$_{50}$ (μM) vs. NMDA[a] |
|---|---|---|
| 3,3-bis(3-fluorophenyl)-1-propylamine (Compound 20) | | 0.070 |

TABLE 6-continued
| Compound | Structure | IC$_{50}$ (μM) vs. NMDA[a] |
|---|---|---|
| 3,3-bis(3-fluorophenyl)-2-methyl-1-propylamine (Compound 21) | 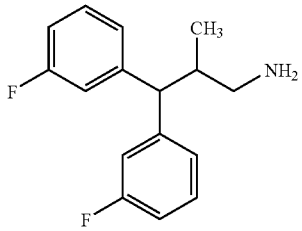 | 0.038 |
| 3,3-bis(3-fluorophenyl)-2-methyl-1-propylamine (Compound 33) | 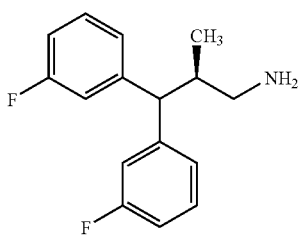 | 0.060 |
| 3,3-bis(3-fluorophenyl)-2-methyl-1-propylamine (Compound 34) | 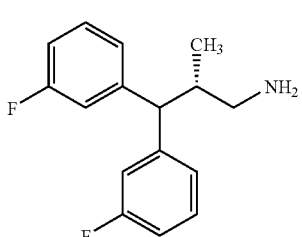 | 0.426 |
| 3,3-bis(3-fluorophenyl)-1-methyl-1-propylamine (Compound 22) | 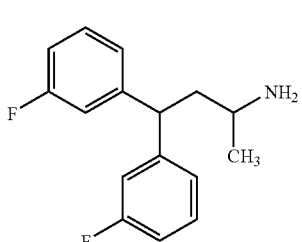 | 0.145 |
| 3,3-bis(3-fluorophenyl)-1-methyl-1-propylamine (Compound 50) | 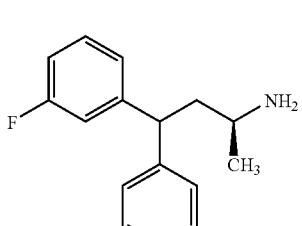 | 0.089 |
| 3,3-bis(3-fluorophenyl)-1-methyl-2-propylamine (Compound 51) | 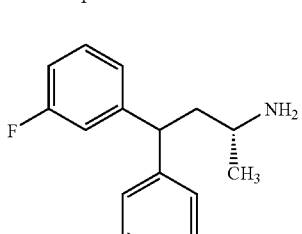 | 1.1 |

TABLE 6-continued

| Compound | Structure | IC$_{50}$ (μM) vs. NMDA[a] |
|---|---|---|
| 3,3-bis(3-fluorophenyl)-2-ethyl-1-propylamine (Compound 55) | 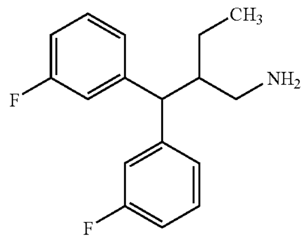 | 0.035 |
| 3,3-bis(3-fluorophenyl)-1-ethyl-1-propylamine (Compound 23) | 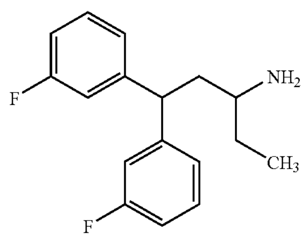 | 0.267 |
| 3,3-bis(3-fluorophenyl)-2-hydroxyethyl-2-propylamine (Compound 54) | 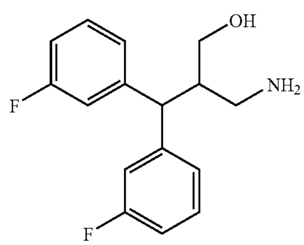 | 0.036 |
| 3,3-bis(3-fluorophenyl)-3-ethyl-1-propylamine (Compound 82) | 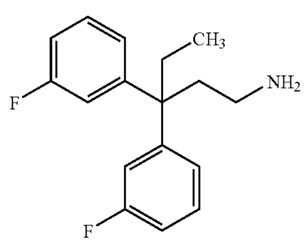 | 0.106 |
| 3,3-bis(3-fluorophenyl)-1,2-dimethyl-1-propylamine (Compound 38) | 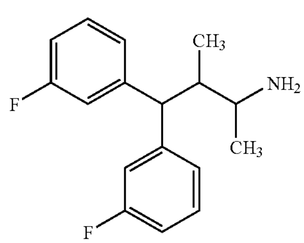 | 0.407 |
| 3,3-bis(3-fluorophenyl)-2,2-dimethyl-1-propylamine (Compound 41) | 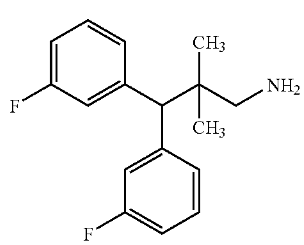 | 0.724 |

TABLE 6-continued

| Compound | Structure | IC$_{50}$ (μM) vs. NMDA[a] |
|---|---|---|
| 3,3-bis(3-fluorophenyl)-2,2-diethyl-2-propylamine (Compound 80) | 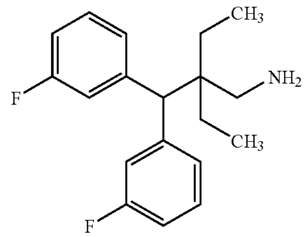 | 28 |

[a]Inhibition of NMDA/glycine-induced increases in intracellular calcium in cultured rat cerebellar granule cells (RCGC's) (see Example 1).

The next series of SAR experiments investigated the effect of incorporation of a double bond within the propyl chain on NMDA receptor antagonist potency in vitro (Table 7). As can be seen in Table 7, the incorporation of a double bond decreased potency in a consistent manner.

TABLE 7

| Compound | Structure | IC$_{50}$ (μM) vs. NMDA[a] |
|---|---|---|
| 3,3-bis(3-fluorophenyl)-1-propylamine (Compound 20) | 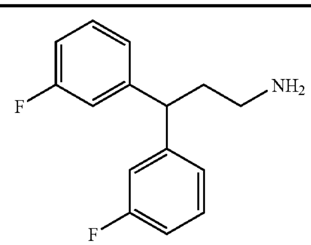 | 0.070 |
| 3,3-bis(3-fluorophenyl)-prop-2-ene-1-amine (Compound 139) | 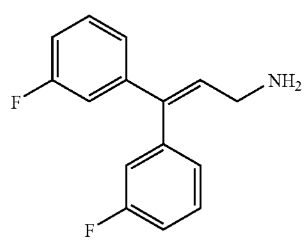 | 1.4 |
| 3,3-diphenyl-1-propylamine (Compound 19) | 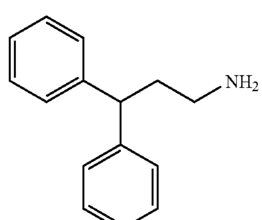 | 0.435 |
| 3,3-diphenyl-prop-2-ene-1-amine (Compound 81) | 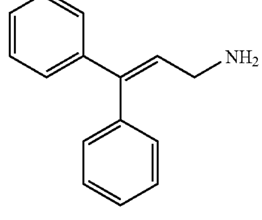 | 1.4 |

TABLE 7-continued

| Compound | Structure | IC$_{50}$ (μM) vs. NMDA[a] |
|---|---|---|
| 3-(3-fluorophenyl)-3-phenyl-1-propylamine (Compound 32) | 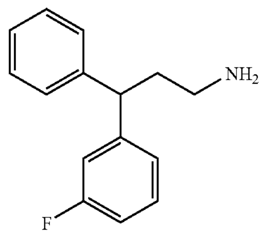 | 0.284 |
| 3-(3-fluorophenyl)-3-phenyl-prop-2-ene-1-amine (Compound 107) | (mixture of 2 compounds) | 2.67 |
| 3,3-bis(3-methoxyphenyl)-1-propylamine (Compound 115) | 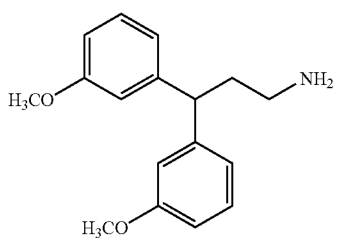 | 1.9 |
| 3,3-bis(3-methoxyphenyl)-prop-2-ene-1-amine (Compound 116) | 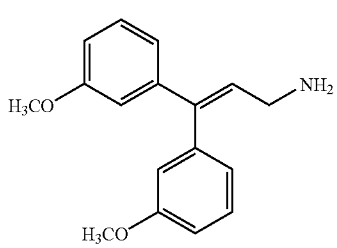 | 4.47 |

[a]Inhibition of NMDA/glycine-induced increases in intracellular calcium in cultured rat cerebellar granule cells (RCGC's) (see Example 1).

The next series of SAR experiments investigated the effect of incorporation of the propylamine chain into a ring structure on NMDA receptor antagonist potency in vitro (Table 8).

TABLE 8

| Compound | Structure | IC$_{50}$ (μM) vs. NMDA[a] |
|---|---|---|
| 3,3-bis(3-fluorophenyl)-1-propylamine (Compound 20) | 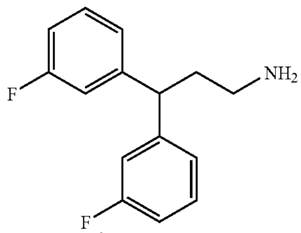 | 0.070 |
| Compound 63 | 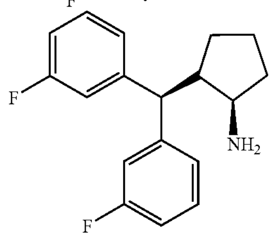 | 0.093 |
| Compound 64 | 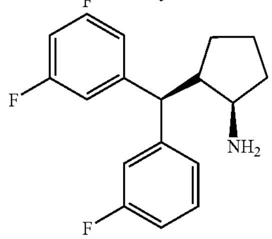 | 0.309 |
| Compound 102 | 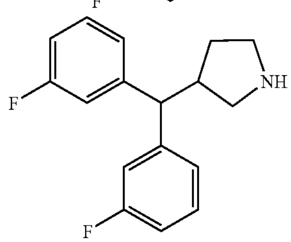 | 1.01 |

TABLE 8-continued

| Compound | Structure | IC$_{50}$ (μM) vs. NMDA[a] |
|---|---|---|
| Compound 84 | 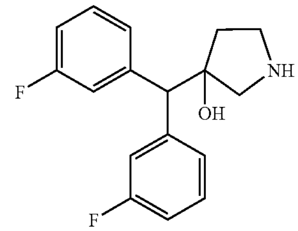 | 7.9 |
| Compound 111 | 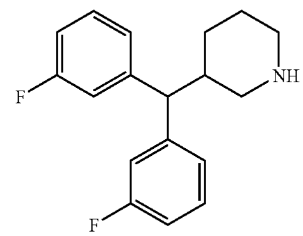 | 0.790 |
| Compound 112 | 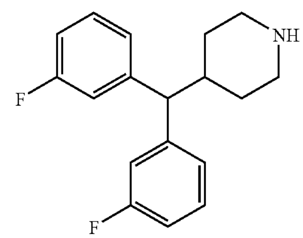 | 28.9 |

[a]Inhibition of NMDA/glycine-induced increases in intracellular calcium in cultured rat cerebellar granule cells (RCGC's) (see Example 1).

The next series of SAR experiments investigated the effect of simple alkyl substitution on the nitrogen on NMDA receptor antagonist potency in vitro (Table 9)

TABLE 9

| Compound | Structure | IC$_{50}$ (μM) vs. NMDA[a] |
|---|---|---|
| 3,3-bis(3-fluorophenyl-1-propylamine (Compound 20) | 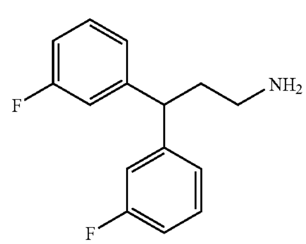 | 0.070 |

TABLE 9-continued

| Compound | Structure | IC$_{50}$ (μM) vs. NMDA[a] |
|---|---|---|
| N-methyl-3,3-bis(3-fluorophenyl)-1-propylamine (Compound 60) | 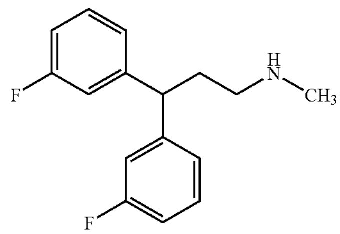 | 0.416 |
| N-ethyl-3,3-bis(3-fluorophenyl)-1-propylamine (Compound 59) | 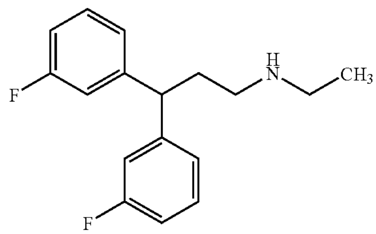 | 0.272 |
| N,N-dimethyl-3,3-bis(3-fluorophenyl)-1-polyamine (Compound 123) | 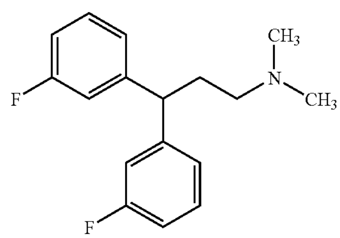 | 9.6 |
| 3-(3-fluorophenyl)-3-phenyl-1-propylamine (Compound 32) | 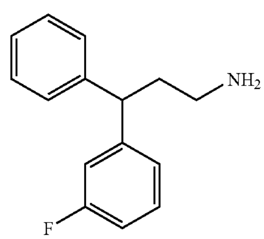 | 0.284 |
| N-methyl-3-(3-fluorophenyl)-3-phenyl-1-propylamine (Compound 108) | 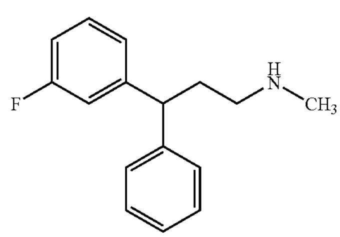 | 1.06 |
| 3,3-diphenylpropylamine (Compound 19) | 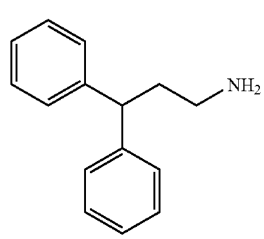 | 0.435 |

TABLE 9-continued

| Compound | Structure | IC$_{50}$ (μM) vs. NMDA[a] |
|---|---|---|
| N-methyl-3,3-diphenylpropylamine (Compound 67) | 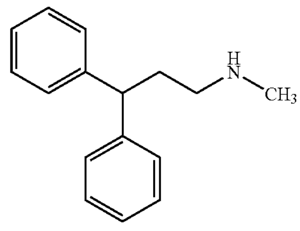 | 10.95 |
| N-ethyl-3,3-diphenylpropylamine (Compound 68) | 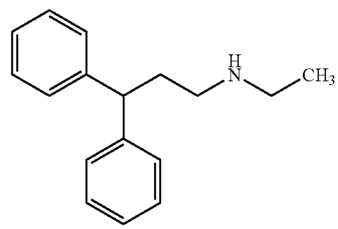 | 2.9 |
| N,N-dimethyl-3,3-diphenylpropylamine (Compound 73) | 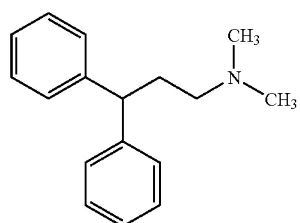 | 12.6 |
| N-isopropyl-3,3-diphenylpropylamine (Compound 72) | 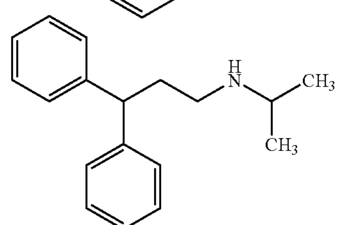 | 7.4 |
| N,N-diethyl-3,3-diphenylpropylamine (Compound 74) | 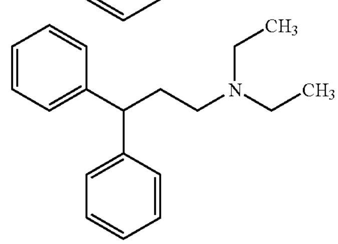 | 27.5 |

[a]Inhibition of NMDA/glycine-induced increases in intracellular calcium in cultured rat cerebellar granule cells (RCGC's) (see Example 1).

Certain simplified arylalkylamine compounds were selected for evaluation of activity in a battery of neurotransmitter receptor binding assays, and for activity against the L-type calcium channel and delayed rectifier potassium channel. The compounds were inactive (less than 50% inhibition at concentrations up to 10 μM) in the following assays: nonselective α2 adrenergic receptor ([$^3$H]RX 821002 binding in rat cortex), H1 histamine receptor ([$^3$H]pyrilamine binding in bovine cerebellum), nonselective sigma receptor ([$^3$H]DTG binding in guinea pig brain), nonselective opiate receptor ([$^3$H]naloxone binding in rat forebrain), monoamine oxidase (MAO) activity, both MAO-A ([$^{14}$C]serotonin metabolism in rat liver mitochondria) and MAO-B ([$^{14}$C]phenylethylamine metabolism in rat liver mitochondria).

As can be seen in Table 10, activity was noted for several compounds at concentrations below 10 μM in the following assays: L-type calcium channel, delayed rectifier potassium channel, central muscarinic cholinergic receptor binding, and monoamine (dopamine, norepinephrine, and serotonin) uptake binding assays. This profile of activity in the central muscarinic cholinergic receptor and monoamine uptake binding assays is not unexpected, given the chemical structures of our simplified arylalkylamines (refer to Table 2 above). With the exceptions, however, of the activity of Compound 19 in the serotonin uptake binding assay, the activity of Compound 34 in the dopamine uptake binding assay, the activity of Compound 50 in the serotonin uptake binding assay, the activity of Compounds 63 and 64 in the dopamine uptake binding assay, and the activity of Compound 60 in the dopamine and serotonin uptake binding assays, the simplified arylalkylamine compounds were most potent at the NMDA receptor.

TABLE 10

| Compound | IC$_{50}$ (μm) vs. NMDA[a] | L-type calcium channel[b] | Delayed rectifier potassium channel[c] | Central muscarinic Cholinergic receptor[d] | Monoamine uptake binding assays[e] |
|---|---|---|---|---|---|
| Compound 19 | 0.435 | 10.2 | 1–10 | 4% at 0.174% at 10 | 7% at 0.1[f]75% at 10[f]3% at 0.1[g]53% at 10[g]18% at 0.1[h]89% at 10[h] |
| Compound 20 | 0.070 | 2.2 | 1–10 | 8% at 0.190% at 10[f] | 6% at 0.1[f]81% at 10[f] 5% at 0.1[g]58% at 10[g]28% at 0.1[h]94% at 10[h] |
| Compound 33 | 0.00 | 1.6 | >10 | 42% at 0.199% at 10 | 23% at 0.1[f]86% at 10[f]2% at 0.1[G]54% at 10[g]14% at 0.1[h]89% at 10[h] |
| Compound 34 | 0.426 | not tested | ~10 | 25% at 0.199% at 10 | 60% at 0.1[f]99% at 10[f]10% at 0.1[g]64% at 10[g]12% at 0.1[h]79% at 10[h] |
| Compound 50 | 0.089 | not tested | ~10 | 11% at 0.184% at 10 | 17% at 0.1[f]93% at 10[f] 10% at 0.1[g]78% at 10[g]75% at 0.1[h]97% at 10[h] |
| Compound 46 | 0.013 | 0.676 | ~3 | 33% at 0.189% at 10 | 40% at 0.1[f]97% at 10[f]7% at 0.1[g]64% at 10[g]10% at 0.1[h]75% at 10[h] |
| Compound 63 | 0.093 | 1.9 | not tested | 11% at 0.181% at 10 | 64% at 0.1[f]98% at 10[f]7% at 0.1[g]76% at 10[g]13% at 0.1[h]85% at 10[h] |
| Compound 64 | 0.309 | not tested | not tested | 11% at 0.183% at 10 | 50% at 0.1[f]99% at 10[f] 8% at 0.1[g]65% at 10[g]29% at 0.1[h]68% at 10[h] |
| Compound 58 | 0.028 | 1.6 | not tested | 1% at 0.148% at 10 | 0% at 0.1[f]45% at 10[f]1% at 0.1[g]67% at 10[g]27% at 0.1[h]95% at 10[h] |
| Compound 59 | 0.272 | not tested | not tested | 9% at 0.187% at 10 | 2% at 0.1[f]78% at 10[f]7% at 0.1[g]51% at 10[g]14% at 0.1[h]86% at 10[h] |
| Compound 60 | 0.416 | 2.3 | not tested | 13% at 0.193% at 10 | 0.914 16% at 0.1[g]64% at 10[g] 0.068[h] |

[a]Inhibition of NMDA/glycine-induced increases in intracellular calcium in cultured rat cerebellar granule cells (RCGC's) (see Example 1).
[b]Inhibition of KCl depolarization-induced increases in intracellular calcium in cultured rat cerebellar granule cells (RCGCs); estimated IC$_{50}$ value in μM.
[c]Inhibition of delayed rectifier potassium channel in cultured N1E-115 neuroblastoma cells; estimated IC$_{50}$ Value in μM.
[d]Inhibition of the binding of [$^3$H] quinuclidinylbenzilate (QNB) to rat cortical membranes; percent block at indicated concentration in μM.
[e]Inhibition of the binding of [$^3$H] WIN-35,428 to guinea pig striatal membranes (dopamine uptake binding assay), [$^3$H] desipramine to rat cortical membranes (norepinephrine uptake binding assay), or [$^3$H] citalopram to rat forebrain membranes (serotonin uptake binding assay); percent block at indicated concentration in μM, or IC$_{50}$ when available.
[f]dopamine uptake binding assay
[g]norepinephrine uptake binding assay
[h]serotonin uptake binding assay Advantageous properties of the arylalkylamine compounds of the present invention are illustrated by the fact that concentrations which suppress NMDA receptor-mediated synaptic transmission fail to inhibit LTP. Furthermore, while compounds such as Compound 9, and 11 do produce a hypotensive response following systemic administration in rats, the hypotensive effect produced by these compounds is of a relatively short duration (approximately 30 min). Additionally, Compounds 12 and 14 have no cardiovascular activity at doses up to 37.3 μmoles/kg i.v. and 15 μmoles/kg i.v., respectively.

TABLE 11

| Compound | Suppresion of NMDA Receptor-Mediated Synaptic Transmission[a] | LTP Assay[b] | Drop in Mean Arterial Blood Pressure[c] |
|---|---|---|---|
| Compound 1 | 10–30 μM | no block at 300 μM | 65 mm Hg at 1.5 μmoles/kg i.v., 60 min duration |

TABLE 11-continued

| Compound | Suppresion of NMDA Receptor-Mediated Synaptic Transmission[a] | LTP Assay[b] | Drop in Mean Arterial Blood Pressure[c] |
|---|---|---|---|
| Compound 2 | 10–30 μM | no block at 100 μM | 40 mm Hg at 1.5 μmoles/kg i.v., 120 min duration |
| Compound 3 | 10–30 μM | not tested | 20 mm Hg at 1 mg/kg s.c., >60 min duration |
| Compound 4 | 10–100 μM | no block at 100 μM | 40 mm Hg at 1.5 μmoles/kg i.v., 120 min duration |
| Compound 9 | 10–100 μM | no block at 100 μM | 75 mm Hg at 4.5 μmoles/kg i.v., 90 min duration |
| Compound 11 | not tested | not tested | 20 mm Hg at 1 mg/kg i.v., 30 min duration |
| Compound 12 | not tested | not tested | no effect at doses up to 37.3 μmoles/kg i.v. |
| Compound 14 | not tested | not tested | no effect at doses up to 15 μmoles/kg i.v. |
| Compound 19 | 100–300 μM | bock at 100 μM | not tested |
| Compound 20 | 30–300 μM | block at 100 μM | no effect at doses up to 15 μmoles/kg i.v. |
| Compound 22 | not tested | not tested | no effect at doses up to 15 μmoles/kg i.v. |

[a]Concentration which suppresses NMDA receptor-mediated synaptic transmission (see Example 5).
[b]Concentration that does not block the induction of LTP (see Example 19).
[c]Drop in systemic blood pressure produced by administration of compound in rats (see Example 22).

Compounds of Formula VIII and Methods of Use

The present invention further provides methods for treating a patient having a neurological disease or disorder, comprising administering a compound of Formula VIII:

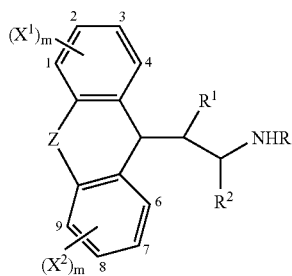

FORMULA VIII wherein:

Z is selected from the group consisting of —CH2CH2-, —CH2CH(CH3)-, —CH═CH—, —O—CH2-, —S—CH2-, —O—, and —S—;

$X^1$ and $X^2$ are independently selected from the group consisting of —F, —Cl, —CH3, —OH, and lower O-alkyl in the 1-, 3-, 7-, or 9-substituent positions;

m is independently an integer from 0 to 2;

—NHR is selected from the group consisting of —NH$_2$, —NHCH$_3$, and —NHC$_2$H$_5$;

$R^1$ is selected from the group consisting of —H, alkyl, hydroxyalkyl, —OH, —O-alkyl, and —O-acyl, and $R^2$ is selected from the group consisting of —H, alkyl, hydroxyalkyl, and pharmaceutically acceptable salts and complexes thereof, wherein the compound is active at an NMDA receptor.

Especially preferred aspects are those embodiments in which:

Z is —CH$_2$CH$_2$—;

$X^1$ or $X^2$ is —F, or both $X^1$ and $X^2$ are —F;

either $R^1$ or $R^2$ is methyl or both $R^1$ and $R^2$ are —H; and

—NHR is selected from the group consisting of —NH2 or —NHCH$_3$.

In further preferred embodiments, the methods of treatment include administration of a compound selected from compounds 156, 182, 183, 184, 187, 193, 194, 195, 196, and 197, and pharmaceutically acceptable salta and complexes thereof. Preferably, said compound is active at an NMDA receptor.

In most preferred embodiments, the methods of treatment include administration of a compound selected from compounds 193, 194, 195, 196, and 197.

The present invention further provides simplified arylalkylamines comprising the compounds of Formula VIII, and all preferred aspects of Formula VIII, as set out above.

Examples of such simplified arylalkylamines include, but are not limited to, Compounds 156, 182, 183, 184, 187, 193, 194, 195, 196, and 197, whose structures are provided herein. Preferably, the compound has an IC$_{50}$ 10 μM at an NMDA receptor. More preferably, the compound has an IC$_{50}$≦5 μM, more preferably ≦2.5 μM, and most preferably ≦0.5 μM at an NMDA receptor.

In preferred embodiments, the compound is selected from the group consisting of Compound 193, 194, 195, 196, and 197, and pharmaceutically acceptable salts and complexes thereof.

In most preferred embodiments, the compound, selected from the group consisting of Compounds 193–197, is active at an NMDA receptor.

Also provided in an aspect of the invention are pharmaceutical compositions of Formula VIII useful for treating a patient having a neurological disease or disorder. The pharmaceutical compositions are provided in a pharmaceutically acceptable carrier and appropriate dose. The pharmaceutical compositions may be in the form of pharmaceutically acceptable salts and complexes, as is known to those skilled in the art.

Preferred pharmaceutical compositions comprise a compound selected from the group consisting of Compound 193, 194, 195, 196, 197, and pharmaceutically acceptable salts and complexes thereof, and a pharmaceutically acceptable carrier. Preferably, the compound has an IC$_{50}$ ≦10 μM at an NMDA receptor. More preferably, the compound has an IC$_{50}$ ≦5 μM, more preferably ≦2.5 μM, and most preferably ≦0.5 μM at an NMDA receptor.

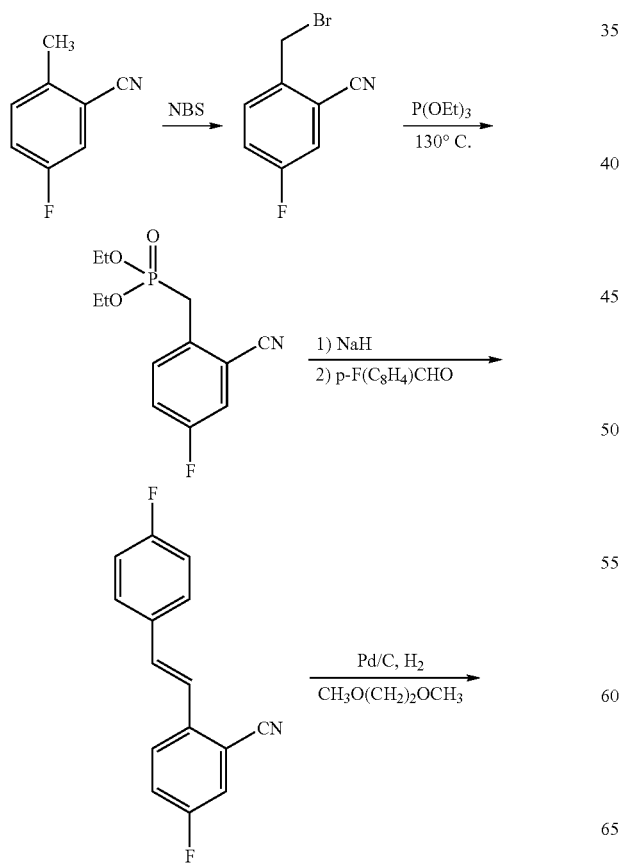

Synthetic Scheme for Compound 195

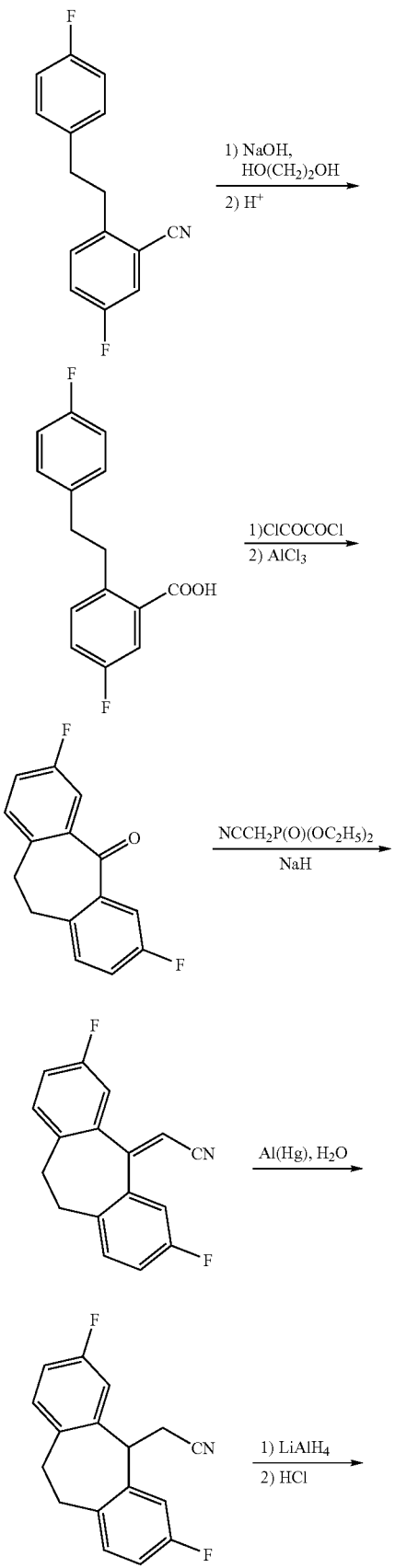

-continued

-continued

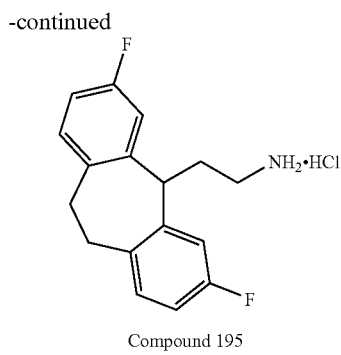

Compound 195

Synthesis of Compound 195

2-Bromomethyl-5-fluorobenzonitrile

A mixture of 5-fluoro-2-methylbenzonitrile (10.0 g, 74.0 mmol), N-bromosuccinimide (NBS, 13.2 g, 74.0 mmol), benzoyl peroxide (0.2 g, 0.82 mmol), and carbon tetrachloride (100 mL) was refluxed for 18 h. The reaction mixture was then cooled to room temperature and filtered through fritted glass. The solid in the funnel was washed with carbon tetrachloride (3×50 mL) and evaporated to dryness under vacuum to provide 16.1 g, 102% yield of product.

Diethyl-2-cyano-4-fluorobenzyl phosphonate

A mixture of 2-bromomethyl-5-fluoro-benzonitrile (16.1 g, 75.2 mmol, 1 equiv) and triethyl phosphite (16.3 mL, 15.8 g, 94.8 mmol, 1.26 equiv) were heated at 130° C. for 1 h, open to the air. The reaction mixture was then heated at 165° C. for 30 min to remove ethyl bromide and excess triethyl phosphite and subsequently cooled to room temperature to provide 24.8 g (122% crude yield) of a light-orange oil.

2-[2(4-Fluorophenyl)ethenyl]-5-fluorobenzonitrile

Sodium hydride (60% in mineral oil; 1.66 g [0.993 g NaH], 1.4 mmol, 1.10 equiv) was added to a solution of diethyl-2-cyano-4-fluorobenzyl phosphonate (10.2 g-equiv, 37.6 mmol, 1.0 equiv) in DMF (40 mL) over a period of 2 min. The reaction was stirred for 20 min at room temperature. 4-Fluorobenzaldehyde (4.67 g, 38 mmol, 1.0 equiv) was then added over a period of 2 min. After stirring for 18 h, H$_2$O (200 mL) and satd. NaCl (50 mL) were added and the resulting mixture was extracted with EtOAc (2×100 mL). The combined organic layers were washed with 1N NaOH (1×100 mL) and H$_2$O (2×100 mL), dried (anhyd. Na$_2$SO$_4$), and rotary evaporated (>100° C., heat gun). The crude, dark-red crystalline/oil (7.49 g, 82.7%) was chromatographed twice on silica gel (50×250 mm, dry pack), eluting first with hexane/EtOAc [4:1] and the second chromatography with [30:1] to provide a TLC-pure, yellow compound (2.1 g, 23.2%).

2-[2-(4-Fluorophenyl)ethyl]-5-fluorobenzonitrile

2-[2-(4-Fluorophenyl)ethenyl]-5-fluorobenzonitrile (2.1 g, 8.7 mmol) was dissolved in ethylene glycol dimethyl ether (100 mL). Palladium on charcoal (10% Pd; 0.20 g) was added, and the reaction mixture was shaken under 60 psig H$_2$ for 1 h. The reaction mixture was then filtered through Celite®, and the filtrate was rotary evaporated (75° C.) to provide 2.1 g (99%) of product as a light-yellow oil.

2-[2-(4-Fluorophenyl)ethyl]-5-fluorobenzoic acid

A mixture of 2-[2-(4-fluorophenyl)ethyl]-5-fluorobenzonitrile (2.12 g, 8.72 mmol, 1 equiv) and aq. NaOH (10N; 3.9 mL, 39.3 mmol, 4.5 equiv) in ethylene glycol (25 mL) was heated at 190° C. for 24 h. After allowing the mixture to cool, H$_2$O (100 mL) was added followed by 12N HCl (8 mL). The cloudy mixture precipitated the desired product as a cream-colored solid. This material was washed with H$_2$O (3×20 mL) and dried under vacuum (18 h, 25° C., 0.1 mm Hg) to provide 2.02 g (88.4%) of a cream-colored solid.

3,7-Difluoro-10,11-dihydro-5H-dibenzo[a,d]cyclohepten-5-one

A mixture of 2-[2-(4-fluorophenyl)ethyl]-5-fluorobenzoic acid (2.02 g, 7.71 mmol, 1 equiv) and oxalyl chloride (1.37 g, 10.8 mmol, 1.4 equiv) in CH$_2$Cl$_2$ (20 mL) was refluxed for 30 min. The resulting solution was then added to a stirring suspension of aluminum chloride (1.44 g, 10.8 mmol, 1.4 equiv) in CH$_2$Cl$_2$ (50 mL). This mixture was refluxed for 1 h. The reaction mixture was then washed with 1N HCL (3×20 mL), aq. satd. NaCl (1×50 mL), and H$_2$O (1×50 mL) The organic layer was dried (anhyd. Na$_2$SO$_4$) and rotary evaporated to provide 1.6 g of a light-orange-colored semi-solid. This material was chromatographed (3:1 hexane/CHCl$_3$) through silica gel (150 mm×25-mm dia.). Evaporation of the combined fractions containing product provided 0.93 g (49%) of the desired product as a light-yellow shiny solid.

3,7-Difluoro-10,11-dihydro-5H-dibenzo[a,d]cyclohepten-5-ylidenenitrile

Diethylcyanomethylphosphonate (1.01 g, 5.72 mmol, 1.50 equiv) was dissolved in DMF (15 mL) and sodium hydride (60% in mineral oil; 0.229 g, 0.137 g NaH, 5.72 mmol, 1.5 equiv) was added. After stirring for 20 min, a solution of 3,7-difluoro-10,11-dihydro-5H-dibenzo[a,d]cyclohepten-5-one (0.930 g, 3.81 mmol, 1 equiv) in DMF (5 mL) was added. After stirring for 2 h, EtOAc (100 mL) was added, and the resulting solution was washed with H$_2$O (4×25 mL), dried (anhyd. Na$_2$SO$_4$), and rotary evaporated (75° C.) to provide 0.86 g (84.5%) of a yellow, crystalline solid.

3,7-Difluoro-10,11-dihydro-5-cyanomethyl-5H-dibenzo[a,d]cycloheptene

Aluminum/mercury amalgam was prepared as follows. To aluminum granules (4.0 g, Aldrich, −10+60 mesh, 99+%) was added 0.5N NaOH (200 mL). The mixture was stirred for 5 min, and then the supernatant was decanted. The etched Al was subsequently washed with H$_2$O (200 mL), and then with EtOH (200 mL). The aluminum was then suspended in EtOH (100 mL) and a solution of Hg$_2$Cl (4.0 g, Aldrich, 99.5%, A.C.S. reagent) dissolved in Et$_2$O (200 mL) was added. The reaction was stirred for 5 min. The supernatant was decanted and the Al(Hg) amalgam was washed with H$_2$O (200 mL), EtOH (200 mL), and, finally, Et$_2$O (200 mL). The amalgam was then covered with Et$_2$O (100 mL) and was ready for use.

A solution of 3,7-difluoro-10,11-dihydro-5H-dibenzo[a,d]cyclohepten-5-ylidenenitrile (0.86 g, 3.22 mmol) dissolved in EtOAc (25 mL) was added to the amalgam. EtOH (25 mL) and then H$_2$O (5 mL) were then added, and the mixture was stirred at room temperature for 1 h. The reaction mixture was subsequently filtered through paper and the filtrate was evaporated to provide 960 mg (110% yield) of crude product as a nearly colorless oil which crystallized on standing. This material was found to be contaminated with a small amount (<5%) of diethylcyanomethyl phosphonate.

3,7-Difluoro-10,11,-dihydro-5-(2-aminoethyl)-5H-dibenzo[a,d]cycloheptene hydrochloride To a suspension of lithium aluminum hydride (339 mg, 8.92 mmol, 2.5 equiv) in anhyd. diethyl ether (10 mL) was added 3,7-difluoro-10,11-dihydro-5-(2-cyanoethyl)-5H-dibenzo[a,d]cycloheptene (0.96 g, 3.57 mmol) dissolved in anhyd. diethyl ether (5 mL) over a period of 2 min. The reaction was then stirred at room temperature for 30 min. Water (0.3 mL) was added followed by 5N NaOH (0.3 mL), followed by H$_2$O (0.9 mL) with stirring to precipitate the inorganic salts. Diethyl ether (20 mL) was added and the reaction was filtered through paper. The filtrate was then rotary-evaporated to provide 0.80 g (82.1%) of product as its free base, a colorless oil which solidified on standing. The free base was dissolved in diethyl ether (50 mL). Excess ethereal hydrogen chloride (1 M) was added to precipitate the corresponding hydrochloride salt as a white solid (0–60 g, 54%).

Synthetic Scheme for Compound 197

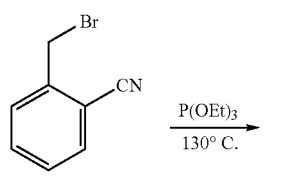
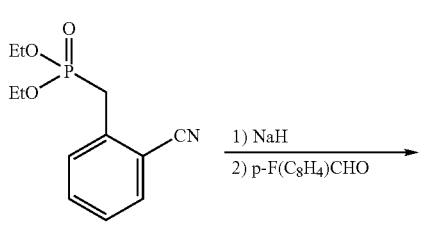
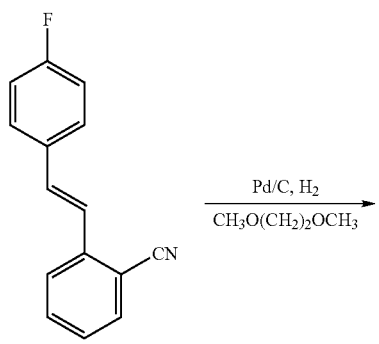
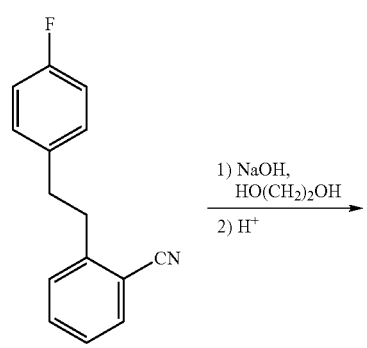
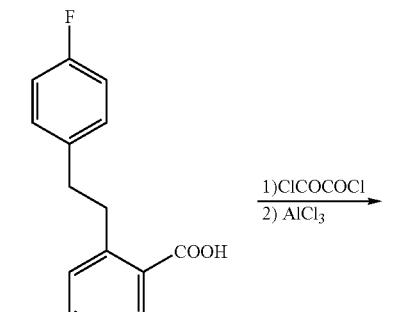
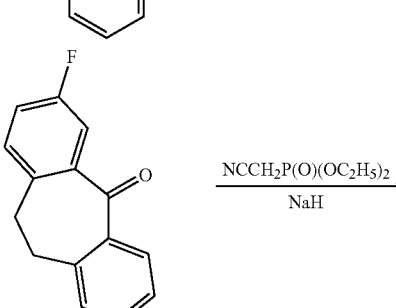
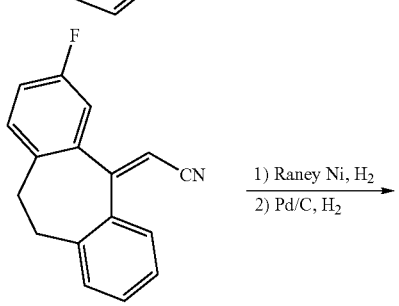
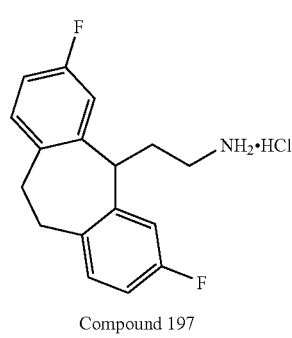

Compound 197

EXAMPLE 2

Synthesis of Compound 197

2-[2-(4-Fluorophenyl)ethenyl]benzonitrile

A mixture of (α-bromo-o-tolunitrile (10.0 g, 51.0 mmol, 1 equiv) and triethyl phosphite (11.0 mL, 10.7 g, 64.1 mmol, 1.26 equiv) was heated to 130° C. in an oil bath for 1 h. The reaction was then heated to 165° C. for 30 min to remove ethyl bromide and excess triethyl phosphite. After allowing the reaction to cool, anh. DMF (40 mL) was added. Sodium hydride (60% dispersion in mineral oil; 2.05 g, 1.23 g NaH, 51.3 mmol, 1.00 equiv) was added over a period of 2 min. The reaction was stirred for 10 min.

The reaction was then placed in a water bath (25° C.) and 4-fluorobenzaldehyde (5.5 mL, 6.4 g, 51 mmol, 1.0 equiv) was added over a period of 2 min. After stirring for 2.5 h, H$_2$O (200 mL) was added and the resulting mixture was extracted with EtOAc (2×100 mL). The combined organic layers were washed with 1N NaOH (1×100 mL) and H$_2$O (2×100 mL), dried (anh. Na$_2$SO$_4$), and rotary evaporated (>100° C., heat gun). While still hot, hexane (25 mL) was added. The product crystallized while stirring as the mixture was allowed to cool to 25° C. The crystals were filtered, washed with hexane (2×25 mL), and allowed to dry in the open air for 16 h. This provided 8.10 g (71.1%) of the desired product as an orange, crystalline solid.

2-[2-(4-Fluorophenyl)ethyl]benzonitrile

2-[2-(4-Fluorophenyl)ethyl]benzonitrile (8.10 g, 36.3 mmol) was dissolved in ethylene glycol dimethyl ether (200 mL). Palladium on charcoal. (10% Pcl; 0.81 g) in H$_2$O (1.0 mL) was added, and the reaction mixture was shaken under 60 psig H$_2$ for 1 h. The reaction mixture was then filtered through Celite®, and the filtrate was rotary evaporated (75° C.). This provided 8.03 g (98.3%) of the product as an orange oil which crystallized on standing.

2-[2-(4-Fluorophenyl)ethyl]benzoic acid

A mixture of 2-[2-(4-fluorophenyl)ethyl]benzonitrile (8.03 g, 35.6 mmol, 1 equiv) and aq. NaOH (10N; 16 mL, 160 mmol, 4.5 equiv) in ethylene glycol (100 mL) was heated to 190 C for 69 h. After allowing the reaction mixture to cool, H$_2$O (300 mL) was added, followed by 12N HCl (16 mL). This mixture was extracted with CHCl$_3$ (1×100 mL) and the organic layer was then washed with H$_2$O (2×50 mL). The organic layer was dried (anh. Na2SO4) and rotary evaporated (90° C.). This provided 7.44 g (85.4%) of a light-yellow solid.

3-Fluoro-10,11-dihydro-5H-dibenzo[a,d]cyclohepten-5-one

A mixture of 2-[2-(4-fluorophenyl)ethyl]benzoic acid (4.00 g, 16.4 mmol, 1 equiv) and oxalyl chloride (2.0 mL, 2.9 g, 23 mmol, 1.4 equiv) in CH$_2$Cl$_2$ (50 mL) was refluxed for 30 min. The resulting solution was then added to a stirring suspension of aluminum chloride (3.0 g, 2.2 mmol, 1.4 equiv) in CH$_2$Cl$_2$ (50 mL). This mixture was refluxed for 1 h. The reaction mixture was then washed with 1N HCl (3×50 mL), aq. satd. NaCl (1×50 mL), and H$_2$O (1×50 mL). The organic layer was dried (anh. Na$_2$SO$_4$) and rotary evaporated (75° C.) to provide 3.7 g of a dark-brown oil. This oil was flash chromatographed (20:1 hexane/EtOAc) through flash silica gel (250 mm×25 mm). Evaporation of the combined fractions of interest provided 1.58 g (42.6%) of the desired product as a yellow oil.

3-Fluoro-10,11-dihydro-5H-dibenzo[a,d]cyclohepten-5-ylidenenitrile

Diethylcyanomethylphosphonate (1.76 g, 9.94 mmol, 1.50 equiv) was dissolved in DMF (15 mL) and sodium hydride (60% in mineral oil; 0.40 g, 0.24 g NaH, 10 mmol, 1.5 equiv) was added. After stirring for 10 min, 3-fluoro-10,11-dihydro-5H-dibenzo[a,d]cyclohepten-5-one (1.50 g, 6.63 mmol, 1 equiv) was transferred in with DMF (5 ML). After stirring for 19 h, H$_2$O (100 mL) was added. The resulting mixture was extracted with EtOAc (2×50 mL). The combined organic layers were washed with aq. satd. NaCl (2×50 mL), dried (anh. Na$_2$SO$_4$), and rotary evaporated (75° C.) to provide 2 g of a dark-brown oil. This material was flash chromatographed (9:1 hexane/EtOAc) through flash silica gel (200 mm×25 mm) to provide 1.60 g (96.8%) of a yellow solid.

3-Fluoro-10,11-dihydro-5-(2-aminoethyl)-5H-dibenzo[a,d]cycloheptene hydrochloride 3-Fluoro-10,11-dihydro-5H-dibenzo[a,d]cyclohepten-5-ylidenenitrile (1.60 g, 6.42 mmol) was dissolved in EtOH (160 mL), and 1N NaOH (16 mL) and Raney nickel (slurry in H$_2$O; 1.6 g) were added. The reaction mixture was shaken under 60 psig H$_2$ at 60° C. for 16 h. At this point, all of the starting material had disappeared, but a significant amount of alkeneamine intermediate remained. The reaction mixture was filtered through Celite® and the solvent was removed by rotary evaporation. The resulting material was dissolved in EtOAc (100 mL), washed with H$_2$O (2×50 mL), dried (anh. Na$_2$SO$_4$), and the EtOAc was removed by rotary evaporation. This material was then dissolved in EtOH (50 mL). Palladium on charcoal (10% Pd; 0.80 g) and 12.1N HCl (~3 mL) were subsequently added. The reaction mixture was then shaken under 60 psig H$_2$ at 70° C. for 24 h. The reaction mixture was filtered through Celite® and the filtrate was rotary evaporated to afford 2.10 g of product as a brown, bubbly solid. This solid was dissolved in CHCl$_3$ (50 mL) and "free-based" with satd. aq. NaHCO$_3$ (25 mL). The aqueous layer (which was full of precipitate) was then extracted with CHCl$_3$ (1×50 mL). The combined organic layers were dried (anh. Na$_2$SO$_4$) and rotary evaporated (75° C.). The resulting dark-brown oil was flash chromatographed (1:10 MeOH/CHCl$_3$) through flash silica gel (250 mm×25 mm). This yielded 0.48 g of free-base product as a light-brown oil. This oil was dissolved in EtOH (2.0 mL), and 1.0 M HCl in Et2O (3.0 mL) was added. This solution was rotary evaporated to yield 0.55 g (29%) of the desired product as a cream-colored, bubbly solid.

Different possible "planar" ring conformations of Compound 20, and Compounds 194 and 195 are presented below. All are considered to be within the scope of the present invention.

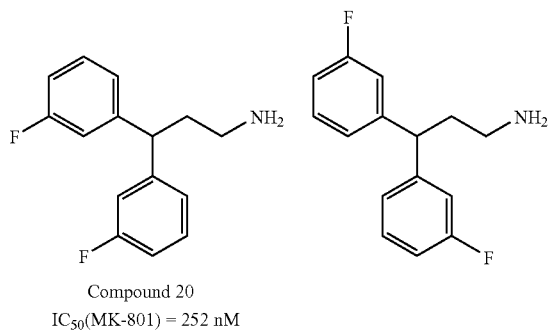

Compound 20
IC$_{50}$(MK-801) = 252 nM

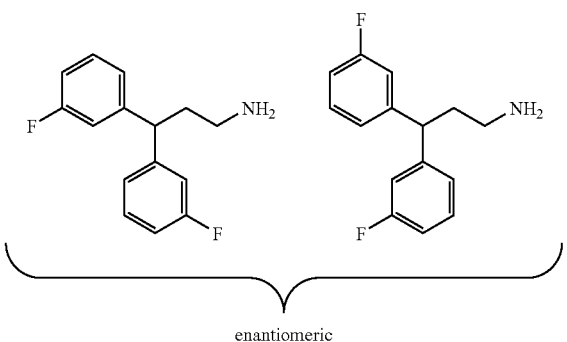

enantiomeric

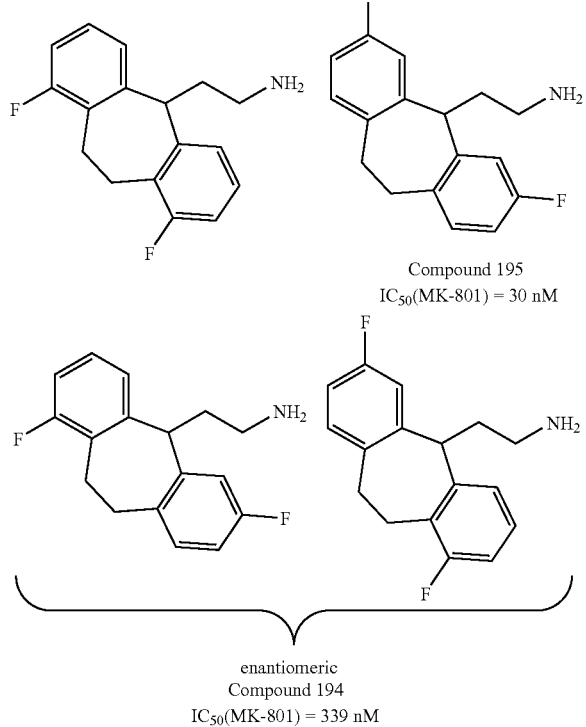

enantiomeric
Compound 194
IC$_{50}$(MK-801) = 339 nM

Compound 195
IC$_{50}$(MK-801) = 30 nM

Physical Data for Compounds 93–97

Gas chromatographic and mass spectral data were obtained using a Hewlett-Packard 5890 Series II Gas Chromatograph with a 5971 Series Mass Selective Detector [Ultra-2 Ultra Performance Capillary Column (crosslinked 5% phenyl methyl silicone); column length, 25 m, column i.d., 0.20 mm; He flow rate, 60 mL/min; injector temp., 250° C.; gradient temperature program, 20° C./min from 125 to 325° C. for 10 min, then held constant at 325° C. for 6 min].

Compound 193, R$_f$=8.79 min, m/z (% rel. int.) 273 (M+,21), 256 (53), 255 (32), 242 (13), 241 (73), 231 (11), 230 (75), 229 (100), 228 (29), 227 (56), 225 (11), 220 (8), 215 (31), 214 (67), 209 (13), 207 (20), 201 (19), 196 (11), 183 (12), 147 (13), 146 (10), 134 (16), 133 (77), 109 (42), 107 (7), 83 (8), 44 (44), 43 (8), 42 (8).

Compound 194, R$_f$=8.79 min, m/z (% rel. int.) 273 (M+,22), 256 (59), 255 (36), 242 (17), 241 (92), 230 (54), 229 (90), 228 (41), 227 (76), 225 (15), 221 (8), 220 (10), 215 (34), 214 (67), 209 (16), 207 (25), 201 (27), 196 (12), 183 (15), 147 (14), 146 (13), 134 (20), 133 (100), 109 (53), 107 (10), 83 (12), 44 (47), 43 (10), 42 (10).

Compound 195, R$_f$=8.84 min, m/z (% rel. int.) 273 (M+,35), 256 (71), 255 (45), 242 (19), 241 (100), 240 (9), 230 (45), 229 (83), 228 (40), 227 (77), 225 (15), 220 (8), 215 (31), 214 (56), 209(14), 207 (18), 201 (22), 196 (10), 183 (12), 147 (16), 146 (11), 134 (18), 133 (87), 109 (47), 107 (8), 83 (10), 44 (45), 43 (9), 42 (9).

Compound 196, R$_f$=8.77 min, m/z (% rel. int.) 255 (M+,13), 238 (43), 237 (30), 224 (11), 223 (57), 220 (7), 212 (42), 211 (100), 210 (31), 209 (52), 208 (8), 207 (20), 197 (23), 196 (67), 191 (10), 189 (16), 183 (30), 178 (7), 170 (9), 165 (8), 134 (9), 133 (40), 116 (7), 115 (39), 109 (15), 91 (17), 63 (7), 44 (14), 42 (7).

Compound 197, R$_f$=8.77 min, m/z (% rel. int.) 255 (M+,17), 237 (39), 224 (14), 223 (73), 220 (17), 219 (10), 212 (36), 211 (100), 210 (38), 209 (64), 208 (11), 207 (25), 205 (12), 197 (27), 196 (71), 194 (12), 193 (24), 191 (20), 189 (20), 183 (34), 178 (18), 170 (10), 165 (13), 133 (49), 116 (10), 115 (60), 109 (19), 91 (24), 44 (19).

Some of the simplified arylalkyl amines disclosed have structural features similar to portions of the following compounds.

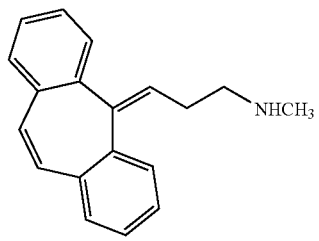

Nortriptyline

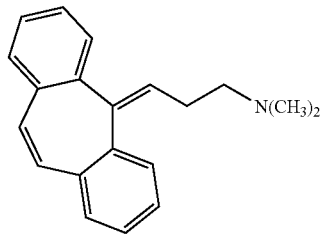

Cyclobenzaprine

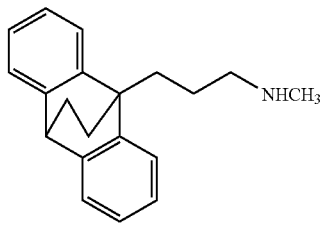

Maprotiline

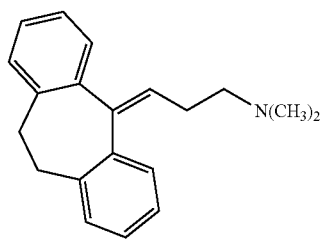

Amitriptyline

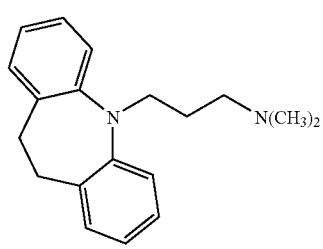

Imipramine

Clomipramine
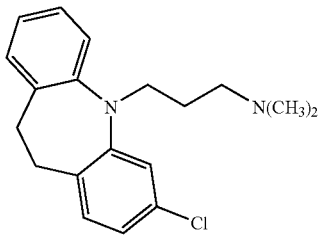

Doxepin
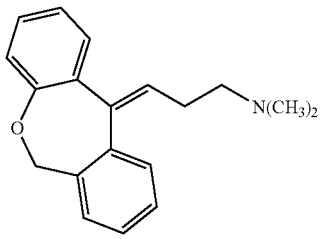

Chlorpromazine
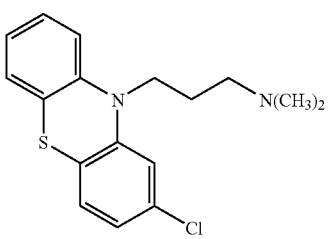

Desipramine
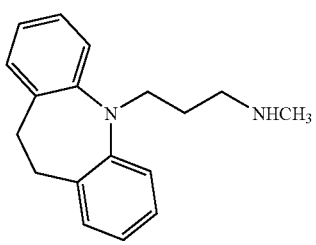

Protrylptyline
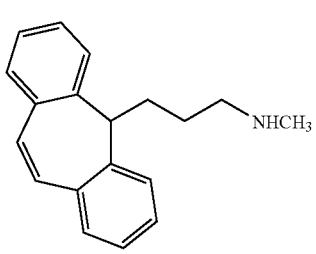

Eli Lilly Compound*
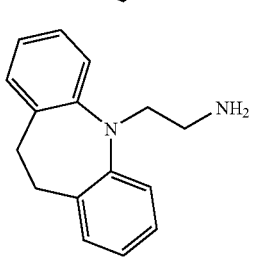

*Disclosed as Compound 1 in McQuaid et al., "Inhibition of [³H]-MK-801 binding and protection against NMDA-induced lethality in mice by a series of imipramine analogs," Res. Commun. Pathol. Pharm. 77:171–178, 1992.

Biological data for certain tricyclic compounds of Formula VIII are provided in Table 12. The data presented in Table 12 was obtained according to the same methods used to obtain the data for Table 1.

TABLE 12

Biological Data for Compounds Claimed

| Compound | IC$_{50}$ (μM) vs. NMDA[a] | IC$_{50}$ (μM) vs. [³H]MK-801[b] |
| --- | --- | --- |
| Compound 156 | 0.069 (3) | 0.081 (3) |
| Compound 182 | 2.6 (1) | 7.05 (1) |
| Compound 183 | 0.676 (1) | 5.01 (1) |
| Compound 184 | 1.5 (1) | 1.65 (2) |
| Compound 187 | 1.78 (1) | 2.06 (2) |
| Compound 193 | not tested | inactive @ 1 μM |
| Compound 194 | not tested | 0.371 (2) |
| Compound 195 | not tested | 0.029 (2) |
| Compound 196 | not tested | 2.24 (1) |
| Compound 197 | not tested | 0.053 (2) |
| Eli Lilly Compd. | 0.609 (2) | 1.17 (3) |
| Amitriptyline | not tested | 14.2 (2) |
| Imipramine | not tested | 6.75 (2) |
| Clomipramine | not tested | 10.0 (2) |
| Doxepin | not tested | 30.4 (1) |
| Chlorpromazine | not tested | 11.2 (1) |
| Desipramine | 2.3 | 3.26 (2) |
| Protriptyline | 73% @ 10 μM | 21.4 (1) |
| Nortriptyline | 3.7 | 5.67 (1) |
| Maprotiline | 5.8 | not tested |
| Cyclobenzaprine | not tested | 14.5 (1) |

[a]Inhibition of NMDA/glycine-induced increases in intracellular calcium in cultured rat cerebellar granule cells (RCGC's). (# in parentheses indicates the number of experiments).
[b]Inhibition of [3H]MK-801 binding in rat cortical/hippocampal washed membrane preparations.

Formulation and Administration

As demonstrated herein, useful compounds of this invention and their pharmaceutically acceptable salts may be used to treat neurological disorders or diseases. While these compounds will typically be used in therapy for human patients, they may also be used to treat similar or identical diseases in other vertebrates such as other primates, farm animals such as swine, cattle and poultry, and sports animals and pets such as horses, dogs and cats.

In therapeutic and/or diagnostic applications, the compounds of the invention can be formulated for a variety of modes of administration, including systemic and topical or localized administration. Techniques and formulations generally may be found in *Remington's Pharmaceutical Sciences*, Mack Publishing Co., Easton Pa. (18th ed. 1990).

Pharmaceutically acceptable salts are generally well known to those of ordinary skill in the art, and may include, by way of example but not limitation, acetate, benzenesulfonate, besylate, benzoate, bicarbonate, bitartrate, calcium edetate, camsylate, carbonate, citrate, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, mucate, napsylate, nitrate, pamoate (embonate), pantothenate, phosphate/disphosphate, polygalacturonate, salicylate, stearate, subacetate, succinate, sulfate, tannate, tartrate, or teoclate. Other pharmaceutically acceptable salts may be found in, for example, Remington's Pharmaceutical Sciences, Mack Publishing Co., Easton, Pa. (18th ed. 1990).

Preferred pharmaceutically acceptable salts include, for example, acetate, benzoate, bromide, carbonate, citrate, gluconate, hydrobromide, hydrochloride, maleate, mesylate, napsylate pamoate (embonate), phosphate, salicylate, succinate, sulfate, or tartrate.

The useful compounds of this invention may also be in the form of pharmaceutically acceptable complexes. Pharmaceutically acceptable complexes are known to those of ordinary skill in the art and include, by way of example but not limitation, 8-chlorotheophyllinate (teoclate).

The exact formulation, route of administration and dosage can be chosen by the individual physician in view of the patient's condition. (See e.g. Fingl et al., in *The Pharmacological Basis of Therapeutics*, 1975, Ch. 1 p. 1).

It should be noted that the attending physician would know how and when to terminate, interrupt, or adjust administration due to toxicity or organ dysfunction. Conversely, the attending physician would also know to adjust treatment to higher levels if the clinical responses were not adequate (precluding toxicity). The magnitude of an administered dose in the management of the disorder of interest will vary with the severity of the condition to be treated and to the route of administration. The severity of the condition may, for example, be evaluated in part, by standard prognostic evaluation methods. Further, the dose and perhaps dose frequency, will also vary according to the age, body weight, and response of the individual patient. A program comparable to that discussed above may be used in veterinary medicine.

Depending on the specific conditions being treated, such agents may be formulated into liquid or solid dosage forms and administered systemically or locally. The agents may be delivered, for example, in a timed or sustained-release form as is known to those skilled in the art. Techniques for formulation and administration may be found in *Remington's Pharmaceutical Sciences*, Mack Publishing Co., Easton, Pa. (18th ed. 1990). Suitable routes may include oral, buccal, sublingual, rectal, transdermal, vaginal, transmucosal, nasal or intestinal administration; parenteral delivery, including intramuscular, subcutaneous, intramedullary injections, as well as intrathecal, direct intraventricular, intravenous, intraperitoneal, intranasal, or intraocular injections, just to name a few.

For injection, the agents of the invention may be formulated in aqueous solutions, preferably in physiologically compatible buffers such as Hank's solution, Ringer's solution, or physiological saline buffer. For such transmucosal administration, penetrants appropriate to the barrier to be permeated are used in the formulation. Such penetrants are generally known in the art.

Use of pharmaceutically acceptable carriers to formulate the compounds herein disclosed for the practice of the invention into dosages suitable for systemic administration is within the scope of the invention. With proper choice of carrier and suitable manufacturing practice, the compositions of the present invention, in particular, those formulated as solutions, may be administered parenterally, such as by intravenous injection. The compounds can be formulated readily using pharmaceutically acceptable carriers well known in the art into dosages suitable for oral administration. Such carriers enable the compounds of the invention to be formulated as tablets, pills, capsules, liquids, gels, syrups, slurries, suspensions and the like, for oral ingestion by a patient to be treated.

Agents intended to be administered intracellularly may be administered using techniques well known to those of ordinary skill in the art. For example, such agents may be encapsulated into liposomes, then administered as described above. Liposomes are spherical lipid bilayers with aqueous interiors. All molecules present in an aqueous solution at the time of liposome formation are incorporated into the aqueous interior. The liposomal contents are both protected from the external microenvironment and, because liposomes fuse with cell membranes, are efficiently delivered into the cell cytoplasm. Additionally, due to their hydrophobicity, small organic molecules may be directly administered intracellularly.

Pharmaceutical compositions suitable for use in the present invention include compositions wherein the active ingredients are contained in an effective amount to achieve its intended purpose. Determination of the effective amounts is well within the capability of those skilled in the art, especially in light of the detailed disclosure provided herein.

In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions.

The pharmaceutical compositions of the present invention may be manufactured in a manner that is itself known, e.g., by means of conventional mixing, dissolving, granulating, dragee-making, levigating, emulsifying, encapsulating, entrapping or lyophilizing processes.

Pharmaceutical formulations for parenteral administration include aqueous solutions of the active compounds in water-soluble form. Additionally, suspensions of the active compounds may be prepared as appropriate oily injection suspension. Suitable lipophilic solvents or vehicles include fatty oils such as sesame oil, or synthetic fatty acid ester, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical preparations for oral use can be obtained by combining the active compounds with solid excipients, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations, for example, maize starch, wheat starch, rice starch, potato starch, gelatin, gum tragacanth, methyl cellulose, hydroxypropylmethyl-cellulose, sodium carboxymethylcellulose (CMC), and/or polyvinylpyrrolidone (PVP: povidone). If desired, disintegrating agents may be added, such as the cross-linked polyvinylpyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinylpyrrolidone, carbopol gel, polyethylene glycol (PEG), and/or titanium dioxide, lacquer solutions, and suitable organic solvents or solvent mixtures. Dye-stuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin, and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols (PEGs). In addition, stabilizers may be added.

Other embodiments are within the following claims.

The invention claimed is:

1. A compound of Formula VIII: wherein:

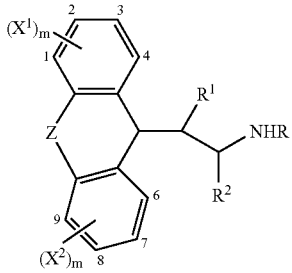

FORMULA VIII

Z is selected from the group consisting of —CH$_2$CH$_2$—, —CH$_2$CH(CH$_3$)—, —CH=CH—, —O—CH$_2$—, —S—CH$_2$—, —O—, and —S—;

X$^1$ and X$^2$ are independently selected from the group consisting of —F, —CH$_3$, —OH, and lower O-alkyl in the 1-, 3-, 7-, or 9-substituent positions;

m can be 1 or 2;

—NHR is selected from the group consisting of —NH$_2$, —NHCH$_3$, and —NHC$_2$H$_5$;

R$^1$ is selected from the group consisting of —H, alkyl, hydroxyalkyl, —OH, —O-alkyl, and —O-acyl;

R$^2$ is selected from the group consisting of —H, alkyl, hydroxyalkyl; and pharmaceutically acceptable salts and complexes thereof;

wherein the compound is active at an NMDA receptor.

2. The compound of claim 1, wherein R$^1$ and R$^2$ are independently selected from the group consisting of —H and alkyl.

3. The compound of claim 1, wherein Z is selected from the group consisting of —CH$_2$CH$_2$—, —CH=CH—, —O—CH$_2$—, —O—, and —S—.

4. The compound of claim 1, wherein Z is selected from the group consisting of —CH$_2$CH$_2$— and —O—CH$_2$—.

5. The compound of claim 2, wherein Z is selected from the group consisting of —CH$_2$CH$_2$—, —CH=CH—, —O—CH$_2$—, —O—, and —S—.

6. The compound of claim 2, wherein Z is selected from the group consisting of —CH$_2$CH$_2$— and —O—CH$_2$—.

* * * * *